US011319368B2

(12) United States Patent
Cook et al.

(10) Patent No.: US 11,319,368 B2
(45) Date of Patent: *May 3, 2022

(54) TREATMENT OF HEPATOTOXICITY WITH IL-11 ANTIBODY

(71) Applicants: Singapore Health Services PTE LTD., Singapore (SG); National University of Singapore, Singapore (SG)

(72) Inventors: Stuart Alexander Cook, Singapore (SG); Sebastian Schaefer, Singapore (SG); Anissa Widjaja, Singapore (SG)

(73) Assignees: Singapore Health Services PTE LTD., Singapore (SG); National University of Singapore, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 16/748,698

(22) Filed: Jan. 21, 2020

(65) Prior Publication Data
US 2020/0262910 A1 Aug. 20, 2020

(30) Foreign Application Priority Data

Jan. 21, 2019 (GB) .................................. 1900811
Jun. 3, 2019 (GB) .................................. 1907839
Oct. 17, 2019 (GB) .................................. 1915003

(51) Int. Cl.
| A61P 1/16 | (2006.01) |
| A61K 39/395 | (2006.01) |
| C07K 16/24 | (2006.01) |
| C07K 14/54 | (2006.01) |
| C07K 16/28 | (2006.01) |
| C12N 15/113 | (2010.01) |
| A61K 31/198 | (2006.01) |
| A61K 38/00 | (2006.01) |

(52) U.S. Cl.
CPC .............. *C07K 16/244* (2013.01); *A61P 1/16* (2018.01); *C07K 14/5431* (2013.01); *C07K 16/2866* (2013.01); *C12N 15/1136* (2013.01); *A61K 31/198* (2013.01); *A61K 38/00* (2013.01); *C07K 2317/76* (2013.01); *C12N 2310/11* (2013.01); *C12N 2310/14* (2013.01)

(58) Field of Classification Search
CPC ........................ A61P 1/16; A61K 2039/55527
See application file for complete search history.

(56) References Cited

U.S. PATENT DOCUMENTS

| 5,679,339 A | 10/1997 | Keith et al. |
| 5,843,509 A | 12/1998 | Calvo Salve et al. |
| 6,126,933 A | 10/2000 | Warne et al. |
| 6,540,993 B1 | 4/2003 | Warne et al. |
| 6,649,192 B2 | 11/2003 | Alonso Fernandez et al. |
| 6,846,907 B1 | 1/2005 | Shaughnessy et al. |
| 6,953,777 B2 | 10/2005 | Keith et al. |
| 6,998,123 B1 | 2/2006 | Shaughnessy et al. |
| 7,993,637 B2 | 8/2011 | Baca |
| 8,182,814 B2 | 5/2012 | Baca et al. |
| 8,361,966 B2 | 1/2013 | Azuma et al. |
| 8,518,888 B2 | 8/2013 | Jenkins et al. |
| 8,540,977 B2 | 9/2013 | Baca |
| 9,340,618 B2 | 5/2016 | Edwards et al. |
| 10,035,852 B2* | 7/2018 | Cook .................... C07K 16/244 |
| 10,106,603 B2 | 10/2018 | Cook et al. |
| 10,870,696 B2* | 12/2020 | Cook ................. C07K 14/7155 |
| 2003/0147849 A1 | 8/2003 | Warne et al. |
| 2004/0126358 A1 | 7/2004 | Warne et al. |
| 2004/0142871 A1 | 7/2004 | Shaughnessy et al. |
| 2006/0062760 A1 | 3/2006 | Keith et al. |
| 2007/0160577 A1 | 7/2007 | Damle et al. |
| 2009/0191147 A1 | 7/2009 | Keith et al. |
| 2009/0202533 A1 | 8/2009 | Baca et al. |
| 2010/0062058 A1 | 3/2010 | Warne et al. |
| 2010/0093976 A1 | 4/2010 | Azuma et al. |
| 2010/0183544 A1 | 7/2010 | Jenkins et al. |
| 2013/0302277 A1 | 11/2013 | Jenkins et al. |
| 2014/0219919 A1 | 8/2014 | Edwards et al. |
| 2016/0031999 A1 | 2/2016 | Edwards et al. |
| 2017/0174759 A1 | 6/2017 | Cook et al. |
| 2018/0186871 A1 | 7/2018 | Cook et al. |
| 2018/0186872 A1 | 7/2018 | Cook et al. |
| 2018/0265579 A1 | 9/2018 | Cook et al. |
| 2018/0362633 A1 | 12/2018 | Cook et al. |
| 2018/0362634 A1 | 12/2018 | Cook et al. |
| 2018/0362635 A1 | 12/2018 | Cook et al. |
| 2018/0362636 A1 | 12/2018 | Cook et al. |
| 2018/0362637 A1 | 12/2018 | Cook et al. |
| 2018/0362638 A1 | 12/2018 | Cook et al. |

(Continued)

FOREIGN PATENT DOCUMENTS

| CN | 105497893 A | 4/2016 |
| EP | 1630232 A2 | 3/2006 |

(Continued)

OTHER PUBLICATIONS

Rudikoff et al. Proc. Natl. Acad. Sci. USA vol. 79, pp. 1979-1983 (Mar. 1982).*
Janeway et al. Immunology, 3rd ed., 1997, Garland Publications, Inc., pp. 3:1-3:11.*
Kovalovich et al (2000), Hepatology, 31:149-159.*
Bourdi et al (2002), 35:289-298.*
Abbas-Terki et al., Lentiviral-mediated RNA interference. Hum Gene Ther. 2002;13(18):2197-2201.
Aceves et al., Airway fibrosis and angiogenesis due to eosinophil trafficking in chronic asthma. Curr Mol Med. 2008;8(5):350-358. doi: 10.2174/156652408785161023.
Agthe et al., Interleukin-11 classic but not trans-signaling is essential for fertility in mice. Placenta. Sep. 2017;57:13-16. doi: 10.1016/j.placenta.2017.05.015. Epub May 28, 2017.

(Continued)

*Primary Examiner* — Prema M Mertz
(74) *Attorney, Agent, or Firm* — Wolf, Greenfield & Sacks, P.C.

(57) ABSTRACT

Methods of treating and preventing hepatotoxicity through inhibiting interleukin 11 (IL-11)-mediated signalling are disclosed, as well as agents for use in such methods.

7 Claims, 64 Drawing Sheets

Specification includes a Sequence Listing.

(56) References Cited

U.S. PATENT DOCUMENTS

| | | |
|---|---|---|
| 2018/0362639 A1 | 12/2018 | Cook et al. |
| 2018/0362640 A1 | 12/2018 | Cook et al. |
| 2018/0362641 A1 | 12/2018 | Cook et al. |
| 2018/0371077 A1 | 12/2018 | Cook et al. |
| 2018/0371078 A1 | 12/2018 | Cook et al. |
| 2019/0002553 A1 | 1/2019 | Cook et al. |
| 2019/0389957 A1 | 12/2019 | Cook et al. |
| 2020/0031918 A1 | 1/2020 | Cook et al. |

FOREIGN PATENT DOCUMENTS

| | | |
|---|---|---|
| KR | 20110047179 A | 5/2011 |
| RU | 2016 125 115 A | 12/2017 |
| RU | 2016 151 730 A | 6/2018 |
| WO | WO 1991/019813 A1 | 12/1991 |
| WO | WO 1996/019574 A1 | 6/1996 |
| WO | WO 1998/36061 A2 | 8/1998 |
| WO | WO 1999/020755 A2 | 4/1999 |
| WO | WO 1999/032619 A1 | 7/1999 |
| WO | WO 1999/059608 A2 | 11/1999 |
| WO | WO 2000/078336 A1 | 12/2000 |
| WO | WO 2001/029058 A1 | 4/2001 |
| WO | WO 2002/020609 A2 | 3/2002 |
| WO | WO 2005/058956 A1 | 6/2005 |
| WO | WO 2005/070446 A1 | 8/2005 |
| WO | WO 2005/098041 A2 | 10/2005 |
| WO | WO 2009/052588 A1 | 4/2009 |
| WO | WO 2014/121325 A1 | 8/2014 |
| WO | WO 2017/103108 A1 | 6/2017 |
| WO | WO 2018/109168 A1 | 6/2018 |
| WO | WO 2018/109170 A2 | 6/2018 |
| WO | WO 2018/109174 A2 | 6/2018 |
| WO | WO 2019/207122 A1 | 10/2019 |
| WO | WO 2019/238882 A1 | 12/2019 |

OTHER PUBLICATIONS

Ahmad et al., Epidemiology and Genetic Risk Factors of Drug Hepatotoxicity. Clin Liver Dis. Feb. 2017;21(1):55-72. doi: 10.1016/j.cld.2016.08.004.

Almagro et al., Humanization of antibodies. Front Biosci. 2008;13:1619-1633. Published Jan. 1, 2008.

Altenhofer et al., Evolution of NADPH Oxidase Inhibitors: Selectivity and Mechanisms for Target Engagement. Antioxid Redox Signal. Aug. 10, 2015;23(5):406-27. doi: 10.1089/ars.2013.5814.

Anguita et al., Selective anti-inflammatory action of interleukin-11 in murine Lyme disease: arthritis decreases while carditis persists. J Infect Dis. Mar. 1999;179(3):734-7.

Augsburger et al., Pharmacological Characterization of the Seven Human NOX Isoforms and their Inhibitors. Redox Biology. 2019;26:1-15. Epub Jul. 11, 2019.

Baeuerle et al., Bispecific T-cell engaging antibodies for cancer therapy. Cancer Res. 2009;69(12):4941-4944.

Balic et al., Interleukin-11-driven gastric tumourigenesis is independent of trans-signalling. Cytokine. Apr. 2017;92:118-123. doi: 10.1016/j.cyto.2017.01.015. Epub Feb. 1, 2017.

Barbas et al., In vitro evolution of a neutralizing human antibody to human immunodeficiency virus type 1 to enhance affinity and broaden strain cross-reactivity. Proc Natl Acad Sci U S A. 1994;91(9):3809-3813.

Barton et al., Retroviral delivery of small interfering RNA into primary cells. Proc Natl Acad Sci U S A. 2002;99(23):14943-14945.

Beaucage et al., Advances in the synthesis of Oligonucleotides by the Phosphoramidte Approach. Tetrahedron. 1992;48(12):2223-2311.

Bernal et al., Acute liver failure. N Engl J Med. Mar. 20, 2014;370(12):1170-1. doi: 10.1056/NEJMc1400974.

Bernstein aet al., Role for a bidentate ribonuclease in the initiation step of RNA interference. Nature. 2001;409(6818):363-366.

Bettaieb et al., Hepatocyte Nicotinamide Adenine Dinucleotide Phosphate Reduced Oxidase 4 Regulates Stress Signaling, Fibrosis, and Insulin Sensitivity During Development of Steatohepatitis in Mice. Gastroenterology. Aug. 2015;149(2):468-80.e10. doi: 10.1053/j.gastro.2015.04.009. Epub Apr. 14, 2015.

Bhushan et al., Liver Regeneration after Acetaminophen Hepatotoxicity: Mechanisms and Therapeutic Opportunities. Am J Pathol. Apr. 2019;189(4):719-729. doi: 10.1016/j.ajpath.2018.12.006. Epub Jan. 14, 2019.

Bockhorn et al., MicroRNA-30c Inhibits Human Breast Tumour Chemotherapy Resistance by Regulating TWF1 and IL-11. Nat Commun. 2013;4:1393. doi: 10.1038/ncomms2393.

Boerma et al., Local administration of interleukin-11 ameliorates intestinal radiation injury in rats. Cancer Res. Oct. 1, 2007;67(19):9501-6.

Bolger et al., Trimmomatic: a flexible trimmer for Illumina sequence data. Bioinformatics. Aug. 1, 2014;30(15):2114-20. doi: 10.1093/bioinformatics/btu170. Epub Apr. 1, 2014.

Borkhardt, Blocking oncogenes in malignant cells by RNA interference—new hope for a highly specific cancer treatment?. Cancer Cell. 2002;2(3):167-168.

Bozza et al., Interleukin-11 modulates Th1/Th2 cytokine production from activated CD4+ T cells. J Interferon Cytokine Res. Jan. 2001;21(1):21-30.

Bozza et al., Interleukin-11 Reduces T-cell-dependent Experimental Liver Injury in Mice. Hepatology. Dec. 1999;30(6):1441-7. doi: 10.1002/hep.510300616.

Brookes et al. The Essence of SNPs. Gene. Jul. 8, 1999;234(2):177-86. doi: 10.1016/s0378-1119(99)00219-x.

Brüggemann et al., Human Antibody Production in Transgenic Animals. Archivum Immunologiae et Therapiae Experimentalis. Apr. 2015;63(2):101-108. Epub Dec. 3, 2014.

Budnitz et al., Emergency Department Visits for Overdoses of Acetaminophen-Containing Products. American Journal of Preventive Medicine. 2011;40(6):585-592.

Castanotto et al., The promises and pitfalls of RNA-interference-based therapeutics. Nature. 2009;457(7228):426-433.

Chan et al., The role of phage display in therapeutic antibody discovery. Int Immunol. 2014;26(12):649-657. doi:10.1093/intimm/dxu082.

Chiew et al., Interventions for paracetamol (acetaminophen) overdose. Cochrane Database Syst Rev. Feb. 23, 2018;2:CD003328. doi: 10.1002/14651858.CD003328.pub3.

Chothani et al., Widespread Translational Control of Fibrosis in the Human Heart by RNA-Binding Proteins. Circulation. Sep. 10, 2019;140(11):937-951. doi: 10.1161/CIRCULATIONAHA.119.039596. Epub Jul. 9, 2019.

Chothia et al., Canonical Structures for the Hypervariable Regions of Immunoglobulins. Journal of Molecular Biology. 1987;196:901-917.

Ciliberto et al. Cytokine Inhibitors: Chapter 8. Marcel Dekker, Inc. 2001.

Clare et al., Genetic Factors Influencing Drug-Induced Liver Injury: Do They Have a Role in Prevention and Diagnosis? Curr Hepatol Rep. 2017;16(3):258-264. doi: 10.1007/s11901-017-0363-9.

Concepcion et al., Label-free detection of biomolecular interactions using BioLayer interferometry for kinetic characterization. Comb Chem High Throughput Screen. Sep. 2009;12(8):791-800. doi: 10.2174/138620709789104915.

Curtis et al., Recombinant Soluble interleukin-11 (IL-11) Receptor Alpha-Chain Can Act as an IL-11 Antagonist. Blood. Dec. 1, 1997;90(11);4403-12.

Czauderna et al., Structural variations and stabilising modifications of synthetic siRNAs in mammalian cells. Nucleic Acids Res. Jun. 1, 2003;31(11):2705-16. doi: 10.1093/nar/gkg393.

Dahlin et al., N-acetyl-p-benzoquinone Imine: A Cytochrome P-450-mediated Oxidation Product of Acetaminophen. Proc Natl Acad Sci U S A. Mar. 1984;81(5):1327-31. doi: 10.1073/pnas.81.5.1327.

De-Chao et al., Soluble Vascular Endothelial Growth Factor Decoy Receptor FP3 Exerts Potent Antiangiogenic Effects. Mol Ther. May 2012;20(5):938-47. doi: 10.1038/mt.2011.285.

Denton et al., Therapeutic interleukin-6 blockade reverses transforming growth factor-beta pathway activation in dermal fibroblasts: insights from the faSScinate clinical trial in systemic scle-

(56) References Cited

OTHER PUBLICATIONS rosis. Ann Rheum Dis. Sep. 2018;77(9):1362-1371. doi: 10.1136/annrheumdis-2018-213031. Epub May 31, 2018.
Devroe et al., Retrovirus-delivered siRNA. BMC Biotechnol. 2002;2:15. Published Aug. 28, 2002. doi:10.1186/1472-6750-2-15.
Dobin et al., STAR: ultrafast universal RNA-seq aligner. Bioinformatics. Jan. 1, 2013;29(1):15-21. doi: 10.1093/bioinformatics/bts635. Epub Oct. 25, 2012.
Du et al., Protective effects of interleukin-11 in a murine model of ischemic bowel necrosis. Am J Physiol. Mar. 1997;272(3 Pt 1):G545-52.
Dzau et al. Gene therapy for cardiovascular disease. Trends Biotechnol. 1993;11(5):205-210.
Elbashir et al., Duplexes of 21-nucleotide RNAs mediate RNA interference in cultured mammalian cells. Nature. 2001;411(6836):494-498.
Elbashir et al., RNA interference is mediated by 21- and 22-nucleotide RNAs. Genes Dev. 2001;15(2):188-200.
Fan et al. Highly Parallel SNP Genotyping. Cold Spring Harb Symp Quant Biol. 2003;68:69-78. doi: 10.1101/sqb.2003.68.69.
Fire et al., Potent and specific genetic interference by double-stranded RNA in Caenorhabditis elegans. Nature. 1998;391(6669):806-811.
Fire, RNA-triggered gene silencing. Trends Genet. 1999;15(9):358-363.
Fontan et al., Interleukin-11 for Treatment of Hepatitis C-associated ITP. Acta Haematol. 2008;119(2):126-32. doi: 10.1159/000125192. Epub Apr. 8, 2008.
French, How to make bispecific antibodies. Methods Mol Med. 2000;40:333-339.
Gibson et al., Interleukin-11 reduces TLR4-induced colitis in TLR2-deficient mice and restores intestinal STAT3 signaling. Gastroenterology. Oct. 2010;139(4):1277-88. doi: 10.1053/j.gastro.2010.06.057. Epub Jun. 25, 2010.
Gicquel et al., Quantitative analysis of acetaminophen and its primary metabolites in small plasma volumes by liquid chromatography-tandem mass spectrometry. J Anal Toxicol. Mar. 2013;37(2):110-6. doi: 10.1093/jat/bks139. Epub Jan. 12, 2013.
Gold et al., Aptamer-based Multiplexed Proteomic Technology for Biomarker Discovery. PLoS One. Dec. 7, 2010;5(12):e15004. doi: 10.1371/journal.pone.0015004.
Gowda et al., A Review on Laboratory Liver Function Tests. Pan Afr Med J. Nov. 22, 2009;3:17.
Greenwood-Van Meerveld et al., Recombinant human interleukin-11 modulates ion transport and mucosal inflammation in the small intestine and colon. Lab Invest. Aug. 2000;80(8):1269-80.
Gunawan et al., c-Jun N-terminal kinase plays a major role in murine acetaminophen hepatotoxicity. Gastroenterology. Jul. 2006;131(1):165-78.
Hahne et al., Visualizing Genomic Data Using Gviz and Bioconductor. Methods Mol Biol. 2016;1418:335-51. doi: 10.1007/978-1-4939-3578-9_16.
Hamilton et al., A species of small antisense RNA in post-transcriptional gene silencing in plants. Science. 1999;286(5441):950-952.
Hammond et al., An RNA-directed nuclease mediates post-transcriptional gene silencing in *Drosophila* cells. Nature. 2000;404(6775):293-296.
Hammond et al., Post-transcriptional gene silencing by double-stranded RNA. Nat Rev Genet. 2001;2(2):110-119.
Hannon et al., RNA interference. Nature. 2002;418(6894):244-251.
Hawkins et al., Selection of phage antibodies by binding affinity. Mimicking affinity maturation. J Mol Biol. 1992;226(3):889-896.
Hearty et al., Measuring antibody-antigen binding kinetics using surface plasmon resonance. Methods Mol Biol. 2012;907:411-42. doi: 10.1007/978-1-61779-974-7_24.
Hecker et al., NADPH oxidase-4 mediates myofibroblast activation and fibrogenic responses to lung injury. Nat Med. Sep. 2009;15(9):1077-81. doi: 10.1038/nm.2005. Epub Aug. 23, 2009.
Herrlinger et al., Randomized, double blind controlled trial of subcutaneous recombinant human interleukin-11 versus prednisolone in active Crohn's disease. Am J Gastroenterol. Apr. 2006;101(4):793-7.
Hill et al., Interleukin-11 promotes T cell polarization and prevents acute graft-versus-host disease after allogeneic bone marrow transplantation. J Clin Invest. Jul. 1, 1998;102(1):115-23.
Hilton et al., Cloning of a Murine IL-11 Receptor Alpha-Chain; Requirement for gp130 for High Affinity Binding and Signal Transduction. EMBO J. Oct. 17, 1994;13(20):4765-75.
Holgate, The airway epithelium is central to the pathogenesis of asthma. Allergol Int. 2008;57(1):1-10. doi:10.2332/allergolint.R-07-154.
Hoogenboom, Selecting and screening recombinant antibody libraries. Nat Biotechnol. 2005;23(9):1105-1116. doi:10.1038/nbt1126.
Hurrell, Monoclonal Hybridoma Antibodies: Techniques and Applications. CRC Press. 1982.
Jackson et al., In vitro antibody maturation. Improvement of a high affinity, neutralizing antibody against IL-1 beta. J Immunol. 1995;154(7):3310-3319.
Jaeschke et al., Acetaminophen: Dose-Dependent Drug Hepatotoxicity and Acute Liver Failure in Patients. Dig Dis. 2015;33(4):464-71. doi: 10.1159/000374090. Epub Jul. 6, 2015.
Jerabek-Willemsen et al., Molecular interaction studies using microscale thermophoresis. Assay and Drug Development Technologies. Aug. 2011;9(4):342-353.
John et al., Human MicroRNA targets [published correction appears in PLoS Biol. Jul. 2005;3(7):e264]. PLoS Biol. 2004;2(11):e363. doi:10.1371/journal.pbio.0020363.
Jollow et al., Acetaminophen-induced Hepatic Necrosis. II. Role of Covalent Binding in Vivo. J Pharmacol Exp Ther. Oct. 1973;187(1):195-202.
Karpovich et al., Expression and Function of interleukin-11 and Its Receptor Alpha in the Human Endometrium. Mol Hum Reprod. Feb. 2003;9(2):75-80. doi: 10.1093/molehr/gag012.
Katoh et al., MAFFT Multiple Sequence Alignment Software Version 7: Improvements in Performance and Usability. Molecular Biology and Evolution. Apr. 2013;30(4):772-780. Epub Jan. 16, 2013.
Khoury et al., Drug Induced Liver Injury: Review With a Focus on Genetic Factors, Tissue Diagnosis, and Treatment Options. J Clin Transl Hepatol. Jun. 28, 2015;3(2):99-108. doi: 10.14218/JCTH.2015.00007.
Klein et al., The IL-6-gp130-STAT3 pathway in hepatocytes triggers liver protection in T cell-mediated liver injury. J Clin Invest. Apr. 2005;115(4):860-9. Epub Mar. 3, 2005.
Knight et al., STAT3 in tissue fibrosis: is there a role in the lung?. Pulm Pharmacol Ther. 2011;24(2):193-198. doi:10.1016/j.pupt.2010.10.005.
Knight et al., The role of gp130/IL-6 cytokines in the development of pulmonary fibrosis: critical determinants of disease susceptibility and progression?. Pharmacol Ther. 2003;99(3):327-338. doi:10.1016/s0163-7258(03)00095-0.
Konner et al., Use of soluble recombinant decoy receptor vascular endothelial growth factor trap (VEGF Trap) to inhibit vascular endothelial growth factor activity. Clin Colorectal Cancer. 2004;4 Suppl 2:S81-S85.
Kontermann, Dual targeting strategies with bispecific antibodies. MAbs. 2012;4(2):182-197.
Kroy et al., Lack of interleukin-6/glycoprotein 130/signal transducers and activators of transcription-3 signaling in hepatocytes predisposes to liver steatosis and injury in mice. Hepatology. Feb. 2010;51(2):463-73. doi: 10.1002/hep.23322.
Kyle et al., Metabolism of Acetaminophen by Cultured Rat Hepatocytes. Depletion of Protein Thiol Groups Without Any Loss of Viability. Biochem Pharmacol. Sep. 15, 1990;40(6):1211-8. doi: 10.1016/0006-2952(90)90385-x.
Lad et al., High-Throughput Kinetic Screening of Hybridomas to Identify High-Affinity Antibodies Using Bio-Layer Interferometry. Journal of Biomolecular Screening. 2015;20(4):498-507.
Langmead et al., Ultrafast and memory-efficient alignment of short DNA sequences to the human genome. Genome Biol. 2009;10(3):R25. doi: 10.1186/gb-2009-10-3-r25. Epub Mar. 4, 2009.

(56) References Cited

OTHER PUBLICATIONS

Lassman et al., Kalign—an accurate and fast multiple sequence alignment algorithm. BMC Bioinformatics. Dec. 2005;6(298) https://doi.org/10.1186/1471-2105, 9 pages.
Lawitz et al., A pilot study of interleukin-11 in subjects with chronic hepatitis C and advanced liver disease nonresponsive to antiviral therapy. Am J Gastroenterol. Dec. 2004;99(12):2359-64.
Lay et al., Interleukin 11 Regulates Endometrial Cancer Cell Adhesion and Migration via STAT3. Int J Oncol. Aug. 2012;41(2):759-64. doi: 10.3892/ijo.2012.1486.
Lee et al., Intravenous N-acetylcysteine improves transplant-free survival in early stage non-acetaminophen acute liver failure. Gastroenterology. Sep. 2009;137(3):856-64, 864.e1. doi: 10.1053/j.gastro.2009.06.006. Epub Jun. 12, 2009.
Lee et al., Transgenic modeling of transforming growth factor-beta(1): role of apoptosis in fibrosis and alveolar remodeling. Proc Am Thorac Soc. 2006;3(5):418-423. doi:10.1513/pats.200602-017AW.
Lee W.M., Acetaminophen and the U.S. Acute Liver Failure study Group: Lowering the Risks of Hepatic Failure. Hepatology. 2004;40(1):6-9.
Leng et al., Interleukin-11. Int J Biochem Cell Biol. 1997;29(8-9):1059-1062. doi:10.1016/s1357-2725(97)00017-4.
Lewis et al., Efficient delivery of siRNA for inhibition of gene expression in postnatal mice. Nat Genet. 2002;32(1):107-108.
Liao et al., featureCounts: an efficient general purpose program for assigning sequence reads to genomic features. Bioinformatics. Apr. 1, 2014;30(7):923-30. doi:10.1093/bioinformatics/btt656. Epub Nov. 13, 2013.
Lo et al., Antibody Engineering. Microbiol Spectr. 2014;2(1):. doi:10.1128/microbiolspec.AID-0007-12.
Lori et al., Gene therapy approaches to HIV infection. Am J Pharmacogenomics. 2002;2(4):245-252.
Maeshima et al., A Protective Role of Interleukin 11 on Hepatic Injury in Acute Endotoxemia. Shock. Feb. 2004;21(2):134-8. doi: 10.1097/01.shk.0000103386.98235.f6.
Marcos et al., Liver regeneration and function in donor and recipient after right lobe adult to adult living donor liver transplantation. Transplantation. Apr. 15, 2000;69(7):1375-9.
Marks et al., By-passing immunization: building high affinity human antibodies by chain shuffling. Biotechnology (N Y). 1992;10(7):779-783.
Martineau P., Affinity Measurements by Competition ELISA. Antibody Engineering. 2010;1:657-665.
Matsuzaki et al., Parallel Genotyping of Over 10,000 SNPs Using a One-Primer Assay on a High-Density Oligonucleotide Array. Genome Res. Mar. 2004;14(3):414-25. doi: 10.1101/gr.2014904.
Matta et al., Use of lentiviral vectors for delivery of small interfering RNA. Cancer Biol Ther. 2003;2(2):206-210.
Matthews et al., Interleukm-6-deficient mice develop hepatic inflammation and systemic insulin resistance. Diabetologia. Nov. 2010;53(11):2431-41. doi: 10.1007/s00125-010-1865-y. Epub Aug. 11, 2010.
McClain et al., Acetaminophen Hepatotoxicity: An Update. Curr Gastroenterol Rep. Feb.-Mar. 1999;1(1):42-9. doi: 10.1007/s11894-999-0086-3.
McManus et al., Gene silencing in mammals by small interfering RNAs. Nat Rev Genet. 2002;3(10):737-747.
Menkhorst et al., IL11 Antagonist Inhibits Uterine Stromal Differentiation, Causing Pregnancy Failure in Mice. Biol Reprod. May 2009;80(5):920-7. doi: 10.1095/biolreprod.108.073601.
Michalopoulos et al., Hepatostat: Liver regeneration and normal liver tissue maintenance. Hepatology. Apr. 2017;65(4):1384-1392. doi: 10.1002/hep.28988. Epub Mar. 6, 2017.
Moore et al., The Toxicity of Acetaminophen and N-acetyl-p-benzoquinone Imine in Isolated Hepatocytes Is Associated With Thiol Depletion and Increased Cytosolic Ca2+. J Biol Chem. Oct. 25, 1985;260(24):13035-40.
Moreland et al., Results of a phase-I/II randomized, masked, placebo-controlled trial of recombinant human interleukin-11 (rhIL-11) in the treatment of subjects with active rheumatoid arthritis. Arthritis Res. 2001;3(4):247-52. Epub Apr. 10, 2001.
Morris et al., Translocating peptides and proteins and their use for gene delivery. Curr Opin Biotechnol. 2000;11(5):461-466.
Morrison et al., Chimeric human antibody molecules: mouse antigen-binding domains with human constant region domains. Proc Natl Acad Sci U S A. 1984;81(21):6851-6855.
Muller et al., Bispecific antibodies for cancer immunotherapy: Current perspectives. BioDrugs. 2010;24(2):89-98.
Murray et al., NADPH oxidase 4 regulates homocysteine metabolism and protects against acetaminophen-induced liver damage in mice. Free Radic Biol Med. Dec. 2015;89:918-30. doi: 10.1016/j.freeradbiomed.2015.09.015. Epub Oct. 22, 2015.
Myers et al., Recombinant Dicer efficiently converts large dsRNAs into siRNAs suitable for gene silencing. Nat Biotechnol. 2003;21(3):324-328.
Nandurkar et al., The Human IL-11 Receptor Requires gp130 for Signalling: Demonstration by Molecular Cloning of the Receptor. Oncogene. Feb. 1, 1996;12(3):585-93.
Neuberger et al. Antibody Engineering. 8th International Biotechnology Symposium Part 2. 1988:792-799.
Ng et al., Interleukin-11 Is a Therapeutic Target in Idiopathic Pulmonary Fibrosis. Sci Transl Med. Sep. 25, 2019;11(511):eaaw1237. doi: 10.1126/scitranslmed.aaw1237.
Njoku et al., Drug-induced Hepatotoxicity: Metabolic, Genetic and Immunological Basis. Int J Mol Sci. Apr. 22, 2014;15(4):6990-7003. doi: 10.3390/ijms15046990.
Nordan et al., Purification and NH2-terminal sequence of a plasmacytoma growth factor derived from the murine macrophage cell line P388D1. J Immunol. 1987;139(3):813-817.
Notredame et al., T-Coffee: A Novel Method for Fast and Accurate Multiple Sequence Alignment. Journal of Molecular Biology. 2000;302:205-217.
Olman, Epithelial cell modulation of airway fibrosis in asthma. Am J Respir Cell Mol Biol. 2003;28(2):125-128. doi:10.1165/rcmb.F257.
Opal et al., Orally administered recombinant human interleukin-11 is protective in experimental neutropenic sepsis. J Infect Dis. Jan. 1, 2003;187(1):70-6. Epub Dec. 13, 2002.
Opal et al., Recombinant human interleukin-11 has anti-inflammatory actions yet does not exacerbate systemic Listeria infection. J Infect Dis. Feb. 2000;181(2):754-6.
Orazi et al., Interleukin-11 prevents apoptosis and accelerates recovery of small intestinal mucosa in mice treated with combined chemotherapy and radiation. Lab Invest. Jul. 1996;75(1):33-42.
Park et al., Paracetamol (Acetaminophen) Poisoning. BMJ Clin Evid. Oct. 19, 2015;2015:2101.
Pasqualini et al., Targeting the interleukin-11 Receptor ? in Metastatic Prostate Cancer: A First-In-Man Study. Cancer. Jul. 15, 2015; 121(14):2411-21. doi: 10.1002/cncr.29344.
Paul et al., Effective expression of small interfering RNA in human cells. Nat Biotechnol. 2002;20(5):505-508.
Petrov et al., RNAcentral: a comprehensive database of non-coding RNA sequences. Nucleic Acids Res. Jan. 4, 2017;45(D1):D128-D134. doi: 10.1093/nar/gkw1008. Epub Oct. 28, 2016.
Pflanz et al., A Fusion Protein of interleukin-11 and Soluble interleukin-11 Receptor Acts as a Superagonist on Cells Expressing gp130. FEBS Lett. Apr. 30, 1999;450(1-2):117-22. doi: 10.1016/s0014-5793(99)00477-9.
Potten et al., Protection of the small intestinal clonogenic stem cells from radiation-induced damage by pretreatment with interleukin 11 also increases murine survival time. Stem Cells. Jul. 1996;14(4):452-9.
Prêle et al., STAT3: a central mediator of pulmonary fibrosis? [published correction appears in Proc Am Thorac Soc. Oct. 2012;9(4):210]. Proc Am Thorac Soc. 2012;9(3):177-182. doi: 10.1513/pats.201201-007AW.
Putoczki et al., More Than a Sidekick: The IL-6 Family Cytokine IL-11 Links Inflammation to Cancer. J Leukoc Biol. Dec. 2010;88(6):1109-17. doi: 10.1189/jlb.0410226.
Qin et al., Inhibiting HIV-1 infection in human T cells by lentiviral-mediated delivery of small interfering RNA against CCR5. Proc Natl Acad Sci U S A. 2003;100(1):183-188.

(56) References Cited

OTHER PUBLICATIONS

Qiu et al., Protection by recombinant human interleukin-11 against experimental TNB-induced colitis in rats. Dig Dis Sci. Aug. 1996;41(8):1625-30.
Retter et al., VBASE2, an integrative V gene database. Nucleic Acids Research. 2005;33:D671-D674.
Reverdatto et al., Peptide Aptamers: Development and Applications. Curr Top Med Chem. 2015;15(12):1082-1101. Author Manuscript, 38 pages.
Rich et al., Extracting kinetic rate constants from surface plasmon resonance array systems. Analytical Biochemistry. 2008;373(1):112-120. Epub Aug. 19, 2007.
Ropeleski et al., Interleukin-11-induced heat shock protein 25 confers intestinal epithelial-specific cytoprotection from oxidant stress. Gastroenterology. May 2003;124(5):1358-68.
Rowe et al., Hepatocyte-derived Snail1 propagates liver fibrosis progression. Mol Cell Biol. Jun. 2011;31(12):2392-403. doi: 10.1128/MCB.01218-10.
Safdari et al., Antibody humanization methods—a review and update. Biotechnol Genet Eng Rev. 2013;29:175-186. doi:10.1080/02648725.2013.801235.
Sands et al., Randomized, controlled trial of recombinant human interleukin-11 in patients with active Crohn's disease. Aliment Pharmacol Ther. Mar. 2002;16(3):399-406.
Scherr et al., Gene silencing mediated by small interfering RNAs in mammalian cells. Curr Med Chem. 2003;10(3):245-256.
Scherr et al., Modulation of gene expression by lentiviral-mediated delivery of small interfering RNA. Cell Cycle. 2003;2(3):251-257.
Schier et al.., Identification of functional and structural amino-acid residues by parsimonious mutagenesis. Gene. 1996;169(2):147-155.
Schleinkofer et al., Identification of the domain in the human interleukin-11 receptor that mediates ligand binding. J Mol Biol. Feb. 16, 2001;306(2):263-74.
Schmidt-Arras et al., IL-6 pathway in the liver: From physiopathology to therapy. J Hepatol. Jun. 2016;64(6):1403-15. doi: 10.1016/j.jhep.2016.02.004. Epub Feb. 8, 2016.
Schroeder et al., Structure and Function of Immunoglobulins. J Allergy Clin Immunol. Feb. 2010;125(202):S41-s52. Author Manuscript, 24 pages.
Schwabe et al., Apoptosis and necroptosis in the liver: a matter of life and death. Nat Rev Gastroenterol Hepatol. Dec. 2018;15(12):738-752. doi: 10.1038/s41575-018-0065-y.
Segal et al., Production of bispecific antibodies. Curr Protoc Immunol. 2001;Chapter 2:. doi:10.1002/0471142735.im0213s14.
Sekiya et al., Glycogen synthase kinase 3 ?-dependent Snail degradation directs hepatocyte proliferation in normal liver regeneration. Proc Natl Acad Sci U S A. Jul. 5, 2011;108(27):11175-80. doi: 10.1073/pnas.1016122108. Epub Jun. 20, 2011.
Sharp, RNA interference—2001. Genes Dev. 2001;15(5):485-490.
Shen et al., Gene silencing by adenovirus-delivered siRNA. FEBS Lett. 2003;539(1-3):111-114.
Sheridan et al., Interleukin-11 attenuates pulmonary inflammation and vasomotor dysfunction in endotoxin-induced lung injury. Am J Physiol. Nov. 1999;277(5):L861-7. doi: 10.1152/ajplung.1999.277.5.L861.
Shin et al., Optimization of linear double-stranded RNA for the production of multiple siRNAs targeting hepatitis C virus. RNA. 2009;15(5):898-910.
Shinagawa et al., Generation of Ski-knockdown mice by expressing a long double-strand RNA from an RNA polymerase II promoter. Genes Dev. 2003;17(11):1340-1345.
Shuey et al., RNAi: gene-silencing in therapeutic intervention. Drug Discov Today. 2002;7(20):1040-1046.
Simeoni et al., Insight into the mechanism of the peptide-based gene delivery system MPG: implications for delivery of siRNA into mammalian cells. Nucleic Acids Res. 2003;31(11):2717-2724.
Sinha et al., Polymer support oligonucleotide synthesis XVIII: use of b-cyanoethyl-N,N-dialkylamino-/Nmorpholino phosphoramidite of deoxynucleosides for the synthesis of DNA fragments simplifying deprotection and isolation of the final product. Nucleic Acids Research. 1984;12(11):4539-4557.
Song et al., RNA interference targeting Fas protects mice from fulminant hepatitis. Nat Med. 2003;9(3);347-351.
Sonis et al., Mitigating effects of interleukin 11 on consecutive courses of 5-fluorouracil-induced ulcerative mucositis in hamsters. Cytokine. Aug. 1997;9(8):605-12.
Sorensen et al., Gene silencing by systemic delivery of synthetic siRNAs in adult mice. J Mol Biol. 2003;327(4):761-766.
Starkel et al., Genetic Factors Predicting Response to Interferon Treatment for Viral Hepatitis C. Gut. Apr. 2008;57(4):440-2. doi: 10.1136/gut.2007.137646.
Söding J., Protein homology detection by HMM-HMM comparison. Bioinformatics. 2005;21(7):951-960. Epub Nov. 5, 2004.
Taki et al., Differential Inhibitory Effects of Indomethacin, Dexamethasone, and Interferon-Gamma (IFN-gamma) on IL-11 Production by Rheumatoid Synovial Cells. Clin Exp Immunol. Apr. 1998;112(1):133-8. doi: 10.1046/j.1365-2249.1998.00552.x.
Tamura et al., The cardioprotective effect of interleukin-11 against ischemia-reperfusion injury in a heart donor model. Ann Cardiothorac Surg. Jan. 2018;7(1):99-105. doi: 10.21037/acs.2017.09.11.
Trepicchio et al., IL-11 regulates macrophage effector function through the inhibition of nuclear factor-kappaB. J Immunol. Dec. 1, 1997;159(11):5661-70.
Trepicchio et al., Interleukin-11 therapy selectively downregulates type I cytokine proinflammatory pathways in psoriasis lesions. J Clin Invest. Dec. 1999;104(11):1527-37.
Trepicchio et al., Recombinant human IL-11 attenuates the inflammatory response through down-regulation of proinflammatory cytokine release and nitric oxide production. J Immunol. Oct. 15, 1996;157(8):3627-34.
Tuerk et al., Systematic Evolution of Ligands by Exponential Enrichment: RNA Ligands to Bacteriophage T4 DNA Polymerase. Science. Aug. 3, 1990;249(4968):505-10. doi: 10.1126/science.2200121.
Tuschl, RNA interference and small interfering RNAs. Chembiochem. 2001;2(4):239-245.
Urban et al., Genetic Basis of Susceptibility to Drug-Induced Liver Injury: What Have We Learned and Where Do We Go From Here? Pharmacogenomics. May 2012;13(7):735-8. doi: 10.2217/pp. 12.45.
Vanwagner et al., Evaluating Elevated Bilirubin Levels in Asymptomatic Adults. JAMA. Feb. 3, 2015;313(5):516-7. doi: 10.1001/jama.2014.12835.
Walmsley et al., An anti-inflammatory role for interleukin-11 in established murine collagen-induced arthritis. Immunology. Sep. 1998;95(1):31-7.
Wang et al., Delivery of siRNA therapeutics: barriers and carriers. AAPS J. 2010;12(4):492-503.
Waxman et al., Targeted lung expression of interleukin-11 enhances murine tolerance of 100% oxygen and diminishes hyperoxia-induced DNA fragmentation. J Clin Invest. May 1, 1998;101(9):1970-82.
Wermuth et al., Abrogation of transforming growth factor-?-induced tissue fibrosis in mice with a global genetic deletion of Nox4. Lab Invest. Apr. 2019;99(4):470-482. doi: 10.1038/s41374-018-0161-1. Epub Nov. 23, 2018.
Widjaja et al., Inhibiting Interleukin 11 Signaling Reduces Hepatocyte Death and Liver Fibrosis, Inflammation, and Steatosis in Mouse Models of Nonalcoholic Steatohepatitis. Gastroenterology. Sep. 2019;157(3):777-792.e14. doi: 10.1053/j.gastro.2019.05.002.
Win et al., New insights into the role and mechanism of c-Jun-N-terminal kinase signaling in the pathobiology of liver diseases. Hepatology. May 2018;67(5):2013-2024. doi: 10.1002/hep.29689. Epub Apr. 6, 2018.
Wozniak-Knopp et al., Introducing antigen-binding sites in structural loops of immunoglobulin constant domains: Fc fragments with engineered HER2/neu-binding sites and antibody properties. Protein Eng Des Sel. 2010;23(4):289-297.
Wright et al., Upregulation of c-MYC in cis through a large chromatin loop linked to a cancer risk-associated single-nucleotide polymorphism in colorectal cancer cells. Mol Cell Biol. 2010;30(6):1411-1420.

(56) References Cited

OTHER PUBLICATIONS

Wuesterfeld et al., Interleukin-6/glycoprotein 130-dependent pathways are protective during liver regeneration. J Biol Chem. Mar. 28, 2003;278(13):11281-8. Epub Dec. 30, 2002.
Xie et al., Inhibitor of apoptosis signal-regulating kinase 1 protects against acetaminophen-induced liver injury. Toxicol Appl Pharmacol. Jul. 1, 2015;286(1):1-9. doi: 10.1016/j.taap.2015.03.019. Epub Mar. 25, 2015.
Yelton et al., Affinity maturation of the BR96 anti-carcinoma antibody by codon-based mutagenesis. J Immunol. 1995;155(4):1994-2004.
Yu et al., Interleukin-11 Protects Mouse Liver From Warm Ischemia/Reperfusion (WI/Rp) Injury. Clin Res Hepatol Gastroenterol. Nov. 2016;40(5):562-570. doi: 10.1016/j.clinre.2015.11.009. Epub Mar. 23, 2016.
Zamore et al., RNAi: double-stranded RNA directs the ATP-dependent cleavage of mRNA at 21 to 23 nucleotide intervals. Cell. 2000;101(1):25-33.
Zhang et al., Reduction of liver Fas expression by an antisense oligonucleotide protects mice from fulminant hepatitis. Nat Biotechnol. Aug. 2000;18(8):862-7.
Zola, Monoclonal Antibodies: A Manual of Techniques. CRC Press. 1988.
International Search Report and Written Opinion for International Patent Application No. PCT/EP2020/051332, dated Apr. 28, 2020.
Bourdi et al., Protection against acetaminophen-induced liver injury and lethality by interleukin 10: role of inducible nitric oxide synthase. Hepatology. Feb. 2002;35(2):289-98.
Chiang et al., Targeting bile acids and lipotoxicity for NASH treatment. Hepatol Commun. Dec. 2017; 1(10): 1002-1004. Epub Dec. 4, 2017. doi: 10.1002/hep4.1127.
Elshabrawy et al., IL-11 facilitates a novel connection between RA joint fibroblasts and endothelial cells. Angiogenesis. May 2018;21(2):215-228. doi: 10.1007/sl0456-017-9589-y. Epub Jan. 11, 2018.
Simpson et al., Inhibition of tumour necrosis factor alpha does not prevent experimental paracetamol-induced hepatic necrosis. J Pathol. Mar. 2000;190(4):489-94.
Underhill-Day et al., Functional Characterization of W147A: A High-Affinity interleukin-11 Antagonist. Endocrinology. Aug. 2003;144(8):3406-14. doi: 10.1210/en.2002-0144.
Widjaja et al., Abstract 00417: Neutralizing Anti-IL-11 Antibodies Protect Against Hepatic Fibrosis in Non-alcoholic Steatohepatitis. 69th Annual Meeting of the American Association for the Stuyd of Liver Diseases, AASLD Nov. 9-13, 2018. Hepatology. Nov. 9, 2018;68(Supplement 1):1348A.
Widjaja et al., Redefining Interleukin 11 as a regeneration-limiting hepatotoxin. BioRxiv. Nov. 4, 2019. Retrieved from https://www.biorxiv.org/content/10.1101/830018v.1.full.pdf. 40 pages.
International Search Report and Written Opinion for PCT/EP2016/081430 dated Apr. 18, 2017.
Chapter II Demand filed Aug. 14, 2017 for International Patent Application No. PCT/EP2016/081430.
International Preliminary Report on Patentability (Chapter II) for International Patent Application No. PCT/EP2016/081430, dated Nov. 6, 2017.
International Search Report and Written Opinion for Application No. PCT/EP2017/083051 dated Aug. 13, 2018.
International Preliminary Report on Patentability (Chapter II) for International Patent Application No. No. PCT/EP2017/083051, dated Jun. 27, 2019.
International Search Report and Written Opinion for Application No. PCT/EP2017/083043 dated Jul. 20, 2018.
International Preliminary Report on Patentability (Chapter II) for International Patent Application No. PCT/EP2017/083043, dated Dec. 6, 2018.
[No Author Listed] Human IL-11 Antibody. Monoclonal Mouse IgG2A. Clone No. 22626. Cat. No. MAB218. R& D Systems: A Biotechne Brand. Rev. Feb. 7, 2018. 1 page.

[No Author Listed] Human Il-11 Rα Antibody. Monoclonal Mouse IgG1. Clone No. 473143. Cat. No. MAB1977. R& D Systems: A Biotechne Brand. Rev. Feb. 7, 2018. 1 page.
[No Author Listed] Recombinant Human anti-human IL11 antibody. 2 pages. May 8, 2018.
[No Author Listed] Section 2, Definition, Pathophsiology and Pathogenesis of Asthma, and Natural History of Asthma. Aug. 28, 2007. 24 pages.
Ancey et al., A fusion protein of the gp130 and interlenkin-6Ralpha ligand-binding domains acts as a potent interleukin-6 inhibitor. J Biol Chem. May 9, 2003;278(19):16968-72.
Blanc et al., Monoclonal antibodies against the human interleukin-11 receptor alpha-chain (IL-11Ralpha) and their use in studies of human mononuclear cells. J Immunol Methods. Jul. 31, 2000;241(1-2):43-59.
Bravo et al., Crystal structure of a cytokine-binding region of gp130. EMBO J. Mar. 16, 1998;17(6):1665-74.
Carr et al., Asthma heterogeneity and severity. World Allergy Organ J. 2016; 9(1): 41. EPub Nov. 29, 2016. doi: 10.1186/s40413-016-0131-2. 8 pages.
Chen et al., Enhancement and destruction of antibody function by somatic mutation: unequal occurrence is controlled by V gene combinatorial associations. The EMBO Journal 1995;14(12):2784-94.
Chen et al., IL-11 receptor alpha in the pathogenesis of IL-13-induced inflammation and remodeling. J Immunol. Feb. 15, 2005;174(4):2305-13.
Cheng et al., Cross-reactivity of antibody against SARS-coronavirus nucleocapsid protein with IL-11. Biochem Biophys Res Commun. Dec. 23, 2005;338(3):1654-60. Epub Oct. 25, 2005.
Chow et al., Structure of an extracellular gp130 cytokine receptor signaling complex. Science. Mar. 16, 2001;291(5511):2150-5.
Colman, Effects of Amino Acid Sequence Changes on Antibody-Antigen Interactions. Research In Immunology. 1994;145:33-6.
Cook et al., Hiding in Plain Sight: Interleukin-11 Emerges as a Master Regulator of Fibrosis, Tissue Integrity and Stromal Inflammation. Annu Rev Med. Jan. 27, 2020;71:263-276. doi: 10.1146/annurev-med-041818-011649.
Deguchi et al., Generation of and characterization of anti-IL-11 antibodies using newly established Il1 1-deficient mice. Biochem Biophys Res Commun. Oct. 28, 2018;505(2):453-459. doi: 10.1016/j.bbrc.2018.09.128. Epub Sep. 26, 2018.
Du et al., A bone marrow stromal-derived growth factor, interleukin-11, stimulates recovery of small intestinal mucosal cells after cytoablative therapy. Blood. Jan. 1, 1994;83(1):33-7.
Du et al., Interleukin-11: review of molecular, cell biology, and clinical use. Blood. Jun. 1, 1997;89(11):3897-908.
Forth, et al., Allgemeine und spezielle Pharmakologie und Toxikologie. 11th Edition. Aktories et al., Editors. Urban & Fischer. Sep. 17, 2013;Chapter 16:362-4.
Friedlander, Fibrosis and diseases of the eye. J Clin Invest. Mar. 2007; 117(3):576-86.
Garbers et al., Interleukin-6 and interleukin-11: same same but different. Biol Chem. Sep. 2013;394(9):1145-61. doi: 10.1515/hsz-2013-0166.
Gu et al., Anti-gp130 transducer monoclonal antibodies specifically inhibiting ciliary neurotrophic factor, interleukin-6, interleukin-11, leukemia inhibitory factor or oncostatin M. J Immunol Methods. Mar. 28, 1996;190(1):21-7.
Halwani et al., Airway remodeling in asthma. Curr Opin Pharmacol. Jun. 2010;10(3):236-45. doi: 10.1016/j.coph.2010.06.004.
Ham et al., Critical role of interleukin-11 in isoflurane-mediated protection against ischemic acute kidney injury in mice. Anesthesiology. Dec. 2013;119(6):1389-401. doi: 10.1097/ALN.0b013e3182a950da.
Hennersdorf, et al., Das Herz bei arterieller Hypertonie. Internist. 2007;48(3): 236-45. https://doi.org/10.1007/s00108-006-1762-0.
Hermann et al., Important immunoregulatory role of interleukin-11 in the inflammatory process in rheumatoid arthritis. Arthritis Rheum. Aug. 1998;41(8):1388-97.
Janeway, Jr et al., Immunobiology: The Immune System in Health and Disease. 3rd Ed. New York: Garland Science. 1997. Part II: The Recognition of Antigen. 3:1-3:11.

(56) References Cited

OTHER PUBLICATIONS

Johnstone et al., Emerging roles for IL-11 signaling in cancer development and progression: Focus on breast cancer. Cytokine Growth Factor Rev. Oct. 2015;26(5):489-98. doi: 10.1016/j.cytogfr.2015.07.015. Epub Jul. 14, 2015.

Kapina et al., Interleukin-11 drives early lung inflammation during Mycobacterium tuberculosis infection in genetically susceptible mice. PLoS One. 2011;6(7):e21878. doi: 10.1371/journal.pone.0021878.

Keith et al., IL-11, a pleiotropic cytokine: exciting new effects of IL-11 on gastrointestinal mucosal biology. Stem Cells. 1994;12 Suppl 1:79-89; discussion 89-90.

Khan et al., Fibrosis in heart disease: understanding the role of transforming growth factor-beta in cardiomyopathy, valvular disease and arrhythmia. Immunology. May 2006;118(1):10-24.

Kimura et al., Identification of cardiac myocytes as the target of interleukin 11, a cardioprotective cytokine. Cytokine. May 2007;38(2):107-15.

King, A scar-y movie, starring IL-11. Science Translational Medicine. Nov. 29, 2017;9(418):eaar2443. doi: 10.1126/scitranslmed.aar2443.

Kussie et al., A single engineered amino acid substitution changes antibody fine specificity. J Immunol. Jan. 1, 1994;152(1):146-52.

Lai et al., Interleukin-11 attenuates nephrotoxic nephritis in Wistar Kyoto rats. J Am Soc Nephrol. Nov. 2001;12(11):2310-20.

Lai et al., Interleukin-11 reduces renal injury and glomerular NF-kappa B activity in murine experimental glomerulonephritis. Nephron Exp Nephrol. 2005;101(4):e146-54. Epub Aug. 30, 2005.

Lee et al., Cysteinyl leukotriene upregulates IL-11 expression in allergic airway disease of mice. J Allergy Clin Immunol. Jan. 2007;119(1):141-9. Epub Oct. 27, 2006.

Lee et al., Endogenous IL-11 signaling is essential in Th2- and IL-13-induced inflammation and mucus production. Am J Respir Cell Mol Biol. Dec. 2008;39(6):739-46. doi: 10.1165/rcmb.2008-0053OC. Epub Jul. 10, 2008.

Lee et al., Interleukin-11 protects against renal ischemia and reperfusion injury. Am J Physiol Renal Physiol. Oct. 15, 2012; 303(8): F1216-F1224. EPub Aug. 1, 2012. doi: 10.1152/ajprenal.00220.2012.

Lemoli et al., Interleukin-11 (IL-11) acts as a synergistic factor for the proliferation of human myeloid leukaemic cells. Br J Haematol. Oct. 1995;91(2):319-26.

Lindahl et al., Microarray profiling reveals suppressed interferon stimulated gene program in fibroblasts from scleroderma-associated interstitial lung disease. Respir Res. Aug. 2, 2013;14:80. doi: 10.1186/1465-9921-14-80.

Lokau et al., Generation of soluble interleukin-11 and interleukin-6 receptors: a crucial function for proteases during inflammation. Mediators of Inflammation. 2016. Article ID:1785021. 10 pages.

Lokau et al., Proteolytic Cleavage Governs Interleukin-11 Trans-signaling. Cell Rep. 2016; 14(7): 1761-1773.

Lokau et al., Signal transduction of Interleukin-11 and Interleukin-6 α-Receptors. Recep Clin Investigation. 2016;3.

McCoy et al., IL-11 produced by breast cancer cells augments osteoclastogenesis by sustaining the pool of osteoclast progenitor cells. BMC Cancer. Jan. 11, 2013;13:16. doi: 10.1186/1471-2407-13-16. 11 pages.

Metz et al., Characterization of the Interleukin (IL)-6 Inhibitor IL-6-RFP: fused receptor domains act as high affinity cytokine-binding proteins. J Biol Chem. Jan. 12, 2007;282(2):1238-48. Epub Nov. 3, 2006.

Minshall et al., IL-11 expression is increased in severe asthma: association with epithelial cells and eosinophils. J Allergy Clin Immunol. Feb. 2000;105(2 Pt 1):232-8.

Molet et al., IL-11 and IL-17 expression in nasal polyps: relationship to collagen deposition and suppression by intranasal fluticasone propionate. Laryngoscope. Oct. 2003;113(10):1803-12.

Muhl, STAT3, a Key Parameter of Cytokine-Driven Tissue Protection during Sterile Inflammation—the Case of Experimental Acetaminophen (Paracetamol)-Induced Liver Damage. Front Immunol. May 2, 2016;7:163. doi: 10.3389/fimmu.2016.00163. eCollection 2016.

Murray et al., Targeting Interleukin-13 with Tralokinumab Attenuates Lung Fibrosis and Epithelial Damage in a Humanized SCID Idiopathic Pulmonary Fibrosis ModelAm. J. Resp. Cell Mol. Biol. 2014; 50(5): 985-994, & Data Suppl.

Nishina et al., Critical Contribution of Nuclear Factor Erythroid 2-related Factor 2 (NRF2) to Electrophile-induced Interleukin-11 Production. J Biol Chem. Jan. 6, 2017;292(1):205-216. doi: 10.1074/jbc.M116.744755. Epub Nov. 21, 2016.

Nishina et al., Interleukin-11 Links Oxidative Stress and Compensatory Proliferation. Sci Signal. Jan. 17, 2012;5(207):ra5. doi: 10.1126/scisignal.2002056.

Obana et al., Therapeutic activation of signal transducer and activator of transcription 3 by interleukin-11 ameliorates cardiac fibrosis after myocardial infarction. Circulation. Feb. 9, 2010;121(5):684-91. doi: 10.1161/CIRCULATIONAHA.109.893677. Epub Jan. 25, 2010.

Obana et al., Therapeutic administration of IL-11 exhibits the postconditioning effects against ischemia-reperfusion injury via STAT3 in the heart. Am J Physiol Heart Circ Physiol. Sep. 1, 2012;303(5):H569-77. doi: 10.1152/ajpheart.00060.2012.

Panka et al., Variable region framework differences result in decreased or increased affinity of variant anti-digoxin antibodies. Proc. Natl. Acad. Sci. USA. 1988; 85(9): 3080-3084.

Park et al., Monoclonal antibody therapy. Advances in Protein Chemistry. 2001;56:369-421. https://doi.org/10.1016/S0065-3233(01)56010-6.

PGR2019-00053, Exhibit No. 1003. Declaration of Peter Bowers in Support of Petition for Post Grant Review for U.S. Pat. No. 10,106,603. Jul. 22, 2019. 106 pages.

PGR2019-00053, Exhibit No. 1004. Barton et al., Interleukin-11 signals through the formation of a hexameric receptor complex. J Biol Chem. Nov. 17, 2000;275(46):36197-203.

PGR2019-00053, Exhibit No. 1004. Declaration of Dr. Stephen Ledbetter, Ph.D. in Support of Petition for Post Grant Review for U.S. Pat. No. 10,106,603. Jul. 22, 2019. 79 pages.

PGR2019-00053, Reviewed Petition for Post Grant Review of U.S. Pat. No. 10,106,603. Issued February 6, 2020. 41 pages.

Putoczki et al., IL-11 signaling as a therapeutic target for cancer. Immunotherapy. 2015;7(4):441-53. doi: 10.2217/imt.15.17.

Putoczki et al., Interleukin-11 is the dominant IL-6 family cytokine during gastrointestinal tumorigenesis and can be targeted therapeutically. Cancer Cell. Aug. 12, 2013;24(2):257-71. doi: 10.1016/j.ccr.2013.06.017.

Ray et al., Regulated overexpression of interleukin 11 in the lung. Use to dissociate development-dependent and -independent phenotypes. J Clin Invest. Nov. 15, 1997;100(10):2501-11.

Redlich et al., IL-11 enhances survival and decreases TNF production after radiation-induced thoracic injury. J Immunol. Aug. 15, 1996;157(4):1705-10.

Relevance of third-party observation dated Aug. 5, 2018. 3 pages.

Rudikoff et al., Single amino acid substitution altering antigen-binding specificity. Proc Natl Acad Sci U S A. Mar. 1982; 79(6): 1979-1983. doi: 10.1073/pnas.79.6.1979.

Schafer et al., IL-11 is a crucial determinant of cardiovascular fibrosis. Nature. 2017;552(7683): 110-115.

Shepelkova et al., Therapeutic Effect of Recombinant Mutated Interleukin 11 in the Mouse Model of Tuberculosis. J Infect Dis. Aug. 1, 2016;214(3):496-501. doi: 10.1093/infdis/jiw176.

Sommer et al., Constitutively active mutant gp130 receptor protein from inflammatory hepatocellular adenoma is inhibited by an anti-gp130 antibody that specifically neutralizes interleukin 11 signaling. J Biol Chem. Apr. 20, 2012;287(17):13743-51. doi: 10.1074/jbc.M111.349167.

Stangou et al., Effect of IL-11 on glomerular expression of TGF-beta and extracellular matrix in nephrotoxic nephritis in Wistar Kyoto rats. J Nephrol. Jan.-Feb. 2011;24(1):106-11. Author Manuscript.

Tang et al., Targeted expression of IL-11 in the murine airway causes lymphocytic inflammation, bronchial remodeling, and airways obstruction. J Clin Invest. Dec. 15, 1996;98(12):2845-53.

(56) References Cited

OTHER PUBLICATIONS

Tang et al., Transforming Growth Factor-b Stimulates Interleukin-11 Transcription via Complex Activating Protein-1-dependent Pathways. J. Biol. Chem. 1998; 273(10): 5506-5513.

Tao et al., Cancer-associated fibroblasts treated with cisplatin facilitates chemoresistance of lung adenocarcinoma through IL-11/IL-11R/STAT3 signaling pathway. Sci Rep. Dec. 6, 2016;6:38408. doi: 10.1038/srep38408. 24 pages.

Third Party Observations for application No. EP20160822941, dated Aug. 5, 2018. 3 pages.

Third Party Submission Under 37 C.F.R. § 1.290 for U.S. Appl. No. 15/381,622, filed Apr. 30, 2018.

Toda et al., Polarized in vivo expression of IL-11 and IL-17 between acute and chronic skin lesions. J Allergy Clin Immunol. Apr. 2003;111(4):875-81.

Trepicchio et al., Protective effect of rhIL-11 in a murine model of acetaminophen-induced hepatotoxicity. Toxicol Pathol. Mar.-Apr. 2001;29(2):242-9.

Trepicchio et al., The therapeutic utility of Interleukin-11 in the treatment of inflammatory disease. Expert Opin Investig Drugs. Sep. 1998;7(9):1501-4.

Winship et al., Targeting Interleukin-11 Receptor-α Impairs Human Endometrial Cancer Cell Proliferation and Invasion In Vitro and Reduces Tumor Growth and Metastasis In Vivo. Mol Cancer Ther. Apr. 2016;15(4):720-30. doi: 10.1158/1535-7163.MCT-15-0677. Epub Feb. 4, 2016.

Wong et al., Endogenous IL-11 is pro-inflammatory in acute methylated bovine serum albumin/interleukin-1-induced (mBSA/IL-1)arthritis. Cytokine. Jan. 21, 2005;29(2):72-6.

Wynn, Cellular and molecular mechanisms of fibrosis. J Pathol. Jan. 2008;214(2):199-210. Author Manuscript.

Wynn, Fibrotic Disease And The Th1/Th2 Paradigm. Nat Rev Immunol. Aug. 2004; 4(8): 583-594. doi: 10.1038/nri1412.

Yashiro et al., Transforming growth factor-beta stimulates interleukin-11 production by human periodontal ligament and gingival fibroblasts. J Clin Periodontol. Mar. 2006;33(3):165-71.

Zheng et al., IL-11: insights in asthma from overexpression transgenic modeling. J Allergy Clin Immunol. Oct. 2001;108(4):489-96.

Zhu et al., IL-11 Attenuates Liver Ischemia/Reperfusion Injury (IRI) through STAT3 Signaling Pathway in Mice. PLoS One. May 6, 2015;10(5):e0126296. doi: 10.1371/journal.pone.0126296.

Zong-Jiang et al., Anti-gp 130 transducer monoclonal antibodies specifically inhibiting ciliary neurotrophic factor, interleukin-6, interleukin-11, leukemia inhibitory factor or oncostatin M. J. Immunol. Methods. 1996; 190(1): 21-27.

\* cited by examiner

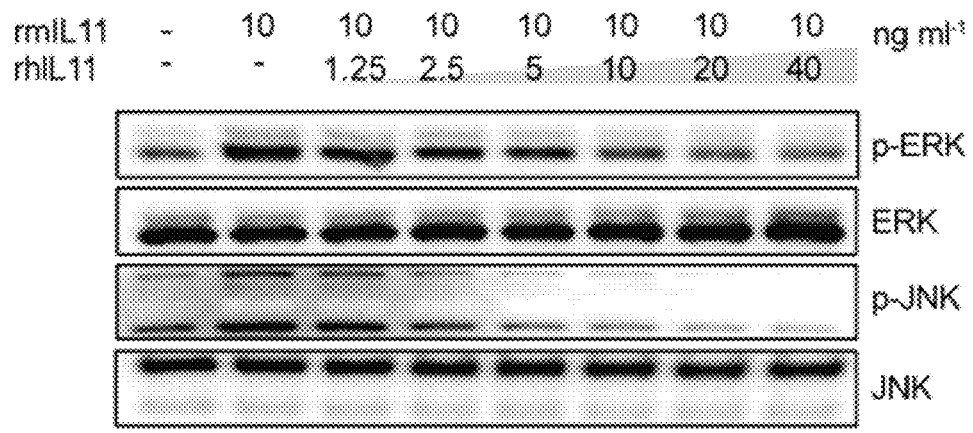
Figure 18E
Figure 18F
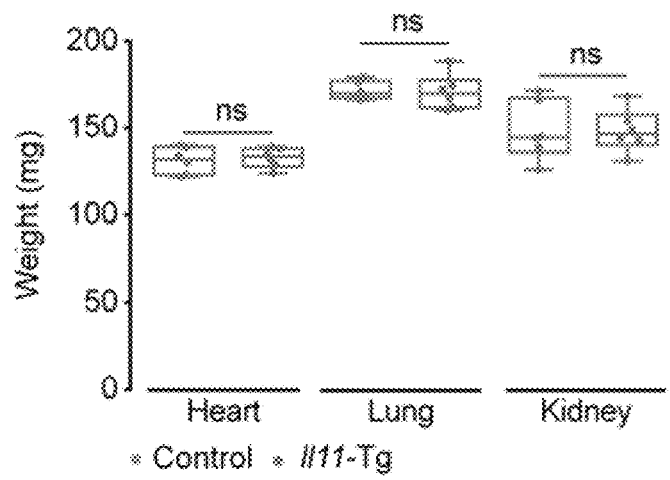
Figure 19A

| | IgG control | X203 anti-IL11 |
|---|---|---|
| Mean | 9360 | 5875 |
| Std. Deviation | 957.8 | 1724 |

TREATMENT OF HEPATOTOXICITY WITH IL-11 ANTIBODY

This application claims priority under 35 U.S.C. § 119 (a)-(d) to United Kingdom Patent Applications GB 1900811.9 filed 21 Jan. 2019, GB 1907839.3 filed 3 Jun. 2019, and GB 1915003.6 filed 17 Oct. 2019, the contents and elements of which are herein incorporated by reference in their entirety for all purposes.

FIELD OF THE INVENTION

The present invention relates to the diagnosis, treatment and prophylaxis of diseases and conditions associated with hepatotoxicity.

BACKGROUND TO THE INVENTION

Hepatotoxicity refers to toxic damage to the liver, specifically dysfunction and death of the hepatocyte cells within the liver. It is often chemical-driven, for example hepatic damage or injury caused by a medicine, chemical (e.g. alcohol), or herbal or dietary supplements. Hepatotoxicity may also be caused by infection (e.g. by a hepatitis virus), malnutrition or genetic disorders.

The analgesic agent acetaminophen (APAP, N-acetyl-p-aminophenol, or paracetamol) is commonly used for reducing fever and mild-to-moderate pain. Overdose of acetaminophen is a prevalent cause of hepatic injury and is responsible for up to 80,000 emergency visits, 2500 hospitalisations and 500 fatal intoxications in the United States annually (Lee W M. Hepatology (2004) 40(1):6-9; Budnitz D S et al. Am J Prev Med (2011) 40(6):585-92). In addition, hepatic injury can be encountered with chronic use of acetaminophen at lower doses, particularly in the presence of other predisposing factors such as chronic alcohol consumption (alcoholism), fasting, malnutrition, HIV infection, hepatitis virus infection, cancer and drug interactions (McClain et al., Curr. Gastroenterol. Rep. 1999; 1:42-49).

The pathophysiology of acetaminophen-induced hepatotoxicity has been studied extensively over the years. Damage to the liver following acetaminophen ingestion is not due to the drug itself, but to a toxic metabolite N-acetyl-p-benzoquinone imine (NAPQI) which is generated through the cytochrome P450 group of enzymes in the liver. NAPQI is harmless under normal conditions and it is removed from the body after conjugating with endogenous glutathione. However, biotransformation of overdosed acetaminophen by Cytochrome P450 (CYP450), predominately the CYP2E1 isoform, leads to the accumulation of excess NAPQI due to glutathione depletion. This in turn causes hepatocellular injury and increasing cell death (Jollow et al., J Pharmacol Exp Ther, 1973 October; 187(1):195-202; Dahlin et al., Proc Natl Acad Sci U.S.A. 1984 March; 81(5): 1327-31; Moore et al., The Journal of Biological Chemistry Vol. 260. No. 24, October 25, pp, 13035-13040, 1985; Kyle et al., Biochemical Pharmacology Volume 40, issue 6, 15 Sep. 1990). Hepatic injury can be limited through administration of N-acetylcysteine, which replenishes liver levels of glutathione. Further therapeutic and prophylactic approaches are needed.

The cytokine interleukin 11 (IL-11) reportedly has a protective effect on acetaminophen-induced liver damage and toxicity (Trepicchio W L et al., Toxicol Pathol. 2001; 29(2):242-9; Nishina T et al., J Biol Chem. 2017; 292(1): 205-216). Activation of the STAT3 pathway by cytokines such as IL-11 has been shown to be capable of driving hepatocyte compensatory proliferation, a key principle of the regenerating liver, and administration of IL-11, among other STAT3-activating cytokines, is suggested as a therapeutic approach to APAP toxicity (Mühl H, Front Immunol. 2016 2; 7:163). Nishina T et al., Sci Signal. 2012; 5 (207):ra5 reports that IL-11 provides a functional link between oxidative stress and compensatory proliferation of hepatocytes, and found that an IL-11 receptor agonist enhanced the proliferation of hepatocytes and ameliorated oxidative stress upon acetaminophen-induced liver injury.

IL-11 treatment has also been reported to protect against and/or treat other liver conditions, such as liver ischemia/reperfusion injury (IRI), immune thrombocytopenic purpura (ITP) associated with chronic hepatitis C (HpC-ITP), acute endotoxemia and T-cell-mediated liver injury (Yu J et al., Clin Res Hepatol Gastroenterol. 2016; 40(5):562-570; Zhu M et al., PLoS ONE 10(5): e0126296; Fontana V et al., Acta Haematol. 2008; 119(2):126-32; Maeshima et al., Shock. (2004) 21(2):134-8; Bozza et al., Hepatology (1999) 30(6): 1441-7).

SUMMARY OF THE INVENTION

In contrast to the reported protective role of IL-11 in liver damage, the present invention relates to the treatment and/or prevention of hepatotoxicity and disorders, diseases or conditions associated with hepatotoxicity through the inhibition of IL-11 signalling.

In one aspect of the present invention there is provided an agent capable of inhibiting interleukin 11 (IL-11)-mediated signalling for use in a method of treating or preventing hepatotoxicity and/or a disorder, disease or condition associated with hepatotoxicity.

In another aspect of the present invention, there is provided the use of an agent capable of inhibiting interleukin 11 (IL-11)-mediated signalling for use in the manufacture of a medicament for use in a method of treating or preventing hepatotoxicity and/or a disorder, disease or condition associated with hepatotoxicity.

In another aspect of the present invention, there is provided a method of treating or preventing hepatotoxicity and/or a disorder, disease or condition associated with hepatotoxicity, the method comprising administering to a subject in need of treatment a therapeutically effective amount of an agent capable of inhibiting interleukin 11 (IL-11)-mediated signalling.

In some embodiments, the agent is an agent capable of preventing or reducing the binding of interleukin 11 (IL-11) to a receptor for interleukin 11 (IL-11R).

In some embodiments, the agent is capable of binding to interleukin 11 (IL-11) or a receptor for interleukin 11 (IL-11R). In some embodiments, the agent is selected from the group consisting of: an antibody or an antigen-binding fragment thereof, a polypeptide, a peptide, a nucleic acid, an oligonucleotide, an aptamer or a small molecule. The agent may be an antibody or an antigen-binding fragment thereof. The agent may be a decoy receptor.

In some embodiments, the agent is an anti-IL-11 antibody antagonist of IL-11-mediated signalling, or an antigen-binding fragment thereof. In some embodiments, the agent is an anti-IL-11Rα antibody antagonist of IL-11-mediated signalling, or an antigen-binding fragment thereof.

In some embodiments, the agent is a decoy receptor for IL-11. In some embodiments the decoy receptor for IL-11 comprises: (i) an amino acid sequence corresponding to the cytokine binding module of gp130 and (ii) an amino acid sequence corresponding to the cytokine binding module of IL-11Rα.

In some embodiments the agent is an IL-11 mutein. In some embodiments the IL-11 mutein is W147A.

In some embodiments, the agent is capable of preventing or reducing the expression of interleukin 11 (IL-11) or a receptor for interleukin 11 (IL-11R). The agent may be an oligonucleotide or a small molecule.

In some embodiments the agent is an antisense oligonucleotide capable of preventing or reducing the expression of IL-11. In some embodiments the antisense oligonucleotide capable of preventing or reducing the expression of IL-11 is siRNA targeted to IL11 comprising the sequence of SEQ ID NO:12, 13, 14 or 15. In some embodiments the agent is an antisense oligonucleotide capable of preventing or reducing the expression of IL-11Rα. In some embodiments the antisense oligonucleotide capable of preventing or reducing the expression of IL-11Rα is siRNA targeted to IL11RA comprising the sequence of SEQ ID NO:16, 17, 18 or 19.

In any embodiments provided herein, the interleukin 11 receptor is or comprises IL-11Rα.

In any embodiments provided herein, the agent may be administered before, in conjunction with, or after the cause of the hepatotoxicity, e.g. administration or consumption of a hepatotoxic medicine or exposure to an environmental source of hepatotoxicity.

In any embodiments provided herein, the disorder, disease or condition associated with hepatotoxicity is a disease in which hepatotoxicity is pathologically implicated.

In some embodiments the disease in which hepatotoxicity is pathologically implicated is selected from: drug-induced liver injury (DILI), acute liver injury (ALI), acute liver failure, acute liver disease, chronic liver disease, liver damage, hepatitis, viral hepatitis, alcoholic hepatitis, liver ischemia-reperfusion injury (IRI), warm ischemia-reperfusion (WIR), radiation-induced liver disease (RILD), idiosyncratic drug-induced liver injury (IDILI), autoimmune liver injury, cholestatic liver disease, HIV, and cancer.

In any embodiments, the agents, uses and methods herein are provided for treating and/or preventing drug-induced liver injury (DILI). The DILI may be intrinsic and/or idiosyncratic hepatotoxicity. In any embodiments, the agents, uses and methods herein are provided for treating and/or preventing acetaminophen (APAP)-induced hepatotoxicity. In some embodiments the method further comprises treatment with N-acetylcysteine.

In any embodiments, the method of treating or preventing comprises administering the agent to a subject in which expression of interleukin 11 (IL-11) or a receptor for IL-11 (IL-11R) is upregulated.

In any embodiments, the method of treating or preventing comprises administering the agent to a subject in expression of interleukin 11 (IL-11) or a receptor for interleukin 11 (IL-11R) has been determined to be upregulated.

In some embodiments the method of treating or preventing comprises determining whether expression of interleukin 11 (IL-11) or a receptor for IL-11 (IL-11R) is upregulated in the subject and administering the agent to a subject in which expression of interleukin 11 (IL-11) or a receptor for IL-11 (IL-11R) is upregulated.

Also provided is a method of determining the suitability of a subject for the treatment or prevention of hepatotoxicity and/or a disorder, disease or condition associated with hepatotoxicity with an agent capable of inhibiting interleukin 11 (IL-11)-mediated signalling, the method comprising determining, optionally in vitro, whether interleukin 11 (IL-11) or a receptor for IL-11 (IL-11R) expression is upregulated in the subject.

Also provided is a method of selecting a subject for the treatment or prevention of hepatotoxicity and/or a disorder, disease or condition associated with hepatotoxicity with an agent capable of inhibiting interleukin 11 (IL-11)-mediated signalling, the method comprising determining, optionally in vitro, whether interleukin 11 (IL-11) or a receptor for IL-11 (IL-11R) expression is upregulated in the subject.

In one aspect there is provided a method of diagnosing hepatotoxicity and/or a disorder, disease or condition associated with hepatotoxicity, or a risk of developing hepatotoxicity and/or a disorder, disease or condition associated with hepatotoxicity in a subject, the method comprising determining, optionally in vitro, the upregulation of interleukin 11 (IL-11) or an receptor for IL-11 (IL-11R) in a sample obtained from the subject. In some embodiments, the method of diagnosing is a method of confirming a diagnosis of hepatotoxicity and/or a disorder, disease or condition associated with hepatotoxicity in a subject suspected of having hepatotoxicity and/or a disorder, disease or condition associated with hepatotoxicity. In some embodiments a method of diagnosing and/or a method of confirming a diagnosis comprises selecting the subject for treatment with an agent capable of inhibiting interleukin 11 (IL-11)-mediated signalling.

Also provided is a method of providing a prognosis for a subject having, or suspected of having, hepatotoxicity and/or a disorder, disease or condition associated with hepatotoxicity, the method comprising determining, optionally in vitro, whether expression of interleukin 11 (IL-11) or a receptor for IL-11 (IL-11R) is upregulated in a sample obtained from the subject and, based on the determination, providing a prognosis for treatment of the subject with an agent capable of inhibiting interleukin 11 (IL-11)-mediated signalling. In some embodiments, a method of providing a prognosis comprises selecting a subject determined to have upregulated expression of expression of interleukin 11 (IL-11) or a receptor for IL-11 (IL-11R) for treatment with an agent capable of inhibiting interleukin 11 (IL-11)-mediated signalling.

In another aspect there is provided a method of diagnosing hepatotoxicity and/or a disorder, disease or condition associated with hepatotoxicity or a risk of developing hepatotoxicity and/or a disorder, disease or condition associated with hepatotoxicity, the method comprising determining, optionally in vitro, one or more genetic factors in the subject that are predictive of upregulation of expression of IL-11 or a receptor for IL-11, or of upregulation of IL-11 mediated signalling. In some embodiments the method comprises selecting the subject for treatment with an agent capable of inhibiting interleukin 11 (IL-11)-mediated signalling.

Also provided is a method of providing a prognosis for a subject having, or suspected of having, hepatotoxicity and/or a disorder, disease or condition associated with hepatotoxicity, the method comprising determining, optionally in vitro, one or more genetic factors in the subject that are predictive of upregulation of expression of IL-11 or a receptor for IL-11, or of upregulation of IL-11 mediated signalling.

DESCRIPTION

There is ongoing demand for effective prevention and treatment of hepatotoxicity, for example hepatotoxicity as a result of drug-induced liver injury (DILI). Liver damage from acetaminophen (APAP) overdose is a common cause of hepatotoxicity.

The cytokine IL-11 is repeatedly reported to have a protective effect on APAP-induced liver damage and hepatotoxicity more generally. In contrast, however, the present inventors have found that inhibition of IL-11 mediated signalling is effective to ameliorate APAP-induced hepatotoxicity, thus presenting new therapeutic and/or prophylactic approaches to treat hepatotoxicity.

Interleukin 11 and Receptors for IL-11

Interleukin 11 (IL-11), also known as adipogenesis inhibitory factor, is a pleiotropic cytokine and a member of the IL-6 family of cytokines that includes IL-6, IL-11, IL-27, IL-31, oncostatin, leukemia inhibitory factor (LIF), cardiotrophin-1 (CT-1), cardiotrophin-like cytokine (CLC), ciliary neurotrophic factor (CNTF) and neuropoetin (NP-1).

Interleukin 11 (IL-11) is expressed in a variety of mesenchymal cell types. IL-11 genomic sequences have been mapped onto chromosome 19 and the centromeric region of chromosome 7, and is transcribed with a canonical signal peptide that ensures efficient secretion from cells. The activator protein complex of IL-11, cJun/AP-1, located within its promoter sequence is critical for basal transcriptional regulation of IL-11 (Du and Williams, Blood 1997, Vol 89: 3897-3908). The immature form of human IL-11 is a 199 amino acid polypeptide whereas the mature form of IL-11 encodes a protein of 178 amino acid residues (Garbers and Scheller, Biol. Chem. 2013; 394(9):1145-1161). The human IL-11 amino acid sequence is available under UniProt accession no. P20809 (P20809.1 GI:124294; SEQ ID NO:1). Recombinant human IL-11 (oprelvekin) is also commercially available. IL-11 from other species, including mouse, rat, pig, cow, several species of bony fish and primates, have also been cloned and sequenced.

In this specification "IL-11" refers to an IL-11 from any species and includes isoforms, fragments, variants or homologues of an IL-11 from any species. In preferred embodiments the species is human (*Homo sapiens*). Isoforms, fragments, variants or homologues of an IL-11 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of immature or mature IL-11 from a given species, e.g. human. Isoforms, fragments, variants or homologues of an IL-11 may optionally be characterised by ability to bind IL-11Rα (preferably from the same species) and stimulate signal transduction in cells expressing IL-11Rα and gp130 (e.g. as described in Curtis et al. Blood, 1997, 90(11); or Karpovich et al. Mol. Hum. Reprod. 2003 9(2): 75-80). A fragment of IL-11 may be of any length (by number of amino acids), although may optionally be at least 25% of the length of mature IL-11 and may have a maximum length of one of 50%, 75%, 80%, 85%, 90%, 91%, 92%, 93%, 94%, 95%, 96%, 97%, 98%, or 99% of the length of mature IL-11. A fragment of IL-11 may have a minimum length of 10 amino acids, and a maximum length of one of 15, 20, 25, 30, 40, 50, 60, 70, 80, 90, 100, 110, 120, 130, 140, 150, 160, 170, 180, 190 or 195 amino acids.

IL-11 signals through a homodimer of the ubiquitously expressed glycoprotein 130 (gp130; also known as glycoprotein 130, IL-6ST, IL-6-beta or CD130). Gp130 is a transmembrane protein that forms one subunit of the type I cytokine receptor with the IL-6 receptor family. Specificity is gained through an individual interleukin 11 receptor subunit alpha (IL-11Rα), which does not directly participate in signal transduction, although the initial cytokine binding event to the α-receptor leads to the final complex formation with gp130.

Human gp130 (including the 22 amino acid signal peptide) is a 918 amino acid protein, and the mature form is 866 amino acids, comprising a 597 amino acid extracellular domain, a 22 amino acid transmembrane domain, and a 277 amino acid intracellular domain. The extracellular domain of the protein comprises the cytokine-binding module (CBM) of gp130. The CBM of gp130 comprises the Ig-like domain D1, and the fibronectin-type III domains D2 and D3 of gp130. The amino acid sequence of human gp130 is available under UniProt accession no. P40189-1 (SEQ ID NO:2).

Human IL-11Rα is a 422 amino acid polypeptide (UniProt Q14626; SEQ ID NO:3) and shares ~85% nucleotide and amino acid sequence identity with the murine IL-11Rα. Two isoforms of IL-11Rα have been reported, which differ in the cytoplasmic domain (Du and Williams, supra). The IL-11 receptor α-chain (IL-11Rα) shares many structural and functional similarities with the IL-6 receptor α-chain (IL-6Rα). The extracellular domain shows 24% amino acid identity including the characteristic conserved Trp-Ser-X-Trp-Ser (WSXWS) motif. The short cytoplasmic domain (34 amino acids) lacks the Box 1 and 2 regions that are required for activation of the JAK/STAT signalling pathway.

The receptor binding sites on murine IL-11 have been mapped and three sites—sites I, II and III—identified. Binding to gp130 is reduced by substitutions in the site II region and by substitutions in the site III region. Site III mutants show no detectable agonist activity and have IL-11Rα antagonist activity (Cytokine Inhibitors Chapter 8; edited by Gennaro Ciliberto and Rocco Savino, Marcel Dekker, Inc. 2001).

In this specification a receptor for IL-11 (IL-11R) refers to a polypeptide or polypeptide complex capable of binding IL-11. In some embodiments an IL-11 receptor is capable of binding IL-11 and inducing signal transduction in cells expressing the receptor.

An IL-11 receptor may be from any species and includes isoforms, fragments, variants or homologues of an IL-11 receptor from any species. In preferred embodiments the species is human (*Homo sapiens*).

In some embodiments the IL-11 receptor may be, or may comprise, IL-11Rα. In some embodiments a receptor for IL-11 may be a polypeptide complex comprising IL-11Rα. In some embodiments the IL-11 receptor may be, or may comprise, gp130. In some embodiments a receptor for IL-11 may be a polypeptide complex comprising gp130. In some embodiments the IL-11 receptor may be a polypeptide complex comprising IL-11Rα and gp130. In some embodiments the IL-11 receptor may be gp130, or a complex comprising gp130 to which IL-11 binds.

Isoforms, fragments, variants or homologues of an IL-11Rα may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of IL-11Rα from a given species, e.g. human. Isoforms, fragments, variants or homologues of an IL-11Rα may optionally be characterised by ability to bind IL-11 (preferably from the same species) and stimulate signal transduction in cells expressing the IL-11Rα and gp130 (e.g. as described in Curtis et al. Blood, 1997, 90(11) or Karpovich et al. Mol. Hum. Reprod. 2003 9(2): 75-80). A fragment of an IL-11 receptor may be of any length (by number of amino acids), although may optionally be at least 25% of the length of the mature IL-11Rα and have a maximum length of one of 50%, 75%, 80%, 85%, 90%, 91%, 92%, 93%, 94%, 95%, 96%, 97%, 98%, or 99% of the length of the mature IL-11Rα. A fragment of an IL-11 receptor fragment may have a minimum length of 10 amino acids, and a maximum length of one of 15, 20, 25, 30, 40, 50, 100, 110, 120, 130, 140, 150, 160, 170, 180, 190, 200, 250, 300, 400, or 415 amino acids.

IL-11 Signalling

IL-11 binds to IL-11Rα with low affinity (Kd ~10 nmol/L), and interaction between these binding partners alone is insufficient to transduce a biological signal. The generation of a high affinity receptor (Kd ~400 to 800 pmol/L) capable of signal transduction requires co-expression of the IL-11Rα and gp130 (Curtis et al Blood 1997; 90 (11):4403-12; Hilton et al., EMBO J 13:4765, 1994; Nandurkar et al., Oncogene 12:585, 1996). Binding of IL-11 to cell-surface IL-11Rα induces heterodimerization, tyrosine phosphorylation, activation of gp130 and downstream signalling, predominantly through the mitogen-activated protein kinase (MAPK)-cascade and the Janus kinase/signal transducer and activator of transcription (Jak/STAT) pathway (Garbers and Scheller, supra).

In principle, a soluble IL-11Rα can also form biologically active soluble complexes with IL-11 (Pflanz et al., 1999 FEBS Lett, 450, 117-122) raising the possibility that, similar to IL-6, IL-11 may in some instances bind soluble IL-11Rα prior to binding cell-surface gp130 (Garbers and Scheller, supra). Curtis et al (Blood 1997 Dec. 1; 90 (11):4403-12) describe expression of a soluble murine IL-11 receptor alpha chain (sIL-11R) and examined signalling in cells expressing gp130. In the presence of gp130 but not transmembrane IL-11R the sIL-11R mediated IL-11 dependent differentiation of M1 leukemic cells and proliferation in Ba/F3 cells and early intracellular events including phosphorylation of gp130, STAT3 and SHP2 similar to signalling through transmembrane IL-11R. Activation of signalling through cell-membrane bound gp130 by IL-11 bound to soluble IL-11Rα has recently been demonstrated (Lokau et al., 2016 Cell Reports 14, 1761-1773). This so-called IL-11 trans signalling may be important for disease pathogenesis, yet its role in human disease has not yet been studied.

As used herein, 'IL-11 trans signalling' is used to refer to signalling which is triggered by binding of IL-11 bound to IL-11Rα, to gp130. The IL-11 may be bound to IL-11Rα as a non-covalent complex. The gp130 is membrane-bound and expressed by the cell in which signalling occurs following binding of the IL-11:IL-11Rα complex to gp130. In some embodiments the IL-11Rα may be a soluble IL-11Rα. In some embodiments, the soluble IL-11Rα is a soluble (secreted) isoform of IL-11Rα (e.g. lacking a transmembrane domain). In some embodiments, the soluble IL-11Rα is the liberated product of proteolytic cleavage of the extracellular domain of cell membrane bound IL-11Rα. In some embodiments, the IL-11Rα may be cell membrane-bound, and signalling through gp130 may be triggered by binding of IL-11 bound to cell-membrane-bound IL-11Rα, termed "IL-11 cis signalling".

IL-11-mediated signalling has been shown to stimulate hematopoiesis and thrombopoiesis, stimulate osteoclast activity, stimulate neurogenesis, inhibit adipogenesis, reduce pro inflammatory cytokine expression, modulate extracellular matrix (ECM) metabolism, and mediate normal growth control of gastrointestinal epithelial cells (Du and Williams, supra).

The physiological role of Interleukin 11 (IL-11) remains unclear. IL-11 has been most strongly linked with activation of haematopoetic cells and with platelet production. IL-11 has also been shown to confer protection against graft-vs-host-disease, inflammatory arthritis and inflammatory bowel disease, leading to IL-11 being considered an anti-inflammatory cytokine (Putoczki and Ernst, J Leukoc Biol 2010, 88(6):1109-1117). However, it is suggested that IL-11 is pro-inflammatory as well as anti-inflammatory, pro-angiogenic and important for neoplasia. Recent studies have shown that IL-11 is readily detectable during viral-induced inflammation in a mouse arthritis model and in cancers, suggesting that the expression of IL-11 can be induced by pathological stimuli. IL-11 is also linked to Stat3-dependent activation of tumour-promoting target genes in neoplastic gastrointestinal epithelium (Putoczki and Ernst, supra).

As used herein, "IL-11 signalling" and "IL-11-mediated signalling" refers to signalling mediated by binding of IL-11, or a fragment thereof having the function of the mature IL-11 molecule, to a receptor for IL-11. It will be appreciated that "IL-11 signalling" and "IL-11 mediated signalling" refer to signalling initiated by IL-11/functional fragment thereof, e.g. through binding to a receptor for IL-11. "Signalling" in turn refers to signal transduction and other cellular processes governing cellular activity.

Hepatotoxicity

Aspects of the present invention relate to the diagnosis, treatment and prophylaxis of hepatotoxicity and disorders, diseases and conditions characterised by hepatotoxicity.

As used herein, "hepatotoxicity and/or a disorder, disease or condition associated with hepatotoxicity" refers to hepatotoxicity, a disorder associated with hepatotoxicity, a disease associated with hepatotoxicity, or a condition associated with hepatotoxicity.

As used herein, hepatotoxicity refers to damage to and/or death of liver cells/tissue. Hepatotoxicity can refer to a state of toxic damage to the liver, specifically with death of the hepatocyte cells within the liver. Hepatotoxicity may be determined/diagnosed by detection of one or more correlates of hepatotoxicity as described hereinbelow.

Hepatotoxicity may arise as a consequence of hepatotoxic insult. As used herein "hepatotoxic insult" refers to any treatment, event or conditions giving rise to hepatotoxicity. For example, hepatotoxic insult may be caused by a chemical/physical treatment/experience, or gaseous conditions. In some embodiments hepatotoxic insult is chemical, e.g. in the case of drug-induced liver injury, e.g. APAP-induced hepatotoxicity. In some embodiments hepatotoxic insult is physical, e.g. in the case of hepatotoxicity arising as a result of surgical damage to liver tissue, which may occur e.g. surgery to treat a disease and/or for liver transplantation (e.g. the hepatotoxicity may have iatrogenic causes). In some embodiments hepatotoxic insult arises from hypoxia, e.g. as a consequence of ischaemia, or may result from reperfusion (e.g. the hepatotoxic insult may arise from IRI).

Hepatotoxicity may be chemical-driven liver damage, for example damage or injury caused by a medicine, chemical, ischaemia, reperfusion, sepsis or herbal or dietary supplements. In some embodiments hepatotoxicity refers to drug-induced liver injury (DILI). In some embodiments hepatotoxicity refers to liver injury caused by a hepatotoxin. A hepatotoxin may be alcohol. Hepatotoxicity may also be termed toxic hepatitis. Hepatotoxicity may refer to acute and/or chronic hepatotoxicity.

Hepatotoxicity may be caused, directly or indirectly, by alcohol ingestion e.g. chronic alcohol consumption. Hepatotoxicity as referred to herein may be caused, directly or indirectly, by fasting, malnutrition, infection by an infectious agent (e.g. a hepatitis virus (e.g. hepatitis A, B, C, D or E), HIV), cancer or drug interactions.

Hepatotoxicity may be present in association with other disorders, diseases and conditions. Disorders, diseases or conditions associated with hepatotoxicity include acute liver injury (ALI), acute liver failure, acute liver disease, chronic liver disease, liver damage, hepatitis e.g. viral hepatitis, alcoholic hepatitis, liver ischemia-reperfusion injury (IRI) e.g. 'warm' ischemia-reperfusion (WIR), radiation-induced liver disease (RILD), drug-induced liver injury (DILI), autoimmune liver injury, cholestatic liver disease, HIV and cancer.

Drug-induced liver injury (DILI) includes intrinsic and idiosyncratic hepatotoxicity, and idiosyncratic DILI further includes allergic and nonallergic reaction. The intrinsic mechanism is related to dose dependent hepatotoxicity, whereas idiosyncratic hepatotoxicity is not dose dependent and may happen in an unpredictable fashion. Allergic idiosyncratic hepatotoxicity is further characterized by the presence of symptoms and signs typical of an adaptive immune system reaction, including fever, skin reactions, eosinophilia, formation of autoantibodies, and a short latency time particularly after re-exposure (Khoury et al., J Clin Transl Hepatol. 2015 Jun. 28; 3(2): 99-108).

Aspects of the present invention relate to the diagnosis, treatment and prophylaxis of acetaminophen (APAP)-induced hepatotoxicity. Acetaminophen is also known as N-acetyl-p-aminophenol or paracetamol, or by the brand names Tylenol and Panadol. Acetaminophen intoxication results in hepatotoxicity associated with increased serum concentrations of hepatocellular leakage enzymes such as aspartate aminotransferase, lactate dehydrogenase, and alanine aminotransferase, centrilobular degeneration and necrosis, and activation of Kupffer cells (Trepicchio W L et al., Toxicol Pathol. 2001; 29(2):242-9).

Agents Capable of Inhibiting the Action of IL-11

Aspects of the present invention involve inhibition of IL-11-mediated signalling.

Herein, 'inhibition' refers to a reduction, decrease or lessening relative to a control condition. For example, inhibition of the action of IL-11 by an agent capable of inhibiting IL-11-mediated signalling refers to a reduction, decrease or lessening of the extent/degree of IL-11-mediated signalling in the absence of the agent, and/or in the presence of an appropriate control agent.

Inhibition may herein also be referred to as neutralisation or antagonism. That is, an agent capable of inhibiting IL-11-mediated signalling (e.g. interaction, signalling or other activity mediated by IL-11 or an IL-11-containing complex) may be said to be a 'neutralising' or 'antagonist' agent with respect to the relevant function or process. For example, an agent which is capable of inhibiting IL-11-mediated signalling may be referred to as an agent which is capable of neutralising IL-11-mediated signalling, or may be referred to as an antagonist of IL-11-mediated signalling.

The IL-11 signalling pathway offers multiple routes for inhibition of IL-11 signalling. An agent capable of inhibiting IL-11-mediated signalling may do so e.g. through inhibiting the action of one or more factors involved in, or necessary for, signalling through a receptor for IL-11.

For example, inhibition of IL-11 signalling may be achieved by disrupting interaction between IL-11 (or an IL-11 containing complex, e.g. a complex of IL-11 and IL-11Rα) and a receptor for IL-11 (e.g. IL-11Rα, a receptor complex comprising IL-11Rα, gp130 or a receptor complex comprising IL-11Rα and gp130). In some embodiments, inhibition of IL-11-mediated signalling is achieved by inhibiting the gene or protein expression of one or more of e.g. IL-11, IL-11Rα and gp130.

In embodiments, inhibition of IL-11-mediated signalling is achieved by disrupting IL-11-mediated cis signalling but not disrupting IL-11-mediated trans signalling, e.g. inhibition of IL-11-mediated signalling is achieved by inhibiting gp130-mediated cis complexes involving membrane bound IL-11Rα. In embodiments, inhibition of IL-11-mediated signalling is achieved by disrupting IL-11-mediated trans signalling but not disrupting IL-11-mediated cis signalling, i.e. inhibition of IL-11-mediated signalling is achieved by inhibiting gp130-mediated trans signalling complexes such as IL-11 bound to soluble IL-11Rα or IL-6 bound to soluble IL-6R. In embodiments, inhibition of IL-11-mediated signalling is achieved by disrupting IL-11-mediated cis signalling and IL-11-mediated trans signalling. Any agent as described herein may be used to inhibit IL-11-mediated cis and/or trans signalling. In preferred embodiments, inhibition of IL-11-mediated signalling is achieved by disrupting IL-11-mediated cis signalling.

In other examples, inhibition of IL-11 signalling may be achieved by disrupting signalling pathways downstream of IL-11/IL-11Rα/gp130. That is, in some embodiments inhibition/antagonism of IL-11-mediated signalling comprises inhibition of a signalling pathway/process/factor downstream of signalling through the IL-11/IL-11 receptor complex.

In some embodiments inhibition/antagonism of IL-11-mediated signalling comprises inhibition of signalling through an intracellular signalling pathway which is activated by the IL-11/IL-11 receptor complex. In some embodiments inhibition/antagonism of IL-11-mediated signalling comprises inhibition of one or more factors whose expression/activity is upregulated as a consequence of signalling through the IL-11/IL-11 receptor complex.

In some embodiments, the methods of the present invention employ agents capable of inhibiting JAK/STAT signalling. In some embodiments, agents capable of inhibiting JAK/STAT signalling are capable of inhibiting the action of JAK1, JAK2, JAK3, TYK2, STAT1, STAT2, STAT3, STAT4, STAT5A, STAT5B and/or STAT6. For example, agents may be capable of inhibiting activation of JAK/STAT proteins, inhibiting interaction of JAK or STAT proteins with cell surface receptors e.g. IL-11Rα or gp130, inhibiting phosphorylation of JAK proteins, inhibiting interaction between JAK and STAT proteins, inhibiting phosphorylation of STAT proteins, inhibiting dimerization of STAT proteins, inhibiting translocation of STAT proteins to the cell nucleus, inhibiting binding of STAT proteins to DNA, and/or promoting degradation of JAK and/or STAT proteins. In some embodiments, a JAK/STAT inhibitor is selected from Ruxolitinib (Jakafi/Jakavi; Incyte), Tofacitinib (Xeljanz/Jakvinus; NIH/Pfizer), Oclacitinib (Apoquel), Baricitinib (Olumiant; Incyte/Eli Lilly), Filgotinib (G-146034/GLPG-0634; Galapagos NV), Gandotinib (LY-2784544; Eli Lilly), Lestaurtinib (CEP-701; Teva), Momelotinib (GS-0387/CYT-387; Gilead Sciences), Pacritinib (SB1518; CTI), PF-04965842 (Pfizer), Upadacitinib (ABT-494; AbbVie), Peficitinib (ASP015K/JNJ-54781532; Astellas), Fedratinib (SAR302503; Celgene), Cucurbitacin I (JSI-124) and CHZ868.

In some embodiments, the methods of the present invention employ agents capable of inhibiting MAPK/ERK signalling. In some embodiments, agents capable of inhibiting MAPK/ERK signalling are capable of inhibiting the action of GRB2, inhibiting the action of RAF kinase, inhibiting the action of MEK proteins, inhibiting the activation of MAP3K/MAP2K/MAPK and/or Myc, and/or inhibiting the phosphorylation of STAT proteins. In some embodiments, agents capable of inhibiting ERK signalling are capable of inhibiting ERK p42/44. In some embodiments, an ERK inhibitor is selected from SCH772984, SC1, VX-11e, DEL-22379, Sorafenib (Nexavar; Bayer/Onyx), SB590885, PLX4720, XL281, RAF265 (Novartis), encorafenib (LGX818/Braftovi; Array BioPharma), dabrafenib (Tafinlar; GSK), vemurafenib (Zelboraf; Roche), cobimetinib (Cotellic; Roche), CI-1040, PD0325901, Binimetinib (MEK162/MEKTOVI; Array BioPharma), selumetinib (AZD6244; Array/AstraZeneca) and Trametinib (GSK1120212/Mekinist; Novartis). In some embodiments, the methods of the present invention employ agents capable of inhibiting c-Jun N-terminal kinase (JNK) signalling/activity. In some embodiments, agents capable of inhibiting JNK signalling/activity are capable of inhibiting the action and/or phosphorylation of a JNK (e.g. JNK1, JNK2). In some embodiments, a JNK inhibitor is selected from SP600125, CEP 1347, TCS JNK 6o, c-JUN peptide, SU3327, AEG 3482, TCS JNK 5a, BI78D3, IQ3, SR3576, IQ1S, JIP-1 (153-163) and CC401 dihydrochloride.

In the present Examples the inventors demonstrate that NOX4 expression and activity is upregulated by signalling through IL-11/IL-11Rα/gp130. NOX4 is an NADPH oxidase, and a source of reactive oxygen species (ROS). Expression of Nox4 is upregulated in transgenic mice with hepatocyte-specific Il11 expression, and primary human hepatocytes stimulated with IL11 upregulate NOX4 expression.

In some embodiments, the present invention employs agents capable of inhibiting NOX4 expression (gene or protein expression) or function. In some embodiments, the present invention employs agents capable of inhibiting IL-11-mediated upregulation of NOX4 expression/function. Agents capable of inhibiting NOX4 expression or function may be referred to herein as NOX4 inhibitors. For example, a NOX4 inhibitor may be capable of reducing expression (e.g. gene and/or protein expression) of NOX4, reducing the level of RNA encoding NOX4, reduce the level of NOX4 protein, and/or reducing the level of a NOX4 activity (e.g. reducing NOX4-mediated NADPH oxidase activity and/or NOX4-mediated ROS production).

NOX4 inhibitors include a NOX4-binding molecules and molecules capable of reducing NOX4 expression. NOX4-binding inhibitors include peptide/nucleic acid aptamers, antibodies (and antibody fragments) and fragments of interaction partners for NOX4 which behave as antagonists of NOX4 function, and small molecules inhibitors of NOX4. Molecules capable of reducing NOX4 expression include antisense RNA (e.g. siRNA, shRNA) to NOX4. In some embodiments, a NOX4 inhibitor is selected from a NOX4 inhibitor described in Altenhofer et al., Antioxid Redox Signal. (2015) 23(5): 406-427 or Augsburder et al., Redox Biol. (2019) 26: 101272, such as GKT137831.

Binding Agents

In some embodiments, agents capable of inhibiting IL-11-mediated signalling may bind to IL-11. In some embodiments, agents capable of inhibiting IL-11-mediated signalling may bind to a receptor for IL-11 (e.g. IL-11Rα, gp130, or a complex containing IL-11Rα and/or gp130). Binding of such agents may inhibit IL-11-mediated signalling by reducing/preventing the ability of IL-11 to bind to receptors for IL-11, thereby inhibiting downstream signalling. Binding of such agents may inhibit IL-11 mediated cis and/or trans-signalling by reducing/preventing the ability of IL-11 to bind to receptors for IL-11, e.g. IL-11Rα and/or gp130, thereby inhibiting downstream signalling. Agents may bind to trans-signalling complexes such as IL-11 and soluble IL-11Rα and inhibit gp130-mediated signalling.

Agents capable of binding to IL-11/an IL-11 containing complex or a receptor for IL-11 may be of any kind, but in some embodiments the agent may be an antibody, an antigen-binding fragment thereof, a polypeptide, a peptide, a nucleic acid, an oligonucleotide, an aptamer or a small molecule. The agents may be provided in isolated or purified form, or may be formulated as a pharmaceutical composition or medicament.

Antibodies and Antigen-Binding Fragments

In some embodiments, an agent capable of binding to IL-11/an IL-11 containing complex or a receptor for IL-11 is an antibody, or an antigen-binding fragment thereof. In some embodiments, an agent capable of binding to IL-11/an IL-11 containing complex or a receptor for IL-11 is a polypeptide, e.g. a decoy receptor molecule. In some embodiments, an agent capable of binding to IL-11/an IL-11 containing complex or a receptor for IL-11 may be an aptamer.

In some embodiments, an agent capable of binding to IL-11/an IL-11 containing complex or a receptor for IL-11 is an antibody, or an antigen-binding fragment thereof. An "antibody" is used herein in the broadest sense, and encompasses monoclonal antibodies, polyclonal antibodies, monospecific and multispecific antibodies (e.g., bispecific antibodies), and antibody fragments, as long as they display binding to the relevant target molecule.

In view of today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimaeric antibodies are discussed by Neuberger et al (1988, 8th International Biotechnology Symposium Part 2, 792-799). Monoclonal antibodies (mAbs) are particularly useful in the methods of the invention, and are a homogenous population of antibodies specifically targeting a single epitope on an antigen.

Polyclonal antibodies are also useful in the methods of the invention. Monospecific polyclonal antibodies are preferred. Suitable polyclonal antibodies can be prepared using methods well known in the art.

Antigen-binding fragments of antibodies, such as Fab and Fab2 fragments may also be used/provided as can genetically engineered antibodies and antibody fragments. The variable heavy (VH) and variable light (VL) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) Proc. Natl. Acad. Sd. USA 81, 6851-6855).

Antibodies and antigen-binding fragments according to the present disclosure comprise the complementarity-determining regions (CDRs) of an antibody which is capable of binding to the relevant target molecule (i.e. IL-11/an IL-11 containing complex/a receptor for IL-11).

Antibodies capable of binding to IL-11 include e.g. monoclonal mouse anti-human IL-11 antibody clone #22626; Catalog No. MAB218 (R&D Systems, MN, USA), used e.g.

in Bockhorn et al. *Nat. Commun.* (2013) 4(0):1393, clone 6D9A (Abbiotec), clone KT8 (Abbiotec), clone M3103F11 (BioLegend), clone 1 F1 (Abnova Corporation), clone 3C6 (Abnova Corporation), clone GF1 (LifeSpan Biosciences), clone 13455 (Source BioScience), 11 h3/19.6.1 (Hermann et al., Arthritis Rheum. (1998) 41(8):1388-97), AB-218-NA (R&D Systems), X203 (Ng et al., Sci Transl Med. (2019) 11(511) pii: eaaw1237) and anti-IL-11 antibodies disclosed in US 2009/0202533 A1, WO 99/59608 A2 and WO 2018/109174 A2.

In particular, anti-IL-11 antibody clone 22626 (also known as MAB218) has been shown to be an antagonist of IL-11 mediated signalling, e.g. in Schaefer et al., Nature (2017) 552(7683): 110-115. Monoclonal antibody 11 h3/19.6.1 is disclosed in Hermann et al., Arthritis Rheum. (1998) 41(8):1388-97 to be a neutralising anti-IL-11 IgG1. AB-218-NA from R&D Systems, used e.g. in McCoy et al., BMC Cancer (2013) 13:16, is another example of neutralizing anti-IL-11 antibody. WO 2018/109174 A2 discloses yet further exemplary anti-IL-11 antibody antagonists of IL-11 mediated signalling.

Antibodies capable of binding to IL-11Rα include e.g. monoclonal antibody clone 025 (Sino Biological), clone EPR5446 (Abcam), clone 473143 (R & D Systems), clones 8E2, 8D10 and 8E4 and the affinity-matured variants of 8E2 described in US 2014/0219919 A1, the monoclonal antibodies described in Blanc et al (*J. Immunol Methods.* 2000 Jul. 31; 241(1-2); 43-59), X209 (Widjaja et al., Gastroenterology (2019) 157(3):777-792) antibodies disclosed in WO 2014121325 A1 and US 2013/0302277 A1, and anti-IL-11Rα antibodies disclosed in US 2009/0202533 A1, WO 99/59608 A2 and WO 2018/109170 A2.

In particular, anti-IL-11Rα antibody clone 473143 (also known as MAB1977) has been shown to be an antagonist of IL-11 mediated signalling, e.g. in Schaefer et al., Nature (2017) 552(7683):110-115. US 2014/0219919 A1 provides sequences for anti-human IL-11Rα antibody clones 8E2, 8D10 and 8E4, and discloses their ability to antagonise IL-11 mediated signalling—see e.g. [0489] to [0490] of US 2014/0219919 A1. US 2014/0219919 A1 moreover provides sequence information for an additional 62 affinity-matured variants of clone 8E2, 61 of which are disclosed to antagonise IL-11 mediated signalling—see Table 3 of US 2014/0219919 A1. WO 2018/109170 A2 discloses yet further exemplary anti-IL-11Rα antibody antagonists of IL-11 mediated signalling.

The skilled person is well aware of techniques for producing antibodies suitable for therapeutic use in a given species/subject. For example, procedures for producing antibodies suitable for therapeutic use in humans are described in Park and Smolen Advances in Protein Chemistry (2001) 56: 369-421 (hereby incorporated by reference in its entirety).

Antibodies to a given target protein (e.g. IL-11 or IL-11Rα) can be raised in model species (e.g. rodents, lagomorphs), and subsequently engineered in order to improve their suitability for therapeutic use in a given species/subject. For example, one or more amino acids of monoclonal antibodies raised by immunisation of model species can be substituted to arrive at an antibody sequence which is more similar to human germline immunoglobulin sequences (thereby reducing the potential for anti-xenogenic antibody immune responses in the human subject treated with the antibody). Modifications in the antibody variable domains may focus on the framework regions in order to preserve the antibody paratope. Antibody humanisation is a matter of routine practice in the art of antibody technology, and is reviewed e.g. in Almagro and Fransson, Frontiers in Bioscience (2008) 13:1619-1633, Safdari et al., Biotechnology and Genetic Engineering Reviews (2013) 29(2): 175-186 and Lo et al., Microbiology Spectrum (2014) 2(1), all of which are hereby incorporated by reference in their entirety. The requirement for humanisation can be circumvented by raising antibodies to a given target protein (e.g. IL-11 or IL-11Rα) in transgenic model species expressing human immunoglobulin genes, such that the antibodies raised in such animals are fully-human (described e.g. in Bruggemann et al., Arch Immunol Ther Exp (Warsz) (2015) 63(2): 101-108, which is hereby incorporated by reference in its entirety).

Phage display techniques may also be employed to the identification of antibodies to a given target protein (e.g. IL-11 or IL-11Rα), and are well known to the skilled person. The use of phage display for the identification of fully human antibodies to human target proteins is reviewed e.g. in Hoogenboom, Nat. Biotechnol. (2005) 23, 1105-1116 and Chan et al., International Immunology (2014) 26(12): 649-657, which are hereby incorporated by reference in their entirety.

The antibodies/fragments may be antagonist antibodies/fragments that inhibit or reduce a biological activity of IL-11. The antibodies/fragments may be neutralising antibodies that neutralise the biological effect of IL-11, e.g. its ability to stimulate productive signalling via an IL-11 receptor. Neutralising activity may be measured by ability to neutralise IL-11 induced proliferation in the T11 mouse plasmacytoma cell line (Nordan, R. P. et al. (1987) *J. Immunol.* 139:813).

IL-11- or IL-11Rα-binding antibodies can be evaluated for the ability to antagonise IL-11-mediated signalling, e.g. using the assay described in US 2014/0219919 A1 or Blanc et al (*J. Immunol Methods.* 2000 Jul. 31; 241(1-2); 43-59. Briefly, IL-11- and IL-11Rα-binding antibodies can be evaluated in vitro for the ability to inhibit proliferation of Ba/F3 cells expressing IL-11Rα and gp130 from the appropriate species, in response to stimulation with IL-11 from the appropriate species. Alternatively, IL-11- and IL-11Rα-binding antibodies can be analysed in vitro for the ability to inhibit the fibroblast-to-myofibroblast transition following stimulation of fibroblasts with TGFβ1, by evaluation of αSMA expression (as described e.g. in WO 2018/109174 A2 (Example 6) and WO 2018/109170 A2 (Example 6), Ng et al., Sci Transl Med. (2019) 11(511) pii: eaaw1237 and Widjaja et al., Gastroenterology (2019) 157(3):777-792).

Antibodies generally comprise six CDRs; three in the light chain variable region (VL): LC-CDR1, LC-CDR2, LC-CDR3, and three in the heavy chain variable region (VH): HC-CDR1, HC-CDR2 and HC-CDR3. The six CDRs together define the paratope of the antibody, which is the part of the antibody which binds to the target molecule. There are several different conventions for defining antibody CDRs, such as those described in Kabat et al., Sequences of Proteins of Immunological Interest, 5th Ed. Public Health Service, National Institutes of Health, Bethesda, Md. (1991), Chothia et al., *J. Mol. Biol.* 196:901-917 (1987), and VBASE2, as described in Retter et al., *Nucl. Acids Res.* (2005) 33 (suppl 1): D671-D674.

Antibodies and antigen-binding fragments according to the present disclosure may be designed and prepared using the sequences of monoclonal antibodies (mAbs) capable of binding to the relevant target molecule. Antigen-binding regions of antibodies, such as single chain variable fragment (scFv), Fab and Fab2 fragments may also be used/provided. An 'antigen-binding region' or 'antigen binding fragment' is any fragment of an antibody which is capable of binding to the target for which the given antibody is specific.

In some embodiments the antibodies/fragments comprise the VL and VH regions of an antibody which is capable of binding to IL-11, an IL-11 containing complex, or a receptor for IL-11. The VL and VH region of an antigen-binding region of an antibody together constitute the Fv region. In some embodiments the antibodies/fragments comprise or consist of the Fv region of an antibody which is capable of binding to IL-11, an IL-11 containing complex, or a receptor for IL-11. The Fv region may be expressed as a single chain wherein the VH and VL regions are covalently linked, e.g. by a flexible oligopeptide. Accordingly, antibodies/fragments may comprise or consist of an scFv comprising the VL and VH regions of an antibody which is capable of binding to IL-11, an IL-11 containing complex, or a receptor for IL-11.

The VL and light chain constant (CL) region, and the VH region and heavy chain constant 1 (CH1) region of an antigen-binding region of an antibody together constitute the Fab region. In some embodiments the antibodies/fragments comprise or consist of the Fab region of an antibody which is capable of binding to IL-11, an IL-11 containing complex, or a receptor for IL-11.

In some embodiments, antibodies/fragments comprise, or consist of, whole antibody capable of binding to IL-11, an IL-11 containing complex, or a receptor for IL-11. A "whole antibody" refers to an antibody having a structure which is substantially similar to the structure of an immunoglobulin (Ig). Different kinds of immunoglobulins and their structures are described e.g. in Schroeder and Cavacini J Allergy Clin Immunol. (2010) 125(202): S41-S52, which is hereby incorporated by reference in its entirety. Immunoglobulins of type G (i.e. IgG) are ~150 kDa glycoproteins comprising two heavy chains and two light chains. From N- to C-terminus, the heavy chains comprise a VH followed by a heavy chain constant region comprising three constant domains (CH1, CH2, and CH3), and similarly the light chain comprises a VL followed by a CL. Depending on the heavy chain, immunoglobulins may be classed as IgG (e.g. IgG1, IgG2, IgG3, IgG4), IgA (e.g. IgA1, IgA2), IgD, IgE, or IgM. The light chain may be kappa (κ) or lambda (λ).

Fab, Fv, ScFv and dAb antibody fragments can all be expressed in and secreted from E. coli, thus allowing the facile production of large amounts of the said fragments.

Whole antibodies, and F(ab')2 fragments are "bivalent". By "bivalent" we mean that the said antibodies and F(ab')2 fragments have two antigen combining sites. In contrast, Fab, Fv, ScFv and dAb fragments are monovalent, having only one antigen combining site. Synthetic antibodies capable of binding to IL-11, an IL-11 containing complex, or a receptor for IL-11 may also be made using phage display technology as is well known in the art.

Antibodies may be produced by a process of affinity maturation in which a modified antibody is generated that has an improvement in the affinity of the antibody for antigen, compared to an unmodified parent antibody. Affinity-matured antibodies may be produced by procedures known in the art, e.g., Marks et al., *Rio/Technology* 10:779-783 (1992); Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):331 0-15 9 (1995); and Hawkins et al, *J. Mol. Biol.* 226:889-896 (1992).

Antibodies/fragments include bi-specific antibodies, e.g. composed of two different fragments of two different antibodies, such that the bi-specific antibody binds two types of antigen. The bispecific antibody comprises an antibody/fragment as described herein capable of binding to IL-11, an IL-11 containing complex, or a receptor for IL-11. The antibody may contain a different fragment having affinity for a second antigen, which may be any desired antigen. Techniques for the preparation of bi-specific antibodies are well known in the art, e.g. see Mueller, D et al., (2010 *Biodrugs* 24 (2): 89-98), Wozniak-Knopp G et al., (2010 *Protein Eng Des* 23 (4): 289-297), and Baeuerle, P A et al., (2009 *Cancer Res* 69 (12): 4941-4944). Bispecific antibodies and bispecific antigen-binding fragments may be provided in any suitable format, such as those formats described in Kontermann MAbs 2012, 4(2): 182-197, which is hereby incorporated by reference in its entirety. For example, a bispecific antibody or bispecific antigen-binding fragment may be a bispecific antibody conjugate (e.g. an IgG2, F(ab')2 or CovX-Body), a bispecific IgG or IgG-like molecule (e.g. an IgG, scFv4-Ig, IgG-scFv, scFv-IgG, DVD-Ig, IgG-sVD, sVD-IgG, 2 in 1-IgG, mAb2, or Tandemab common LC), an asymmetric bispecific IgG or IgG-like molecule (e.g. a kih IgG, kih IgG common LC, CrossMab, kih IgG-scFab, mAb-Fv, charge pair or SEED-body), a small bispecific antibody molecule (e.g. a Diabody (db), dsDb, DART, scDb, tandAbs, tandem scFv (taFv), tandem dAb/VHH, triple body, triple head, Fab-scFv, or F(ab')2-scFv2), a bispecific Fc and CH3 fusion protein (e.g. a taFv-Fc, Di-diabody, scDb-CH3, scFv-Fc-scFv, HCAb-VHH, scFv-kih-Fc, or scFv-kih-CH3), or a bispecific fusion protein (e.g. a scFv2-albumin, scDb-albumin, taFv-toxin, DNL-Fab3, DNL-Fab4-IgG, DNL-Fab4-IgG-cytokine2). See in particular FIG. 2 of Kontermann MAbs 2012, 4(2): 182-19.

Methods for producing bispecific antibodies include chemically crosslinking antibodies or antibody fragments, e.g. with reducible disulphide or non-reducible thioether bonds, for example as described in Segal and Bast, 2001. Production of Bispecific Antibodies. Current Protocols in Immunology. 14:IV:2.13:2.13.1-2.13.16, which is hereby incorporated by reference in its entirety. For example, N-succinimidyl-3-(-2-pyridyldithio)-propionate (SPDP) can be used to chemically crosslink e.g. Fab fragments via hinge region SH— groups, to create disulfide-linked bispecific F(ab)2 heterodimers.

Other methods for producing bispecific antibodies include fusing antibody-producing hybridomas e.g. with polyethylene glycol, to produce a quadroma cell capable of secreting bispecific antibody, for example as described in D. M. and Bast, B. J. 2001. Production of Bispecific Antibodies. Current Protocols in Immunology. 14:IV:2.13:2.13.1-2.13.16.

Bispecific antibodies and bispecific antigen-binding fragments can also be produced recombinantly, by expression from e.g. a nucleic acid construct encoding polypeptides for the antigen binding molecules, for example as described in Antibody Engineering: Methods and Protocols, Second Edition (Humana Press, 2012), at Chapter 40: Production of Bispecific Antibodies: Diabodies and Tandem scFv (Hornig and Färber-Schwarz), or French, How to make bispecific antibodies, Methods Mol. Med. 2000; 40:333-339.

For example, a DNA construct encoding the light and heavy chain variable domains for the two antigen binding domains (i.e. the light and heavy chain variable domains for the antigen binding domain capable of binding to IL-11, an IL-11 containing complex, or a receptor for IL-11, and the light and heavy chain variable domains for the antigen binding domain capable of binding to another target protein), and including sequences encoding a suitable linker or dimerization domain between the antigen binding domains can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

Decoy Receptors

Peptide or polypeptide based agents capable of binding to IL-11 or IL-11 containing complexes may be based on the IL-11 receptor, e.g. an IL-11 binding fragment of an IL-11 receptor.

In some embodiments, the binding agent may comprise an IL-11-binding fragment of the IL-11Rα chain, and may preferably be soluble and/or exclude one or more, or all, of the transmembrane domain(s). In some embodiments, the binding agent may comprise an IL-11-binding fragment of gp130, and may preferably be soluble and/or exclude one or more, or all, of the transmembrane domain(s). Such molecules may be described as decoy receptors. Binding of such agents may inhibit IL-11 mediated cis and/or trans-signalling by reducing/preventing the ability of IL-11 to bind to receptors for IL-11, e.g. IL-11Rα or gp130, thereby inhibiting downstream signalling.

Curtis et al (Blood 1997 Dec. 1; 90 (11):4403-12) report that a soluble murine IL-11 receptor alpha chain (sIL-11R) was capable of antagonizing the activity of IL-11 when tested on cells expressing the transmembrane IL-11R and gp130. They proposed that the observed IL-11 antagonism by the sIL-11R depends on limiting numbers of gp130 molecules on cells already expressing the transmembrane IL-11R.

The use of soluble decoy receptors as the basis for inhibition of signal transduction and therapeutic intervention has also been reported for other signalling molecule:receptor pairs, e.g. VEGF and the VEGF receptor (De-Chao Yu et al., Molecular Therapy (2012); 20 5, 938-947; Konner and Dupont Clin Colorectal Cancer 2004 October; 4 Suppl 2:S81-5).

As such, in some embodiments a binding agent may be a decoy receptor, e.g. a soluble receptor for IL-11 and/or IL-11 containing complexes. Competition for IL-11 and/or IL-11 containing complexes provided by a decoy receptor has been reported to lead to IL-11 antagonist action (Curtis et al., supra). Decoy IL-11 receptors are also described in WO 2017/103108 A1 and WO 2018/109168 A1, which are hereby incorporated by reference in their entirety.

Decoy IL-11 receptors preferably bind IL-11 and/or IL-11 containing complexes, and thereby make these species unavailable for binding to gp130, IL-11Rα and/or gp130: IL-11Rα receptors. As such, they act as 'decoy' receptors for IL-11 and IL-11 containing complexes, much in the same way that etanercept acts as a decoy receptor for TNFα. IL-11-mediated signalling is reduced as compared to the level of signalling in the absence of the decoy receptor.

Decoy IL-11 receptors preferably bind to IL-11 through one or more cytokine binding modules (CBMs). The CBMs are, or are derived from or homologous to, the CBMs of naturally occurring receptor molecules for IL-11. For example, decoy IL-11 receptors may comprise, or consist of, one or more CBMs which are from, are derived from or homologous to the CBM of gp130 and/or IL-11Rα.

In some embodiments, a decoy IL-11 receptor may comprise, or consist of, an amino acid sequence corresponding to the cytokine binding module of gp130. In some embodiments, a decoy IL-11 receptor may comprise an amino acid sequence corresponding to the cytokine binding module of IL-11Rα. Herein, an amino acid sequence which 'corresponds' to a reference region or sequence of a given peptide/polypeptide has at least 60%, e.g. one of at least 65%, 70%, 75%, 80%, 85%, 90%, 91%, 92%, 93%, 94%, 95%, 96%, 97%, 98% or 99% sequence identity to the amino acid sequence of the reference region/sequence.

In some embodiments a decoy receptor may be able to bind IL-11, e.g. with binding affinity of at least 100 μM or less, optionally one of 10 μM or less, 1 μM or less, 100 nM or less, or about 1 to 100 nM. In some embodiments a decoy receptor may comprise all or part of the IL-11 binding domain and may optionally lack all or part of the transmembrane domains. The decoy receptor may optionally be fused to an immunoglobulin constant region, e.g. IgG Fc region.

Inhibitors

The present invention contemplates the use of inhibitor molecules capable of binding to one or more of IL-11, an IL-11 containing complex, IL-11Rα, gp130, or a complex containing IL-11Rα and/or gp130, and inhibiting IL-11 mediated signalling.

In some embodiments the agent is a peptide- or polypeptide-based binding agent based on IL-11, e.g. mutant, variant or binding fragment of IL-11. Suitable peptide or polypeptide based agents may bind to a receptor for IL-11 (e.g. IL-11Rα, gp130, or a complex containing IL-11Rα and/or gp130) in a manner that does not lead to initiation of signal transduction, or which produces sub-optimal signalling. IL-11 mutants of this kind may act as competitive inhibitors of endogenous IL-11.

For example, W147A is an IL-11 antagonist in which the amino acid 147 is mutated from a tryptophan to an alanine, which destroys the so-called 'site III' of IL-11. This mutant can bind to IL-11Rα, but engagement of the gp130 homodimer fails, resulting in efficient blockade of IL-11 signalling (Underhill-Day et al., 2003; Endocrinology 2003 August; 144(8):3406-14). Lee et al (Am J respire Cell Mol Biol. 2008 December; 39(6):739-746) also report the generation of an IL-11 antagonist mutant (a "mutein") capable of specifically inhibiting the binding of IL-11 to IL-11Rα. IL-11 muteins are also described in WO 2009/052588 A1.

Menkhorst et al (Biology of Reproduction May 1, 2009 vol. 80 no. 5 920-927) describe a PEGylated IL-11 antagonist, PEGIL11A (CSL Limited, Parkvill, Victoria, Australia) which is effective to inhibit IL-11 action in female mice.

Pasqualini et al. Cancer (2015) 121(14):2411-2421 describe a ligand-directed, peptidomimetic drug, bone metastasis-targeting peptidomimetic-11 (BMTP-11) capable of binding to IL-11Rα.

In some embodiments a binding agent capable of binding to a receptor for IL-11 may be provided in the form of a small molecule inhibitor of one of IL-11Rα, gp130, or a complex containing IL-11Rα and/or gp130. In some embodiments a binding agent may be provided in the form of a small molecule inhibitor of IL-11 or an IL-11 containing complex, e.g. IL-11 inhibitor described in Lay et al., Int. J. Oncol. (2012); 41(2): 759-764, which is hereby incorporated by reference in its entirety.

Aptamers

In some embodiments, an agent capable of binding to IL-11/an IL-11 containing complex or a receptor for IL-11 (e.g. IL-11Rα, gp130, or a complex containing IL-11Rα and/or gp130) is an aptamer. Aptamers, also called nucleic acid/peptide ligands, are nucleic acid or peptide molecules characterised by the ability to bind to a target molecule with high specificity and high affinity. Almost every aptamer identified to date is a non-naturally occurring molecule.

Aptamers to a given target (e.g. IL-11, an IL-11 containing complex or a receptor for IL-11) may be identified and/or produced by the method of Systematic Evolution of Ligands by EXponential enrichment (SELEX™), or by developing SOMAmers (slow off-rate modified aptamers) (Gold L et al. (2010) *PLoS ONE* 5(12):e15004). Aptamers and SELEX are described in Tuerk and Gold, *Science* (1990) 249(4968):505-10, and in WO 91/19813. Applying the SELEX and the SOMAmer technology includes for instance adding functional groups that mimic amino acid side chains to expand the aptamer's chemical diversity. As a result high affinity aptamers for a target may be enriched and identified.

Aptamers may be DNA or RNA molecules and may be single stranded or double stranded. The aptamer may comprise chemically modified nucleic acids, for example in which the sugar and/or phosphate and/or base is chemically modified. Such modifications may improve the stability of the aptamer or make the aptamer more resistant to degradation and may include modification at the 2' position of ribose.

Aptamers may be synthesised by methods which are well known to the skilled person. For example, aptamers may be chemically synthesised, e.g. on a solid support. Solid phase synthesis may use phosphoramidite chemistry. Briefly, a solid supported nucleotide is detritylated, then coupled with a suitably activated nucleoside phosphoramidite to form a phosphite triester linkage. Capping may then occur, followed by oxidation of the phosphite triester with an oxidant, typically iodine. The cycle may then be repeated to assemble the aptamer (e.g., see Sinha, N. D.; Biernat, J.; McManus, J.; Köster, H. Nucleic Acids Res. 1984, 12, 4539; and Beaucage, S. L.; Lyer, R. P. (1992). Tetrahedron 48 (12): 2223).

Suitable nucleic acid aptamers may optionally have a minimum length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. Suitable nucleic acid aptamers may optionally have a maximum length of one of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides. Suitable nucleic acid aptamers may optionally have a length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

Aptamers may be peptides selected or engineered to bind specific target molecules. Peptide aptamers and methods for their generation and identification are reviewed in Reverdatto et al., *Curr Top Med Chem.* (2015) 15(12):1082-101, which is hereby incorporated by reference in its entirety. Peptide aptamers may optionally have a minimum length of one of 2, 3, 4, 5, 6, 7, 8, 9 or 10 amino acids. Peptide aptamers may optionally have a maximum length of one of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids. Suitable peptide aptamers may optionally have a length of one of 2-30, 2-25, 2-20, 5-30, 5-25 or 5-20 amino acids.

Aptamers may have $K_D$'s in the nM or pM range, e.g. less than one of 500 nM, 100 nM, 50 nM, 10 nM, 1 nM, 500 μM, 100 μM.

Properties of IL-11 Binding Agents

Agents capable of binding to IL-11/an IL-11 containing complex or a receptor for IL-11 according to the present invention may exhibit one or more of the following properties:

Specific binding to IL-11/IL-11 containing complex or a receptor for IL-11;

Binding to IL-11/IL-11 containing complex, or a receptor for IL-11, with a KD of 10 μM or less, preferably one of ≤5 μM≤1 μM, ≤500 nM, ≤100 nM, ≤10 nM, ≤1 nM or ≤100 μM;

Inhibition of interaction between IL-11 and IL-11Rα;

Inhibition of interaction between IL-11 and gp130;

Inhibition of interaction between IL-11 and IL-11Rα: gp130 receptor complex;

Inhibition of interaction between IL-11:IL-11Rα complex and gp130.

These properties can be determined by analysis of the relevant agent in a suitable assay, which may involve comparison of the performance of the agent to suitable control agents. The skilled person is able to identify an appropriate control conditions for a given assay.

For example, a suitable negative control for the analysis of the ability of a test antibody/antigen-binding fragment to bind to IL-11/an IL-11 containing complex/a receptor for IL-11 may be an antibody/antigen-binding fragment directed against a non-target protein (i.e. an antibody/antigen-binding fragment which is not specific for IL-11/an IL-11 containing complex/a receptor for IL-11). A suitable positive control may be a known, validated (e.g. commercially available) IL-11- or IL-11 receptor-binding antibody. Controls may be of the same isotype as the putative IL-11/IL-11 containing complex/IL-11 receptor-binding antibody/antigen-binding fragment being analysed, and may e.g. have the same constant regions.

In some embodiments, the agent may be capable of binding specifically to IL-11 or an IL-11 containing complex, or a receptor for IL-11 (e.g. IL-11Rα, gp130, or a complex containing IL-11Rα and/or gp130). An agent which specifically binds to a given target molecule preferably binds the target with greater affinity, and/or with greater duration than it binds to other, non-target molecules.

In some embodiments the agent may bind to IL-11 or an IL-11 containing complex with greater affinity than the affinity of binding to one or more other members of the IL-6 cytokine family (e.g. IL-6, leukemia inhibitory factor (LIF), oncostatin M (OSM), cardiotrophin-1 (CT-1), ciliary neurotrophic factor (CNTF) and cardiotrophin-like cytokine (CLC)). In some embodiments the agent may bind to a receptor for IL-11 (e.g. IL-11Rα, gp130, or a complex containing IL-11Rα and/or gp130) with greater affinity than the affinity of binding to one or more other members of the IL-6 receptor family. In some embodiments the agent may bind with greater affinity to IL-11Rα than the affinity of binding to one or more of IL-6Rα, leukemia inhibitory factor receptor (LIFR), oncostatin M receptor (OSMR), ciliary neurotrophic factor receptor alpha (CNTFRα) and cytokine receptor-like factor 1 (CRLF1).

In some embodiments, the extent of binding of a binding agent to an non-target is less than about 10% of the binding of the agent to the target as measured, e.g., by ELISA, SPR, Bio-Layer Interferometry (BLI), MicroScale Thermophoresis (MST), or by a radioimmunoassay (RIA). Alternatively, the binding specificity may be reflected in terms of binding affinity, where the binding agent binds to IL-11, an IL-11 containing complex or a receptor for IL-11 with a $K_D$ that is at least 0.1 order of magnitude (i.e. 0.1×10n, where n is an integer representing the order of magnitude) greater than the $K_D$ towards another, non-target molecule. This may optionally be one of at least 0.2, 0.3, 0.4, 0.5, 0.6, 0.7, 0.8, 0.9, 1.0, 1.5, or 2.0.

Binding affinity for a given binding agent for its target is often described in terms of its dissociation constant ($K_D$). Binding affinity can be measured by methods known in the art, such as by ELISA, Surface Plasmon Resonance (SPR; see e.g. Hearty et al., *Methods Mol Biol*(2012) 907:411-442; or Rich et al., *Anal Biochem.* 2008 Feb. 1; 373(1):112-20), Bio-Layer Interferometry (see e.g. Lad et al., (2015) *J Biomol Screen* 20(4): 498-507; or Concepcion et al., *Comb Chem High Throughput Screen.* 2009 September; 12(8):791-800), MicroScale Thermophoresis (MST) analysis (see e.g. Jerabek-Willemsen et al., *Assay Drug Dev Technol.* 2011 August; 9(4): 342-353), or by a radiolabelled antigen binding assay (RIA).

In some embodiments, the agent is capable of binding to IL-11 or an IL-11 containing complex, or a receptor for IL-11 with a $K_D$ of 50 μM or less, preferably one of ≤10 μM, ≤5 μM, ≤4 μM, ≤3 μM, ≤2 μM, ≤1 μM, ≤500 nM, ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM ≤3 nM, ≤2 nM, ≤1 nM, ≤500 μM, ≤400 μM, ≤300 μM, ≤200 μM, or ≤100 μM.

In some embodiments, the agent binds to IL-11, an IL-11 containing complex or a receptor for IL-11 with an affinity of binding (e.g. as determined by ELISA) of EC50=10,000 ng/ml or less, preferably one of ≤5,000 ng/ml, ≤1000 ng/ml, ≤900 ng/ml, ≤800 ng/ml, ≤700 ng/ml, ≤600 ng/ml, ≤500 ng/ml, ≤400 ng/ml, ≤300 ng/ml, ≤200 ng/ml, ≤100 ng/ml, ≤90 ng/ml, ≤80 ng/ml, ≤70 ng/ml, ≤60 ng/ml, ≤50 ng/ml, ≤40 ng/ml, ≤30 ng/ml, ≤20 ng/ml, ≤15 ng/ml, ≤10 ng/ml, ≤7.5 ng/ml, ≤5 ng/ml, ≤2.5 ng/ml, or ≤1 ng/ml. Such ELISAs can be performed e.g. as described in Antibody Engineering, vol. 1 (2nd Edn), Springer Protocols, Springer (2010), Part V, pp 657-665.

In some embodiments, the agent binds to IL-11 or an IL-11-containing complex in a region which is important for binding to a receptor for the IL-11 or IL-11-containing complex, e.g. gp130 or IL-11Rα, and thereby inhibits interaction between IL-11 or an IL-11-containing complex and a receptor for IL-11, and/or signalling through the receptor. In some embodiments, the agent binds to a receptor for IL-11 in a region which is important for binding to IL-11 or an IL-11-containing complex, and thereby inhibits interaction between IL-11 or an IL-11-containing complex and a receptor for IL-11, and/or signalling through the receptor.

The ability of a given binding agent (e.g. an agent capable of binding IL-11/an IL-11 containing complex or a receptor for IL-11) to inhibit interaction between two proteins can be determined for example by analysis of interaction in the presence of, or following incubation of one or both of the interaction partners with, the binding agent. An example of a suitable assay to determine whether a given binding agent is capable of inhibiting interaction between two interaction partners is a competition ELISA.

A binding agent which is capable of inhibiting a given interaction (e.g. between IL-11 and IL-11Rα, or between IL-11 and gp130, or between IL-11 and IL-11Rα:gp130, or between IL-11:IL-11Rα and gp130) is identified by the observation of a reduction/decrease in the level of interaction between the interaction partners in the presence of—or following incubation of one or both of the interaction partners with—the binding agent, as compared to the level of interaction in the absence of the binding agent (or in the presence of an appropriate control binding agent). Suitable analysis can be performed in vitro, e.g. using recombinant interaction partners or using cells expressing the interaction partners. Cells expressing interaction partners may do so endogenously, or may do so from nucleic acid introduced into the cell. For the purposes of such assays, one or both of the interaction partners and/or the binding agent may be labelled or used in conjunction with a detectable entity for the purposes of detecting and/or measuring the level of interaction. For example, the agent may be labelled with a radioactive atom or a coloured molecule or a fluorescent molecule or a molecule which can be readily detected in any other way. Suitable detectable molecules include fluorescent proteins, luciferase, enzyme substrates, and radiolabels. The binding agent may be directly labelled with a detectable label or it may be indirectly labelled. For example, the binding agent may be unlabelled, and detected by another binding agent which is itself labelled. Alternatively, the second binding agent may have bound to it biotin and binding of labelled streptavidin to the biotin may be used to indirectly label the first binding agent.

Ability of a binding agent to inhibit interaction between two binding partners can also be determined by analysis of the downstream functional consequences of such interaction, e.g. IL-11-mediated signalling. For example, downstream functional consequences of interaction between IL-11 and IL-11Rα:gp130 or between IL-11:IL-11Rα and gp130 may include e.g. a process mediated by IL-11, or gene/protein expression of e.g. collagen or IL-11.

Inhibition of interaction between IL-11 or an IL-11 containing complex and a receptor for IL-11 can be analysed using 3H-thymidine incorporation and/or Ba/F3 cell proliferation assays such as those described in e.g. Curtis et al. *Blood,* 1997, 90(11) and Karpovich et al. *Mol. Hum. Reprod.* 2003 9(2): 75-80. Ba/F3 cells co-express IL-11Rα and gp130.

In some embodiments, the binding agent may be capable of inhibiting interaction between IL-11 and IL-11Rα to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and IL-11Rα in the absence of the binding agent (or in the presence of an appropriate control binding agent). In some embodiments, the binding agent may be capable of inhibiting interaction between IL-11 and IL-11Rα to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and IL-11Rα in the absence of the binding agent (or in the presence of an appropriate control binding agent).

In some embodiments, the binding agent may be capable of inhibiting interaction between IL-11 and gp130 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and gp130 in the absence of the binding agent (or in the presence of an appropriate control binding agent). In some embodiments, the binding agent may be capable of inhibiting interaction between IL-11 and gp130 to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and gp130 in the absence of the binding agent (or in the presence of an appropriate control binding agent).

In some embodiments, the binding agent may be capable of inhibiting interaction between IL-11 and IL-11Rα:gp130 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and IL-11Rα:gp130 in the absence of the binding agent (or in the presence of an appropriate control binding agent). In some embodiments, the binding agent may be capable of inhibiting interaction between IL-11 and IL-11Rα:gp130 to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, 50.45 times, ≤0.4 times, ≤0.35 times, ≤0.3 times, ≤0.25 times, ≤0.2 times, ≤0.15 times, ≤0.1 times the level of interaction between IL-11 and IL-11Rα: gp130 in the absence of the binding agent (or in the presence of an appropriate control binding agent).

In some embodiments, the binding agent may be capable of inhibiting interaction between IL-11:IL-11Rα complex and gp130 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11:IL-11Rα complex and gp130 in the absence of the binding agent (or in the presence of an appropriate control binding agent). In some embodiments, the binding agent is capable of inhibiting interaction between IL-11:IL-11Rα complex and gp130 to less than 1 times, e.g. one of ≤0.99 times, 50.95 times, ≤0.9 times, ≤0.85 times, ≤0.8 times, ≤0.75 times, 50.7 times, ≤0.65 times, 50.6 times, 50.55 times, ≤0.5 times, 50.45 times, ≤0.4 times, ≤0.35 times, ≤0.3 times, ≤0.25 times, ≤0.2 times, ≤0.15 times, 50.1 times the level of interaction between IL-11:IL-11Rα complex and gp130 in the absence of the binding agent.

Agents Capable of Reducing Expression of IL-11 or an IL-11 Receptor

In aspects of the present invention the agent capable of inhibiting IL-11-mediated signalling may be capable of preventing or reducing the expression of one or more of IL-11, IL-11Rα or gp130.

Expression may be gene or protein expression, and may be determined as described herein or by methods in the art that will be well known to a skilled person. Expression may be by a cell/tissue/organ/organ system of a subject.

Suitable agents may be of any kind, but in some embodiments an agent capable of preventing or reducing the expression of one or more of IL-11, IL-11Rα or gp130 may be a small molecule or an oligonucleotide.

An agent capable of preventing or reducing of the expression of one or more of IL-11, IL-11Rα or gp130 may do so e.g. through inhibiting transcription of the gene encoding IL-11, IL-11Rα or gp130, inhibiting posttranscriptional processing of RNA encoding IL-11, IL-11Rα or gp130, reducing the stability of RNA encoding IL-11, IL-11Rα or gp130, promoting degradation of RNA encoding IL-11, IL-11Rα or gp130, inhibiting post-translational processing of IL-11, IL-11Rα or gp130 polypeptide, reducing the stability of IL-11, IL-11Rα or gp130 polypeptide or promoting degradation of IL-11, IL-11Rα or gp130 polypeptide.

Taki et al. *Clin Exp Immunol* (1998) April; 112(1): 133-138 reported a reduction in the expression of IL-11 in rheumatoid synovial cells upon treatment with indomethacin, dexamethasone or interferon-gamma (IFNγ).

The present invention contemplates the use of antisense nucleic acid to prevent/reduce expression of IL-11, IL-11Rα or gp130. In some embodiments, an agent capable of preventing or reducing the expression of IL-11, IL-11Rα or gp130 may cause reduced expression by RNA interference (RNAi).

In some embodiments, the agent may be an inhibitory nucleic acid, such as antisense or small interfering RNA, including but not limited to shRNA or siRNA.

In some embodiments the inhibitory nucleic acid is provided in a vector. For example, in some embodiments the agent may be a lentiviral vector encoding shRNA for one or more of IL-11, IL-11Rα or gp130.

Oligonucleotide molecules, particularly RNA, may be employed to regulate gene expression. These include antisense oligonucleotides, targeted degradation of mRNAs by small interfering RNAs (siRNAs), post transcriptional gene silencing (PTGs), developmentally regulated sequence-specific translational repression of mRNA by micro-RNAs (miRNAs) and targeted transcriptional gene silencing.

An antisense oligonucleotide is an oligonucleotide, preferably single-stranded, that targets and binds, by complementary sequence binding, to a target oligonucleotide, e.g. mRNA. Where the target oligonucleotide is an mRNA, binding of the antisense to the mRNA blocks translation of the mRNA and expression of the gene product. Antisense oligonucleotides may be designed to bind sense genomic nucleic acid and inhibit transcription of a target nucleotide sequence.

In view of the known nucleic acid sequences for IL-11, IL-11Rα and gp130 (e.g. the known mRNA sequences available from GenBank under Accession Nos.: BC012506.1 GI:15341754 (human IL-11), BC134354.1 GI:126632002 (mouse IL-11), AF347935.1 GI:13549072 (rat IL-11), NM_001142784.2 GI:391353394 (human IL-11Rα), NM_001163401.1 GI:254281268 (mouse IL-11Rα), NM_139116.1 GI:20806172 (rat IL-11Rα), NM_001190981.1 GI:300244534 (human gp130), NM_010560.3 GI:225007624 (mouse gp130), NM_001008725.3 GI:300244570 (rat gp130)) oligonucleotides may be designed to repress or silence the expression of IL-11, IL-11Rα or gp130.

Such oligonucleotides may have any length, but may preferably be short, e.g. less than 100 nucleotides, e.g. 10-40 nucleotides, or 20-50 nucleotides, and may comprise a nucleotide sequence having complete- or near-complementarity (e.g. 80%, 85%, 90%, 91%, 92%, 93%, 94%, 95%, 96%, 97%, 98%, 99% or 100% complementarity) to a sequence of nucleotides of corresponding length in the target oligonucleotide, e.g. the IL-11, IL-11Rα or gp130 mRNA. The complementary region of the nucleotide sequence may have any length, but is preferably at least 5, and optionally no more than 50, nucleotides long, e.g. one of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

Repression of expression of IL-11, IL-11Rα or gp130 will preferably result in a decrease in the quantity of IL-11, IL-11Rα or gp130 expressed by a cell/tissue/organ/organ system/subject. For example, in a given cell the repression of IL-11, IL-11Rα or gp130 by administration of a suitable nucleic acid will result in a decrease in the quantity of IL-11, IL-11Rα or gp130 expressed by that cell relative to an untreated cell. Repression may be partial. Preferred degrees of repression are at least 50%, more preferably one of at least 60%, 70%, 80%, 85% or 90%. A level of repression between 90% and 100% is considered a 'silencing' of expression or function.

A role for the RNAi machinery and small RNAs in targeting of heterochromatin complexes and epigenetic gene silencing at specific chromosomal loci has been demonstrated. Double-stranded RNA (dsRNA)-dependent post transcriptional silencing, also known as RNA interference (RNAi), is a phenomenon in which dsRNA complexes can target specific genes of homology for silencing in a short period of time. It acts as a signal to promote degradation of mRNA with sequence identity. A 20-nt siRNA is generally long enough to induce gene-specific silencing, but short enough to evade host response. The decrease in expression of targeted gene products can be extensive with 90% silencing induced by a few molecules of siRNA. RNAi based therapeutics have been progressed into Phase I, II and III clinical trials for a number of indications (*Nature* 2009 Jan. 22; 457(7228):426-433).

In the art, these RNA sequences are termed "short or small interfering RNAs" (siRNAs) or "microRNAs" (miRNAs) depending on their origin. Both types of sequence may be used to down-regulate gene expression by binding to complementary RNAs and either triggering mRNA elimination (RNAi) or arresting mRNA translation into protein. siRNA are derived by processing of long double stranded RNAs and when found in nature are typically of exogenous origin. Micro-interfering RNAs (miRNA) are endogenously encoded small non-coding RNAs, derived by processing of short hairpins. Both siRNA and miRNA can inhibit the translation of mRNAs bearing partially complimentary target sequences without RNA cleavage and degrade mRNAs bearing fully complementary sequences.

siRNA ligands are typically double stranded and, in order to optimise the effectiveness of RNA mediated down-regulation of the function of a target gene, it is preferred that the length of the siRNA molecule is chosen to ensure correct recognition of the siRNA by the RISC complex that mediates the recognition by the siRNA of the mRNA target and so that the siRNA is short enough to reduce a host response.

miRNA ligands are typically single stranded and have regions that are partially complementary enabling the ligands to form a hairpin. miRNAs are RNA genes which are transcribed from DNA, but are not translated into protein. A DNA sequence that codes for a miRNA gene is longer than the miRNA. This DNA sequence includes the miRNA sequence and an approximate reverse complement. When this DNA sequence is transcribed into a single-stranded RNA molecule, the miRNA sequence and its reverse-complement base pair to form a partially double stranded RNA segment. The design of microRNA sequences is discussed in John et al, *PLoS Biology*, 11(2), 1862-1879, 2004.

Typically, the RNA ligands intended to mimic the effects of siRNA or miRNA have between 10 and 40 ribonucleotides (or synthetic analogues thereof), more preferably between 17 and 30 ribonucleotides, more preferably between 19 and 25 ribonucleotides and most preferably between 21 and 23 ribonucleotides. In some embodiments of the invention employing double-stranded siRNA, the molecule may have symmetric 3' overhangs, e.g. of one or two (ribo)nucleotides, typically a UU of dTdT 3' overhang. Based on the disclosure provided herein, the skilled person can readily design suitable siRNA and miRNA sequences, for example using resources such the Ambion siRNA finder. siRNA and miRNA sequences can be synthetically produced and added exogenously to cause gene downregulation or produced using expression systems (e.g. vectors). In a preferred embodiment the siRNA is synthesized synthetically.

Longer double stranded RNAs may be processed in the cell to produce siRNAs (see for example Myers (2003) Nature Biotechnology 21:324-328). The longer dsRNA molecule may have symmetric 3' or 5' overhangs, e.g. of one or two (ribo)nucleotides, or may have blunt ends. The longer dsRNA molecules may be 25 nucleotides or longer. Preferably, the longer dsRNA molecules are between 25 and 30 nucleotides long. More preferably, the longer dsRNA molecules are between 25 and 27 nucleotides long. Most preferably, the longer dsRNA molecules are 27 nucleotides in length. dsRNAs 30 nucleotides or more in length may be expressed using the vector pDECAP (Shinagawa et al., Genes and Dev., 17, 1340-5, 2003).

Another alternative is the expression of a short hairpin RNA molecule (shRNA) in the cell. shRNAs are more stable than synthetic siRNAs. A shRNA consists of short inverted repeats separated by a small loop sequence. One inverted repeat is complimentary to the gene target. In the cell the shRNA is processed by DICER into a siRNA which degrades the target gene mRNA and suppresses expression. In a preferred embodiment the shRNA is produced endogenously (within a cell) by transcription from a vector. shRNAs may be produced within a cell by transfecting the cell with a vector encoding the shRNA sequence under control of a RNA polymerase III promoter such as the human H1 or 7SK promoter or a RNA polymerase II promoter. Alternatively, the shRNA may be synthesised exogenously (in vitro) by transcription from a vector. The shRNA may then be introduced directly into the cell. Preferably, the shRNA molecule comprises a partial sequence of IL-11, IL-11Rα or gp130. Preferably, the shRNA sequence is between 40 and 100 bases in length, more preferably between 40 and 70 bases in length. The stem of the hairpin is preferably between 19 and 30 base pairs in length. The stem may contain G-U pairings to stabilise the hairpin structure.

siRNA molecules, longer dsRNA molecules or miRNA molecules may be made recombinantly by transcription of a nucleic acid sequence, preferably contained within a vector. Preferably, the siRNA molecule, longer dsRNA molecule or miRNA molecule comprises a partial sequence of IL-11, IL-11Rα or gp130.

In one embodiment, the siRNA, longer dsRNA or miRNA is produced endogenously (within a cell) by transcription from a vector. The vector may be introduced into the cell in any of the ways known in the art. Optionally, expression of the RNA sequence can be regulated using a tissue specific (e.g. heart, liver, or kidney specific) promoter. In a further embodiment, the siRNA, longer dsRNA or miRNA is produced exogenously (in vitro) by transcription from a vector.

Suitable vectors may be oligonucleotide vectors configured to express the oligonucleotide agent capable of IL-11, IL-11Rα or gp130 repression. Such vectors may be viral vectors or plasmid vectors. The therapeutic oligonucleotide may be incorporated in the genome of a viral vector and be operably linked to a regulatory sequence, e.g. promoter, which drives its expression. The term "operably linked" may include the situation where a selected nucleotide sequence and regulatory nucleotide sequence are covalently linked in such a way as to place the expression of a nucleotide sequence under the influence or control of the regulatory sequence. Thus a regulatory sequence is operably linked to a selected nucleotide sequence if the regulatory sequence is capable of effecting transcription of a nucleotide sequence which forms part or all of the selected nucleotide sequence.

Viral vectors encoding promoter-expressed siRNA sequences are known in the art and have the benefit of long term expression of the therapeutic oligonucleotide. Examples include lentiviral (*Nature* 2009 Jan. 22; 457 (7228):426-433), adenovirus (Shen et al., *FEBS Lett* 2003 Mar. 27; 539(1-3)111-4) and retroviruses (Barton and Medzhitov *PNAS* Nov. 12, 2002 vol. 99, no. 23 14943-14945).

In other embodiments a vector may be configured to assist delivery of the therapeutic oligonucleotide to the site at which repression of IL-11, IL-11Rα or gp130 expression is required. Such vectors typically involve complexing the oligonucleotide with a positively charged vector (e.g., cationic cell penetrating peptides, cationic polymers and dendrimers, and cationic lipids); conjugating the oligonucleotide with small molecules (e.g., cholesterol, bile acids, and lipids), polymers, antibodies, and RNAs; or encapsulating the oligonucleotide in nanoparticulate formulations (Wang et al., *AAPS J.* 2010 December; 12(4): 492-503).

In one embodiment, a vector may comprise a nucleic acid sequence in both the sense and antisense orientation, such that when expressed as RNA the sense and antisense sections will associate to form a double stranded RNA.

Alternatively, siRNA molecules may be synthesized using standard solid or solution phase synthesis techniques which are known in the art. Linkages between nucleotides may be phosphodiester bonds or alternatives, for example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through-O-or-S—.

Modified nucleotide bases can be used in addition to the naturally occurring bases, and may confer advantageous properties on siRNA molecules containing them.

For example, modified bases may increase the stability of the siRNA molecule, thereby reducing the amount required for silencing. The provision of modified bases may also provide siRNA molecules which are more, or less, stable than unmodified siRNA.

The term 'modified nucleotide base' encompasses nucleotides with a covalently modified base and/or sugar.

For example, modified nucleotides include nucleotides having sugars which are covalently attached to low molecular weight organic groups other than a hydroxyl group at the 3'position and other than a phosphate group at the 5'position. Thus modified nucleotides may also include 2'substituted sugars such as 2'-O-methyl-; 2'-O-alkyl; 2'-O-allyl; 2'-S-alkyl; 2'-S-allyl; 2'-fluoro-; 2'-halo or azido-ribose, carbocyclic sugar analogues, a-anomeric sugars; epimeric sugars such as arabinose, xyloses or lyxoses, pyranose sugars, furanose sugars, and sedoheptulose.

Modified nucleotides are known in the art and include alkylated purines and pyrimidines, acylated purines and pyrimidines, and other heterocycles. These classes of pyrimidines and purines are known in the art and include pseudoisocytosine, N4,N4-ethanocytosine, 8-hydroxy-N6-methyladenine, 4-acetylcytosine,5-(carboxyhydroxylmethyl) uracil, 5 fluorouracil, 5-bromouracil, 5-carboxymethylaminomethyl-2-thiouracil, 5-carboxymethylaminomethyl uracil, dihydrouracil, inosine, N6-isopentyl-adenine, 1-methyladenine, 1-methylpseudouracil, 1-methylguanine, 2,2-dimethylguanine, 2-methyladenine, 2-methylguanine, 3-methylcytosine, 5-methylcytosine, N6-methyladenine, 7-methylguanine, 5-methylaminomethyl uracil, 5-methoxy amino methyl-2-thiouracil, -D-mannosylqueosine, 5-methoxycarbonylmethyluracil, 5methoxyuracil, 2 methyl-thio-N6-isopentenyladenine, uracil-5-oxyacetic acid methyl ester, pseudouracil, 2-thiocytosine, 5-methyl-2 thiouracil, 2-thiouracil, 4-thiouracil, 5methyluracil, N-uracil-5-oxyacetic acid methylester, uracil 5-oxyacetic acid, queosine, 2-thiocytosine, 5-propyluracil, 5-propylcytosine, 5-ethyluracil, 5ethylcytosine, 5-butyluracil, 5-pentyluracil, 5-pentylcytosine, and 2,6,diaminopurine, methylpsuedouracil, 1-methylguanine, 1-methylcytosine.

Methods relating to the use of RNAi to silence genes in *C. elegans, Drosophila*, plants, and mammals are known in the art (Fire A, et al., 1998 *Nature* 391:806-811; Fire, A. *Trends Genet.* 15, 358-363 (1999); Sharp, P. A. *RNA interference* 2001. Genes Dev. 15, 485-490 (2001); Hammond, S. M., et al., *Nature Rev. Genet.* 2, 110-1119 (2001); Tuschl, T. *Chem. Biochem.* 2, 239-245 (2001); Hamilton, A. et al., *Science* 286, 950-952 (1999); Hammond, S. M., et al., *Nature* 404, 293-296 (2000); Zamore, P. D., et al., *Cell* 101, 25-33 (2000); Bernstein, E., et al., *Nature* 409, 363-366 (2001); Elbashir, S. M., et al., *Genes Dev.* 15, 188-200 (2001); WO0129058; WO9932619, and Elbashir S M, et al., 2001 *Nature* 411:494-498).

Accordingly, the invention provides nucleic acid that is capable, when suitably introduced into or expressed within a mammalian, e.g. human, cell that otherwise expresses IL-11, IL-11Rα or gp130, of suppressing IL-11, IL-11Rα or gp130 expression by RNAi.

Nucleic acid sequences for IL-11, IL-11Rα and gp130 (e.g. the known mRNA sequences available from GenBank under Accession Nos.: BC012506.1 GI:15341754 (human IL-11), BC134354.1 GI:126632002 (mouse IL-11), AF347935.1 GI:13549072 (rat IL-11), NM_001142784.2 GI:391353394 (human IL-11Rα), NM_001163401.1 GI:254281268 (mouse IL-11Rα), NM_139116.1 GI:20806172 (rat IL-11Rα), NM_001190981.1 GI:300244534 (human gp130), NM_010560.3 GI:225007624 (mouse gp130), NM_001008725.3 GI:300244570 (rat gp130)) oligonucleotides may be designed to repress or silence the expression of IL-11, IL-11Rα or gp130.

The nucleic acid may have substantial sequence identity to a portion of IL-11, IL-11Rα or gp130 mRNA, e.g. as defined in GenBank accession no. NM_000641.3 GI:391353405 (IL-11), NM_001142784.2 GI:391353394 (IL-11Rα), NM_001190981.1 GI:300244534 (gp130) or the complementary sequence to said mRNA.

The nucleic acid may be a double-stranded siRNA. (As the skilled person will appreciate, and as explained further below, a siRNA molecule may include a short 3' DNA sequence also.)

Alternatively, the nucleic acid may be a DNA (usually double-stranded DNA) which, when transcribed in a mammalian cell, yields an RNA having two complementary portions joined via a spacer, such that the RNA takes the form of a hairpin when the complementary portions hybridise with each other. In a mammalian cell, the hairpin structure may be cleaved from the molecule by the enzyme DICER, to yield two distinct, but hybridised, RNA molecules.

In some preferred embodiments, the nucleic acid is generally targeted to the sequence of one of SEQ ID NOs 4 to 7 (IL-11) or to one of SEQ ID NOs 8 to 11 (IL-11Rα).

Only single-stranded (i.e. non self-hybridised) regions of an mRNA transcript are expected to be suitable targets for RNAi. It is therefore proposed that other sequences very close in the IL-11 or IL-11Rα mRNA transcript to the sequence represented by one of SEQ ID NOs 4 to 7 or 8 to 11 may also be suitable targets for RNAi. Such target sequences are preferably 17-23 nucleotides in length and preferably overlap one of SEQ ID NOs 4 to 7 or 8 to 11 by at least 1, 2, 3, 4, 5, 6, 7, 8, 9, 10, 11, 12, 13, 14, 15, 16, 17, 18 or all 19 nucleotides (at either end of one of SEQ ID NOs 4 to 7 or 8 to 11).

Accordingly, the invention provides nucleic acid that is capable, when suitably introduced into or expressed within a mammalian cell that otherwise expresses IL-11 or IL-11Rα, of suppressing IL-11 or IL-11Rα expression by RNAi, wherein the nucleic acid is generally targeted to the sequence of one of SEQ ID NOs 4 to 7 or 8 to 11.

By "generally targeted" the nucleic acid may target a sequence that overlaps with SEQ ID NOs 4 to 7 or 8 to 11. In particular, the nucleic acid may target a sequence in the mRNA of human IL-11 or IL-11Rα that is slightly longer or shorter than one of SEQ ID NOs 4 to 7 or 8 to 11 (preferably from 17-23 nucleotides in length), but is otherwise identical to one of SEQ ID NOs 4 to 7 or 8 to 11.

It is expected that perfect identity/complementarity between the nucleic acid of the invention and the target sequence, although preferred, is not essential. Accordingly, the nucleic acid of the invention may include a single mismatch compared to the mRNA of IL-11 or IL-11Rα. It is expected, however, that the presence of even a single mismatch is likely to lead to reduced efficiency, so the absence of mismatches is preferred. When present, 3' overhangs may be excluded from the consideration of the number of mismatches.

The term "complementarity" is not limited to conventional base pairing between nucleic acid consisting of naturally occurring ribo- and/or deoxyribonucleotides, but also includes base pairing between mRNA and nucleic acids of the invention that include non-natural nucleotides.

In one embodiment, the nucleic acid (herein referred to as double-stranded siRNA) includes the double-stranded RNA sequences shown in SEQ ID NOs 12 to 15. In another embodiment, the nucleic acid (herein referred to as double-stranded siRNA) includes the double-stranded RNA sequences shown in SEQ ID NOs 16 to 19.

However, it is also expected that slightly shorter or longer sequences directed to the same region of IL-11 or IL-11Rα mRNA will also be effective. In particular, it is expected that double-stranded sequences between 17 and 23 bp in length will also be effective.

The strands that form the double-stranded RNA may have short 3' dinucleotide overhangs, which may be DNA or RNA. The use of a 3' DNA overhang has no effect on siRNA activity compared to a 3' RNA overhang, but reduces the cost of chemical synthesis of the nucleic acid strands (Elbashir et al., 2001c). For this reason, DNA dinucleotides may be preferred.

When present, the dinucleotide overhangs may be symmetrical to each other, though this is not essential. Indeed, the 3' overhang of the sense (upper) strand is irrelevant for RNAi activity, as it does not participate in mRNA recognition and degradation (Elbashir et al., 2001a, 2001b, 2001c).

While RNAi experiments in *Drosophila* show that antisense 3' overhangs may participate in mRNA recognition and targeting (Elbashir et al. 2001c), 3' overhangs do not appear to be necessary for RNAi activity of siRNA in mammalian cells. Incorrect annealing of 3' overhangs is therefore thought to have little effect in mammalian cells (Elbashir et al. 2001c; Czauderna et al. 2003).

Any dinucleotide overhang may therefore be used in the antisense strand of the siRNA. Nevertheless, the dinucleotide is preferably -UU or -UG (or -TT or -TG if the overhang is DNA), more preferably -UU (or -TT). The -UU (or -TT) dinucleotide overhang is most effective and is consistent with (i.e. capable of forming part of) the RNA polymerase III end of transcription signal (the terminator signal is TTTTT). Accordingly, this dinucleotide is most preferred. The dinucleotides AA, CC and GG may also be used, but are less effective and consequently less preferred.

Moreover, the 3' overhangs may be omitted entirely from the siRNA.

The invention also provides single-stranded nucleic acids (herein referred to as single-stranded siRNAs) respectively consisting of a component strand of one of the aforementioned double-stranded nucleic acids, preferably with the 3'-overhangs, but optionally without. The invention also provides kits containing pairs of such single-stranded nucleic acids, which are capable of hybridising with each other in vitro to form the aforementioned double-stranded siRNAs, which may then be introduced into cells.

The invention also provides DNA that, when transcribed in a mammalian cell, yields an RNA (herein also referred to as an shRNA) having two complementary portions which are capable of self-hybridising to produce a double-stranded motif, e.g. including a sequence selected from the group consisting of SEQ ID NOs: 12 to 15 or 16 to 19 or a sequence that differs from any one of the aforementioned sequences by a single base pair substitution.

The complementary portions will generally be joined by a spacer, which has suitable length and sequence to allow the two complementary portions to hybridise with each other. The two complementary (i.e. sense and antisense) portions may be joined 5'-3' in either order. The spacer will typically be a short sequence, of approximately 4-12 nucleotides, preferably 4-9 nucleotides, more preferably 6-9 nucleotides.

Preferably the 5' end of the spacer (immediately 3' of the upstream complementary portion) consists of the nucleotides -UU- or -UG-, again preferably -UU- (though, again, the use of these particular dinucleotides is not essential). A suitable spacer, recommended for use in the pSuper system of OligoEngine (Seattle, Wash., USA) is UUCAAGAGA. In this and other cases, the ends of the spacer may hybridise with each other, e.g. elongating the double-stranded motif beyond the exact sequences of SEQ ID NOs 12 to 15 or 16 to 19 by a small number (e.g. 1 or 2) of base pairs.

Similarly, the transcribed RNA preferably includes a 3' overhang from the downstream complementary portion. Again, this is preferably -UU or -UG, more preferably -UU.

Such shRNA molecules may then be cleaved in the mammalian cell by the enzyme DICER to yield a double-stranded siRNA as described above, in which one or each strand of the hybridised dsRNA includes a 3' overhang.

Techniques for the synthesis of the nucleic acids of the invention are of course well known in the art. The skilled person is well able to construct suitable transcription vectors for the DNA of the invention using well-known techniques and commercially available materials. In particular, the DNA will be associated with control sequences, including a promoter and a transcription termination sequence.

Of particular suitability are the commercially available pSuper and pSuperior systems of OligoEngine (Seattle, Wash., USA). These use a polymerase-III promoter (H1) and a T5 transcription terminator sequence that contributes two U residues at the 3' end of the transcript (which, after DICER processing, provide a 3' UU overhang of one strand of the siRNA).

Another suitable system is described in Shin et al. (RNA, 2009 May; 15(5): 898-910), which uses another polymerase-III promoter (U6).

The double-stranded siRNAs of the invention may be introduced into mammalian cells in vitro or in vivo using known techniques, as described below, to suppress expression of IL-11 or a receptor for IL-11.

Similarly, transcription vectors containing the DNAs of the invention may be introduced into tumour cells in vitro or in vivo using known techniques, as described below, for transient or stable expression of RNA, again to suppress expression of IL-11 or a receptor for IL-11.

Accordingly, the invention also provides a method of suppressing expression of IL-11 or a receptor for IL-11 in a mammalian, e.g. human, cell, the method comprising administering to the cell a double-stranded siRNA of the invention or a transcription vector of the invention.

Similarly, the invention further provides a method of treating hepatotoxicity and/or a disorder, disease or condition associated with hepatotoxicity, the method comprising administering to a subject a double-stranded siRNA of the invention or a transcription vector of the invention.

The invention further provides the double-stranded siRNAs of the invention and the transcription vectors of the invention, for use in a method of treatment, preferably a method of treating hepatotoxicity and/or a disorder, disease or condition associated with hepatotoxicity.

The invention further provides the use of the double-stranded siRNAs of the invention and the transcription vectors of the invention in the preparation of a medicament for the treatment of hepatotoxicity and/or a disorder, disease or condition associated with hepatotoxicity.

The invention further provides a composition comprising a double-stranded siRNA of the invention or a transcription vector of the invention in admixture with one or more pharmaceutically acceptable carriers.

Suitable carriers include lipophilic carriers or vesicles, which may assist in penetration of the cell membrane.

Materials and methods suitable for the administration of siRNA duplexes and DNA vectors of the invention are well known in the art and improved methods are under development, given the potential of RNAi technology.

Generally, many techniques are available for introducing nucleic acids into mammalian cells. The choice of technique will depend on whether the nucleic acid is transferred into cultured cells in vitro or in vivo in the cells of a patient. Techniques suitable for the transfer of nucleic acid into mammalian cells in vitro include the use of liposomes, electroporation, microinjection, cell fusion, DEAE, dextran and calcium phosphate precipitation. In vivo gene transfer techniques include transfection with viral (typically retroviral) vectors and viral coat protein-liposome mediated transfection (Dzau et al. (2003) *Trends in Biotechnology* 11, 205-210).

In particular, suitable techniques for cellular administration of the nucleic acids of the invention both in vitro and in vivo are disclosed in the following articles:

General reviews: Borkhardt, A. 2002. Blocking oncogenes in malignant cells by RNA interference—new hope for a highly specific cancer treatment? Cancer Cell. 2:167-8. Hannon, G. J. 2002. RNA interference. Nature. 418:244-51. McManus, M. T., and P. A. Sharp. 2002. Gene silencing in mammals by small interfering RNAs. Nat Rev Genet. 3:737-47. Scherr, M., M. A. Morgan, and M. Eder. 2003b. Gene silencing mediated by small interfering RNAs in mammalian cells. Curr Med Chem. 10:245-56. Shuey, D. J., D. E. McCallus, and T. Giordano. 2002. RNAi: gene-silencing in therapeutic intervention. Drug Discov Today. 7:1040-6.

Systemic delivery using liposomes: Lewis, D. L., J. E. Hagstrom, A. G. Loomis, J. A. Wolff, and H. Herweijer. 2002. Efficient delivery of siRNA for inhibition of gene expression in postnatal mice. Nat Genet. 32:107-8. Paul, C. P., P. D. Good, I. Winer, and D. R. Engelke. 2002. Effective expression of small interfering RNA in human cells. Nat Biotechnol. 20:505-8. Song, E., S. K. Lee, J. Wang, N. Ince, N. Ouyang, J. Min, J. Chen, P. Shankar, and J. Lieberman. 2003. RNA interference targeting Fas protects mice from fulminant hepatitis. Nat Med. 9:347-51. Sorensen, D. R., M. Leirdal, and M. Sioud. 2003. Gene silencing by systemic delivery of synthetic siRNAs in adult mice. J Mol Biol. 327:761-6.

Virus mediated transfer: Abbas-Terki, T., W. Blanco-Bose, N. Deglon, W. Pralong, and P. Aebischer. 2002. Lentiviral-mediated RNA interference. Hum Gene Ther. 13:2197-201. Barton, G. M., and R. Medzhitov. 2002. Retroviral delivery of small interfering RNA into primary cells. Proc Natl Acad Sci USA. 99:14943-5. Devroe, E., and P. A. Silver. 2002. Retrovirus-delivered siRNA. BMC Biotechnol. 2:15. Lori, F., P. Guallini, L. Galluzzi, and J. Lisziewicz. 2002. Gene therapy approaches to HIV infection. Am J Pharmacogenomics. 2:245-52. Matta, H., B. Hozayev, R. Tomar, P. Chugh, and P. M. Chaudhary. 2003. Use of lentiviral vectors for delivery of small interfering RNA. Cancer Biol Ther. 2:206-10. Qin, X. F., D. S. An, I. S. Chen, and D. Baltimore. 2003. Inhibiting HIV-1 infection in human T cells by lentiviral-mediated delivery of small interfering RNA against CCR5. Proc Natl Acad Sci USA. 100:183-8. Scherr, M., K. Battmer, A. Ganser, and M. Eder. 2003a. Modulation of gene expression by lentiviral-mediated delivery of small interfering RNA. Cell Cycle. 2:251-7. Shen, C., A. K. Buck, X. Liu, M. Winkler, and S. N. Reske. 2003. Gene silencing by adenovirus-delivered siRNA. FEBS Lett. 539:111-4.

Peptide delivery: Morris, M. C., L. Chaloin, F. Heitz, and G. Divita. 2000. Translocating peptides and proteins and their use for gene delivery. Curr Opin Biotechnol. 11:461-6. Simeoni, F., M. C. Morris, F. Heitz, and G. Divita. 2003. Insight into the mechanism of the peptide-based gene delivery system MPG: implications for delivery of siRNA into mammalian cells. Nucleic Acids Res. 31:2717-24. Other technologies that may be suitable for delivery of siRNA to the target cells are based on nanoparticles or nanocapsules such as those described in U.S. Pat. Nos. 6,649,192B and 5,843,509B.

Inhibition of IL-11-Mediated Signalling

In embodiments of the present invention, agents capable of inhibiting the action of IL-11 may possess one or more of the following functional properties:

Inhibition of signalling mediated by IL-11;
Inhibition of signalling mediated by binding of IL-11 to IL-11Rα:gp130 receptor complex;
Inhibition of signalling mediated by binding of IL-11:IL-11Rα complex to gp130 (i.e. IL-11 trans signalling);
Inhibition of a process mediated by IL-11;
Inhibition of gene/protein expression of IL-11, IL-11Rα and/or gp130.

These properties can be determined by analysis of the relevant agent in a suitable assay, which may involve comparison of the performance of the agent to suitable control agents. The skilled person is able to identify an appropriate control conditions for a given assay.

IL-11-mediated signalling and/or processes mediated by IL-11 includes signalling mediated by fragments of IL-11 and polypeptide complexes comprising IL-11 or fragments thereof. IL-11-mediated signalling may be signalling mediated by human IL-11 and/or mouse IL-11. Signalling mediated by IL-11 may occur following binding of IL-11 or an IL-11 containing complex to a receptor to which IL-11 or said complex binds.

In some embodiments, an agent may be capable of inhibiting the biological activity of IL-11 or an IL-11-containing complex.

In some embodiments, the agent is an antagonist of one or more signalling pathways which are activated by signal transduction through receptors comprising IL-11Rα and/or gp130, e.g. IL-11Rα:gp130. In some embodiments, the agent is capable of inhibiting signalling through one or more immune receptor complexes comprising IL-11Rα and/or gp130, e.g. IL-11Rα:gp130. In various aspects of the present invention, an agent provided herein is capable of inhibiting IL-11-mediated cis and/or trans signalling. In some embodiments in accordance with the various aspects of the present invention an agent provided herein is capable of inhibiting IL-11-mediated cis signalling.

In some embodiments, the agent may be capable of inhibiting IL-11-mediated signalling to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of signalling in the absence of the agent (or in the presence of an appropriate control agent). In some embodiments, the agent is capable of reducing IL-11-mediated signalling to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of signalling in the absence of the agent (or in the presence of an appropriate control agent).

In some embodiments, the IL-11-mediated signalling may be signalling mediated by binding of IL-11 to IL-11Rα:gp130 receptor. Such signalling can be analysed e.g. by treating cells expressing IL-11Rα and gp130 with IL-11, or by stimulating IL-11 production in cells which express IL-11Rα and gp130.

The $IC_{50}$ for an agent for inhibition of IL-11-mediated signalling may be determined, e.g. by culturing Ba/F3 cells expressing IL-11Rα and gp130 in the presence of human IL-11 and the agent, and measuring 3H-thymidine incorporation into DNA. In some embodiments, the agent may exhibit an $IC_{50}$ of 10 µg/ml or less, preferably one of <5 µg/ml, ≤4 µg/ml, ≤3.5 µg/ml, ≤3 µg/ml, ≤2 µg/ml, ≤1 µg/ml, ≤0.9 µg/ml, ≤0.8 µg/ml, ≤0.7 µg/ml, ≤0.6 µg/ml, or ≤0.5 µg/ml in such an assay.

In some embodiments, the IL-11-mediated signalling may be signalling mediated by binding of IL-11:IL-11Rα complex to gp130. In some embodiments, the IL-11:IL-11Rα complex may be soluble, e.g. complex of extracellular domain of IL-11Rα and IL-11, or complex of soluble IL-11Rα isoform/fragment and IL-11. In some embodiments, the soluble IL-11Rα is a soluble (secreted) isoform of IL-11Rα, or is the liberated product of proteolytic cleavage of the extracellular domain of cell membrane bound IL-11Rα.

In some embodiments, the IL-11:IL-11Rα complex may be cell-bound, e.g. complex of cell-membrane bound IL-11Rα and IL-11. Signalling mediated by binding of IL-11:IL-11Rα complex to gp130 can be analysed by treating cells expressing gp130 with IL-11:IL-11Rα complex, e.g. recombinant fusion protein comprising IL-11 joined by a peptide linker to the extracellular domain of IL-11Rα, e.g. hyper IL-11. Hyper IL-11 was constructed using fragments of IL-11Rα (amino acid residues 1 to 317 consisting of domain 1 to 3; UniProtKB: Q14626) and IL-11 (amino acid residues 22 to 199 of UniProtKB: P20809) with a 20 amino acid long linker (SEQ ID NO:20). The amino acid sequence for Hyper IL-11 is shown in SEQ ID NO:21.

In some embodiments, the agent may be capable of inhibiting signalling mediated by binding of IL-11:IL-11Rα complex to gp130, and is also capable of inhibiting signalling mediated by binding of IL-11 to IL-11Rα:gp130 receptor.

In some embodiments, the agent may be capable of inhibiting a process mediated by IL-11.

In some embodiments, the agent may be capable of inhibiting gene/protein expression of IL-11 and/or IL-11Rα. Gene and/or protein expression can be measured as described herein or by methods in the art that will be well known to a skilled person.

In some embodiments, the agent may be capable of inhibiting gene/protein expression of IL-11 and/or IL-11Rα to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of expression in the absence of the agent (or in the presence of an appropriate control agent). In some embodiments, the agent is capable of inhibiting gene/protein expression of IL-11 and/or IL-11Rα to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, 50.25 times, ≤0.2 times, ≤0.15 times, ≤0.1 times the level of expression in the absence of the agent (or in the presence of an appropriate control agent).

Treatment/Prevention of Hepatotoxicity

The present invention provides methods and articles (agents and compositions) for the treatment/prevention of hepatotoxicity and disorders, diseases and conditions associated with hepatotoxicity, e.g. as described herein. Also provided are methods for the treatment/prevention of hepatotoxicity and disorders, diseases and conditions associated with hepatotoxicity, e.g. as described herein.

Treatment is achieved by inhibition of IL-11-mediating signalling (i.e. antagonism of IL-11-mediated signalling). That is, the present invention provides for the treatment/prevention of hepatotoxicity and disorders, diseases and conditions associated with hepatotoxicity through inhibition of IL-11 mediated signalling, in e.g. a cell, tissue/organ/organ system/subject. In some embodiments, inhibition of IL-11-mediated signalling in accordance with the present disclosure comprises inhibition of IL-11-mediated signalling in cells of the liver (e.g. hepatocytes).

Provided is an agent capable of inhibiting interleukin 11 (IL-11)-mediated signalling for use in a method of treating or preventing hepatotoxicity and/or a disorder, disease or condition associated with hepatotoxicity.

Also provided is use of an agent capable of inhibiting interleukin 11 (IL-11)-mediated signalling for use in the manufacture of a medicament for use in a method of treating or preventing hepatotoxicity and/or a disorder, disease or condition associated with hepatotoxicity.

Further provided is a method of treating or preventing hepatotoxicity and/or a disorder, disease or condition associated with hepatotoxicity, the method comprising administering to a subject in need of treatment a therapeutically effective amount of an agent capable of inhibiting interleukin 11 (IL-11)-mediated signalling.

In some embodiments, the present invention provides for the treatment/prevention of hepatotoxicity-related pathology in a disease/condition. That is, the present invention provides for the treatment/prevention of a disease/condition in which hepatotoxicity is pathologically implicated. Hepatotoxicity-related pathology is described herein.

It will be clear to the person skilled in the art that the therapeutic and prophylactic utility of the present invention extends to essentially disease/condition which would benefit from a reduction in hepatotoxicity and/or hepatotoxicity-related pathology. The therapeutic and prophylactic utility of the present invention extends to any subject suffering from hepatotoxicity and/or a disorder, disease or condition associated with hepatotoxicity. The therapeutic and prophylactic utility of the present invention also extends to any subject suffering from a disease in which hepatotoxicity-related pathology is present.

In some embodiments, the present invention provides for the treatment/prevention of diseases/conditions that are caused/exacerbated by hepatotoxicity. In some embodiments, there is provided the treatment/prevention of diseases/conditions in a subject in which hepatotoxicity provides a poor prognosis.

In some embodiments, hepatotoxicity and/or a disorder, disease or condition associated with hepatotoxicity to be treated/prevented may be characterised by one or more of the following in an affected organ/tissue/subject e.g. as compared to normal, unaffected organ/tissue/subject (i.e. not affected by hepatotoxicity and/or a disorder, disease or condition associated with hepatotoxicity):

Reduced liver function
Elevated serum concentration of liver enzymes such as alanine aminotransferase (ALT/SGPT), lactate dehydrogenase (LDH), and/or aspartate aminotransferase (AST/SGOT);
An AST/ALT ratio greater than 0.5, greater than 1, or greater than 2;
Elevated levels of blood alkaline phosphatase (ALP);
Elevated levels of gamma glutamyl transpeptidase (GGT);
Elevated serum concentration of cytokines such as TNFα and IL-1β and IFNγ;
Reduced levels of serum albumin;
Increase in total bilirubin (unconjugated (indirect) and conjugated (direct)) e.g. in context with the reference ranges described in VanWagner L B, *JAMA*. 313 (5): 516-517, which is hereby incorporated by reference in its entirety;
Loss of liver mass;
Increased formation of hepatocyte actin stress fibres;
Increased centrilobular necrosis (i.e. necrosis of the centrilobular tissue of the hepatic lobule).

The characteristics recited in the preceding paragraph may also be referred to herein as symptoms/correlates of hepatotoxicity.

Reference levels for laboratory liver tests can be found in e.g. Gowda S et al., Pan Afr Med J. 2009; 3: 17, which is hereby incorporated by reference in its entirety.

In some embodiments, hepatotoxicity and/or a disorder, disease or condition associated with hepatotoxicity to be treated/prevented may be characterised by an increase in one or more of the following in an organ/tissue/subject affected by hepatotoxicity and/or a disorder, disease or condition associated with hepatotoxicity e.g. as compared to normal organ/tissue/subject (i.e. without hepatotoxicity or a disorder, disease or condition associated with hepatotoxicity): expression of one or more of IL-11, and IL-11Rα.

In some embodiments, the present invention provides for the treatment/prevention of hepatotoxicity in the context of a disease/disorder/condition associated with hepatotoxicity e.g. as described herein. In some embodiments, the present invention provides for the treatment/prevention of hepatotoxicity and an underlying disease/disorder/condition associated with hepatotoxicity. For example, inhibition of IL-11-mediated signalling has utility in antagonising the role of IL-11 in chemotherapy-associated hepatotoxicity, as well as antagonising the role of IL-11 in the cancer itself.

Treatment/prevention of hepatotoxicity and/or a disorder, disease or condition associated with hepatotoxicity according to the present invention may be of hepatotoxicity and/or a disorder, disease or condition associated with hepatotoxicity that is associated with an upregulation of IL-11, e.g. an upregulation of IL-11 in cells or tissue in which the symptoms of the disease/disorder/condition manifests or may occur, or upregulation of extracellular IL-11 or IL-11Rα.

The disorder, disease or condition associated with hepatotoxicity may affect any tissue or organ or organ system. In some embodiments, the disease/disorder/condition may affect several tissues/organs/organ systems. In some embodiments, the disease/disorder/condition affects the liver.

In some embodiments, the disorder, disease or condition associated with hepatotoxicity affects one or more of: the cardiovascular system, the digestive system, the excretory system, the respiratory system, the renal system, the reproductive system, the circulatory system, the muscular system, the endocrine system, the exocrine system, the lymphatic system, the immune system, the nervous system, and/or the skeletal system.

In some embodiments, the present invention provides for the treatment/prevention of hepatotoxicity-related pathology in acute liver injury (ALI), acute liver failure, acute liver disease, chronic liver disease, liver damage, hepatitis e.g. viral hepatitis, alcoholic hepatitis, liver ischemia-reperfusion injury (IRI) e.g. 'warm' ischemia-reperfusion (WIR), radiation-induced liver disease (RILD), drug-induced liver injury (DILI), idiosyncratic drug-induced liver injury (IDILI), autoimmune liver injury, cholestatic liver disease, HIV, and cancer.

Treatment may be effective to prevent progression of hepatotoxicity and/or a disorder, disease or condition associated with hepatotoxicity, e.g. to reduce/delay/prevent worsening of, or to reduce/delay/prevent development of, hepatotoxicity and/or a disorder, disease or condition associated with hepatotoxicity. In some embodiments treatment may lead to an improvement, e.g. a reduction in the severity of, and/or a reversal of, the symptoms of hepatotoxicity and/or a disorder, disease or condition associated with hepatotoxicity. In some embodiments treatment may increase survival. In some embodiments treatment is effective to reverse the effects and/or symptoms of hepatotoxicity and/or a disorder, disease or condition associated with hepatotoxicity.

In particular, the inventors have demonstrated that through antagonism of IL-11 mediated signalling it is possible to reduce the symptoms of (i.e. reverse) hepatotoxicity, acute liver failure (ALF) and ALF-associated mortality.

Prevention may refer to prevention of development of hepatotoxicity and/or a disorder, disease or condition associated with hepatotoxicity, and/or prevention of worsening of hepatotoxicity and/or a disorder, disease or condition associated with hepatotoxicity, e.g. prevention of progression of hepatotoxicity and/or a disorder, disease or condition associated with hepatotoxicity to a later or chronic stage.

In some embodiments, the present invention provides for the treatment/prevention of hepatotoxicity in the context of liver transplantation. The antagonist of IL-11 mediated signalling may be administered to a donor subject prior to transplant harvest to minimise damage to the graft. The antagonist of IL-11 mediated signalling may be administered to a donor subject prior to and/or after transplant harvest to treat/prevent hepatotoxicity in the donor subject. The antagonist of IL-11 mediated signalling may be administered to a recipient subject prior to and/or after transplantation to treat/prevent hepatotoxicity in the recipient subject. In some embodiments, treatment may be effective to improve transplant acceptance/reduce transplant rejection.

In accordance with various aspects of the present invention, a method of treating and/or preventing a hepatotoxicity and/or a disorder, disease or condition associated with hepatotoxicity according to the present invention may comprise one or more of the following:

Reducing damage to liver tissue;
Reducing hepatocyte death;
Reducing IL-11-mediated signalling in hepatocytes;
Reducing CASP3 activation in the liver;
Increasing liver function;
Reducing serum ALT level;
Reducing serum AST level;
Increasing liver GSH level;
Reducing acute liver failure;
Reducing fulminant liver failure;
Reducing acute liver failure-associated mortality;
Increasing liver weight;
Regenerating liver tissue;
Reducing ERK and/or JNK activation (i.e. phosphorylation) in the liver;
Reducing pro-inflammatory gene/protein expression in the liver;
Reducing NOX4 gene/protein expression;
Reducing ROS production in the liver;
Increasing gene gene/expression of PCNA, cyclin D1, cyclin D3 and/or cyclin E1 in the liver;
Increasing Rb activation (phosphorylation) in the liver.

The present invention also provide agents capable of inhibiting IL-11-mediated signalling for use to: reduce damage to liver tissue, reduce hepatocyte death, reduce IL-11-mediated signalling in hepatocytes, reduce CASP3 activation in the liver, increase liver function; reduce serum ALT level; reduce serum AST level; increase liver GSH level; reduce acute liver failure; reduce fulminant liver failure; reduce acute liver failure-associated mortality; increase liver weight; regenerate liver tissue; reduce ERK and/or JNK activation (i.e. phosphorylation) in the liver; reduce pro-inflammatory gene/protein expression in the liver; reduce NOX4 gene/protein expression; reduce ROS production in the liver; increase gene/protein expression of PCNA, cyclin D1, cyclin D3 and/or cyclin E1 in the liver; and/or increase Rb activation (phosphorylation) in the liver.

In some embodiments, the present invention provides for the treatment/prevention of acute liver injury (ALI), acute liver failure, acute liver disease, chronic liver disease, liver damage, hepatitis e.g. viral hepatitis, alcoholic hepatitis, liver ischemia-reperfusion injury (IRI) e.g. 'warm' ischemia-reperfusion (WIR), radiation-induced liver disease (RILD), drug-induced liver injury (DILI), idiosyncratic drug-induced liver injury (IDILI), autoimmune liver injury, cholestatic liver disease, HIV, and cancer.

A "cancer" as referred to herein may be any unwanted cell proliferation (or any disease manifesting itself by unwanted cell proliferation), neoplasm or tumour or increased risk of or predisposition to the unwanted cell proliferation, neoplasm or tumour. The cancer may be benign or malignant and may be primary or secondary (metastatic). A neoplasm or tumour may be any abnormal growth or proliferation of cells and may be located in any tissue. Examples of tissues include the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node (including abdominal lymph node, axillary lymph node, cervical lymph node, inguinal lymph node, mediastinal lymph node, pelvic lymph node, periaortic lymph node), lymphoblast, maxilla, mediastinum, mesentery, myometrium, nasopharynx, omentume, oral cavity, ovary, pancreas, parotid gland, peripheral nervous system peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

Cancers may be of a particular type. Examples of types of cancer include astrocytoma, carcinoma (e.g. adenocarcinoma, hepatocellular carcinoma, medullary carcinoma, papillary carcinoma, squamous cell carcinoma), glioma, lymphoma, medulloblastoma, melanoma, myeloma, meningioma, neuroblastoma, sarcoma (e.g. angiosarcoma, chrondrosarcoma, osteosarcoma).

A "cancer" as used herein can comprise any one or more of the following: acute lymphocytic leukemia (ALL), acute myeloid leukemia (AML), adrenocortical cancer, anal cancer, bladder cancer, blood cancer, bone cancer, brain tumor, breast cancer, cancer of the female genital system, cancer of the male genital system, central nervous system lymphoma, cervical cancer, childhood rhabdomyosarcoma, childhood sarcoma, chronic lymphocytic leukemia (CLL), chronic myeloid leukemia (CML), colon and rectal cancer, colon cancer, endometrial cancer, endometrial sarcoma, esophageal cancer, eye cancer, gallbladder cancer, gastric cancer, gastrointestinal tract cancer, hairy cell leukemia, head and neck cancer, hepatocellular cancer, Hodgkin's disease, hypopharyngeal cancer, Kaposi's sarcoma, kidney cancer, laryngeal cancer, leukemia, leukemia, liver cancer, lung cancer, malignant fibrous histiocytoma, malignant thymoma, melanoma, mesothelioma, multiple myeloma, myeloma, nasal cavity and paranasal sinus cancer, nasopharyngeal cancer, nervous system cancer, neuroblastoma, non-Hodgkin's lymphoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, prostate cancer, rectal cancer, respiratory system, retinoblastoma, salivary gland cancer, skin cancer, small intestine cancer, soft tissue sarcoma, stomach cancer, stomach cancer, testicular cancer, thyroid cancer, urinary system cancer, uterine sarcoma, vaginal cancer, vascular system, Waldenstrom's macroglobulinemia and Wilms' tumor.

In particular embodiments the present invention provides for the prevention of hepatotoxicity. In some embodiments inhibition of IL-11 mediated signalling is provided to protect against hepatotoxicity prior to hepatotoxic insult (which may e.g. be physical and/or chemical). Inhibition of IL-11 mediated signalling prior to hepatotoxic insult may reduce one or more symptoms of hepatotoxicity following hepatotoxic insult.

In particular embodiments the present invention provides for the treatment of hepatotoxicity. In some embodiments inhibition of IL-11 mediated signalling is provided to reduce hepatotoxicity following hepatotoxic insult (which may e.g. be physical, perfusion-related and/or chemical). Inhibition of IL-11 mediated signalling following hepatotoxic insult may reduce one or more symptoms of hepatotoxicity.

In further aspects, the present invention provides an agent capable of inhibiting IL-11-mediated signalling for use in combination with other therapeutic/prophylactic intervention for the treatment/prevention of hepatotoxicity (e.g. drug-induced liver injury, e.g. APAP-induced hepatotoxicity). Therapeutic/prophylactic intervention for APAP-overdose (and by extension, APAP-induced hepatotoxicity) is reviewed e.g. in Park et al., BMJ Clin Evid. (2015) 2015: 2101, which is hereby incorporated by reference in its entirety.

Such interventions include treatments/procedures aimed at minimising APAP uptake from the gastrointestinal tract after ingestion. Such treatments/procedures include gastric lavage, administration of an emetic, or administration of activated charcoal.

Further interventions include treatments/procedures aimed at maintaining/increasing glutathione levels. Such treatments/procedures include administration of acetylcysteine (e.g. N-acetylcysteine; NAC), methionine, cysteamine or calcitrol.

Further interventions include treatments/procedures aimed at providing the subject with functional liver tissue, e.g. following, or in anticipation of, liver failure. Such treatments/procedures include liver transplantation.

In another aspect, the present invention provides an agent capable of inhibiting IL-11-mediated signalling for use in a method of treating/preventing APAP-induced hepatotoxicity in a subject, the method comprising administering (i) an agent capable of inhibiting IL-11-mediated signalling and (ii) another (different) agent useful for the treatment/prevention of APAP-induced hepatotoxicity to the subject. Also provided is a combination (e.g. a composition) comprising: an agent capable of inhibiting IL-11-mediated signalling and another (different) agent useful for the treatment/prevention of APAP-induced hepatotoxicity, for use in a method of treating/preventing APAP-induced hepatotoxicity in a subject, the method comprising administering the combination to the subject.

Also provided is the use of an agent capable of inhibiting IL-11-mediated signalling in the manufacture of a medicament for treating/preventing APAP-induced hepatotoxicity in a subject, the method comprising administering (i) an agent capable of inhibiting IL-11-mediated signalling and (ii) another (different) agent useful for the treatment/prevention of APAP-induced hepatotoxicity to the subject. Also provided is the use of a combination (e.g. a composition) comprising: an agent capable of inhibiting IL-11-mediated signalling and another (different) agent useful for the treatment/prevention of APAP-induced hepatotoxicity in the manufacture of a medicament for treating/preventing APAP-induced hepatotoxicity in a subject, the method comprising administering the combination to the subject.

Also provided is a method for treating/preventing APAP-induced hepatotoxicity in a subject, the method comprising administering (i) an agent capable of inhibiting IL-11-mediated signalling and (ii) another (different) agent useful for the treatment/prevention of APAP-induced hepatotoxicity to the subject. Also provided is a method for treating/preventing APAP-induced hepatotoxicity in a subject, the method comprising administering a combination (e.g. a composition) comprising: (i) an agent capable of inhibiting IL-11-mediated signalling, and (ii) another (different) agent useful for the treatment/prevention of APAP-induced hepatotoxicity, to the subject.

In some embodiments in accordance with aspects described herein, an agent useful for the treatment/prevention of APAP-induced hepatotoxicity (other than an agent capable of inhibiting IL-11-mediated signalling) is selected from: acetylcysteine (e.g. NAC), methionine, cysteamine, calcitrol, an emetic or activated charcoal. In particular embodiments, an agent useful for the treatment/prevention of APAP-induced hepatotoxicity (other than an agent capable of inhibiting IL-11-mediated signalling) is acetylcysteine (e.g. NAC).

In some embodiments, aspects employing an agent capable of inhibiting IL-11-mediated signalling and another (different) agent useful for the treatment/prevention of APAP-induced hepatotoxicity provide an improved treatment effect as compared to the effect observed when either agent is used alone (i.e. as a monotherapy). In some embodiments, aspects employing an agent capable of inhibiting IL-11-mediated signalling and another (different) agent useful for the treatment/prevention of APAP-induced hepatotoxicity achieve a synergistic (i.e. super-additive) treatment effect as compared to the effect observed when either agent is used alone.

Administration

Administration of an agent capable of inhibiting IL-11-mediated signalling is preferably in a "therapeutically effective" or "prophylactically effective" amount, this being sufficient to show benefit to the subject.

In some embodiments, the agent may be administered before, in conjunction with, or after hepatotoxic insult (i.e. the cause of the hepatotoxicity). In some embodiments the hepatotoxic insult is chemical, e.g. administration or consumption of a hepatotoxic agent (e.g. a hepatotoxic medicine, e.g. APAP). In some embodiments the cause of the hepatotoxicity is physical, e.g. physical damage to liver cells/tissue, e.g. as a result of surgery, ischemia/reperfusion or physical injury. In some embodiments the hepatotoxic insult is an environmental source of hepatotoxicity.

In some embodiments, the agent capable of inhibiting IL-11-mediated signalling is administered prior to hepatotoxic insult. The agent may be administered in anticipation of hepatotoxic insult. The agent may be administered to prevent/reduce hepatotoxicity resulting from subsequent hepatotoxic insult. In some embodiments the agent is administered within a specified time prior to hepatotoxic insult. In some embodiments the agent is administered within 1 week prior to hepatotoxic insult, e.g. within one of 72 hours, 60 hours, 48 hours, 36 hours, 24 hours, 16 hours, 12 hours, 10 hours, 8 hours, 6 hours, 4 hours, 2 hours, 1 hour or 30 minutes prior to hepatotoxic insult.

In some embodiments, the agent capable of inhibiting IL-11-mediated signalling is administered concurrently with (i.e. at the same time as) hepatotoxic insult. The agent may be administered in to prevent/reduce hepatotoxicity resulting from hepatotoxic insult. In some embodiments the agent is administered at the same time as the hepatotoxic insult, e.g. within 6 hours, 4 hours, 2 hours, 1 hour or 30 minutes before/after hepatotoxic insult.

In some embodiments, the agent capable of inhibiting IL-11-mediated signalling is administered after hepatotoxic insult. The agent may be administered to prevent/reduce hepatotoxicity resulting from prior hepatotoxic insult. The agent may be administered after the onset of hepatotoxicity. The agent may be administered following detection of a correlate of hepatotoxicity. In some embodiments the agent is administered within a specified time after hepatotoxic insult. In some embodiments the agent is administered within 1 month after hepatotoxic insult, e.g. within 3 weeks, 2 weeks, 1 week, 6 days, 5 days, 4 days, 72 hours, 60 hours, 48 hours, 36 hours, 24 hours, 16 hours, 12 hours, 8 hours, 6 hours, 4 hours, 2 hours, 1 hour or 30 minutes after hepatotoxic insult. In some embodiments the agent is administered more than 30 minutes, 1 hour, 2 hours, 4 hours, 6 hours, 8 hours, 12 hours, 16 hours, 24 hours, 36 hours, 48 hours, 60 hours, 72 hours, 4 days, 5 days, 6 days, 1 week, 2 weeks, 3 weeks or 1 month after hepatotoxic insult.

In particular embodiments the hepatotoxic insult is administration/consumption of a hepatotoxic agent. In some embodiments the hepatotoxic agent is a chemical which directly or indirectly cause hepatotoxicity. In some embodiments the hepatotoxic agent is acetaminophen.

In some embodiments the agent is administered within 48 hours, 36 hours, 24 hours, 16 hours, 12 hours, 8 hours, 6 hours, 4 hours, 2 hours, 1 hour or 30 minutes after acetaminophen overdose. In some embodiments the agent is administered more than 30 minutes, 1 hour, 2 hours, 4 hours, 6 hours, 8 hours, 12 hours, 16 hours, 24 hours, 36 hours or 48 hours after acetaminophen overdose.

The actual amount administered, and rate and time-course of administration, will depend on the nature and severity of the hepatotoxicity and the nature of the agent. Prescription of treatment, e.g. decisions on dosage etc., is within the responsibility of general practitioners and other medical doctors, and typically takes account of the disease/condition to be treated, the condition of the individual subject, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Multiple doses of the agent may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

In therapeutic applications, agents capable of inhibiting IL-11-mediated signalling are preferably formulated as a medicament or pharmaceutical together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Suitable carriers, adjuvants, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 2nd edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulations may be prepared for topical, parenteral, systemic, intravenous, intra-arterial, intramuscular, intrathecal, intraocular, intra-conjunctival, subcutaneous, oral or transdermal routes of administration which may include injection. Injectable formulations may comprise the selected agent in a sterile or isotonic medium. The formulation and mode of administration may be selected according to the agent and disease/disorder/condition to be treated.

In some cases, an article (e.g. agent/composition) as described herein is administered for treatment as described herein in conjunction with treatment for a disease/disorder/condition associated with hepatotoxicity. Suitable treatments for a disease/disorder/condition associated with hepatotoxicity are known in the art. A composition may be administered alone or in combination with other treatments, either simultaneously or sequentially dependent upon the disease/disorder/condition to be treated. For example, the article may be administered before, at the same time as, or after the treatment. The article and the treatment may be formulated together, e.g. in a formulation described above, or formulated separately.

In some embodiments in accordance with aspects employing combinations of agents, the agents may be administered simultaneously or sequentially. Simultaneous administration refers to administration as a composition containing both agents (combined preparation), or immediately after each other and optionally via the same route of administration, e.g. to the same artery, vein or other blood vessel. Sequential administration refers to administration of one of agents followed after a given time interval by separate administration of the other agent. It is not required that the two agents are administered by the same route, although this is the case in some embodiments. The time interval may be any time interval.

Detection of IL-11 and Receptors for IL-11

Some aspects and embodiments of the present invention concern detection of expression of IL-11 or a receptor for IL-11 (e.g. IL-11Rα, gp130, or a complex containing IL-11Rα and/or gp130) in a sample obtained from a subject.

In some aspects and embodiments the present invention concerns the upregulation of expression (overexpression) of IL-11 or a receptor for IL-11 (as a protein or oligonucleotide encoding the respective IL-11 or receptor for IL-11) and detection of such upregulation as an indicator of suitability for treatment with an agent capable of inhibiting the action of IL-11 or with an agent capable of preventing or reducing the expression of IL-11 or a receptor for IL-11.

Upregulated expression comprises expression at a level that is greater than would normally be expected for a cell or tissue of a given type. Upregulation may be determined by measuring the level of expression of the relevant factor in a cell or tissue. Comparison may be made between the level of expression in a cell or tissue sample from a subject and a reference level of expression for the relevant factor, e.g. a value or range of values representing a normal level of expression of the relevant factor for the same or corresponding cell or tissue type. In some embodiments reference levels may be determined by detecting expression of IL-11 or a receptor for Il-11 in a control sample, e.g. in corresponding cells or tissue from a healthy subject or from healthy tissue of the same subject. In some embodiments reference levels may be obtained from a standard curve or data set.

Levels of expression may be quantitated for absolute comparison, or relative comparisons may be made.

In some embodiments upregulation of IL-11 or a receptor for IL-11 (e.g. IL-11Rα, gp130, or a complex containing IL-11Rα and/or gp130) may be considered to be present when the level of expression in the test sample is at least 1.1 times that of a reference level. More preferably, the level of expression may be selected from one of at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4 at least 2.5, at least 2.6, at least 2.7, at least 2.8, at least 2.9, at least 3.0, at least 3.5, at least 4.0, at least 5.0, at least 6.0, at least 7.0, at least 8.0, at least 9.0, or at least 10.0 times that of the reference level.

Expression levels may be determined by one of a number of known in vitro assay techniques, such as PCR based assays, in situ hybridisation assays, flow cytometry assays, immunological or immunohistochemical assays.

By way of example suitable techniques involve a method of detecting the level of IL-11 or a receptor for IL-11 in a sample by contacting the sample with an agent capable of binding IL-11 or a receptor for IL-11 and detecting the formation of a complex of the agent and IL-11 or receptor for IL-11. The agent may be any suitable binding molecule, e.g. an antibody, polypeptide, peptide, oligonucleotide, aptamer or small molecule, and may optionally be labelled to permit detection, e.g. visualisation, of the complexes formed. Suitable labels and means for their detection are well known to those in the art and include fluorescent labels (e.g. fluorescein, rhodamine, eosine and NDB, green fluorescent protein (GFP), chelates of rare earths such as europium (Eu), terbium (Tb) and samarium (Sm), tetramethyl rhodamine, Texas Red, 4-methyl umbelliferone, 7-amino-4-methyl coumarin, Cy3, Cy5), isotope markers, radioisotopes (e.g. 32P, 33P, 35S), chemiluminescence labels (e.g. acridinium ester, luminol, isoluminol), enzymes (e.g. peroxidase, alkaline phosphatase, glucose oxidase, beta-galactosidase, luciferase), antibodies, ligands and receptors. Detection techniques are well known to those of skill in the art and can be selected to correspond with the labelling agent. Suitable techniques include PCR amplification of oligonucleotide tags, mass spectrometry, detection of fluorescence or colour, e.g. upon enzymatic conversion of a substrate by a reporter protein, or detection of radioactivity.

Assays may be configured to quantify the amount of IL-11 or receptor for IL-11 in a sample. Quantified amounts of IL-11 or receptor for IL-11 from a test sample may be compared with reference values, and the comparison used to determine whether the test sample contains an amount of IL-11 or receptor for IL-11 that is higher or lower than that of the reference value to a selected degree of statistical significance.

Quantification of detected IL-11 or receptor for IL-11 may be used to determine up- or down-regulation or amplification of genes encoding IL-11 or a receptor for IL-11. In cases where the test sample contains fibrotic cells, such up-regulation, down-regulation or amplification may be compared to a reference value to determine whether any statistically significant difference is present.

A sample obtained from a subject may be of any kind. A biological sample may be taken from any tissue or bodily fluid, e.g. a blood sample, blood-derived sample, serum sample, lymph sample, semen sample, saliva sample, synovial fluid sample. A blood-derived sample may be a selected fraction of a patient's blood, e.g. a selected cell-containing fraction or a plasma or serum fraction. A sample may comprise a tissue sample or biopsy; or cells isolated from a subject. Samples may be collected by known techniques, such as biopsy or needle aspirate. Samples may be stored and/or processed for subsequent determination of IL-11 expression levels.

Samples may be used to determine the upregulation of IL-11 or receptor for IL-11 in the subject from which the sample was taken.

In some preferred embodiments a sample may be a tissue sample, e.g. biopsy, taken from hepatic tissue, cardiac tissue, visceral organ tissue, respiratory system organ tissue, or urinary/renal system tissue. A sample may contain cells.

A subject may be selected for therapy/prophylaxis in accordance with the present invention based on determination that the subject has an upregulated level of expression of IL-11 or of a receptor for IL-11 (e.g. IL-11Rα, gp130, or a complex containing IL-11Rα and/or gp130). Upregulated expression of IL-11 or of a receptor for IL-11 may serve as a marker of hepatotoxicity and/or a disorder, disease or condition associated with hepatotoxicity suitable for treatment with an agent capable of inhibiting IL-11 mediated signalling.

Upregulation may be in a given tissue or in selected cells from a given tissue. A preferred tissue may be hepatic tissue. Upregulation of expression of IL-11 or of a receptor for IL-11 may also be determined in a circulating fluid, e.g. blood, or in a blood derived sample. Upregulation may be of extracellular IL-11 or IL-11Rα. In some embodiments expression may be locally or systemically upregulated.

Following selection, a subject may be administered with an agent capable of inhibiting IL-11 mediated signalling.

Diagnosis and Prognosis

Detection of upregulation of expression of IL-11 or a receptor for IL-11 (e.g. IL-11Rα, gp130, or a complex containing IL-11Rα and/or gp130) may also be used in a method of diagnosing hepatotoxicity and/or a disorder, disease or condition associated with hepatotoxicity, identifying a subject at risk of developing hepatotoxicity and/or a disorder, disease or condition associated with hepatotoxicity, and in methods of prognosing or predicting a subject's response to treatment with an agent capable of inhibiting IL-11 mediated signalling.

"Developing", "development" and other forms of "develop" may refer to the onset of a disorder/disease, or the continuation or progression of a disorder/disease.

In some embodiments a subject may be suspected of having or suffering from hepatotoxicity and/or a disorder, disease or condition associated with hepatotoxicity, e.g. based on the presence of other symptoms indicative of hepatotoxicity and/or a disorder, disease or condition associated with hepatotoxicity in the subject's body or in selected cells/tissues of the subject's body, or be considered at risk of developing hepatotoxicity and/or a disorder, disease or condition associated with hepatotoxicity, e.g. because of genetic predisposition or exposure to environmental conditions, known to be risk factors for hepatotoxicity and/or a disorder, disease or condition associated with hepatotoxicity. Determination of upregulation of expression of IL-11 or a receptor for IL-11 may confirm a diagnosis or suspected diagnosis, or may confirm that the subject is at risk of developing hepatotoxicity and/or a disorder, disease or condition associated with hepatotoxicity. The determination may also diagnose hepatotoxicity and/or a disorder, disease or condition associated with hepatotoxicity or predisposition as one suitable for treatment with an agent capable of inhibiting IL-11-mediated signalling.

As such, a method of providing a prognosis for a subject having, or suspected of having hepatotoxicity and/or a disorder, disease or condition associated with hepatotoxicity may be provided, the method comprising determining whether the expression of IL-11 or a receptor for IL-11 is upregulated in a sample obtained from the subject and, based on the determination, providing a prognosis for treatment of the subject with an agent capable of inhibiting IL-11-mediated signalling.

In some aspects, methods of diagnosis or methods of prognosing or predicting a subject's response to treatment with an agent capable of inhibiting IL-11-mediated signalling may not require determination of the expression of IL-11 or a receptor for IL-11, but may be based on determining genetic factors in the subject that are predictive of upregulation of expression or activity. Such genetic factors may include the determination of genetic mutations, single nucleotide polymorphisms (SNPs) or gene amplification in IL-11, IL-11Rα and/or gp130 which are correlated with and/or predictive of upregulation of expression or activity and/or IL-11 mediated signalling. The use of genetic factors to predict predisposition to a disease state or response to treatment is known in the art, e.g. see Peter Stärkel Gut 2008; 57:440-442; Wright et al., Mol. Cell. Biol. March 2010 vol. 30 no. 6 1411-1420.

Genetic factors may be assayed by methods known to those of ordinary skill in the art, including PCR based assays, e.g. quantitative PCR, competitive PCR. By determining the presence of genetic factors, e.g. in a sample obtained from a subject, a diagnosis may be confirmed, and/or a subject may be classified as being at risk of developing hepatotoxicity and/or a disorder, disease or condition associated with hepatotoxicity, and/or a subject may be identified as being suitable for treatment with an agent capable of inhibiting IL-11 mediated signalling.

Some methods may comprise determination of the presence of one or more SNPs linked to secretion of IL-11 or susceptibility to development of hepatotoxicity and/or a disorder, disease or condition associated with hepatotoxicity. SNPs are usually bi-allelic and therefore can be readily determined using one of a number of conventional assays known to those of skill in the art (e.g. see Anthony J. Brookes. The essence of SNPs. Gene Volume 234, Issue 2, 8 Jul. 1999, 177-186; Fan et al., Highly Parallel SNP Genotyping. Cold Spring Harb Symp Quant Biol 2003. 68: 69-78; Matsuzaki et al., Parallel Genotyping of Over 10,000 SNPs using a one-primer assay on a high-density oligonucleotide array. Genome Res. 2004. 14: 414-425).

The methods may comprise determining which SNP allele is present in a sample obtained from a subject. In some embodiments determining the presence of the minor allele may be associated with increased IL-11 secretion or susceptibility to development of hepatotoxicity and/or a disorder, disease or condition associated with hepatotoxicity.

Accordingly, in one aspect of the present invention a method for screening a subject is provided, the method comprising:

obtaining a nucleic acid sample from the subject;
determining which allele is present in the sample at the polymorphic nucleotide position of one or more of the SNPs listed in FIG. 33, FIG. 34, or FIG. 35 of WO 2017/103108 A1 (incorporated by reference herein), or a SNP in linkage disequilibrium with one of the listed SNPs with an $r^2 \geq 0.8$.

The determining step may comprise determining whether the minor allele is present in the sample at the selected polymorphic nucleotide position. It may comprise determining whether 0, 1 or 2 minor alleles are present.

The screening method may be, or form part of, a method for determining susceptibility of the subject to development of hepatotoxicity and/or a disorder, disease or condition associated with hepatotoxicity, or a method of diagnosis or prognosis as described herein.

The method may further comprise the step of identifying the subject as having susceptibility to, or an increased risk of, developing hepatotoxicity and/or a disorder, disease or condition associated with hepatotoxicity, e.g. if the subject is determined to have a minor allele at the polymorphic nucleotide position. The method may further comprise the step of selecting the subject for treatment with an agent capable of inhibiting IL-11 mediated signalling and/or administering an agent capable of inhibiting IL-11 mediated signalling to the subject in order to provide a treatment for hepatotoxicity and/or a disorder, disease or condition associated with hepatotoxicity in the subject or to prevent development or progression of hepatotoxicity and/or a disorder, disease or condition associated with hepatotoxicity in the subject.

SNPs that may be determined include one or more of the SNPs listed in FIG. 33, FIG. 34, or FIG. 35 of WO 2017/103108 A1 (incorporated by reference herein). SNPs may be selected for determination as having a low P value or FDR (false discovery rate).

In some embodiments the methods described herein may comprise determining the presence or absence of hepatotoxicity-related genetic factors in the subject such as those described in e.g Njoku D B Int J Mol Sci. 2014; 15(4): 6990-7003; Khoury T et al., J Clin Transl Hepatol. 2015; 3(2): 99-108; Ahmad J and Odin J A, Clin Liver Dis. 2017; 21(1):55-72; Clare et al., Curr Hepatol Rep. 2017; 16(3): 258-264 and Urban T J et al., Pharmacogenomics. 2012 May; 13(7): 735-738, which are hereby incorporated by reference in their entirety. In some embodiments the methods described herein may comprise determining whether a subject to be treated is heterozygous or homozygous for Cytochrome P450 (CYP450) isoform CYP2E1. Methods and uses according to the present invention may comprise a step of determining the CYP2E1 genotype of the subject and/or selecting a subject for treatment that is heterozygous or homozygous for CYP2E1.

In some embodiments, a method of diagnosing hepatotoxicity and/or a disorder, disease or condition associated with hepatotoxicity, identifying a subject at risk of developing hepatotoxicity and/or a disorder, disease or condition associated with hepatotoxicity, and methods of prognosing or predicting a subject's response to treatment with an agent capable of inhibiting IL-11 mediated signalling employs an indicator that is not detection of upregulation of expression of IL-11 or a receptor for IL-11, or genetic factors.

In some embodiments, a method of diagnosing hepatotoxicity and/or a disorder, disease or condition associated with hepatotoxicity, identifying a subject at risk of developing hepatotoxicity and/or a disorder, disease or condition associated with hepatotoxicity, and methods of prognosing or predicting a subject's response to treatment with an agent capable of inhibiting IL-11 mediated signalling is based on detecting, measuring and/or identifying one or more of the following indicators:

Elevated serum concentration of liver enzymes such as alanine aminotransferase (ALT/SGPT), lactate dehydrogenase (LDH), and/or aspartate aminotransferase (AST/SGOT);

An AST/ALT ratio greater than 0.5, greater than 1, or greater than 2;

Elevated levels of blood alkaline phosphatase (ALP);

Elevated levels of gamma glutamyl transpeptidase (GGT);

Elevated serum concentration of cytokines such as TNFα and IL-1β and IFNγ;

Reduced levels of serum albumin;

Increase in total bilirubin (unconjugated (indirect) and conjugated (direct)) e.g. in context with the reference ranges described in VanWagner L B, *JAMA*. 313 (5): 516-517, which is hereby incorporated by reference in its entirety;

Loss of liver mass;

Increased formation of hepatocyte actin stress fibres;

Increased centrilobular necrosis (i.e. necrosis of the centrilobular tissue of the hepatic lobule);

Yellowing of the skin and whites of the eyes (jaundice);

Itching;

Abdominal pain in the upper right portion of the abdomen;

Fatigue;

Loss of appetite;

Nausea and vomiting;

Rash;

Weight loss;

Dark or tea-colored urine.

Reference levels for laboratory liver tests can be found in e.g. Gowda S et al., Pan Afr Med J. 2009; 3: 17, which is hereby incorporated by reference in its entirety.

Methods of diagnosis or prognosis may be performed in vitro on a sample obtained from a subject, or following processing of a sample obtained from a subject. Once the sample is collected, the patient is not required to be present for the in vitro method of diagnosis or prognosis to be performed and therefore the method may be one which is not practised on the human or animal body. The sample obtained from a subject may be of any kind, as described herein above.

Other diagnostic or prognostic tests may be used in conjunction with those described here to enhance the accuracy of the diagnosis or prognosis or to confirm a result obtained by using the tests described here.

Subjects

Subjects may be animal or human. Subjects are preferably mammalian, more preferably human. The subject may be a non-human mammal, but is more preferably human. The subject may be male or female. The subject may be a patient. The patient may have hepatotoxicity and/or a disorder, disease or condition associated with hepatotoxicity as described herein. A subject may have been diagnosed with hepatotoxicity and/or a disorder, disease or condition associated with hepatotoxicity requiring treatment, may be suspected of having such hepatotoxicity and/or a disorder, disease or condition associated with hepatotoxicity, or may be at risk from developing hepatotoxicity and/or a disorder, disease or condition associated with hepatotoxicity.

In embodiments according to the present invention the subject is preferably a human subject. In embodiments according to the present invention, a subject may be selected for treatment according to the methods based on characterisation for one or more markers (correlates/symptoms) of hepatotoxicity and/or a disorder, disease or condition associated with hepatotoxicity.

In some embodiments, a subject may selected for treatment in accordance with the present invention based on determination that the subject has experienced, will experience, or is experiencing hepatotoxic insult. In some embodiments, a subject may selected for treatment in accordance with the present invention in advance of anticipated intervention which will or may cause hepatotoxicity (e.g. surgery, e.g. treatment with an agent associated with hepatotoxicity). In some embodiments, a subject may selected for treatment in accordance with the present invention following determination that they have experienced or are experiencing hepatotoxicity or hepatotoxic insult.

Further Methods and Uses Provided

The present invention also provides an agent capable of inhibiting IL-11-mediated signalling for use, or the use of an agent capable of inhibiting IL-11-mediated signalling, in a method of: reducing damage to liver tissue; reducing hepatocyte death; increasing liver function; reducing serum ALT level; increasing liver weight; regenerating liver tissue or reducing ERK and/or JNK activation (i.e. phosphorylation) in the liver.

The present invention also provides use of an agent capable of inhibiting IL-11-mediated signalling for use in the manufacture of a composition for use in a method of: reducing damage to liver tissue; reducing hepatocyte death; increasing liver function; reducing serum ALT level; increasing liver weight; regenerating liver tissue or reducing ERK and/or JNK activation (i.e. phosphorylation) in the liver.

The present invention also provides method of: reducing damage to liver tissue; reducing hepatocyte death; increasing liver function; reducing serum ALT level; increasing liver weight; regenerating liver tissue or reducing ERK and/or JNK activation (i.e. phosphorylation) in the liver, the method comprising administering an effective amount of an agent capable of inhibiting IL-11-mediated signalling to a subject.

Sequence Identity

Pairwise and multiple sequence alignment for the purposes of determining percent identity between two or more amino acid or nucleic acid sequences can be achieved in various ways known to a person of skill in the art, for instance, using publicly available computer software such as ClustalOmega (Söding, J. 2005, *Bioinformatics* 21, 951-960), T-coffee (Notredame et al. 2000, *J. Mol. Biol.* (2000) 302, 205-217), Kalign (Lassmann and Sonnhammer 2005, *BMC Bioinformatics*, 6(298)) and MAFFT (Katoh and Standley 2013, *Molecular Biology and Evolution*, 30(4) 772-780 software. When using such software, the default parameters, e.g. for gap penalty and extension penalty, are preferably used.

| SEQ ID NO: DESCRIPTION | SEQUENCE |
|---|---|
| 1 Human IL-11 (UniProt P20809) | MNCVCRLVLVVLSLWPDTAVAPGPPPGPPRVSPDPRAELDSTVLLTRSLLADTRQLA AQLRDKFPADGDHNLDSLPTLAMSAGALGALQLPGVLTRLRADLLSYLRHVQWLRR AGGSSLKTLEPELGTLQARLDRLLRRLQLLMSRLALPQPPPDPPAPPLAPPSSAWG GIRAAHAILGGLHLTLDWAVRGLLLLKTRL |
| 2 Human gp130 (UniProt P40189-1) | MLTLQTWLVQALFIFLTTESTGELLDPCGYISPESPVVQLHSNFTAVCVLKEKCMDYF HVNANYIVWKTNHFTIPKEQYTIINRTASSVTFTDIASLNIQLTCNILTFGQLEQNVYGIT IISGLPPEKPKNLSCIVNEGKKMRCEWDGGRETHLETNFTLKSEWATHKFADCKAKR DTPTSCTVDYSTVYFVNIEVWVEAENALGKVTSDHINFDPVYKVKPNPPHNLSVINSE ELSSILKLTWTNPSIKSVIILKYNIQYRTKDASTWSQIPEDTASTRSSFTVQDLKPFTE YVFRIRCMKEDGKGYWSDWSEEASGITYEDRPSKAPSFWYKIDPSHTQGYRTVQLV WKTLPPFEANGKILDYEVTLTRWKSHLQNYTVNATKLTVNLTNDRYLATLTVRNLVG KSDAAVLTIPACDFQATHPVMDLKAFPKDNMLWVEWTTPRESVKKYILEWCVLSDK APCITDWQQEDGTVHRTYLRGNLAESKCYLITVTPVYADGPGSPESIKAYLKQAPPS KGPTVRTKKVGKNEAVLEWDQLPVDVQNGFIRNYTIFYRTIIGNETAVNVDSSHTEYT LSSLTSDTLYMVRMAAYTDEGGKDGPEFTFTTPKFAQGEIEAIVVPVCLAFLLTTLLG VLFCFNKRDLIKKHIWPNVPDPSKSHIAQWSPHTPPRHNFNSKDQMYSDGNFTDVS VVEIEANDKKPFPEDLKSLDLFKKEKINTEGHSSGIGGSSCMSSSRPSISSSDENESS QNTSSTVQYSTVVHSGYRHQVPSVQVFSRSESTQPLLDSEERPEDLQLVDHVDGG DGILPRQQYFKQNCSQHESSPDISHFERSKQVSSVNEEDFVRLKQQISDHISQSCGS GQMKMFQEVSAADAFGPGTEGQVERFETVGMEAATDEGMPKSYLPQTVRQGGYM PQ |
| 3 Human IL11RA (UniProt Q14626) | MSSSCSGLSRVLVAVATALVSASSPCPQAWGPPGVQYGQPGRSVKLCCPGVTAGD PVSWFRDGEPKLLQGPDSGLGHELVLAQADSTDEGTYICQTLDGALGGTVTLQLGY PPARPVVSCQAADYENFSCTWSPSQISGLPTRYLTSYRKKTVLGADSQRRSPSTGP WPCPQDPLGAARCVVHGAEFWSQYRINVTEVNPLGASTRLLDVSLQSILRPDPPQG LRVESVPGYPRRLRASWTYPASWPCQPHFLLKFRLQYRPAQHPAWSTVEPAGLEE VITDAVAGLPHAVRVSARDFLDAGTWSTWSPEAWGTPSTGTIPKEIPAWGQLHTQP EVEPQVDSPAPPRPSLQPHPRLLDHRDSVEQVAVLASLGILSFLGLVAGALALGLWL RLRRGGKDGSPKPGFLASVIPVDRRPGAPNL |
| 4 siRNA target IL-11 | CCTTCCAAAGCCAGATCTT |
| 5 siRNA target IL-11 | GCCTGGGCAGGAACATATA |
| 6 siRNA target IL-11 | CCTGGGCAGGAACATATAT |
| 7 siRNA target IL-11 | GGTTCATTATGGCTGTGTT |
| 8 siRNA target IL-11 Rα | GGACCATACCAAAGGAGAT |
| 9 siRNA target IL-11 Rα | GCGTCTTTGGGAATCCTTT |
| 10 siRNA target IL-11 Rα | GCAGGACAGTAGATCCCT |
| 11 siRNA target IL-11 Rα | GCTCAAGGAACGTGTGTAA |
| 12 siRNA to IL-11 (NM_000641.3) | CCUUCCAAAGCCAGAUCUUdTdT-AAGAUCUGGCUUUGGAAGGdTdT |
| 13 siRNA to IL-11 (NM_000641.3) | GCCUGGGCAGGAACAUAUAdTdT-UAUAUGUUCCUGCCCAGGCdTdT |
| 14 siRNA to IL-11 (NM_000641.3) | CCUGGGCAGGAACAUAUAUdTdT-AUAUAUGUUCCUGCCCAGGdTdT |
| 15 siRNA to IL-11 (NM_000641.3) | GGUUCAUUAUGGCUGUGUUdTdT-AACACAGCCAUAAUGAACCdTdT |
| 16 siRNA to IL-11 Rα (U32324.1) | GGACCAUACCAAAGGAGAUdTdT-AUCUCCUUUGGUAUGGUCCdTdT |
| 17 siRNA to IL-11 Rα (U32324.1) | GCGUCUUUGGGAAUCCUUUdTdT-AAAGGAUUCCCAAAGACGCdTdT |
| 18 siRNA to IL-11 Rα (U32324.1) | GCAGGACAGUAGAUCCCUAdTdT-UAGGGAUCUACUGUCCUGCdTdT |
| 19 siRNA to IL-11 Rα (U32324.1) | GCUCAAGGAACGUGUGUAAdTdT-UUACACACGUUCCUUGAGCdTdT |
| 20 20 amino acid linker | GPAGQSGGGGSGGGGSGGGSV |

-continued

Sequences

| SEQ ID NO | DESCRIPTION | SEQUENCE |
|---|---|---|
| 21 | Hyper IL-11 (IL-11RA:IL-11 fusion) | MSSSCSGLSRVLVAVATALVSASSPCPQAWGPPGVQYGQPGRSVKLCCPGVTAGD PVSWFRDGEPKLLQGPDSGLGHELVLAQADSTDEGTYICQTLDGALGGTVTLQLGY PPARPVVSCQAADYENFSCTWSPSQISGLPTRYLTSYRKKTVLGADSQRRSPSTGP WPCPQDPLGAARCVVHGAEFWSQYRINVTEVNPLGASTRLLDVSLQSILRPDPPQG LRVESVPGYPRRLRASWTYPASWPCQPHFLLKFRLQYRPAQHPAWSTVEPAGLEE VITDAVAGLPHAVRVSARDFLDAGTWSTWSPEAWGTPSTGPAGQSGGGGSGGG SGGGSVPGPPPGPPRVSPDPRAELDSTVLLTRSLLADTRQLAAQLRDKFPADGDHN LDSLPTLAMSAGALGALQLPGVLTRLRADLLSYLRHVQWLRRAGGSSLKTLEPELGT LQARLDRLLRRLQLLMSRLALPQPPPDPPAPPLAPPSSAWGGIRAAHAILGGLHLTLD WAVRGLLLLKTRL |
| 22 | Il11 genotyping primer F | GGAGGGAGGGGACGCCAATGACC |
| 23 | Il11 genotyping primer R | TCTGCCTCCCCTGCCTGTTTCTCG |
| 24 | Il11-Luciferase genotyping primer F | AATTCCGTGGTGTTGTCG |
| 25 | Il11-Luciferase genotyping primer R | TCTGCCTCCCCTGCCTGTTTCTG |
| 26 | Il11-EGFP genotyping primer F | GAAATGAGAGCCTAGAGTCCAGAG |
| 27 | Il11-EGFP genotyping primer R | GAGGCTTGGAAGAATGCACAATTA |

The invention includes the combination of the aspects and preferred features described except where such a combination is clearly impermissible or expressly avoided.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value.

Similarly, when values are expressed as approximations, by the use of the antecedent "about," it will be understood that the particular value forms another embodiment. The term "about" in relation to a numerical value is optional and means for example +/−10%.

Methods disclosed herein may be performed, or products may be present, in vitro, ex vivo, or in vivo. The term "in vitro" is intended to encompass experiments with materials, biological substances, cells and/or tissues in laboratory conditions or in culture whereas the term "in vivo" is intended to encompass experiments and procedures with intact multi-cellular organisms. "Ex vivo" refers to something present or taking place outside an organism, e.g. outside the human or animal body, which may be on tissue (e.g. whole organs) or cells taken from the organism.

Where a nucleic acid sequence is disclosed herein, the reverse complement thereof is also expressly contemplated.

For standard molecular biology techniques, see Sambrook, J., Russel, D. W. Molecular Cloning, A Laboratory Manual. 3 ed. 2001, Cold Spring Harbor, New York: Cold Spring Harbor Laboratory Press Aspects and embodiments of the present invention will now be discussed with reference to the accompanying figures. Further aspects and embodiments will be apparent to those skilled in the art. All documents mentioned in this text are incorporated herein by reference. While the invention has been described in conjunction with the exemplary embodiments described below, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

BRIEF DESCRIPTION OF THE FIGURES

Embodiments and experiments illustrating the principles of the invention will now be discussed with reference to the accompanying figures.

Figure 1A:
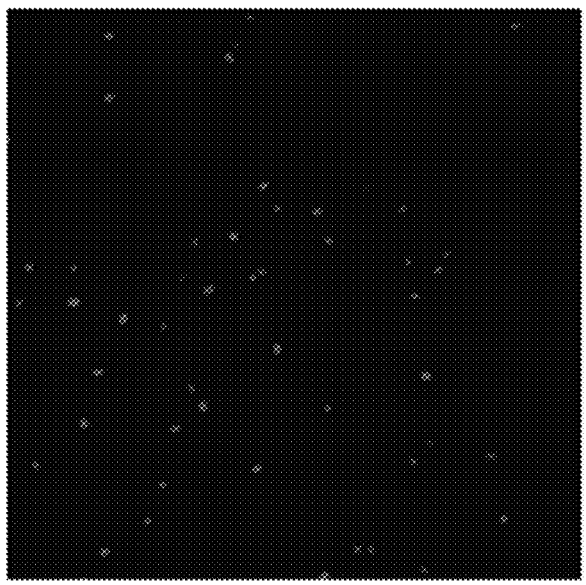
FIGS. 1A to 1C. The effect of IL-11 on hepatocytes. (1A) Primary human hepatocytes express the IL-11Rα receptor. (1B) Dose-dependent increase in ALT levels in the supernatant and increase in number of actin stress fibres in hepatocytes following IL-11 treatment (0.019-10 ng/ml). (1C) $H_2O_2$-induced IL-11 expression.
Figure 1A:
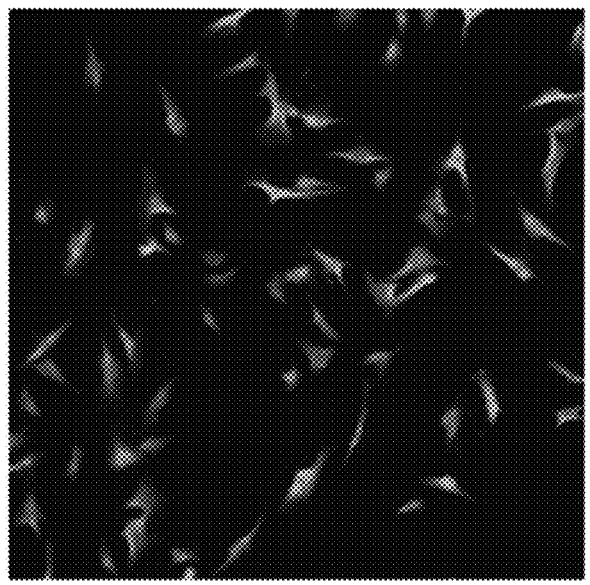

(dark gray points, upper line) and rhIL11 (light gray points, lower line) by competition ELISA. Dose-dependent inhibition effect of rhIL11 on rmIL11-induced (K) ALT secretion and (L) CASP3 activation by mouse hepatocytes. (A, B, K, L) 24 h. (B, K) Data are shown as mean±SD; (E, G) Data are shown as box-and-whisker with median (middle line), 25th-75th percentiles (box), and minimum-maximum values (whiskers). (B, K) Two-tailed, Tukey-corrected Student's t-test; (E) two-tailed Student's t-test; (G) two-tailed Dunnett's test. FC: fold change FIGS. 11A to 11Q. Schematic, images and graphs showing that IL11 causes liver failure through NOX4-dependent glutathione depletion. (A) Schematic of Rosa26$^{fl11/+}$ mice receiving a single intravenous injection of either AAV8-ALB-Null (control) or AAV8-ALB-Cre (Il11-Tg) to specifically induce Il11 overexpression in albumin-expressing cells (hepatocytes); ALB: ALBUMIN. (B) Representative gross anatomy of livers, (C) liver weights, (D) serum ALT levels, (E) representative H&E-stained liver images (scale bars, 100 μm), (F) western blotting of p-ERK, p-JNK, and Cl. CASP3, (G) liver GSH levels, and (H) Nox4 mRNA expression levels in control and Il11-Tg mice 3 weeks after injection. (I) Time course GSH levels, (J) dose-dependent decrease in GSH levels, and (K) western blots showing increased NOX4 protein expression in rhIL11-treated primary human hepatocytes. (L) Western blots of NOX4 in rhIL11 or rmIL11-stimulated mouse hepatocytes. (M) Western blots of NOX4 expression and (N) GSH levels in IgG and X209-treated APAP-stimulated human hepatocytes (20 mM). (O) Dose-dependent inhibition effect of GKT-13781 on GSH levels and CASP3 activation in rhIL11-stimulated human hepatocytes. Effect of siNOX4 on rhIL11-induced (P) ERK, JNK, and CASP3 activation and (Q) GSH depletion levels in human hepatocytes. (1-Q) rhIL11/rmIL11 (10 ng ml$^{-1}$, unless otherwise specified), APAP (20 mM), IgG/X209 (2 μg ml$^{-1}$), siNT (non-targeting siRNA control)/siNOX4 (50 nM). (I-K, M-Q) primary human hepatocytes, (L) primary mouse hepatocytes. (J, L-Q) 24 h. (C-D, G-J, N, O, Q) Data are shown as box-and-whisker with median (middle line), 25th-75th percentiles (box), and minimum-maximum values (whiskers). (C-D, G-H) Two-tailed Student's t-test; (I-J) two-tailed Dunnett's test; (N, O, Q) two-tailed, Tukey-corrected Student's t-test.

FIGS. 12A to 12H. Schematic, images and graphs showing that hepatocyte-specific Il11ra1 deletion protects mice from APAP-induced liver damage. (A) Schematic of induction of APAP injury in Il11ra1$^{loxP/loxP}$ mice. Il11ra1$^{loxP/loxP}$ mice were intravenously injected with either AAV8-ALB-Null (control) or AAV8-ALB-Cre (CKO) to specifically delete Il11ra1 in hepatocytes. Overnight-fasted control and CKO mice were injected with APAP (400 mg kg$^{-1}$) or saline, 3 weeks following virus administration. ALB: Albumin. (B) Representative liver gross anatomy and (C) H&E images (scale bars, 500 μm) from saline and APAP-injected control and CKO mice. (D) Serum ALT levels, (E) serum AST levels, (F) liver GSH levels, (G) western blots of IL11Rα, p-ERK, ERK, p-JNK, JNK, Cl. CASP3, CASP3 and GAPDH, and (H) relative liver mRNA expression levels of proinflammatory genes. (D-F, H) Data are shown as box-and-whisker with median (middle line), 25th-75th percentiles (box), and minimum-maximum values (whiskers); Sidak-corrected Student's t-test.

FIGS. 13A to 13L. Schematics, images and graphs showing the treatment of APAP-induced liver damage with anti-IL11Rα antibody and/or NAC. (A) Schematic of anti-IL11Rα (X209) preventive dosing in APAP OD mice; X209 or IgG (10 mg kg$^{-1}$) was administered at the beginning of fasting period, 16 h prior to APAP (400 mg kg$^{-1}$) injection; control mice received saline injection. (B) Serum ALT levels, (C) representative H&E images (scale bars, 500 μm), and hepatic GSH levels for the experiments shown in FIG. 13A. (E) Schematic of anti-IL11Rα (X209) dose finding experiments; X209 (2.5-10 mg kg$^{-1}$) or IgG (10 mg kg-1) was administered to mice 3 h following APAP injection. (F) Serum ALT levels (the values of saline are the same as those used in 5B), (G) hepatic GSH levels, and (H) Western blots of hepatic ERK and JNK activation from experiments shown in FIG. 13E. (I) Schematic showing therapeutic comparison of X209 and N-acetyl-cysteine (NAC, 500 mg kg$^{-1}$) alone or in combination with X209 (5 mg kg$^{-1}$). Overnight-fasted mice were treated with IgG, NAC, or NAC+X209 3 h post APAP injection for data shown in (J-L). Effect of NAC, NAC+X209 treatment on (H) serum ALT levels, on (I) hepatic GSH levels, and on (J) p-ERK, p-JNK, and Cl. CASP3 expression levels (B, C, F, G, J, K) Data are shown as box-and-whisker with median (middle line), 25th-75th percentiles (box), and minimum-maximum values (whiskers); two-tailed, Tukey-corrected Student's t-test.

Figure 13A:
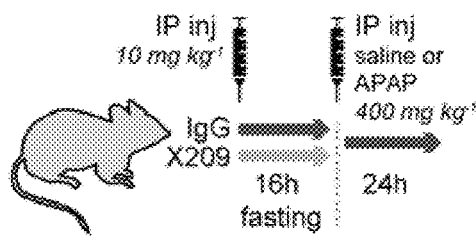
Figure 13B:
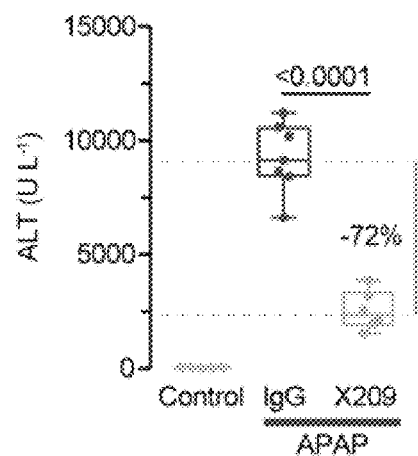
Figure 13C:
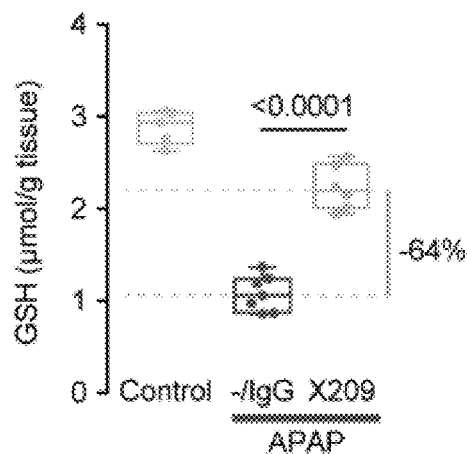
Figure 13D:
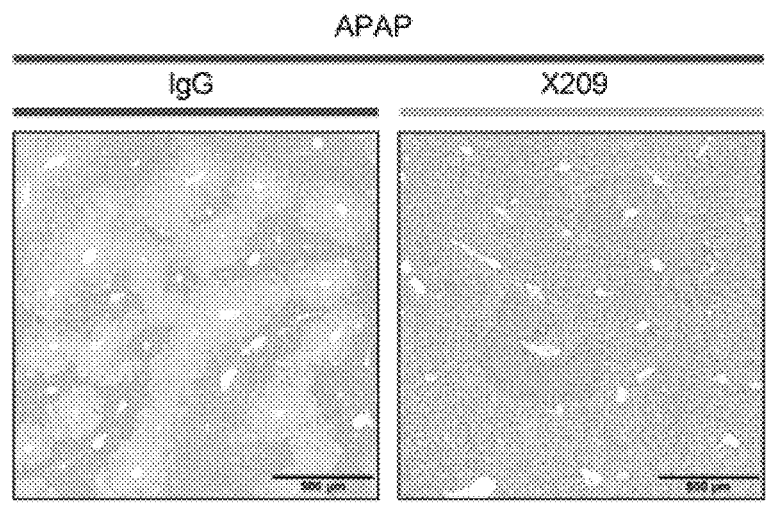
Figure 13E:
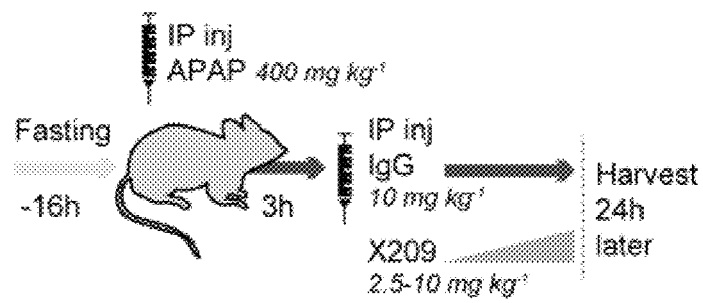
Figure 13F:
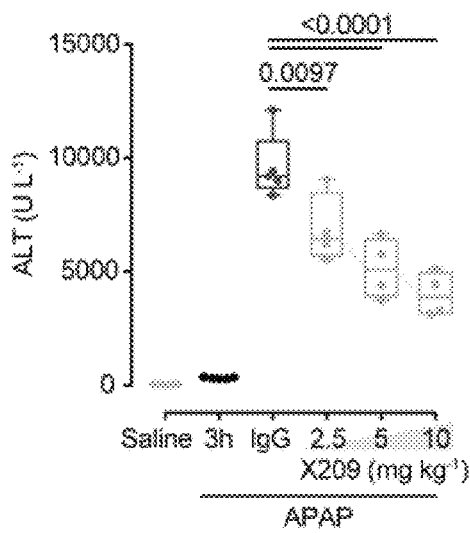
Figure 13G:
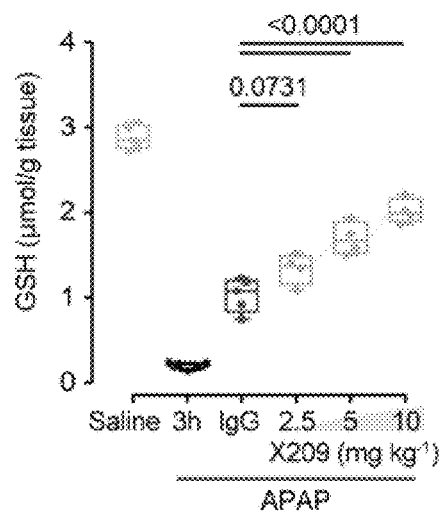
Figure 13H:
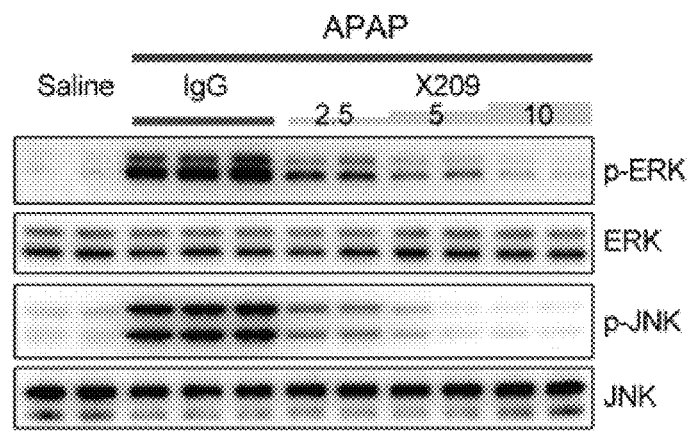
Figure 14A:
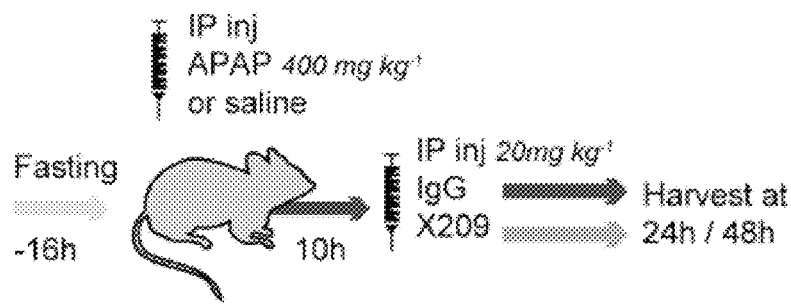
Figure 14B:
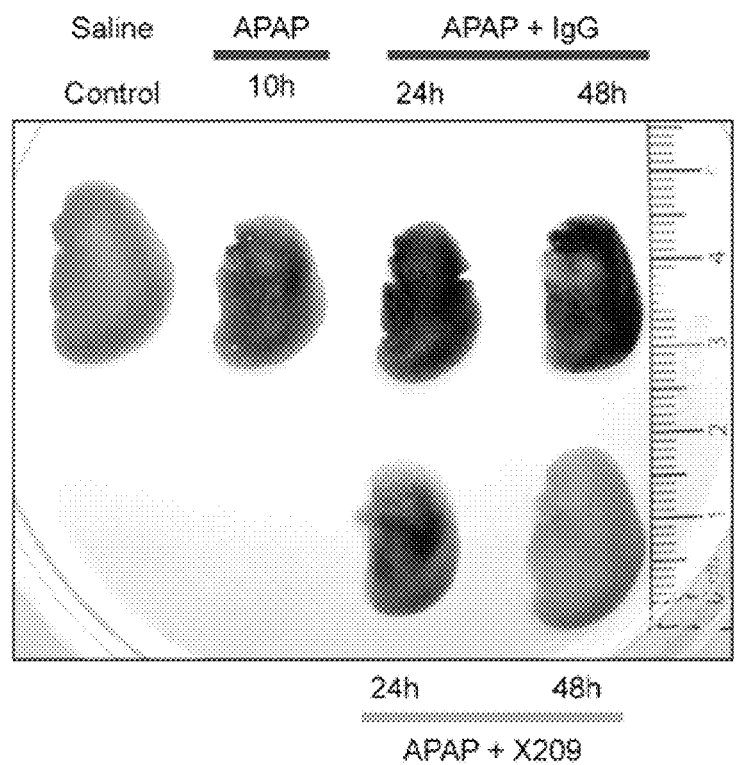
Figure 14C:
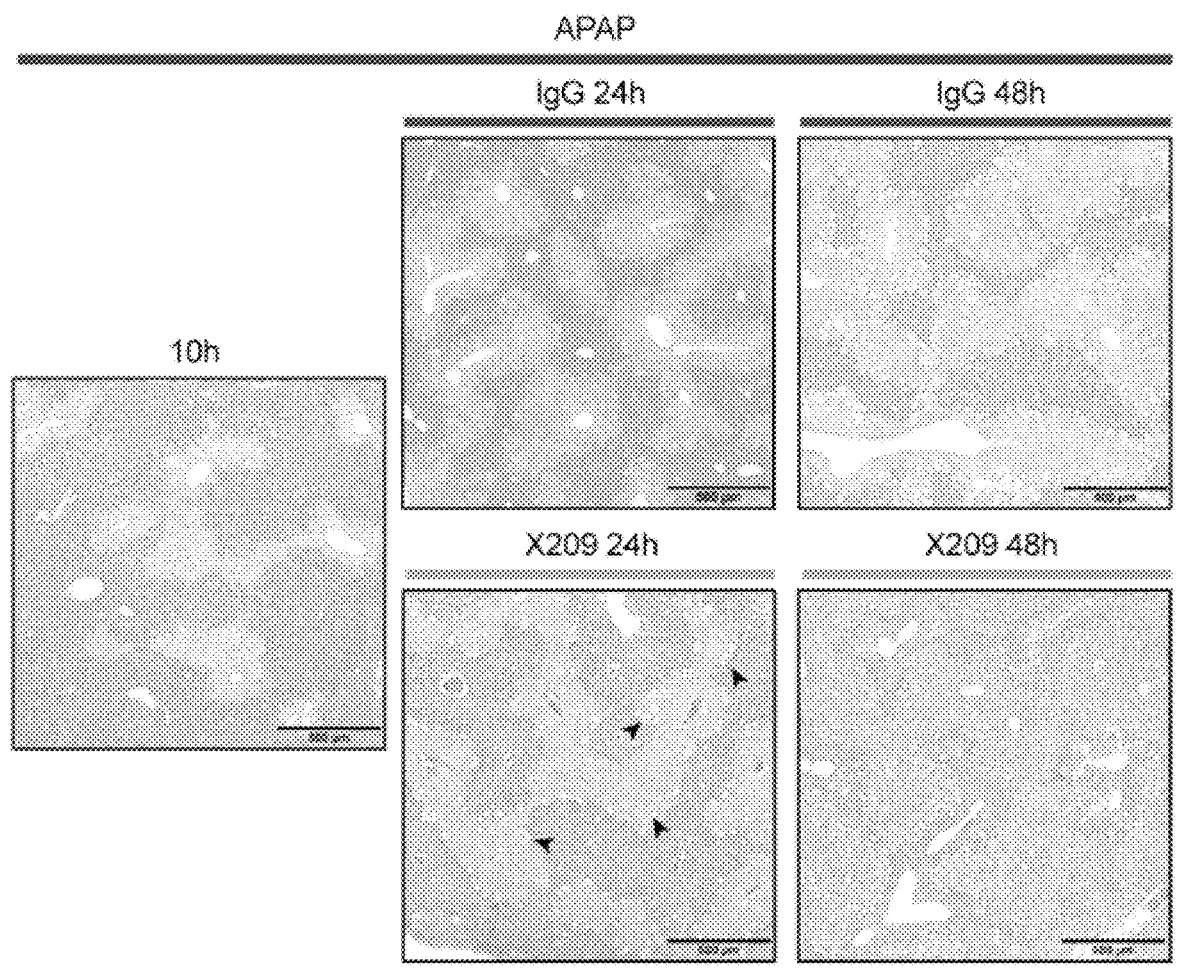
Figure 14D:
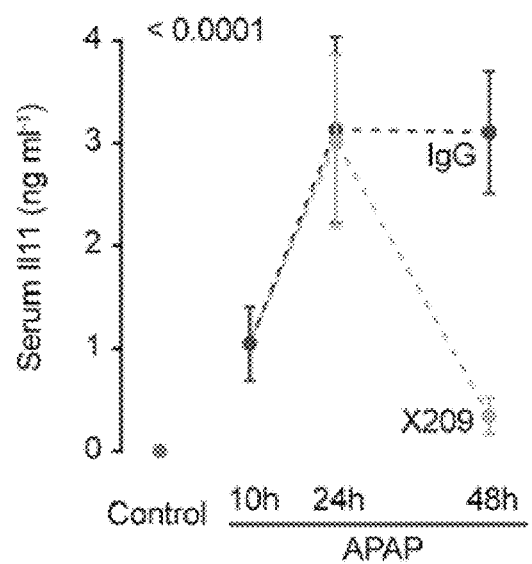
Figure 14E:
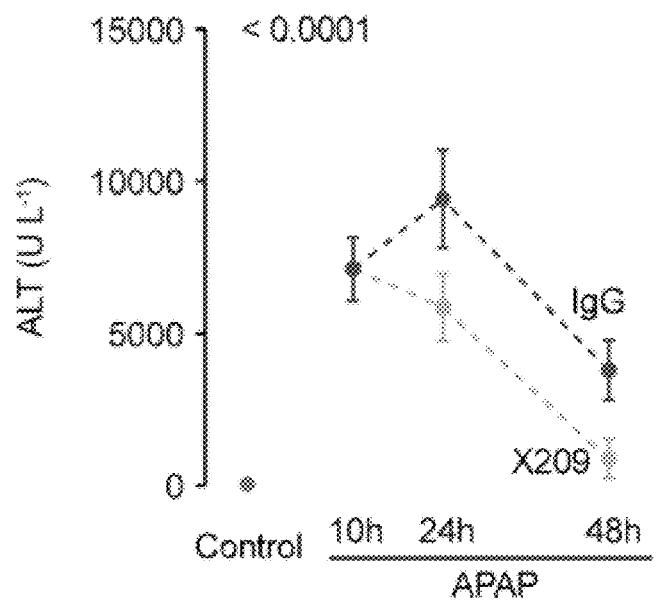

FIGS. 14A to 14K. Schematics, images and graphs showing hepatic regeneration and reversal of liver failure with late anti-IL11Rα therapy. (A) Schematic showing late therapeutic dosing of APAP-injured mice. Overnight fasted mice were administered IgG/X209 (20 mg kg$^{-1}$) 10 h post-APAP. (B) Representative liver gross anatomy, (C) representative H&E-stained liver images (scale bars, 500 μm), (D) serum Il11 levels, (E) serum ALT levels, (F) western blots of p-ERK, p-JNK, Cl. CASP3, PCNA, Cyclin D1/D3/E1, and p-RB, (G) representative EdU-stained liver images (scale bars, 100 μm) from APAP mice receiving a late X209 dose (10 h post APAP) as shown in FIG. 14A. (H) Western blots showing PCNA, Cyclin D1/D3/E1, p-RB protein expression levels in livers from APAP mice treated with either NAC or NAC+X209 (FIG. 13G). (I) Schematic of mice receiving X209 (20 mg kg$^{-1}$) treatment 10 h following a lethal APAP OD (550 mg kg$^{-1}$) for data shown in (J-K). (J) Survival curves of mice treated with either IgG or X209 10 h post lethal APAP OD. (K) Gross liver anatomy of control (D8), IgG (24 h) and X209-treated mice (D8). (D, E) Data are mean±SD; 2-way ANOVA; (J) Gehan-Breslow-Wilcoxon test.

Figure 15:
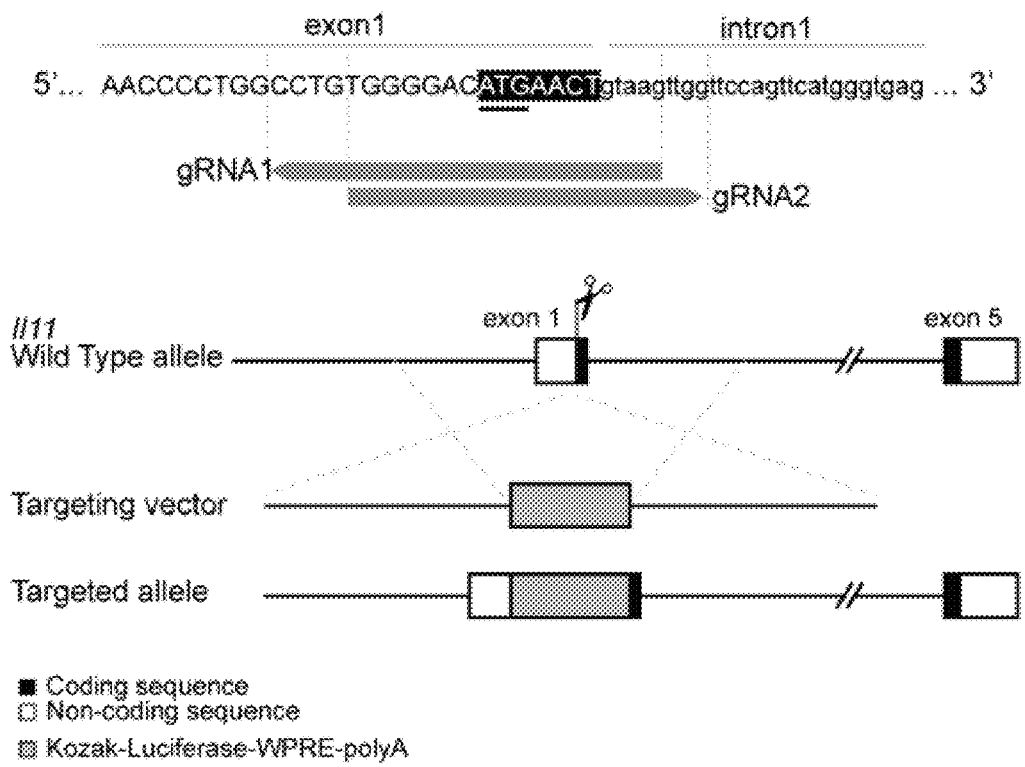

FIG. 15. Schematic relating to the generation of Il11-Luciferase knock-in mice. Knock-in strategy for Kozak-Luciferase-WPRE-polyA into exon 1 of Il11 locus using CRISPR/Cas9. Woodchuck Hepatitis Virus (WHP) Posttranscriptional Regulatory Element (WPRE).

Figure 16:
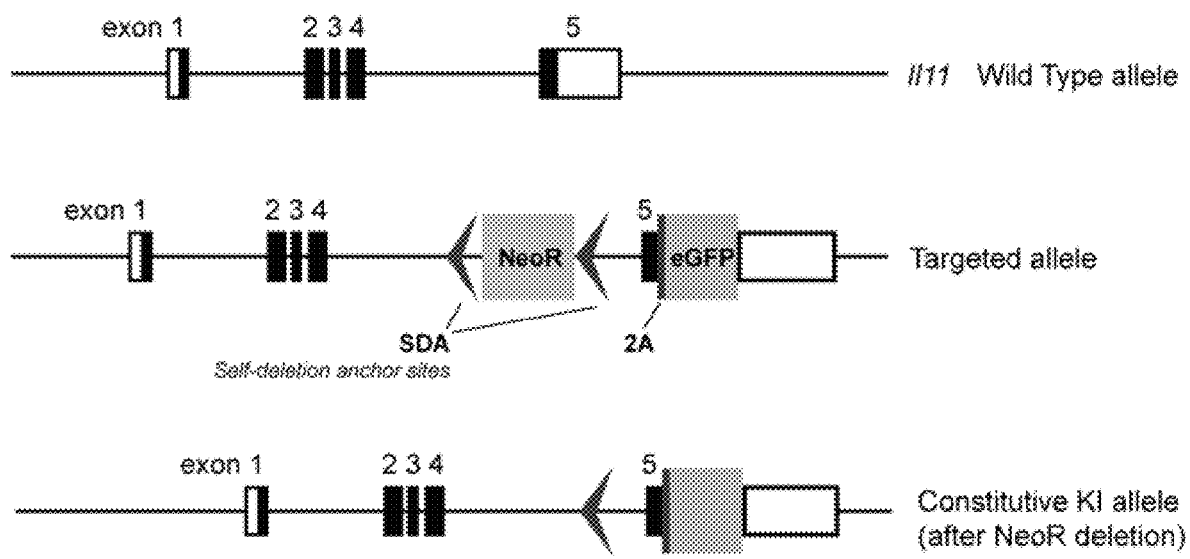

FIG. 16. Schematic relating to the generation of Il11-EGFP knock-in mice. Knock-in strategy for 2A-EGFP cassette into exon 5 of Il11 gene, replacing the TGA stop codon resulting in the translation of Il11-2A-EGFP protein. The 2A linker is cleaved resulting in retention of EGFP in cells that express and secrete Il11.

Figure 17A:
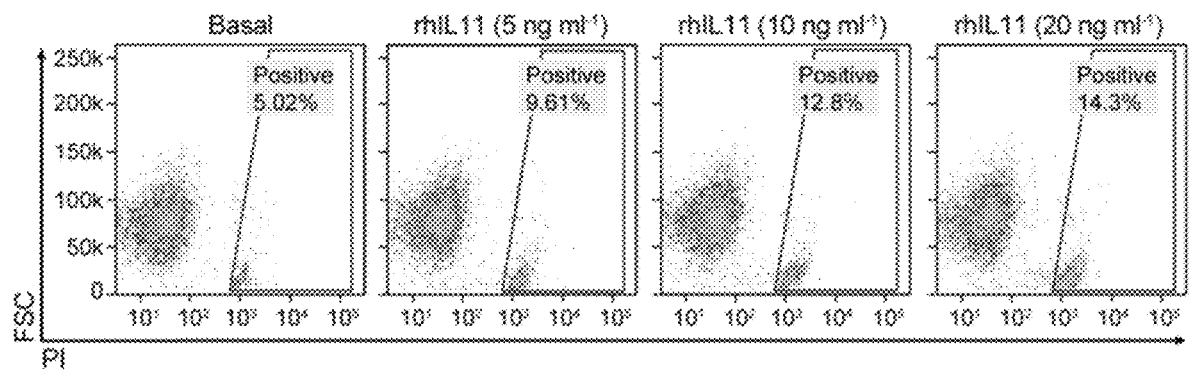
Figure 17B:
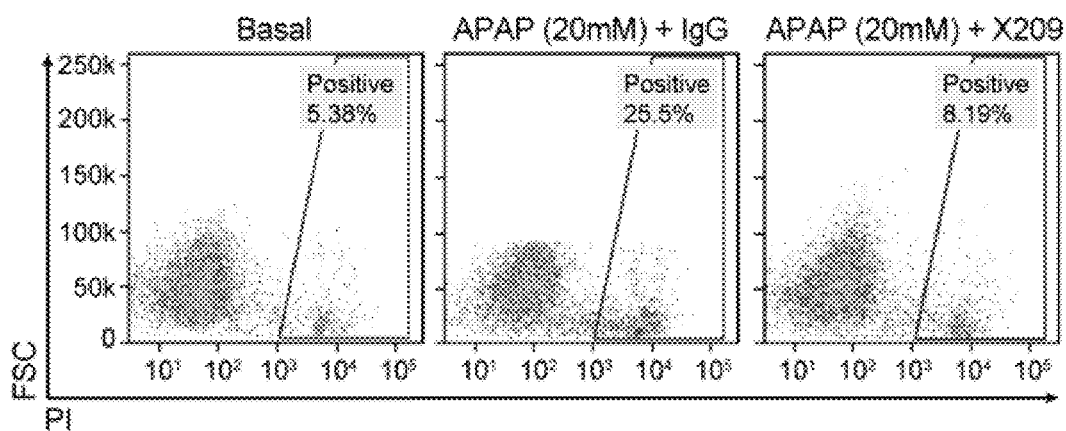

FIGS. 17A and 17B. Scatterplots showing the hepatotoxic effects of IL11. Representative flow cytometry forward scatter (FSC) plots of Propidium Iodide (PI) staining of primary human hepatocytes stimulated with (A) increasing dose of rhIL11 and (B) APAP in the presence of either IgG or X209 (2 μg ml$^{-1}$).

FIGS. 18A to 18F. Images graphs and table showing the species-specific effects of human or mouse IL11 on human or mouse hepatocytes. (A) Effect of recombinant human IL11 (rhIL11, 10 ng ml$^{-1}$) or recombinant mouse IL11 (rmIL11, 10 ng ml$^{-1}$) on ERK, JNK and CASP3 activation status in human hepatocytes. (B) ALT levels in the supernatant of human hepatocytes stimulated with either rhIL11

(10 ng ml-1) or increasing dose of rmIL11 (1, 5, 10, 15 and 20 ng ml$^{-1}$). (C) Effect of rhIL11 and rmIL11 treatment alone (FIG. 10C) or (D) with APAP administration (FIG. 10F) on serum AST levels in the mice; for each time period (6 h, 24 h), boxes from left to right correspond to saline, rmIL11 and rhIL11 treatments. (E) Binding affinity and kinetic constants for mouse IL11Rα interaction with either mouse IL11 or human IL11 and for human IL11Rα interaction with human IL11. (F) Western blots showing dose-dependent inhibition effect of rhIL11 on p-ERK, ERK, p-JNK, JNK in mouse hepatocytes stimulated with rmIL11 (10 ng ml$^{-1}$, 24 h), (B) Data are shown as mean±SD; (C,D) Data are shown as box-and-whisker with median (middle line), 25th-75th percentiles (box), and minimum-maximum values (whiskers). (B) Two-tailed, Tukey-corrected Student's t-test; (C) two-tailed Student's t-test; (D) two-tailed Dunnett's test. FC: fold change.

Figure 11A:
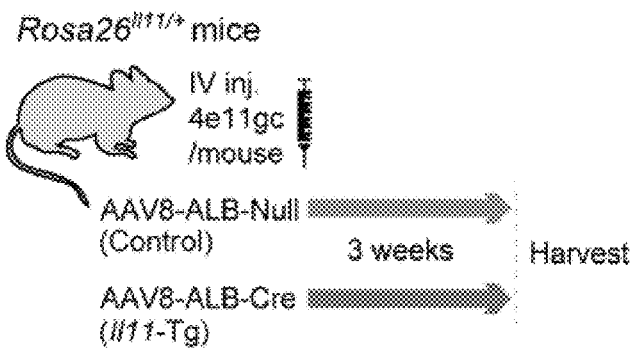
Figure 11B:
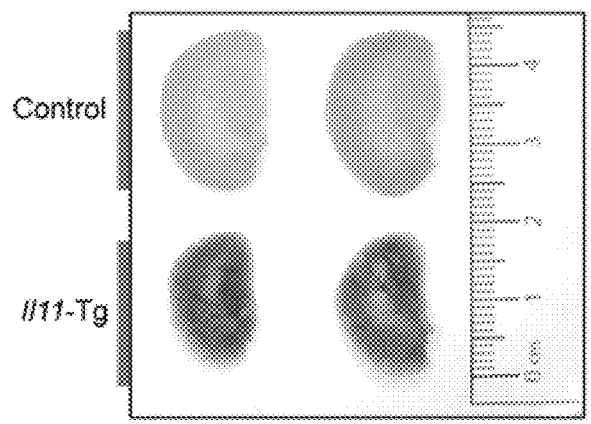
Figure 11C:
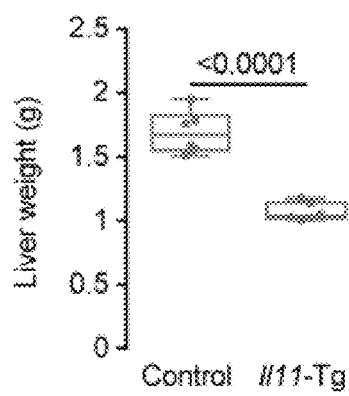
Figure 11D:
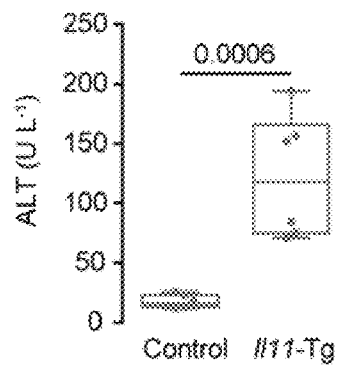

FIGS. 19A to 19E. Graphs and image showing that hepatocyte-specific Il11 overexpression causes liver necro-inflammation. (A) Weight of heart, lung, kidney, (B) serum AST levels, (C) quantification of portal vein diameter, (D) Western blots of total ERK, total JNK, and CASP3, and (E) relative liver mRNA expression levels of pro-inflammatory markers of control and Il11-Tg mice (FIG. 11A). (A-C, E) Data are shown as box-and-whisker with median (middle line), 25th-75th percentiles (box), and minimum-maximum values (whiskers); two-tailed Student's t-test.

Figure 10A:
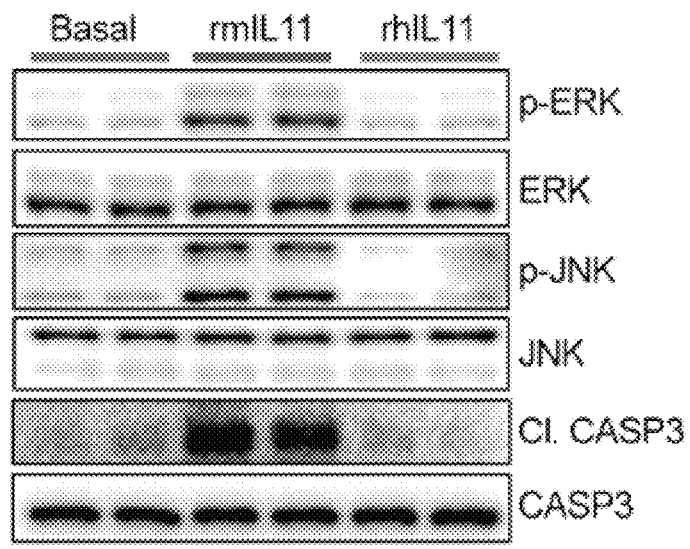
FIGS. 10A to 10L. Images, graphs and schematics showing that recombinant human IL11 inhibits mouse IL11 effects in mouse hepatocytes. (A) Effect of recombinant human IL11 (rhIL11, 10 ng $ml^{-1}$) or recombinant mouse IL11 (rmIL11, 10 ng $ml^{-1}$) on ERK, JNK and CASP3 activation status in mouse hepatocytes. (B) ALT levels in mouse hepatocyte supernatant following stimulation by rmIL11 (10 ng $ml^{-1}$) or by increasing doses of rhIL11 (1, 5, 10, 15 and 20 ng $ml^{-1}$). (C) Schematic of mice receiving a single subcutaneous injection of either saline, rhIL11, or rmIl11 (500 μg $kg^{-1}$). (D) Western blot analysis of hepatic p-ERK, p-JNK, and Cl. CASP3 and (E) serum ALT levels of the experiments shown in FIG. 10C; for each time period (6 h, 24 h), boxes from left to right correspond to saline, rmIL11 and rhIL11 treatments (F) Schematic of mice receiving a subcutaneous injection of either saline, rhIL11, or rmIL11 2 h prior to APAP OD. Effect of rhIL11 or rmIL11 injection prior to APAP OD on (G) serum ALT measurement at 6 and 24 h (for each time period (6 h, 24 h), boxes from left to right correspond to saline, rmIL11 and rhIL11 treatments) and on (H) hepatic ERK and JNK activation at 24 h following APAP administration. (I) Sensorgrams showing binding of mIL11Rα 1 to immobilized rhIL11 (left) and rmIL11 (middle), and binding of hIL11Rα to rhIL11 (right). Experimental data and theoretically fitted curves (1:1 Langmuir) are shown. (J) Binding of biotinylated rmIL11 to mIL11Rα1 in the presence of two-fold dilutions of rmIL11
Figure 10B:
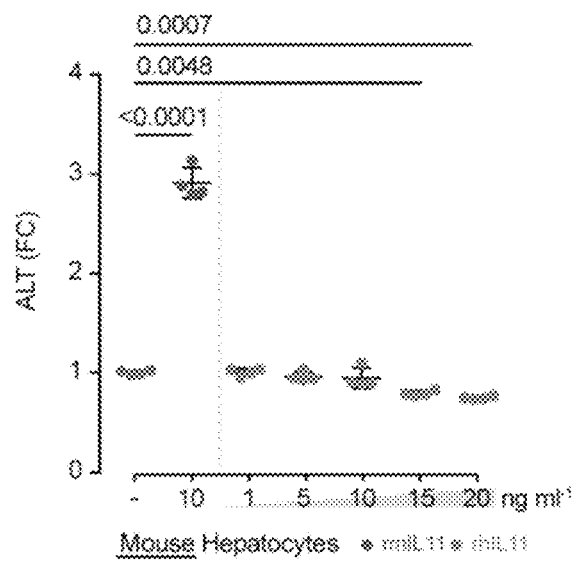
Figure 10C:
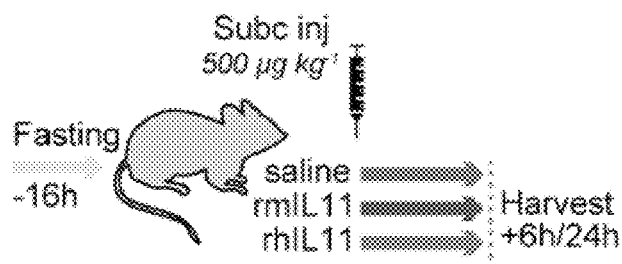
Figure 10D:
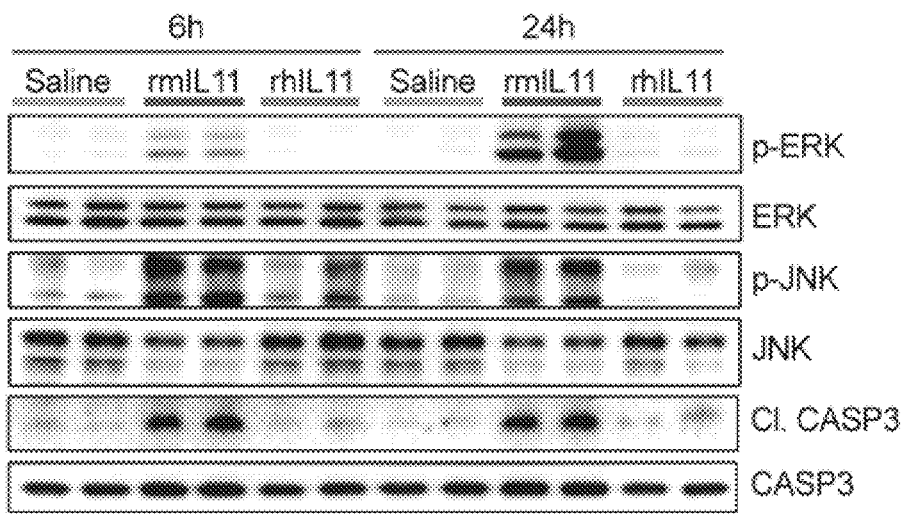
Figure 10E:
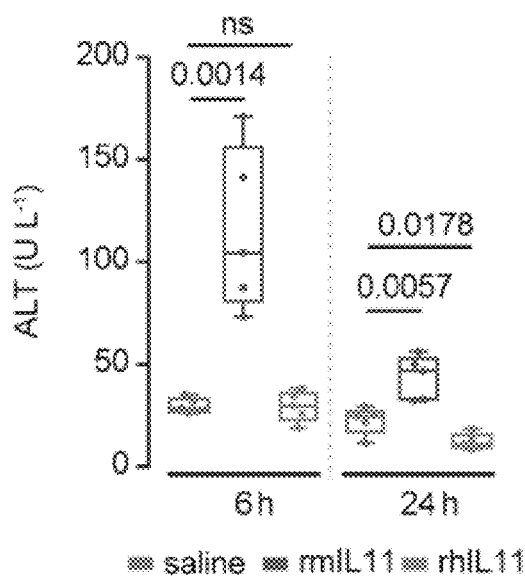
Figure 10F:
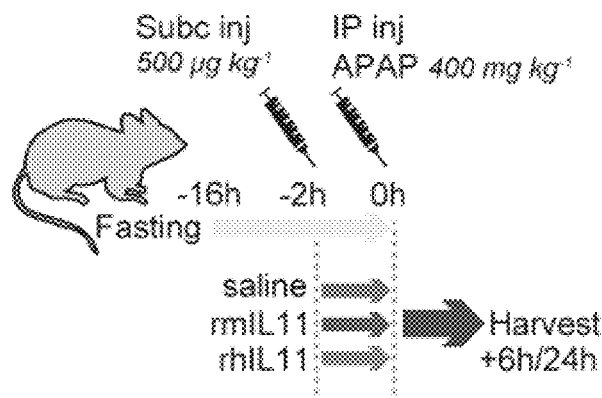

FIGS. 20A to 20D. Image and graphs showing that only species-specific IL11 induces NOX4 and glutathione depletion in hepatocytes. Effect of rhIL11 and rmIL11 (10 ng ml$^{-1}$) on (A) NOX4 protein expression, (B) GSH levels in human hepatocytes, (C) GSH levels in mouse hepatocytes. (D) Hepatic GSH levels following rhIL11 or rmIL11 administration to mice (FIG. 10C); for each time period (6 h, 24 h), boxes from left to right correspond to saline, rmIL11 and rhIL11 treatments. (B-D) Data are shown as box-and-whisker with median (middle line), 25th-75th percentiles (box), and minimum-maximum values (whiskers); two-tailed Dunnett's test FIGS. 21A and 21B. Graphs showing that recombinant human IL11 (rhIL11) restores GSH levels in injured mouse liver. (A) Dose-dependent inhibition effect of rhIL11 on GSH levels in primary mouse hepatocytes stimulated with rmIL11; two-tailed, Tukey-corrected Student's t-test. (B) Effect of rhIL11 or rmIL11 on murine hepatic GSH levels following APAP injury, as shown in FIG. 10F; two-tailed Dunnett's test. For each time period (6 h, 24 h), boxes from left to right correspond to saline, rmIL11 and rhIL11 treatments. (A, B) Data are shown as box-and-whisker with median (middle line), 25th-75th percentiles (box), and minimum-maximum values (whiskers).

Figure 22A:
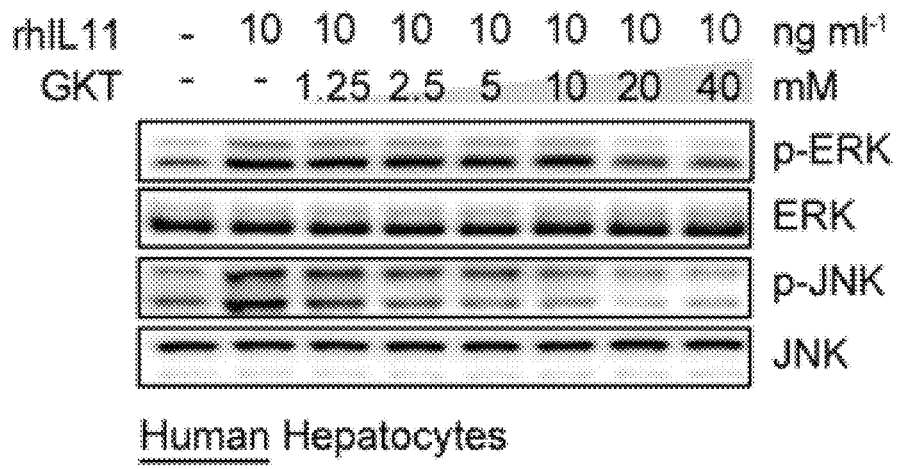
Figure 22B:
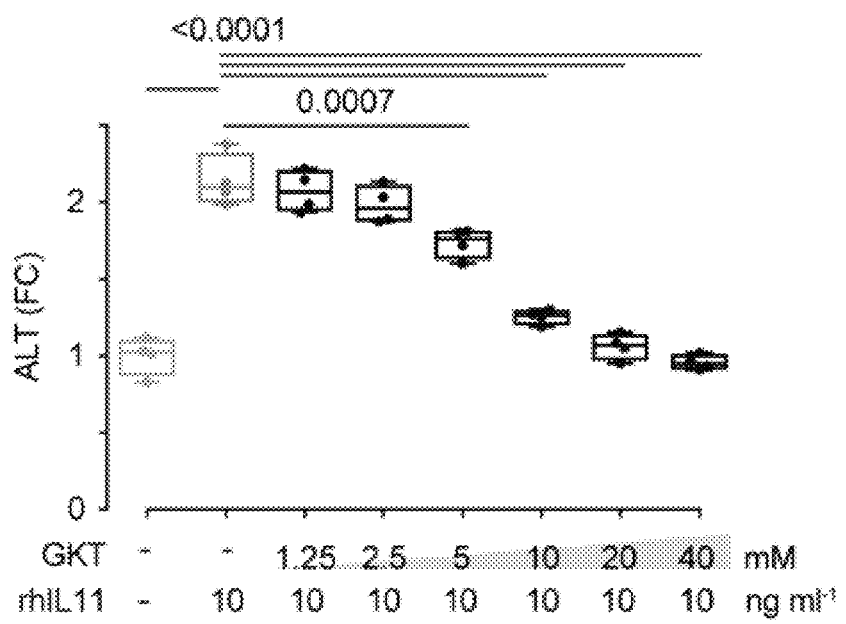

FIGS. 22A and 22B. Image and graph showing that the NOX4 inhibitor GKT-137831 prevents the hepatotoxic effects of IL11. Dose-dependent inhibition effect of GKT-137831, a NOX4 inhibitor, on (A) ERK and JNK activation and on (B) ALT secretion from human hepatocytes stimulated with rhIL11 (10 ng ml$^{-1}$, 24 h). (B) Data are shown as box-and-whisker with median (middle line), 25th-75th percentiles (box), and minimum-maximum values (whiskers); two-tailed, Tukey-corrected Student's t-test. FC: fold change.

Figure 23A:
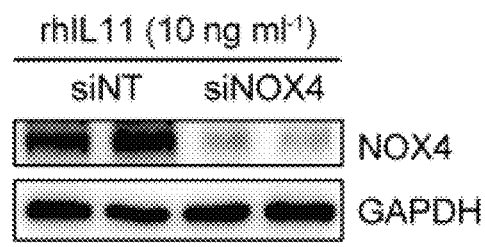
Figure 23B:
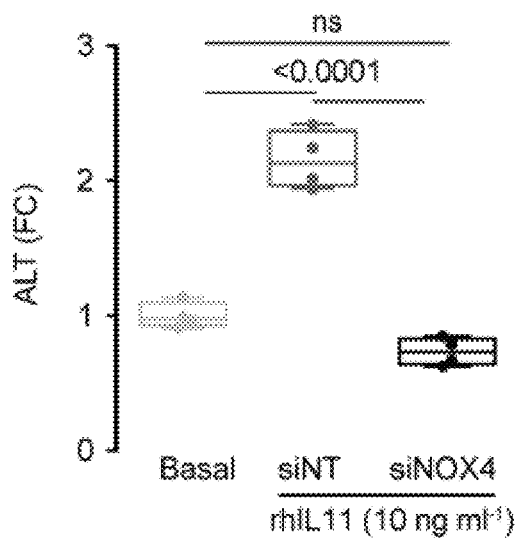

FIGS. 23A and 23B. Image and graph showing that NOX4 is critical for the hepatotoxic effect of IL11. (A) Western blots showing the knockdown efficiency of siNOX4. (B) Effect of siNOX4 on rhIL11-induced primary human hepatocyte death and release of ALT. (A-B) rhIL11 (10 ng ml-1), siNT (non-targeting siRNA control)/siNOX4 (50 nM); 24 h; data are shown as box-and-whisker with median (middle line), 25th-75th percentiles (box), and minimum-maximum values (whiskers); two-tailed, Tukey-corrected Student's t-test. FC: fold change.

Figure 24A:
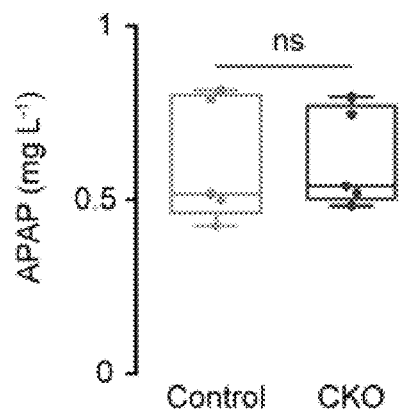
Figure 24B:
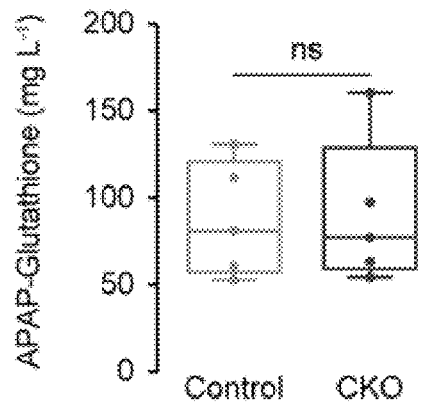

FIGS. 24A and 24B. Graphs showing that control and CKO mice have similar serum levels of APAP and APAP-Glutathione 24 h after APAP administration. LC-MS/MS Quantification of (A) APAP and (B) APAP-Glutathione in the serum of control and CKO mice. Data are shown as box-and-whisker with median (middle line), 25th-75th percentiles (box), and minimum-maximum values (whiskers); two-tailed Student's t-test.

Figure 25A:
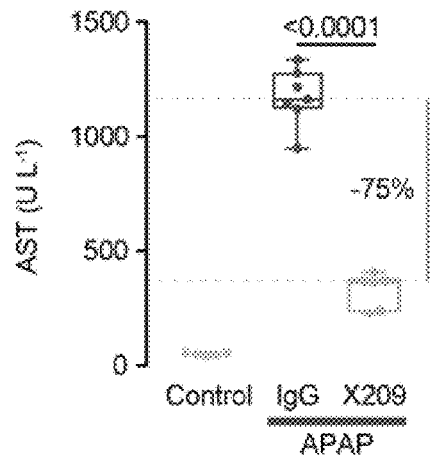
Figure 25B:
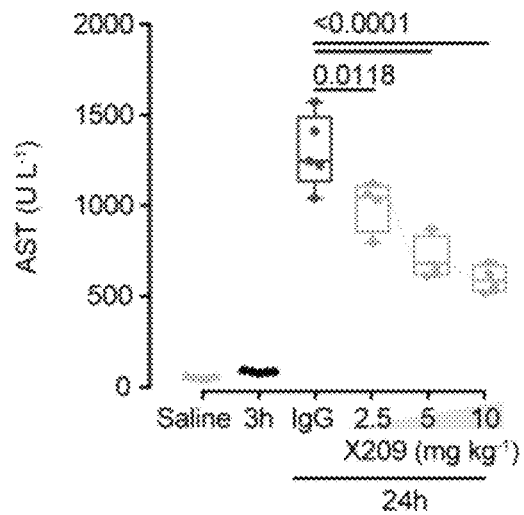
Figure 25C:
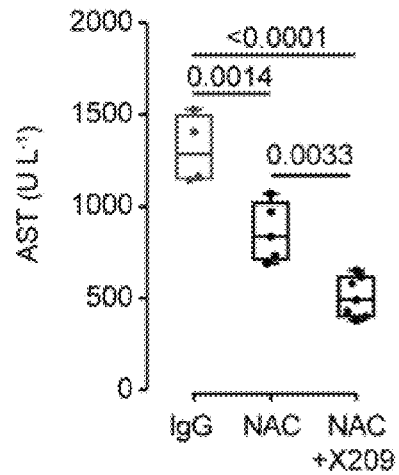

FIGS. 25A to 25C. Graphs showing that anti-IL11Rα antibody (X209) lowers serum AST after APAP injury. (A) Serum AST levels in saline and APAP mice receiving a preventive dose of X209 (10 mg kg$^{-1}$), 16 h prior to APAP (FIG. 13A). (B) Dose-dependent effect of X209 on serum AST levels in APAP mice receiving a therapeutic dose of X209, 3 h post APAP administration (FIG. 13D, the values of saline are the same as those used in S11A). (C) Serum AST levels in mice treated with NAC (500 mg kg$^{-1}$) alone or in combination with X209 (5 mg kg$^{-1}$) 3 h after APAP injury (FIG. 13G). (A-C) Data are shown as box-and-whisker with median (middle line), 25th-75th percentiles (box), and minimum-maximum values (whiskers); two-tailed, Tukey-corrected Student's t-test.

Figure 26A:
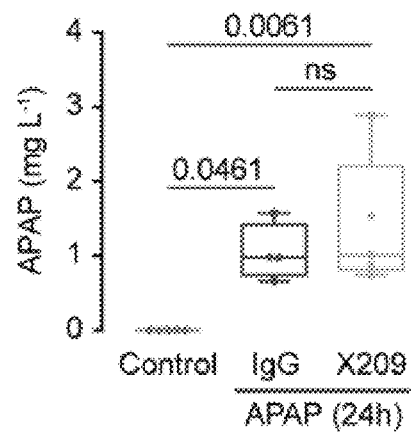
Figure 26B:
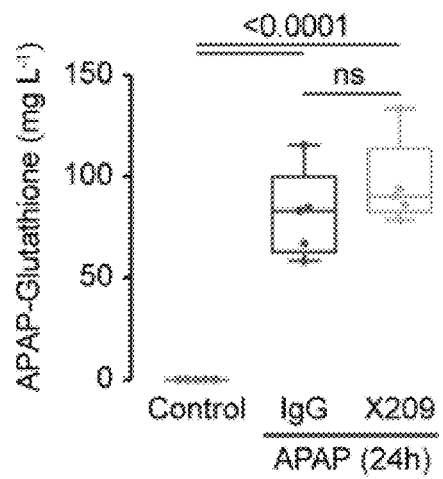

FIGS. 26A and 26B. Graphs showing serum levels of APAP and APAP-Glutathione in the mice serum 24 h post APAP OD. LC-MS/MS Quantification of (A) APAP and (B) APAP-Glutathione in saline control mice, and in IgG and X209-treated mice 24 h following APAP administration. Data are shown as box-and-whisker with median (middle line), 25th-75th percentiles (box), and minimum-maximum values (whiskers); Two-tailed, Tukey-corrected Student's t-test.

Figure 27A:
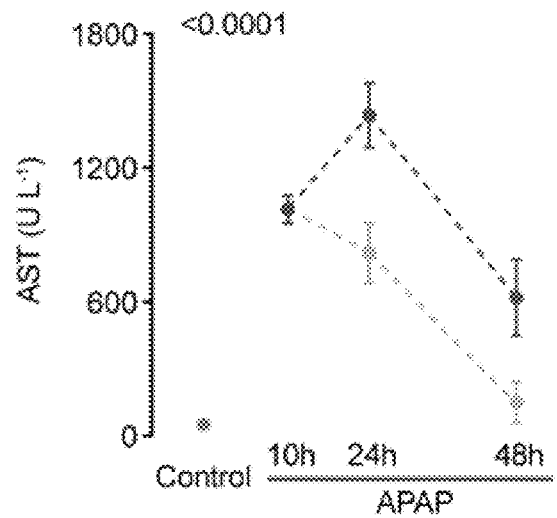
Figure 27B:
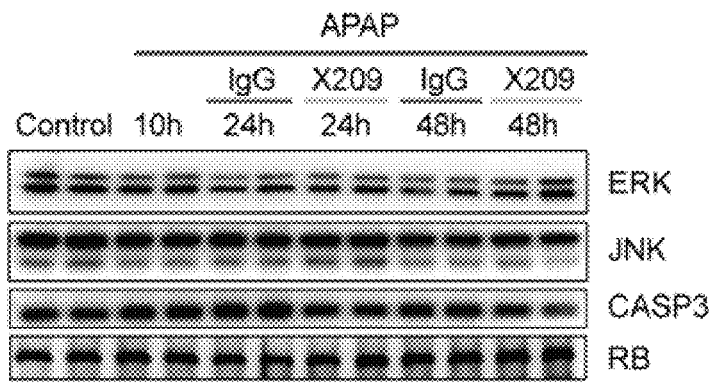

FIGS. 27A and 27B. Graph and image showing that X209 reverses APAP-induced liver damage. (A) Serum AST levels and (B) Western blots showing hepatic content of total ERK, JNK, CASP3, and RB from mice in reversal experimental groups as shown in FIG. 14A.

Figure 28A:
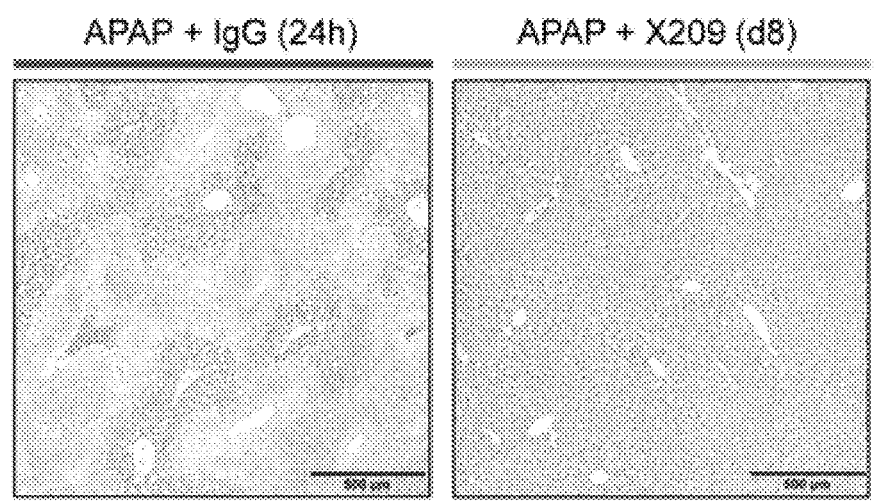
Figure 28B:
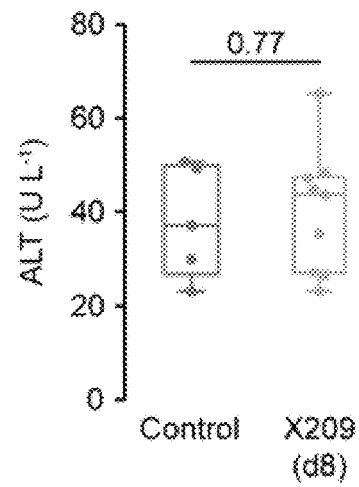

FIGS. 28A and 28B. Image and graph showing the recovery of X209-treated mice following administration of lethal APAP dose. (A) Representative H&E images (scale bars, 500 µm) of livers from IgG (24 h post APAP) and X209-treated mice (D8 post APAP). (B) Serum ALT levels of saline-control and X209-treated mice (D8 post APAP).

Figure 29:
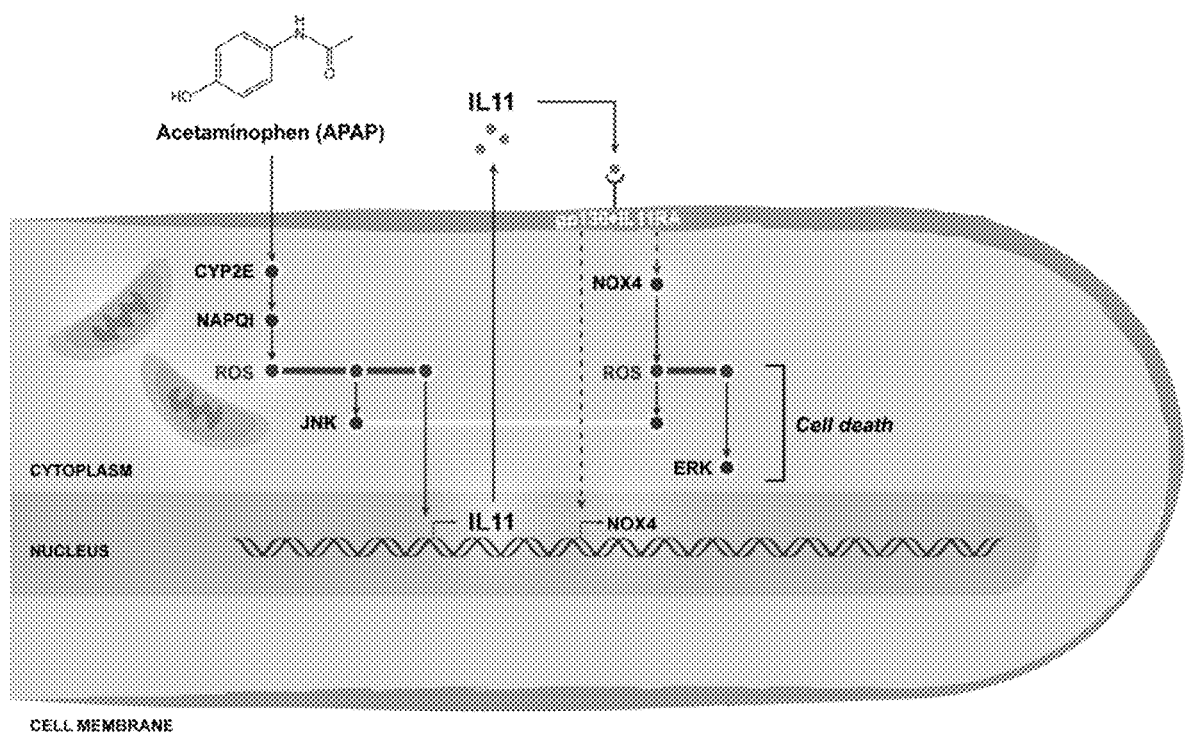

FIG. 29. Schematic of the proposed mechanism and role of IL11 in APAP-induced hepatotoxicity. Metabolizing APAP in the liver leads to ROS production via NAPQI and triggers IL11 secretion. The autocrine IL11 signaling loop on hepatocytes and continues to generate ROS via NOX4, which drives sustained cell death and limits hepatic regeneration independently of APAP and its metabolites. If the IL11 pathway is blocked either genetically or therapeutically, hepatocyte cell death can be prevented and liver regeneration is restored.

Figure 30A:
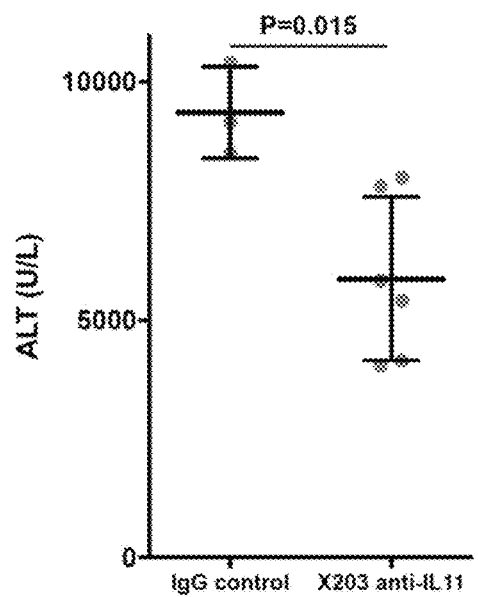
Figure 30B:
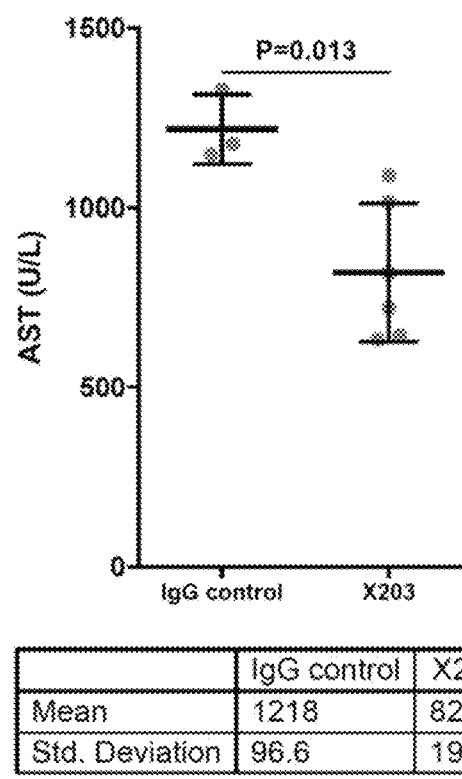

FIGS. 30A and 30B. Box plots showing that anti-IL11 therapy given 16 hours before APAP overdose prevents acute liver injury. A severe APAP overdose (400 mg/kg) was administered to mice 16 hours after IP administration of 20 mg/kg anti-IL11 antibody (ENx203) or IgG control antibody. After 24 hours mice were euthanized. (30A) Serum alanine aminotransferase (ALT) and (30B) aspartate aminotransferase (AST) were measured as correlates of acute liver damage and hepatocyte cell death.

FIGS. 31A to 31K. Scatterplots, box plots histograms and images relating to the expression of receptors for IL-11 and IL-6 and the effects of IL-11 and IL-6 signalling in primary human hepatocytes. (31A) Representative flow cytometry forward scatter (FSC) and fluorescence intensity plots of IL11Rα, IL6R and gp130 staining on hepatocytes. (31B) Abundance of IL11RA1 and IL6R reads in hepatocytes at basal based on RNA-seq (left) and Ribo-seq (right) (Transcripts per million, TPM). (31C and 31D) Read coverage of (31C) IL11RA1 and (31D) IL6R transcripts based on RNA-seq and Ribo-seq of human hepatocytes (n=3). (31E and 31F) (31E) Western blots showing ERK, JNK and STAT3 activation status and (31F) ALT secretion by hepatocytes following stimulation of either hyperIL11 or hyperIL6 over a dose range. (31G) ALT levels in the supernatants of hepatocytes stimulated with hyperIL11 alone or in the presence of increasing amounts of soluble gp130 (sgp130). (31H and 31I) Western blots of hepatocyte lysates showing (31H) phosphorylated ERK and JNK and their respective total expression in response to hyperIL11 stimulation alone or with sgp130 and (31I) phosphorylated STAT3 and total STAT3 in response to hyperIL6 stimulation with and without sgp130. (31J) Representative FSC plots of propidium Iodide (PI) staining of IL11-stimulated hepatocytes in the presence of sgp130 or soluble IL11Rα (sIL11Rα). (31K) Western blots showing p-ERK, p-JNK and their respective total expression in hepatocytes in response to IL11 stimulation alone or in the presence of sgp130 or sIL11Rα. (31A-31K) primary human hepatocytes; (31E-31K) 24 h stimulation; (31E-31K) hyperIL11, hyperIL6, IL11 (20 ng/ml), sgp130, sIL11Rα (1 µg/ml). (31B, 31F-31G) Data are shown as box-and-whisker with median (middle line), $25^{th}$-$75^{th}$ percentiles (box) and min-max values (whiskers).

FIGS. 32A to 32H. Scatterplots, box plots histograms, images and graphs relating to the expression of receptors for IL-11 and IL-6 and the effects of IL-11 and IL-6 signalling in primary human hepatocytes. (32A) Representative FSC plots of IL-11Rα, IL6R, and gp130 staining on activated THP-1 cells. (32B) gp130 transcripts in primary human hepatocytes based on RNA-seq and Ribo-seq (Transcripts per million, TPM). (32C) Read coverage of gp130 transcripts based on RNA-seq and Ribo-seq of primary human hepatocytes (n=3). (32D) Immunofluorescence images (scale bars, 100 µm) of IL11Rα, IL6R, gp130, and Albumin expression in primary human hepatocytes and activated THP-1 cells. (32E) Basal levels of soluble IL6R in the hepatocyte media. (32F) Quantification of PI staining on IL11-stimulated primary human hepatocytes (PI+ve cells) in the presence of sgp130 or sIL11Rα. (32G) Dose-dependent effect of increasing concentration of IL11 in the presence of 1 µg/ml of sgp130 or sIL11Rα on ALT levels secreted by primary human hepatocytes. (32H) Dose-dependent effect of increasing concentration of either sgp130 or sIL-11Rα on IL11-induced ALT secretion. (32B, 32G-32H) Data are shown as box-and-whisker with median (middle line), $25^{th}$-$75^{th}$ percentiles (box) and min-max values (whiskers); (32E-32F) data are shown as mean±SEM; (32F-32H) Tukey-corrected Student's t-test.

EXAMPLES

In the following examples, the inventors demonstrate that IL-11 directly impairs hepatocyte survival and that anti-IL-11 therapy can ameliorate hepatotoxicity. The inventors demonstrate the ability of IL-11 antagonist administered prior to DILI to protect against hepatocyte death and preserve liver function, and also show that IL-11 antagonist administered after DILI can reverse symptoms of liver damage and restore liver function.

Example 1: Effect of IL-11 on Hepatocytes

To investigate the effect of IL-11 on hepatocytes, experiments were performed with primary human hepatocytes in cell culture.

Human hepatocytes (5200, ScienCell) were grown and maintained at 37° C. and 5% $CO_2$. Hepatocyte medium (5201, ScienCell) supplemented with 2% fetal bovine serum and 1% Penicillin-streptomycin was renewed every 2-3 days and cells were passaged at 80% confluence using standard trypsinization techniques. All the experiments were carried out at low cell passage (P2-P3) and cells were serum-starved for 16 hours prior to respective stimulations (24 hours) that were performed in serum-free hepatocyte media. Stimulated cells were compared to unstimulated cells that have been grown for the same duration under the same conditions (serum-free hepatocyte media), but without the stimuli.

IL-11Rα expression from human hepatocytes was determined by immunofluorescence staining. Human hepatocytes were seeded on 8-well chamber slides (1.5×104 cells per well) 24 hours before the staining. Cells were fixed in 4% PFA for 20 minutes, washed with PBS, and non-specific sites were blocked with blocking buffer (5% BSA in PBS) for 2 hours. Cells were incubated with anti-IL11Rα antibody [EPR5446](ab125015, Abcam, 1:100) overnight (4C), followed by incubation with Goat Anti-Rabbit IgG H&L (Alexa Fluor 488) (ab150077, Abcam, 1:200) for 1 hour. Chamber slides were dried in the dark and 5 drops of mounting medium with DAPI were added to the slides for 15 minutes prior to imaging by fluorescence microscope (Leica). Negative control sample was exposed to the same procedure excluding anti-IL11Rα antibody incubation step.

IL-11 mediated hepatocyte cell death was measured by determining the levels of alanine transaminase (ALT) in hepatocyte supernatant after treatment with a range of IL-11 doses (0.019-10 ng/ml). ALT levels were measured using ALT Activity Assay Kit (ab105134, Abcam) according to the manufacturer's protocol. Concurrent number of stress fibres 24 h after IL-11 stimulation was detected by rhodamine-phalloidin staining.

The effect of reactive oxygen species (ROS; stimulated by hydrogen peroxide (0.2 mM $H_2O_2$, 24 hours, 31642, Sigma)) on primary human hepatocytes was investigated.

Figure 1B:
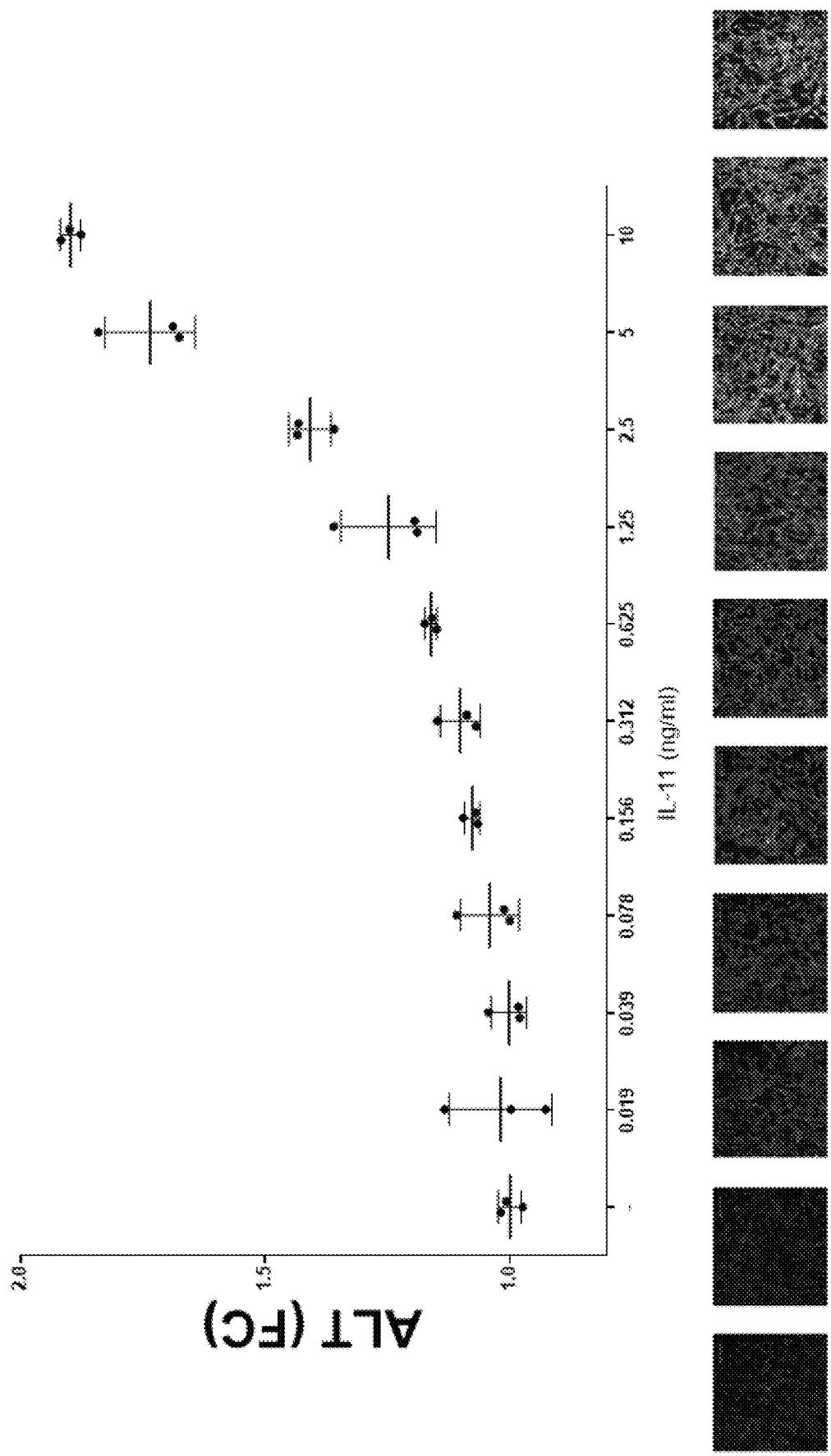
Figure 1C:
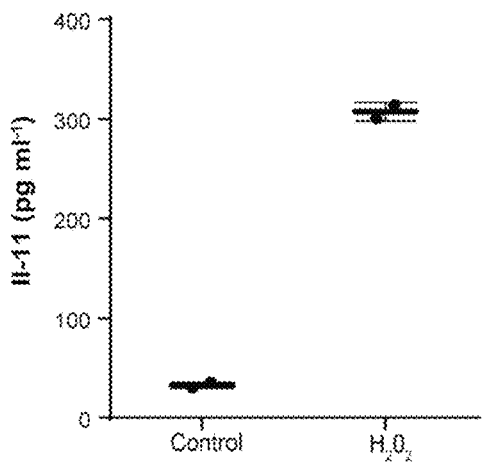

The results are shown in FIGS. 1A to 1C. IL-11 was found to directly impair hepatocyte survival.

Primary human hepatocytes were found to highly express the IL-11Rα receptor (1A). IL-11 stimulation was found to induce dose-dependent hepatocyte cell death as evidenced by a progressive increase in alanine aminotransferase (ALT) over the physiologically relevant dose range (1B). In addition, over the dose range IL-11 progressively stimulated an increase in actin stress fibres in hepatocytes (1B; micrographs from across the dose range), which reflects a partial epithelial-to-mesenchymal transformation of hepatocytes that is known to cause hepatocyte dysfunction (Grant Rowe et al. *Molecular and Cellular Biology* 2011; 31 (12): 2392-2403).

As APAP is known to induce liver injury in ROS-dependent manner, we stimulated human hepatocytes with $H_2O_2$ and found that IL-11 was upregulated by 10-fold in the supernatant (1C). Hence, IL-11 directly causes hepatocyte cell death and drives hepatocyte to dysfunctional partial epithelial-mesenchymal cell transition (EMT) state that is known to limit the regenerative capacity of the liver (Grant Rowe et al. supra).

Example 2: Effect of Anti-IL-11 Therapy on Hepatotoxicity

A mouse model of acetaminophen (APAP)-induced liver injury was employed to investigate the effect of anti-IL-11 therapy on hepatotoxicity.

This animal procedures were approved and conducted in accordance with the SingHealth Institutional Animal Care and Use Committee (IACUC). All mice were provided food and water ad libitum, unless during the starvation period.

Briefly, 12-14 weeks old male mice were starved and intraperitoneally (IP) injected with 10 mg/kg of anti-IL-11Rα antibody or IgG isotype control 16 hours prior to APAP (A3035, Sigma) injection (IP, 400 mg/kg). Mice were sacrificed 24 hours post-APAP administration.

The levels of IL-11 in mouse serum and hepatocyte supernatant were quantified using Mouse IL-11 DuoSet (DY418 and DY008, R&D Systems) and Human IL-11 Quantikine ELISA kit D1100, R&D Systems), respectively, according to the manufacturer's protocol.

Liver samples were excised and fixed for 48 hours at room temperature in 10% neutral-buffered formalin (NBF), dehydrated, embedded in paraffin blocks and sectioned at 7 μm. Sections were stained with Hematoxylin&Eosin (H&E) according to standard protocol and examined by light microscopy.

Figure 2A:
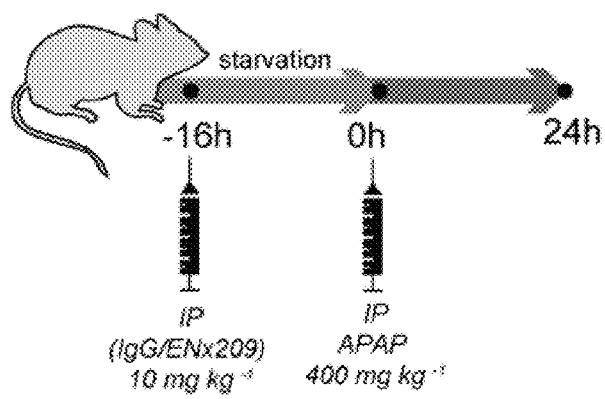
FIGS. 2A to 2E. The effect of anti-IL-11 therapy on hepatotoxicity in a mouse model of APAP-induced liver injury. IgG antibody was used as a control. (2A) Schematic showing the therapeutic regimen. (2B) Serum IL-11 levels following APAP-induced toxicity. (2C) ALT levels showing extent of liver damage. (2D) Extent of APAP-induced loss of liver mass. (2E) Hematoxylin&Eosin (H&E) staining showing the extent of centrilobular necrosis in liver tissue from mice treated with anti-IL11Rα antibody or IgG control.
Figure 2B:
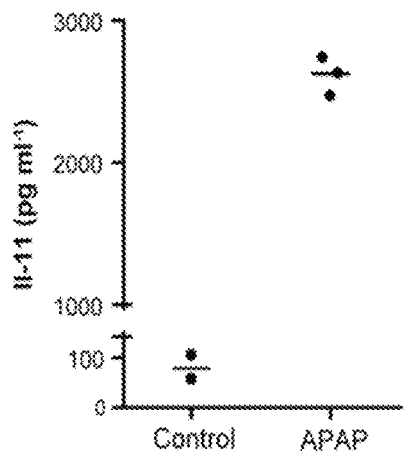
Figure 2C:
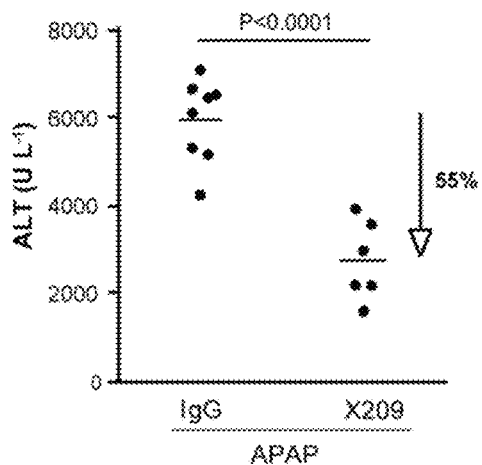
Figure 2D:
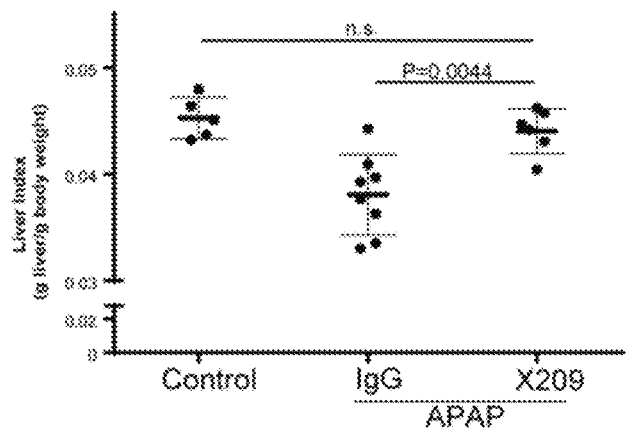
Figure 2E:
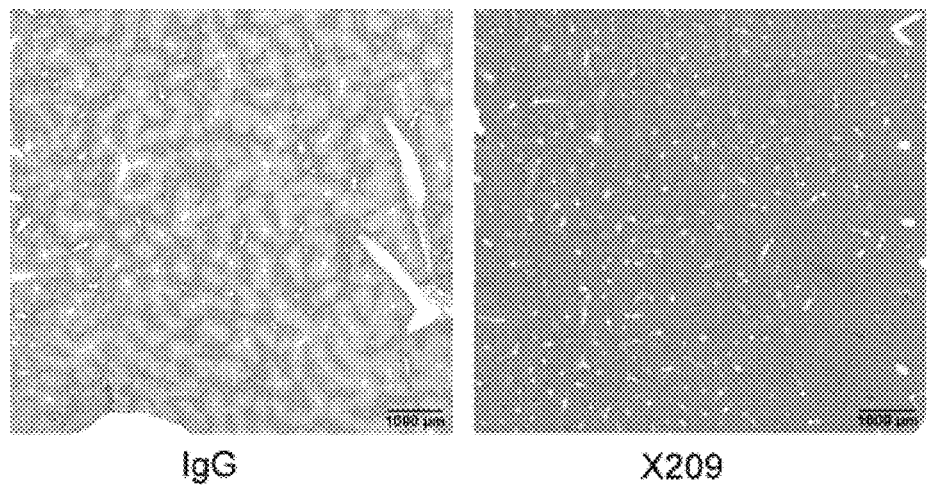

The results are shown in FIGS. 2A to 2E. A schematic showing the therapeutic regimen is shown in FIG. 2A.

As shown above, marked elevation of IL-11 was found in the serum following APAP toxicity (2B), mean±SD, control, n=2; APAP, n=3. Mice receiving a single dose of anti-IL11Rα antibody therapy were found to have significantly lower ALT levels (55% lower compared to IgG control; 2C), i.e. markedly reduced the extent of liver damage. Anti-IL-11 therapy was also found to prevent APAP-induced loss in liver mass, which reflects destruction of liver cells, as compared to 24% loss of liver mass with IgG control antibody (liver index; 2D). (E) Liver histology by Hematoxylin&Eosin (H&E) staining showed severe centrilobular necrosis in IgG-treated mice, a typical histological feature of APAP toxicity, which was found to be reduced with anti-IL11Rα therapy.

The mobility and activity of the mice treated with IgG control or anti-IL-11Rα antibody was observed at 24 hours post-APAP treatment. Control IgG-treated mice were found to be static/moribund with visible features of ill health (e.g. piloerection, hunched posture), whereas mice treated with anti-IL-11Rα antibody had normal mobility and activity.

Hence inhibiting IL-11 signalling by blocking IL-11Rα prevents hepatotoxicity in the accepted, translational model of APAP-induced liver injury (DILI).

Example 3: Antagonism of IL-11 Mediated Signalling Protects Hepatocytes Against Drug-Induced Cell Death The effects of antagonism of IL-11 mediated signalling on hepatocyte viability was analysed in vitro.

Human hepatocytes (5200, ScienCell) cultured at 37° C. and 5% $CO_2$ in hepatocyte medium (5201, ScienCell) supplemented with 2% fetal bovine serum and 1% Penicillin-streptomycin. Medium was replaced every 2-3 days, and cells were passaged at 80% confluence using standard trypsinization techniques. All experiments were carried out at low cell passage (P2-P3). Cells were serum-starved for 16 hours prior to their used in experiments, by culture in serum-free hepatocyte medium.

In a first experiment, hepatocytes were treated with APAP (A3035, Sigma) at a final concentration of 20 mM for 24 hours, in the absence (baseline, BL) or presence of antagonist anti-IL11Rα antibody (X209, 2 μg/ml) or isotype-matched IgG control antibody (IgG, 2 μg/ml).

Hepatocytes were then stained using the FITC Annexin V/Dead Cell Apoptosis Kit (V13242, Thermo Fisher) according to the manufacturer's instructions, and Annexin V-FITC/PI-stained cells were analysed by flow cytometry using a BD LSRFortessa flow cytometer (BD Bioscience). 10,000 cells were analyzed per sample. Data was analyzed using FlowJo version 7 software.

Figure 3:
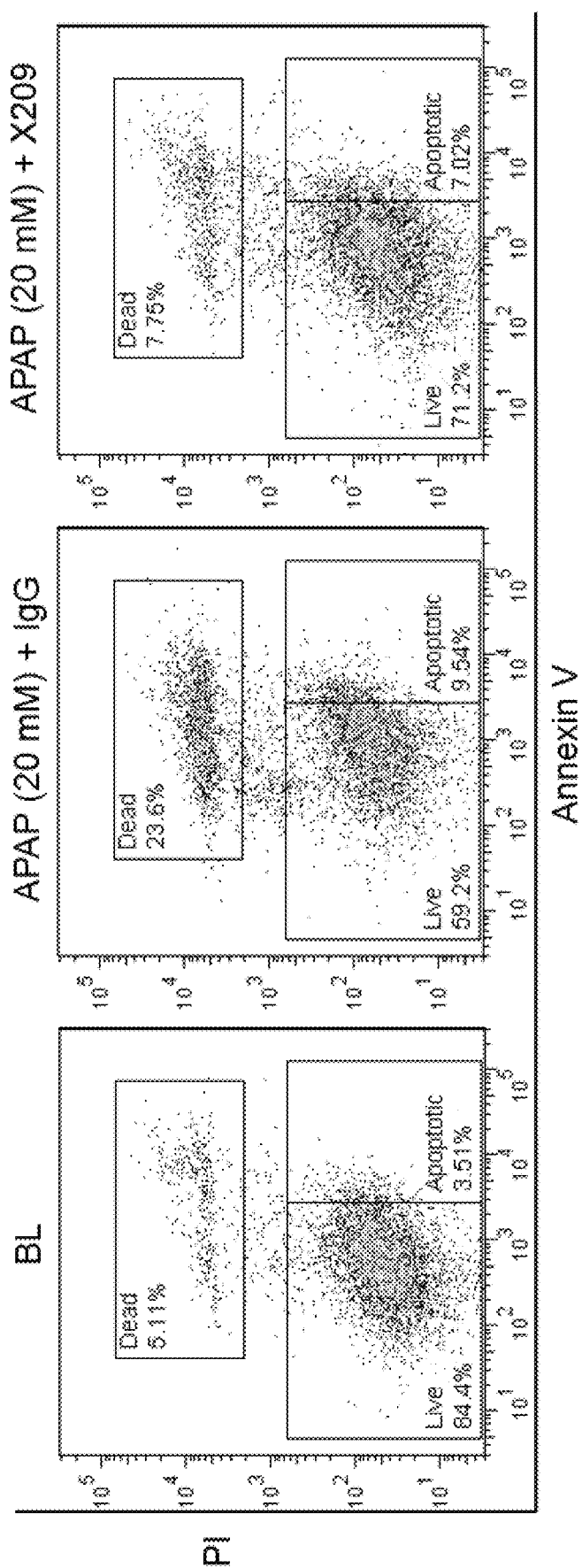
FIG. 3. Scatterplot showing that anti-IL11Rα antibody prevents APAP-mediated hepatocyte death. Human hepatocytes were treated with APAP (20 mM) in the presence or absence (BL) of anti-IL11Rα (X209, 2 μg/ml) or IgG control antibody. Cells were subsequently stained with Annexin V and PI, and cell death was analysed by flow cytometry. BL=baseline.

The results are shown in FIG. 3. Treatment of the hepatocytes with antagonist antibody inhibitor of IL-11 mediated signalling was found to substantially reduce the proportion of dead hepatocytes.

In a separate experiment, hepatocytes were treated with APAP (A3035, Sigma) at a final concentration of 10 mM for 24 hours, in the absence (baseline, BL) or presence of antagonist anti-IL11Rα antibody (X209, 2 μg/ml) or isotype-matched IgG control antibody (IgG, 2 μg/ml).

Protein extracts were prepared from the hepatocytes using radioimmunoprecipitation assay (RIPA) buffer containing protease and phosphatase inhibitors (Thermo Scientifics), followed by centrifugation to clear the lysate. Protein concentrations were determined by Bradford assay (Bio-Rad). Equal amounts of protein lysates were separated by SDS-PAGE, transferred to PVDF membrane, and subjected to immunoblot analysis for the indicated primary antibodies (ERK, pERK, pJNK). Proteins were visualized using the ECL detection system (Pierce) with the appropriate secondary antibodies.

Figure 4:
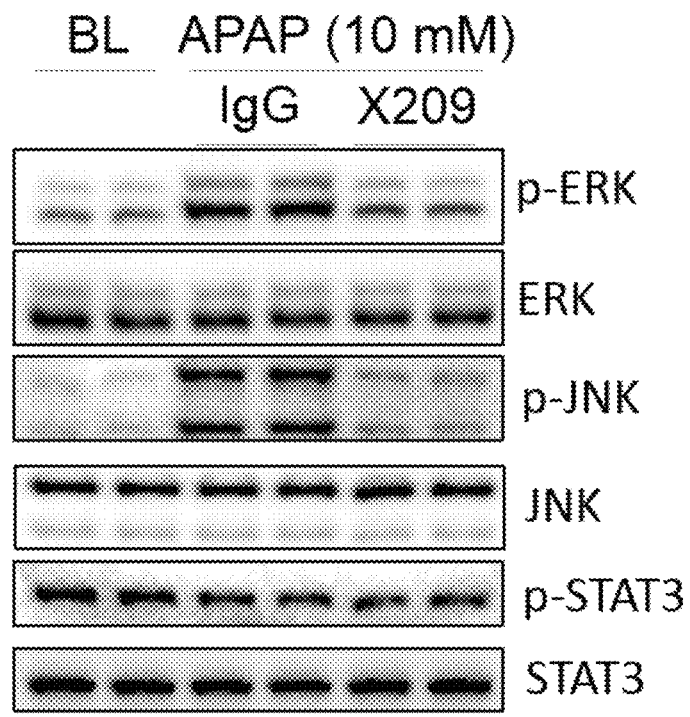
FIG. 4. Image of a western blot showing that anti-IL11Rα antibody prevents APAP-mediated activation of Erk and Jnk. Human hepatocytes were treated with APAP (10 mM) in the presence or absence (BL) of anti-IL11Rα (X209, 2 μg/ml) or IgG control antibody. Cell extracts were prepared and western blots were performed to assess the activation (phosphorylation) status of the Erk and Jnk kinases. BL=baseline.

The results are shown in FIG. 4. Treatment of hepatocytes with APAP was found to significantly upregulate levels of p-ERK and pJNK (cf. BL vs. IgG). Treatment of hepatocytes with antagonist antibody inhibitor of IL-11 mediated signalling was found to substantially reduce the levels of p-ERK and pJNK (cf. IgG vs. X209).

Example 4: Antagonism of IL-11 Mediated Signalling Protects Against Drug-Induced Liver Injury A severe APAP overdose (400 mg/kg) or an equivalent volume of saline was administered to 12-14 weeks old male mice by IP injection, 16 hours after IP administration of 20 mg/kg of antagonist anti-IL11Rα antibody (X209) or isotype-matched IgG control antibody.

24 hours after APAP administration, mice were euthanized. Serum alanine aminotransferase (ALT) levels were measured using ALT Activity Assay Kit (ab105134, Abcam) according to the manufacturer's instructions, and livers were harvested, fixed for 48 h at room temperature in 10% neutral-buffered formalin (NBF), dehydrated, embedded in paraffin blocks and sectioned at 7 μm. Sections were stained with Hematoxylin&Eosin (H&E) according to standard protocol and examined by light microscopy.

Figure 5A:
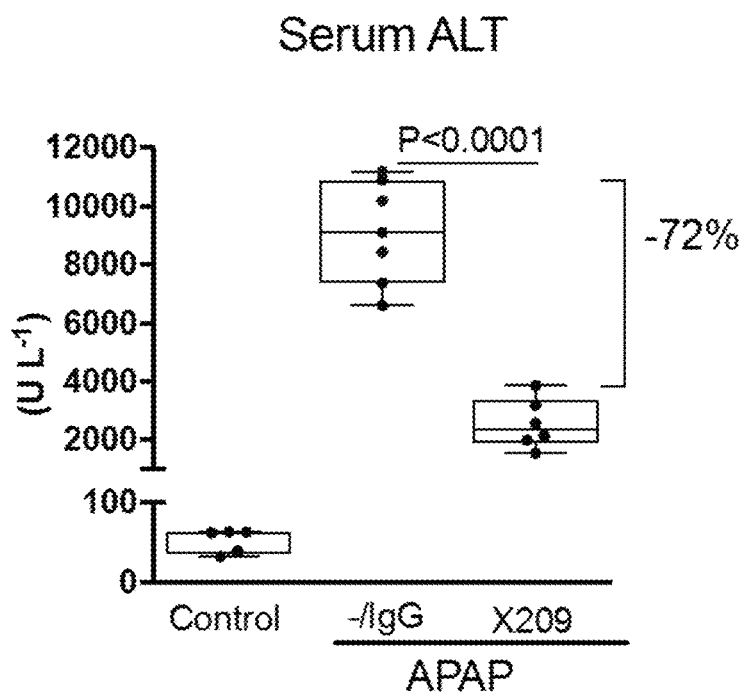
FIGS. 5A and 5B. Box plot and images showing that anti-IL11Rα therapy given 16 hours before APAP overdose prevents acute liver injury. A severe APAP overdose (400 mg/kg) was administered to mice 16 hours after IP administration of 20 mg/kg anti-IL11Rα antibody (ENx209) or IgG control antibody. After 24 hours mice were euthanized. (5A) Serum alanine aminotransferase (ALT) was measured as a marker of acute liver damage and hepatocyte cell death. (5B) Livers were harvested, fixed in 10% neutral-buffered formalin, dehydrated, embedded in paraffin blocks, sectioned and then stained with hematoxylin and eosin to visualize the characteristic centrilobular hepatocyte necrosis seen in APAP overdose.
Figure 5B:
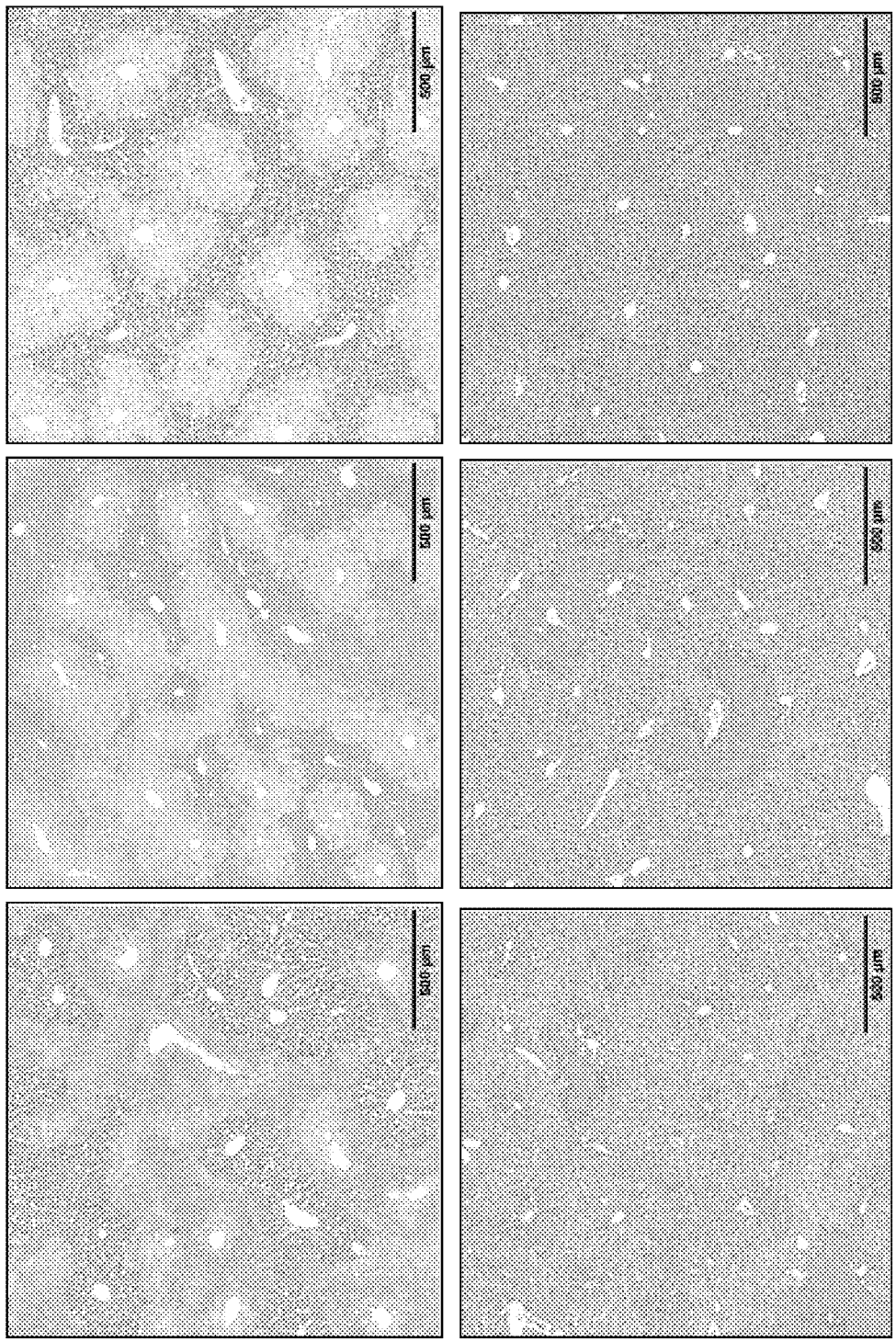

The results are shown in FIGS. 5A and 5B. Pre-treatment with antagonist anti-IL-11Rα antibody inhibitor of IL-11 mediated signalling was shown to significantly protect mice from DILI-associated inhibition of liver function, as determined by a substantial reduction in serum ALT levels (FIG. 5A). The livers of mice pre-treated with antagonist antibody inhibitor of IL-11 mediated signalling also displayed substantially less hepatocyte necrosis as compared to livers from IgG-treated controls (FIG. 5B).

In a further experiment, a severe APAP overdose (400 mg/kg) was administered to 12-14 weeks old male mice by IP injection, 16 hours after IP administration of 20 mg/kg of antagonist anti-IL11 antibody (X203) or isotype-matched IgG control antibody.

24 hours after APAP administration, the levels of alanine transaminase (ALT) and aspartate aminotransferase (AST) in mouse serum were measured using ALT Activity (ab105134, Abcam) and AST (ab105135, Abcam) Assay Kits according to the manufacturer's protocol.

The results are shown in FIGS. 30A and 30B. Pretreatment with antagonist anti-IL-11 antibody inhibitor of IL-11 mediated signalling was shown to significantly protect mice from DILI-associated inhibition of liver function, as evidenced by a substantial reduction in serum ALT and AST levels.

Example 5: Antagonism of IL-11 Mediated Signalling after Drug-Induced Liver Injury Reverse Symptoms of Liver Damage and Restores Liver Function A severe APAP overdose (400 mg/kg) or an equivalent volume of saline was administered to 12-14 weeks old male mice by IP injection, and 10 hours later mice were administered IP with 20 mg/kg of antagonist anti-IL11Rα antibody (X209), isotype-matched IgG control antibody, or untreated.

Mice were euthanized at 24, 36 and 48 hours. Serum ALT levels were analysed as described in Example 4.

Livers were harvested, and fixed as described in Example 4, and digital photographs were taken.

Figure 6A:
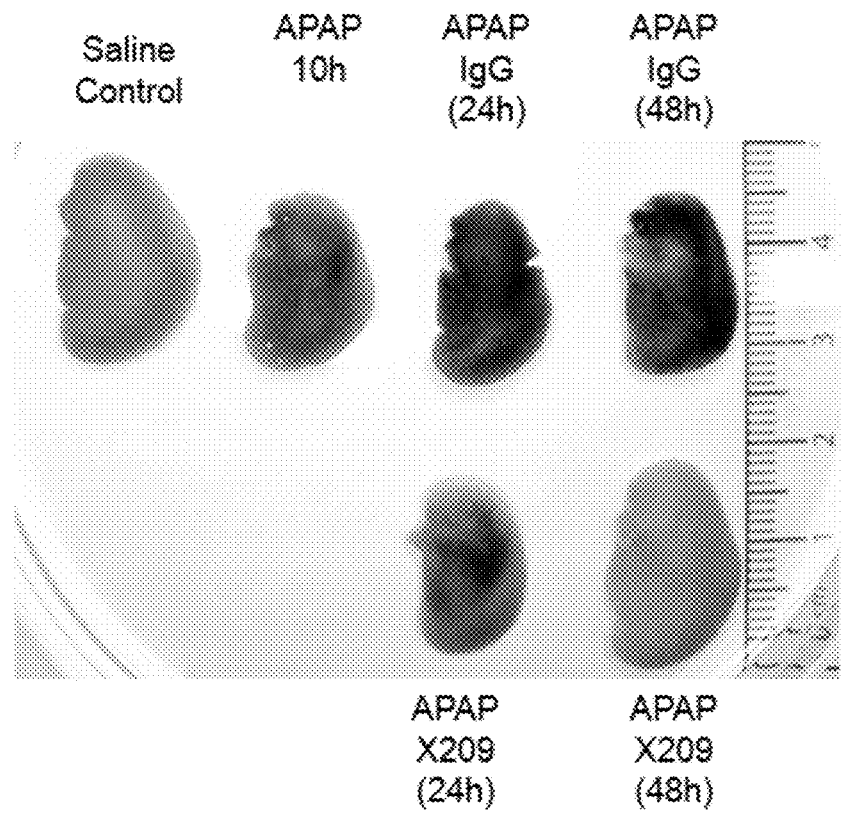
FIGS. 6A and 6B. Image and box plot showing that anti-IL11Rα therapy given 10 hours after APAP overdose treats acute liver injury. A severe APAP overdose (400 mg/kg) was administered to mice, and 10 hours later mice were administered IP with 20 mg/kg anti-IL11Rα antibody (ENx209) or IgG control antibody. (6A) Livers were harvested at the indicated time points fixed in 10% neutral-buffered formalin and gross morphology and appearance was documented. (6B) serum alanine aminotransferase (ALT) was measured as a marker of acute liver damage and hepatocyte cell death at the indicated time points.
Figure 6B:
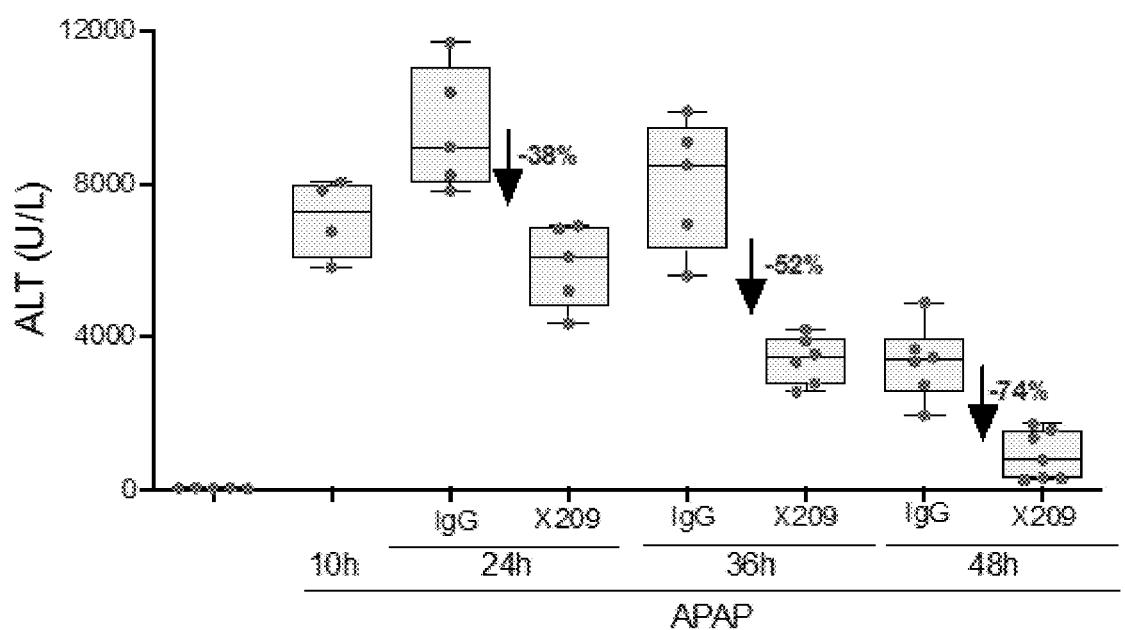

The results are shown in FIGS. 6A and 6B. Antagonist antibody inhibitor of IL-11 mediated signalling administered 10 hours after severe APAP overdose was shown to restore gross liver morphology to that mice which had not been treated with APAP (FIG. 6A). Antagonist antibody inhibitor of IL-11 mediated signalling administered 10 hours after severe APAP overdose was furthermore demonstrated to rescue mice from DILI-associated inhibition of liver function, as determined by substantial reduction in serum ALT levels (FIG. 6B).

Western blots were also performed on protein extracts prepared from the livers of the mice. Liver tissue was homogenized in radioimmunoprecipitation assay (RIPA) buffer containing protease and phosphatase inhibitors (Thermo Scientifics), and lysates were subsequently separated by SDS-PAGE and analysed by western blot as described in Example 3.

Figure 7:
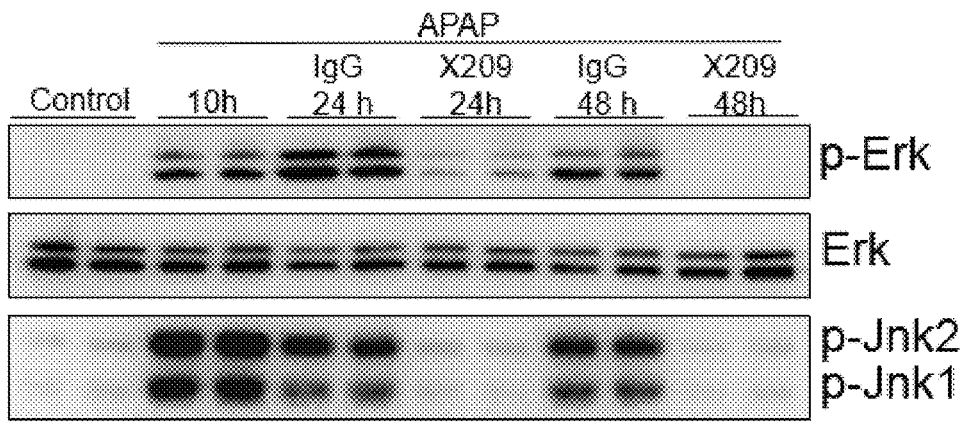
FIG. 7. Image of a western blot showing that anti-IL11Rα therapy given 10 hours after APAP overdose inhibits activation of Jnk and ERK. A severe APAP overdose (400 mg/kg) was administered to mice, and 10 hours later mice were administered IP with 20 mg/kg anti-IL11Rα antibody (ENx209) or IgG control antibody. Livers were harvested at the indicated time points and western blots were performed to assess the activation (phosphorylation) status of the Erk and Jnk kinases.

The results are shown in FIG. 7. APAP overdose significantly upregulated levels of p-ERK, pJNK1 and pJNK2 (cf. Control vs. 10 h). Subsequent treatment with antagonist antibody inhibitor of IL-11 mediated signalling substantially reduced the levels of p-ERK, pJNK1 and pJNK2 (cf. IgG vs. X209).

In further experiments, a lethal APAP overdose (550 mg/kg) or an equivalent volume of saline was administered to 12-14 weeks old male mice by IP injection, and 10 hours later mice were administered IP with 20 mg/kg of antagonist anti-IL11Rα antibody (X209), isotype-matched IgG control antibody, or untreated.

Figure 8A:
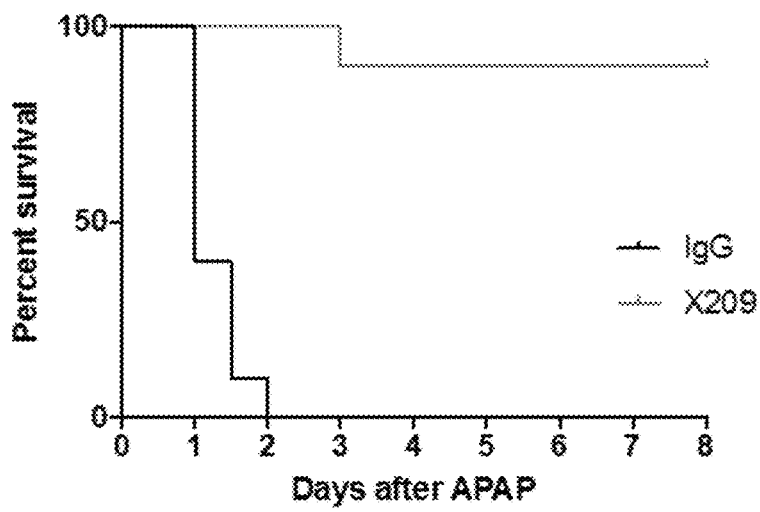
FIGS. 8A to 8C. Graph, images and box plot showing that anti-IL11Rα therapy given 10 hours after APAP overdose prevents death due to acute liver injury, and restores liver function. A lethal APAP overdose (550 mg/kg) was administered to mice, and 10 hours later mice were administered IP with 20 mg/kg anti-IL11Rα antibody (ENx209) or IgG control antibody. (8A) Graph showing mortality over the 8 days post-overdose in the two treatment groups. (8B) Livers were harvested at the indicated time points fixed in 10% neutral-buffered formalin and gross morphology and appearance was documented. (8C) Serum alanine aminotransferase (ALT) was measured as a marker of liver damage and hepatocyte cell death at 8 days post overdose in ENx209 treated mice and compared with levels in normal control mice.

Survival of mice was monitored for 8 days after APAP/saline administration, and the results are shown in FIG. 8A. Treatment with antagonist antibody inhibitor of IL-11 mediated signalling significantly improved survival of mouse administered with a lethal dose of APAP relative to IgG-treated controls.

Mice were euthanized at 24 hours and 192 hours (8 days). Serum ALT levels were analysed as described in Example 4. Livers were harvested, and fixed as described in Example 4, and digital photographs were taken.

Figure 8B:
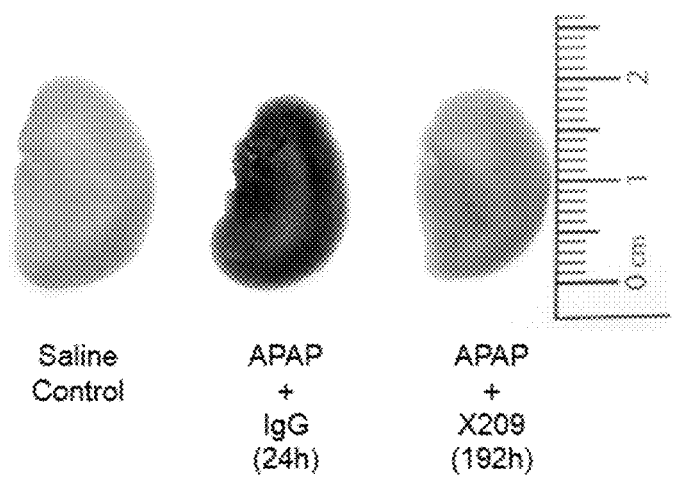
Figure 8C:
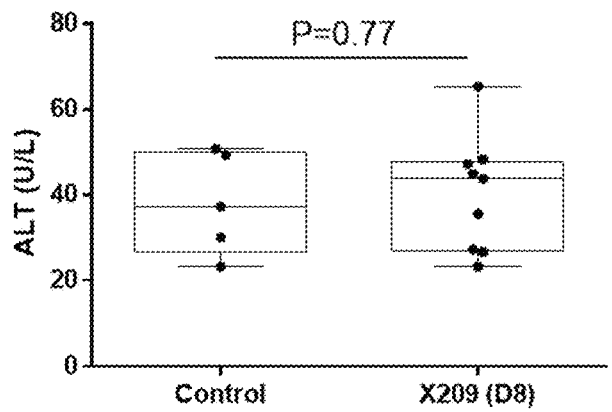

The results are shown in FIGS. 8B and 8C. Antagonist antibody inhibitor of IL-11 mediated signalling administered 10 hours after lethal APAP overdose was shown to restore gross liver morphology to that mice which had not been treated with APAP after 8 days (FIG. 8B). Antagonist antibody inhibitor of IL-11 mediated signalling administered 10 hours after lethal APAP overdose was furthermore demonstrated to rescue mice from DILI-associated inhibition of liver function; serum ALT levels were not significantly different to the levels of normal (saline administered) control mice after 8 days (FIG. 8C).

The ability of treatment with antagonist of IL-11 mediated signalling administered 10 hours after hepatotoxic insult to reverse DILI-associated hepatotoxicity and prevent death of subjects administered a severe/lethal APAP overdose was a truly remarkable result. 10 hours after overdose in mice is thought to be equivalent to about 24 hours after overdose in humans.

The results identify antagonism of IL-11 mediated signalling as an extremely promising therapeutic strategy for reducing liver injury and associated morbidity/mortality following hepatotoxic insult.

Example 6: Antagonism of IL-11 Mediated Signalling after Drug-Induced Liver Injury Reverse Symptoms of Liver Damage and Restores Liver Function 6.1 Overview Acetaminophen (APAP) overdose is a leading cause of liver failure. In the mouse model of APAP-induced liver injury (AILI), the administration of recombinant human interleukin 11 (rhIL11) is protective.

The present disclosure shows that the beneficial effect of rhIL11 in mouse AILI is due to an unexpected inhibitory effect of foreign rhIL11 on endogenous mouse IL11 activity. Contrary to the accepted paradigm, IL11 is secreted by damaged hepatocytes to drive apoptosis and inhibit liver regeneration.

Mice with hepatocyte-specific Il11 expression spontaneously develop liver damage whereas those with Il11ra1 deletion are robustly protected from AILI. Neutralizing anti-IL11R antibodies administered to moribund mice 10 hours post lethal APAP overdose results in 90% survival.

The data of the present disclosure overturn a misconception, indicate a disease mechanism and identify a therapeutic target.

6.2 Introduction

Acetaminophen (N-acetyl-p-aminophenol, APAP) is an over-the-counter analgesic that is commonly taken as an overdose (OD) leading to APAP-induced liver injury (AILI), a major cause of acute liver failure (1). The antioxidant N-acetyl cysteine (NAC) is beneficial for patients presenting early (2), but there is no drug-based treatment beyond eight hours post-OD and death can ensue if liver transplantation is not possible (3, 4).

In hepatocytes, APAP is metabolized to N-Acetyl-p-benzochinonimin (NAPQI) which depletes cellular glutathione (GSH) levels and damages mitochondrial proteins leading to reactive oxygen species (ROS) production and JNK activation (5). ROS-related JNK activation results in a combination of necrotic, apoptotic and other forms of hepatocyte cell death causing liver failure (1, 6, 7). JNK and ASK1 inhibitors have partial protective effects against AILI in mouse models, but this has not translated to the clinic (8, 9). Liver regeneration has fascinated humans since the stories of Prometheus and can be truly profound, as seen after partial hepatic resection in rodents and humans (10, 11). However, in the setting of AILI, liver regeneration is persistently suppressed resulting in permanent injury and patient mortality. Targeting the pathways that hinder the liver's extraordinary regenerative capacity may trigger natural regeneration, which could be particularly useful in AILI (12, 13).

Interleukin 11 (IL11) is a scarcely studied cytokine that is of critical importance for myofibroblast activation and fibrosis of the heart, kidney, lung, and liver (14-16). It is established that IL11 is secreted from injured hepatocytes and Il11 can be detected at high levels in the serum of the mouse model of AILI, where its expression is considered compensatory and cytoprotective (17). In keeping with this paradigm, administration of recombinant human IL11 (rhIL11) is effective in treating the mouse model of AILI and also protects against liver ischemia, endotoxemia or inflammation (17-22). As recently as 2016, rhIL11 has been proposed as a treatment for patients with AILI (23).

In studies of liver fibrosis the inventors made the unexpected observation that, in the context of some models of fibro-inflammatory liver disease, IL11 may be detrimental for hepatocyte function (14). This apparent discrepancy with the previous literature prompted the inventors to look in more detail at the effects of IL11 on hepatocytes independent of fibrosis, and they chose to do so in the mouse model of AILI, where Il11 is largely upregulated (17).

6.3 IL11 Drives APAP-Induced Hepatocyte Cell Death

Figure 9A:
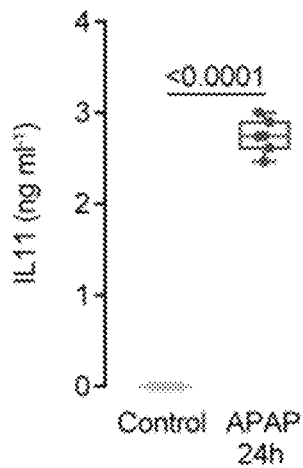
FIGS. 9A to 9J. Graphs and images showing that acetaminophen-induced IL11 secretion from injured hepatocytes causes cell death. (A) Serum IL11 levels in APAP-treated mice. (B) Liver Il11 mRNA following APAP injury. (C) Representative images of luciferase activity in a liver from control and APAP-challenged Il11-Luciferase mice. (D) Western blots showing hepatic IL11 expression in APAP-treated mice. (E) Representative immunofluorescence images (scale bars, 100 μm) of EGFP and cleaved Caspase3 (Cl. CASP3) expression in the livers of Il11-EGFP mice post APAP. (A-E) APAP, 400 mg $kg^{-1}$. (F) ELISA of IL11 secretion from APAP-stimulated hepatocytes. (G) Western blots of phosphorylated ERK, JNK and Cl. CASP3 protein and their respective total expression in hepatocytes in response to rhIL11 stimulation. (H) Quantification of propidium iodide positive ($PI^{+ve}$) cells from rhIL11-stimulated hepatocytes. (I) Western blots showing ERK, JNK, and CASP3 activation status and (J) quantification of $PI^{+ve}$ cells in APAP-treated hepatocytes (20 mM) in the presence of IgG or anti-IL11Rα (X209; 2 μg $ml^{-1}$). (F-J) primary human hepatocytes (F, H-J) 24 h. (A, B, F, H-I) Data are shown as box-and-whisker with median (middle line), 25th-75th percentiles (box), and minimum-maximum values (whiskers). (A, B) Two-tailed Student's t-test; (F, H) two-tailed Dunnett's test; (J) two-tailed, Tukey-corrected Student's t-test.
Figure 9B:
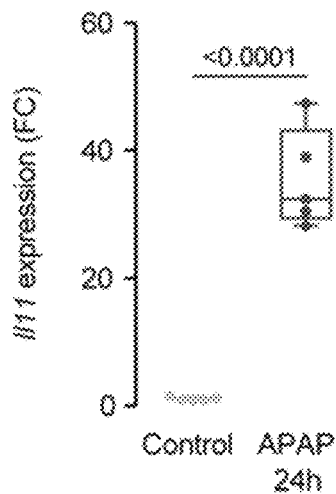
Figure 9C:
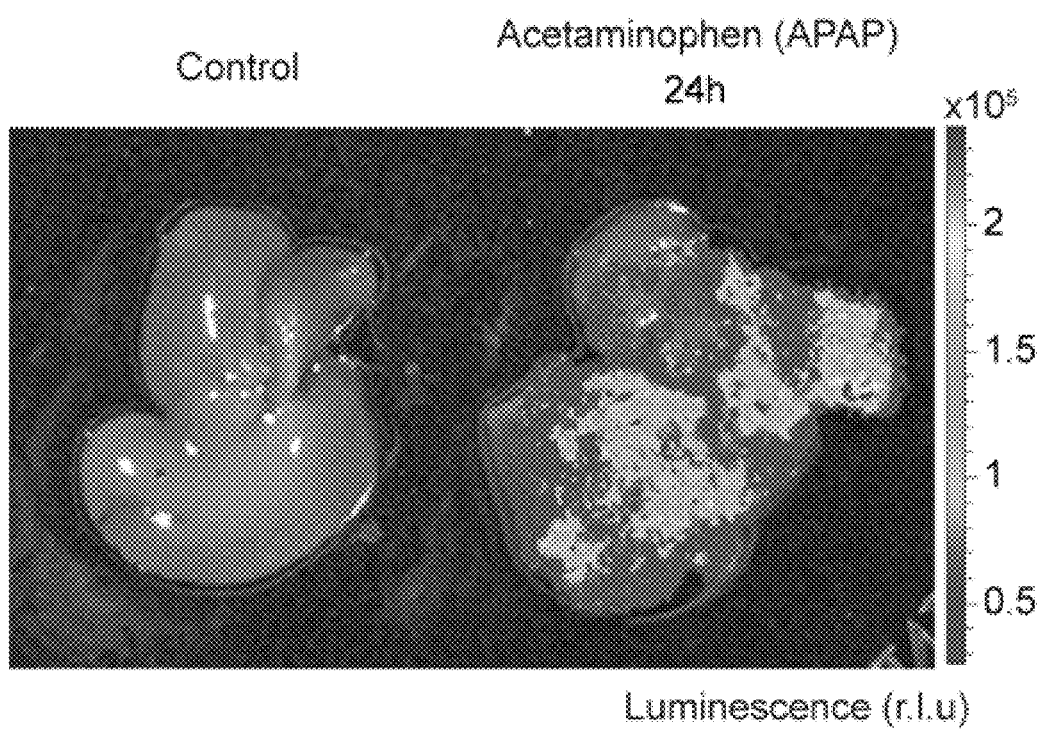
Figure 9D:
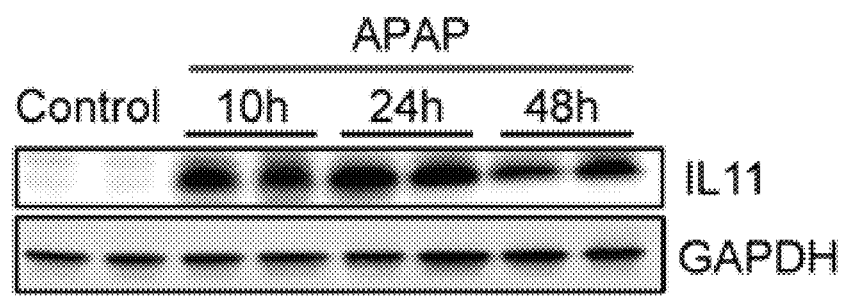
Figure 9E:
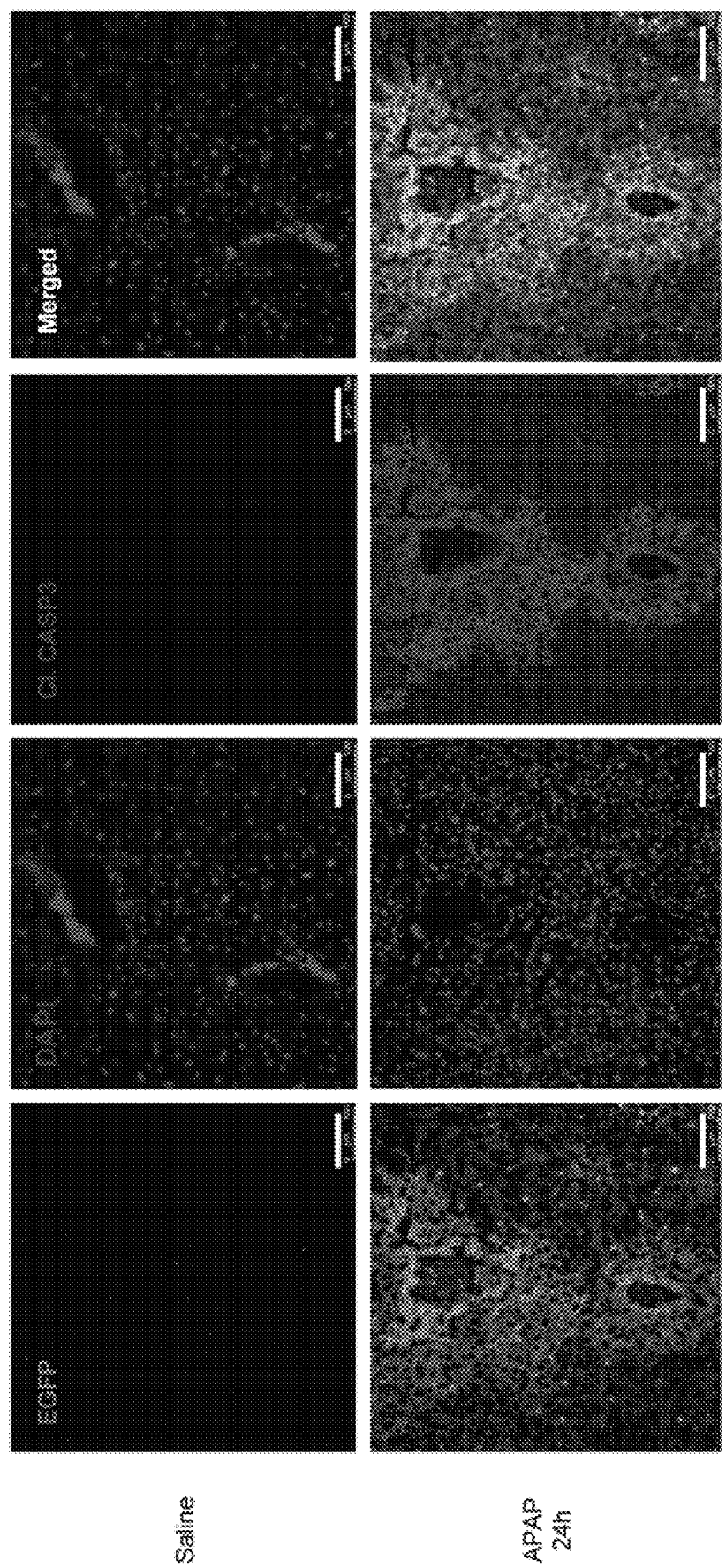

As reported previously (17), AILI was confirmed to be characterized by elevated IL11 serum levels in injured mice (FIG. 9A). The inventors then addressed whether the elevated IL11 serum levels in the mouse AILI model originated in the liver. APAP induced a strong upregulation of hepatic Il11 transcripts (35-fold, P<0.0001). Bioluminescent imaging of a reporter mouse with luciferase cloned into the start codon of Il11 indicated IL11 expression throughout the liver (FIGS. 9B and 9C, and FIG. 15). Western blotting confirmed IL11 upregulation at the protein level across a time course of AILI (FIG. 9D). Experiments using a second reporter mouse with an EGFP reporter construct inserted into the 3'UTR of Il11 (FIG. 16) showed that following APAP, IL11 protein is highly expressed in necrotic centrilobular hepatocytes, the pathognomonic feature of AILI, coincident with cleaved caspase 3 (Cl. CASP3) (FIG. 9E).

Figure 9F:
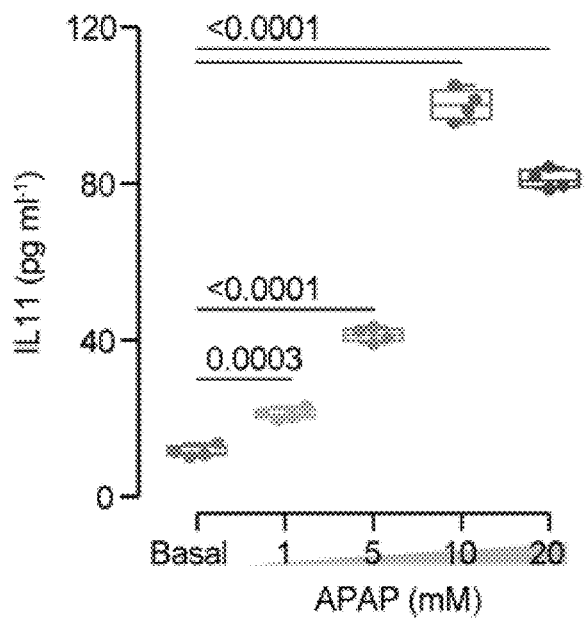
Figure 9G:
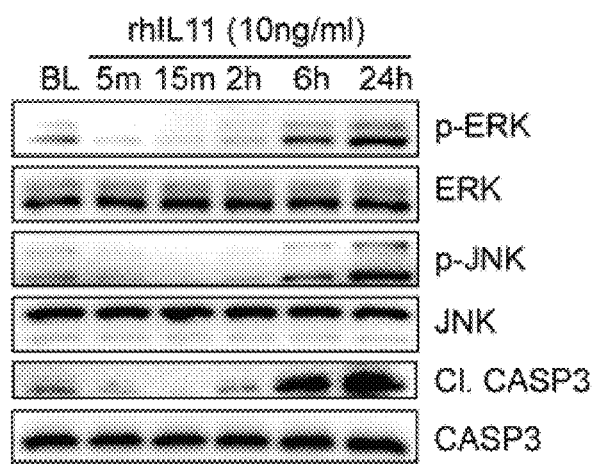
Figure 9H:
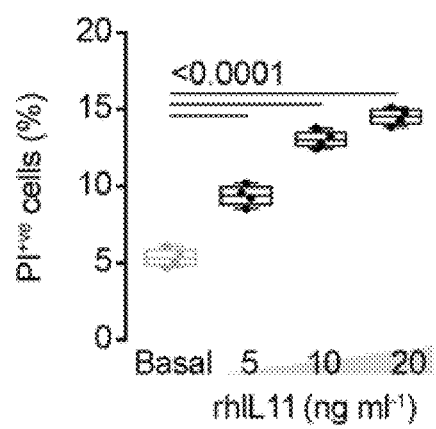
Figure 9I:
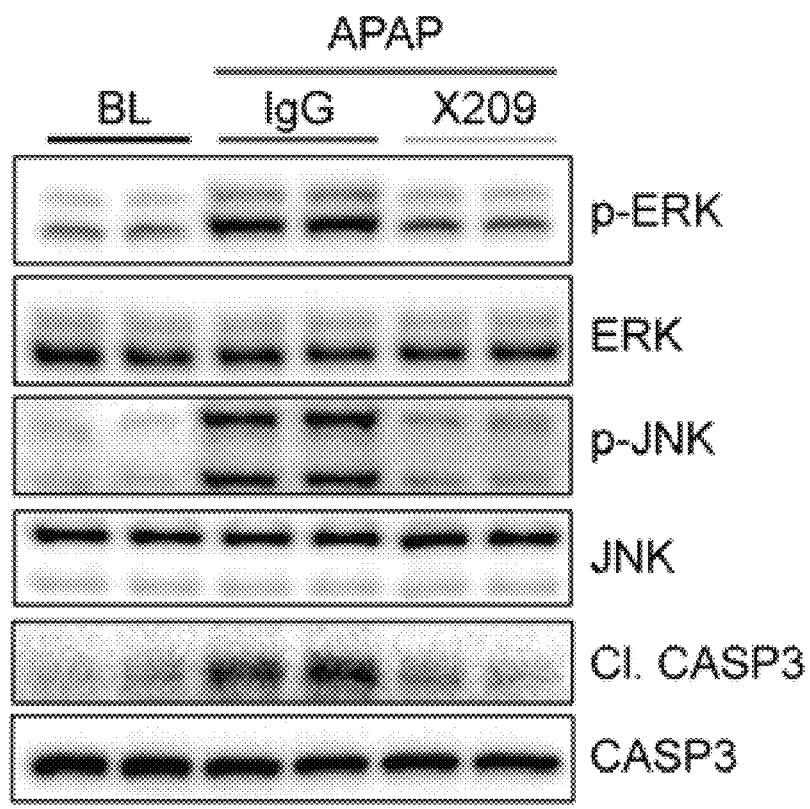
Figure 9J:
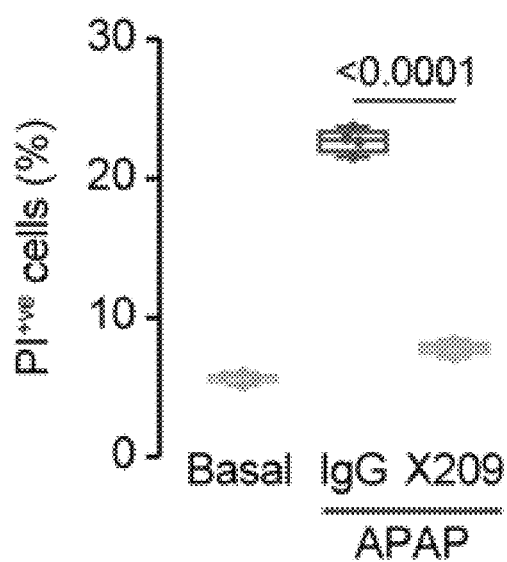

Having identified the source of Il11 upregulation during AILI in vivo, the inventors conducted in vitro experiments to study underlying mechanisms. Exposure of primary human hepatocytes to APAP resulted in the dose-dependent secretion of IL11 (FIG. 9F). Hepatocytes express interleukin 11 receptor subunit alpha (IL11Rα) and it is known that IL11 activates ERK in some cell types (14), hence the inventors explored the effect of IL11 on ERK and JNK, important in AILI, activation in hepatocytes. IL11 induced late (>6 h) and sustained ERK and JNK activation that was concurrent with CASP3 cleavage (FIG. 9G). FACS-based analyses showed dose-dependent IL11-induced hepatocyte cell death (FIG. 9H and FIG. 17A). To explore the role of IL11 signaling in APAP-challenged hepatocytes, the inventors used an IL11Rα neutralizing antibody (X209) (14), which inhibited CASP3 cleavage and cell death, as well as ERK and JNK activation (FIGS. 9I and 9J, and FIG. 17B). While these data confirm the upregulation of IL11 in AILI, they challenge the common perception that this effect is compensatory and protective in the injured liver.

Figure 18A:
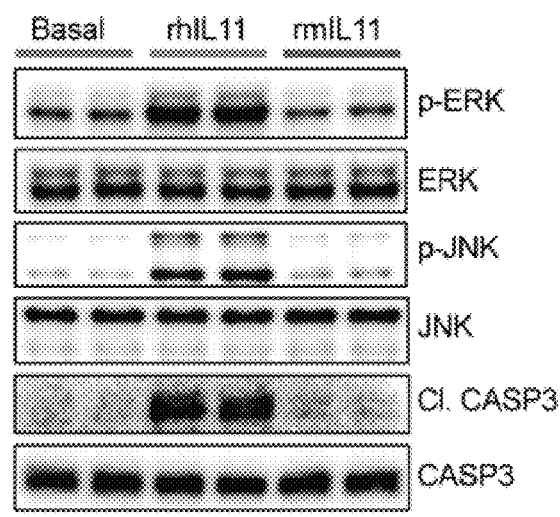
Figure 18B:
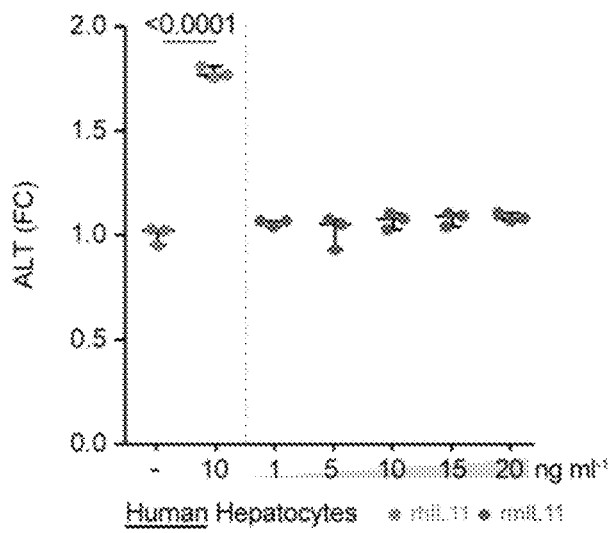

6.4 Species-Specific Effects of Recombinant Human IL11 rhIL11 is consistently reported to be protective in rodent models of liver damage (17-20, 23), yet the results described in Example 6.3 suggested rhIL11 has the exact opposite effect on human hepatocytes in vitro (FIG. 9). This prompted the inventors to test for potential inconsistencies when rhIL11 protein is used in foreign species, as human and mouse IL11 share only 82% protein sequence homology. First, they compared the effects of rhIL11 versus recombinant mouse IL11 (rmIL11) on mouse hepatocytes. While the species-matched rmIL11 stimulated ERK and JNK phosphorylation and induced CASP3 cleavage in mouse hepatocytes, rhIL11 had no effect (FIG. 10A). Similarly, while rmIL11 induced mouse hepatocyte cell death, rhIL11 did not. Indeed, at higher doses rhIL11 trended towards inhibiting mouse hepatocyte death (FIG. 10A). In reciprocal experiments in human hepatocytes, the inventors found that rhIL11 stimulated ERK and JNK signaling and hepatocyte death, whereas rmIL11 did not (FIGS. 18A and 18B).

Figure 18C:
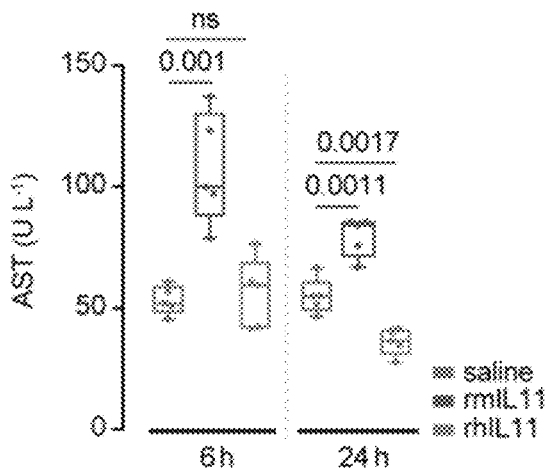

This showed that the role of IL11 signaling in hepatocyte death is conserved across species, but that recombinant IL11 protein has species-specific effects and does not activate the pathway in foreign species. This hypothesis was tested in vivo by injecting either rmIL11 or rhIL11 into mice (FIG. 10C). Injection of rmIL11 resulted in gradual ERK and immediate JNK activation. In contrast, rhIL11 had no effect on ERK or JNK phosphorylation (FIG. 10D). Injection of rmIL11 also caused liver damage with elevated ALT and AST (FIG. 10E and FIG. 18C). In stark contrast, rhIL11 injection in naive mice was associated with slightly lower ALT and AST levels 24 h post-injection (ALT, P=0.018; AST, P=0.0017).

Figure 10G:
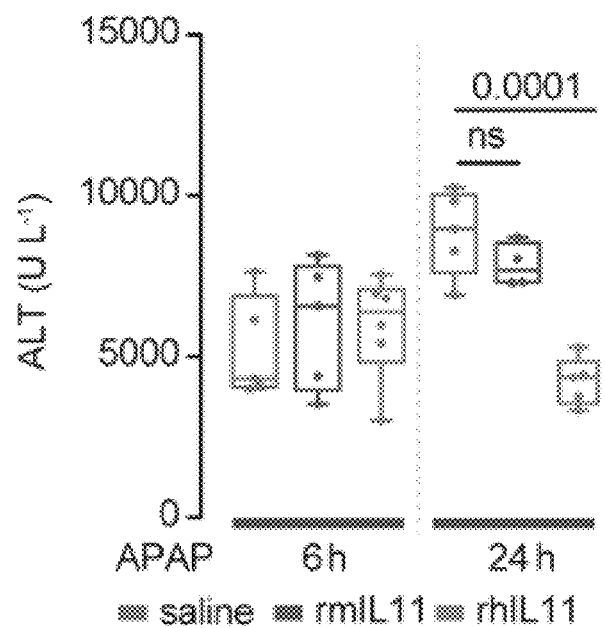
Figure 18D:
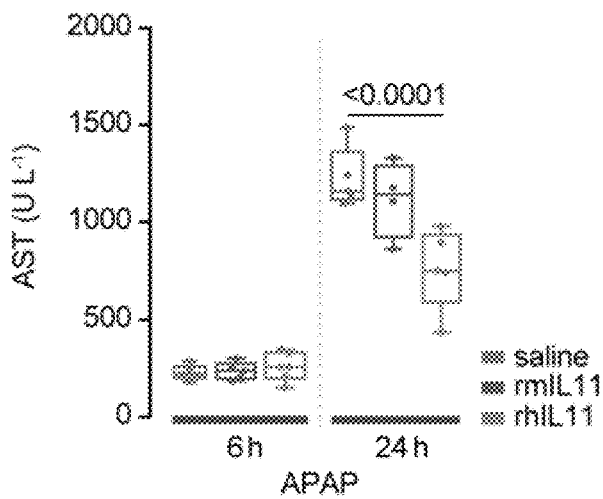

To follow up on the potential protective effect of rhIL11 in the mouse, a protocol similar to the AILI study of 2001 (20) was performed, where rhIL11 was injected into the mouse after APAP OD (FIG. 10F). This confirmed that rhIL11 reduces the severity of AILI in mice (reduction: ALT, 52%, P=0.0001; AST, 39%, P<0.0001), whereas species-matched rmIL11 was not protective in the mouse (FIG. 10G and FIG. 18D).

Figure 10H:
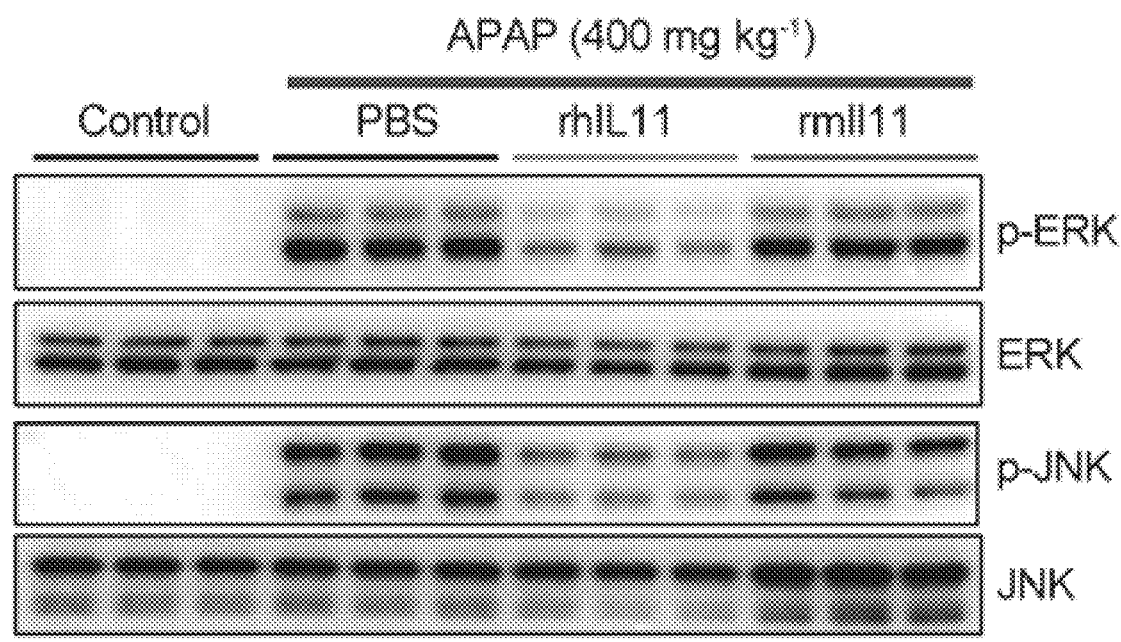

The therapeutic effect of rhIL11 was accompanied by a reduction in hepatic ERK and JNK activation (FIG. 10H), which shows that rhIL11 blocks IL11-driven signaling pathways in the liver similar to IL11Rα antibodies (FIG. 9I).

Figure 10I:
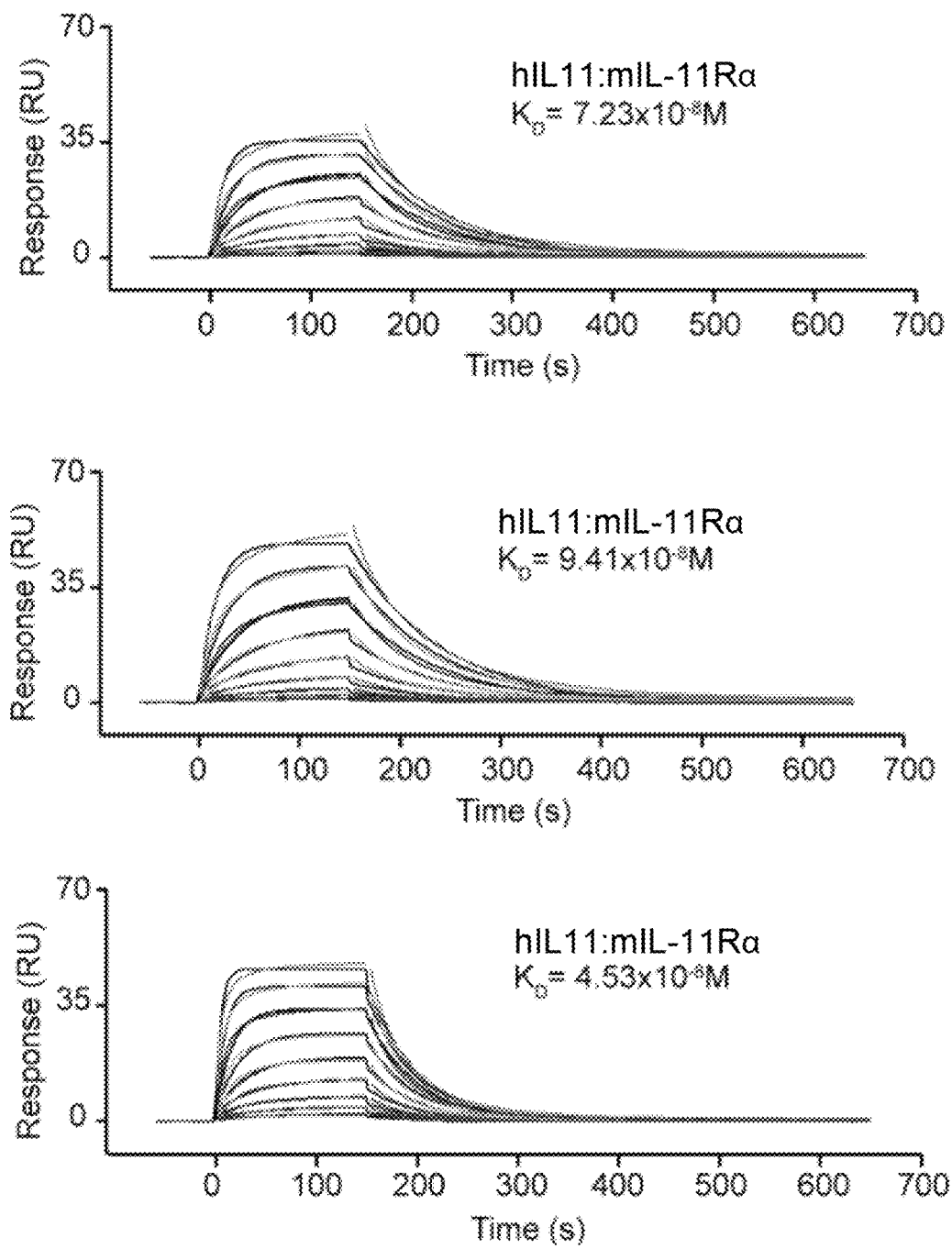
Figure 10J:
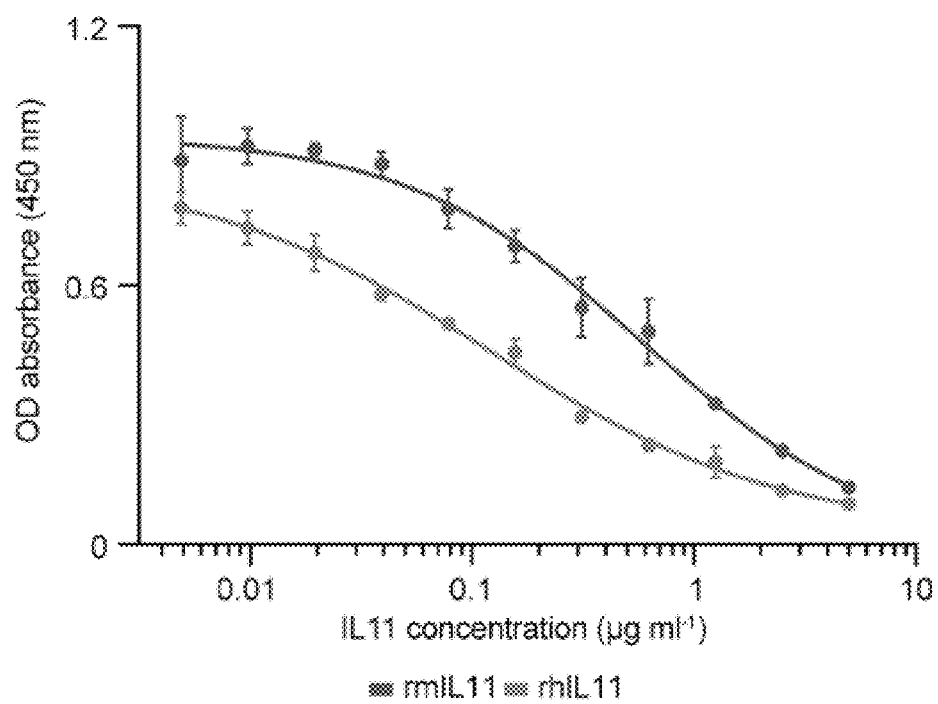
Figure 10K:
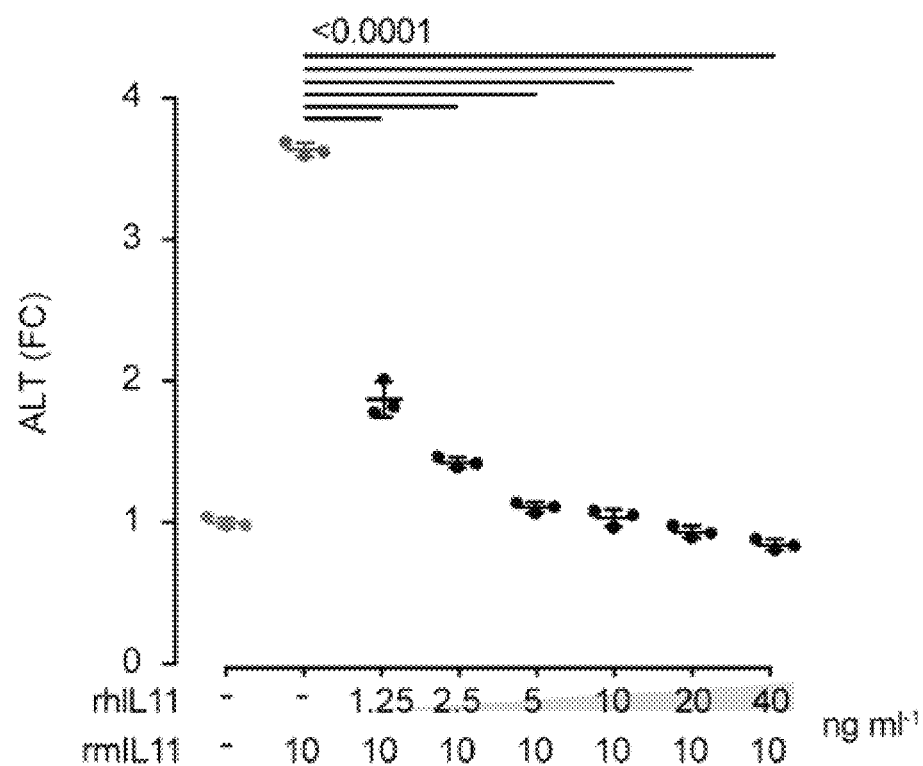
Figure 10L:
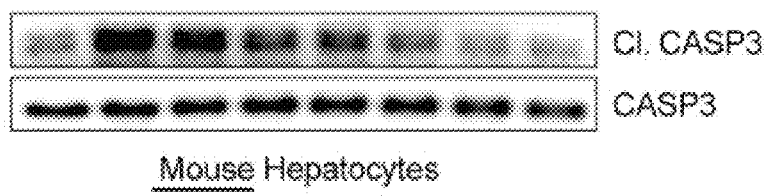

Using surface plasmon resonance (SPR), rhIL11 was found to bind to mouse interleukin 11 receptor alpha chain 1 (mIL11Rα1) with a KD of 72 nM, which is slightly stronger than the rmIL11:mIL11Rα1 interaction (94 nM) and close to that reported previously for rhIL11:hIL11Rα (50 nM), which was reconfirmed (FIG. 10I and FIG. 18E) (24). The inventors then performed a competition ELISA assay and found that rhIL11 competed with rmIL11 for binding to mIL11Rα1 and was a very effective blocker as suggested by the higher affinity to mIL11Rα1 (FIG. 10J). In mouse hepatocytes, rhIL11 was a potent, dose-dependent inhibitor of rmIL11-induced signaling pathways and cytotoxic activity (FIGS. 10K and 10L, and FIG. 18F). Thus, paradoxically, foreign rhIL11 acts as a neutralizer of mouse IL11 both in vitro as in vivo and these observations challenge the understanding of the role of IL11 in liver injury and in disease more broadly.

6.5 Hepatocyte-Specific Expression of Il11 Causes Spontaneous Liver Failure

Figure 11E:
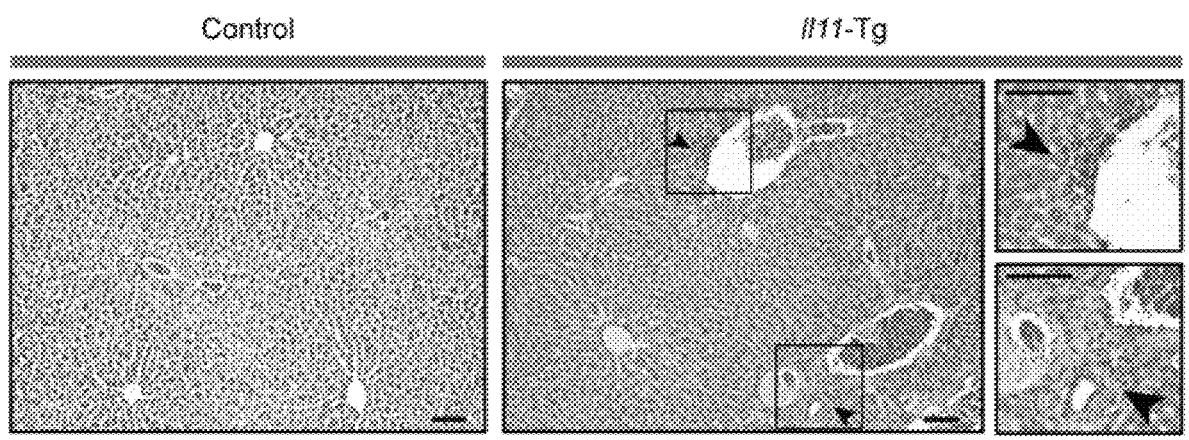
Figure 11F:
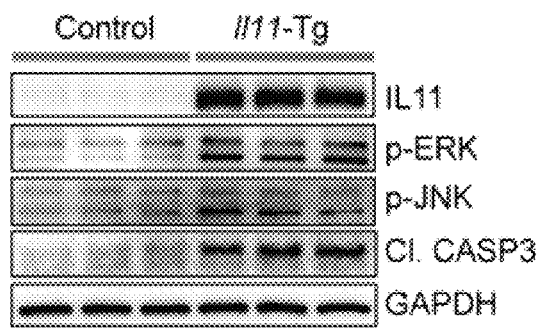
Figure 19B:
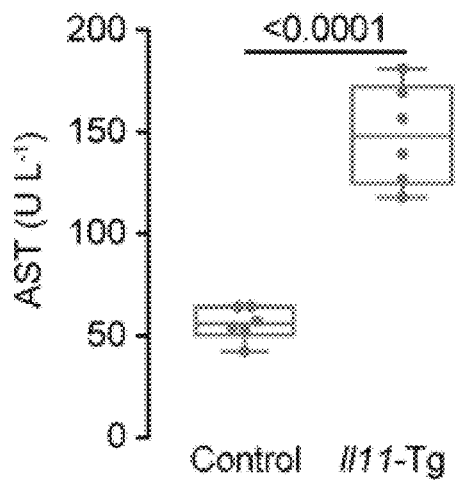
Figure 19C:
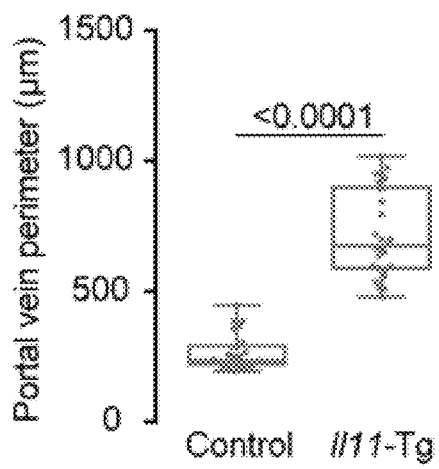
Figure 19D:
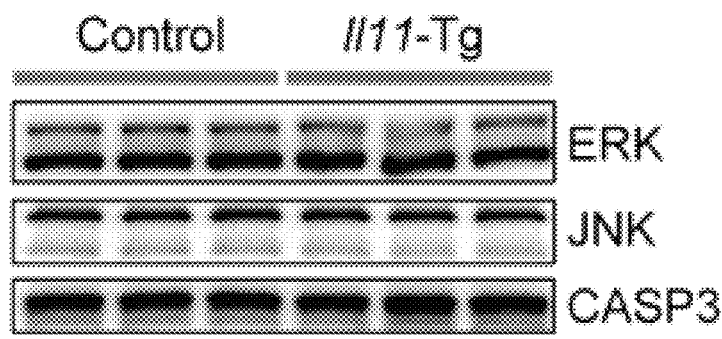
Figure 19E:
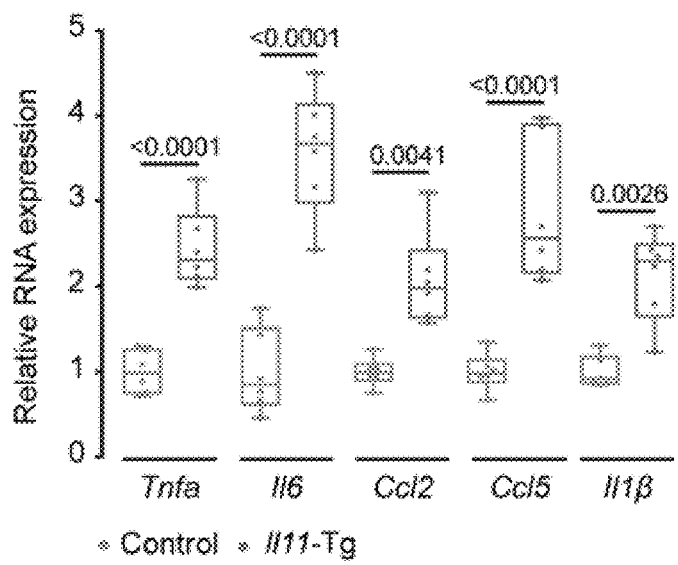
Figure 20A:
Figure 20B:
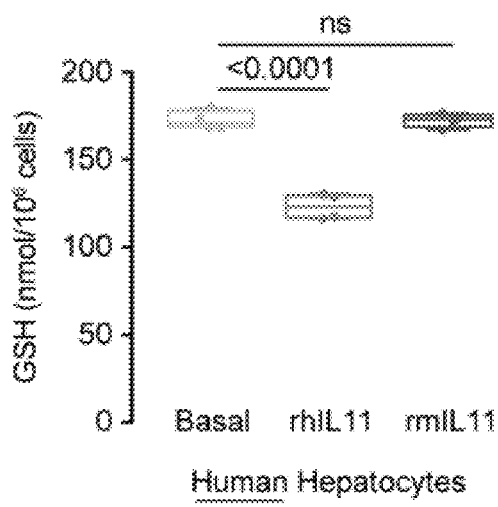
Figure 20C:
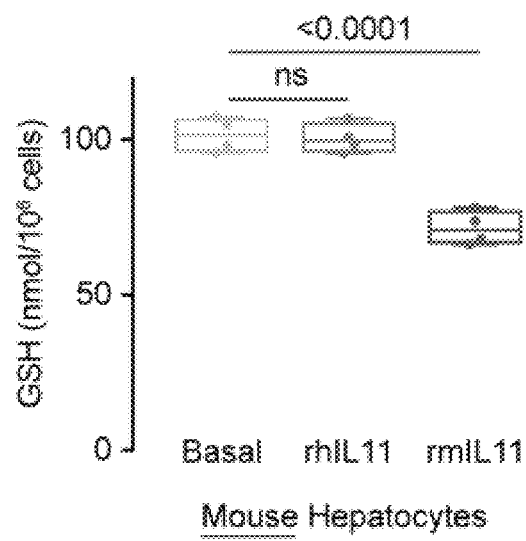
Figure 20D:
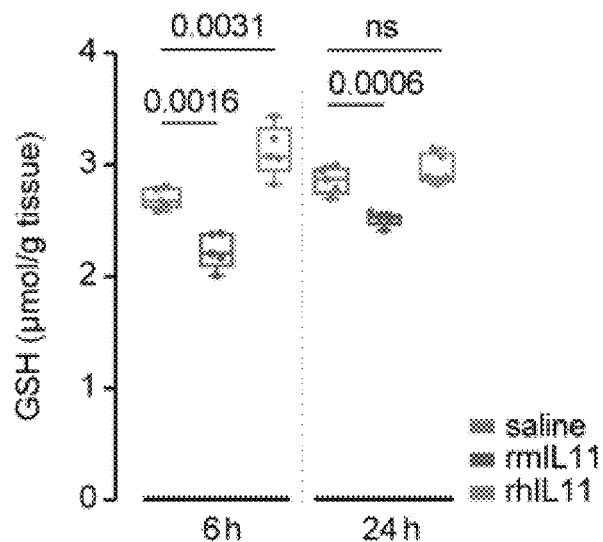

To test the effects of endogenous mouse IL11 secreted from hepatocytes in vivo, an Il11 transgene was expressed specifically in hepatocytes by injecting Rosa26$^{Il11/+}$ mice (15, 16) with AAV8 virus encoding an albumin promoter-driven Cre construct (Il11-Tg mice, FIG. 11A). Three weeks after transgene induction, Il11-Tg mice had grossly abnormal and smaller (38%, P<0.0001) livers with elevated serum ALT and AST levels, while other organs were unaffected (FIGS. 11A to 11D and FIGS. 19A and 19B). Histologically, there was marked portal vein dilatation and blood accumulation in the sinusoids—suggestive of a sinusoidal obstruction syndrome—as well as infiltrates around the portal triad (FIG. 11E and FIG. 19C). Molecular analyses of Il11-Tg livers revealed activation of ERK, JNK, and CASP3 cleavage along with increased pro-inflammatory gene expression (FIG. 11F and FIGS. 19D and 19E). Thus, secretion of IL11 from hepatocytes, as seen with APAP toxicity (FIG. 9), is hepatotoxic.

6.6 IL11 Stimulates NOX4-Mediated Reactive Oxygen Species Production

Figure 11G:
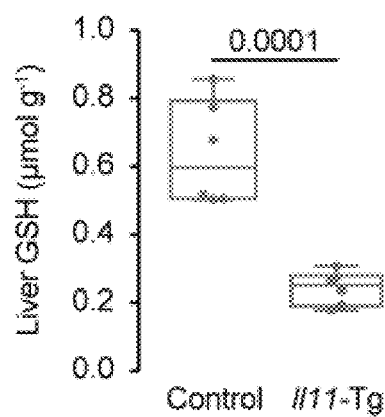

IL11 signaling is required for APAP-driven JNK activation in vitro (FIGS. 9I and 9J), which is known to follow ROS production and GSH depletion. Liver GSH levels were examined in Il11-Tg mice, and found to be diminished (62%, P<0.0001), indicating that IL11 signaling—directly or indirectly—induces ROS (FIG. 11G).

Figure 11H:
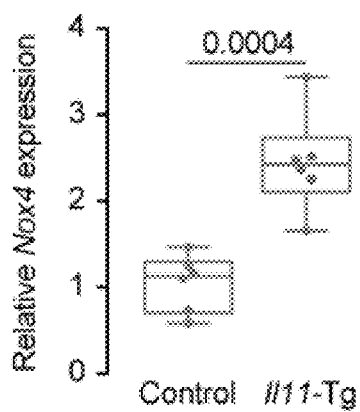
Figure 11I:
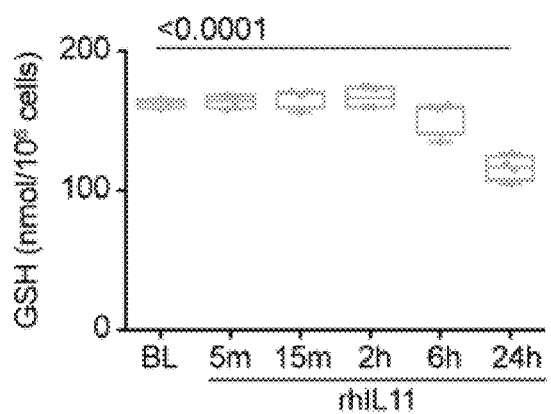
Figure 11J:
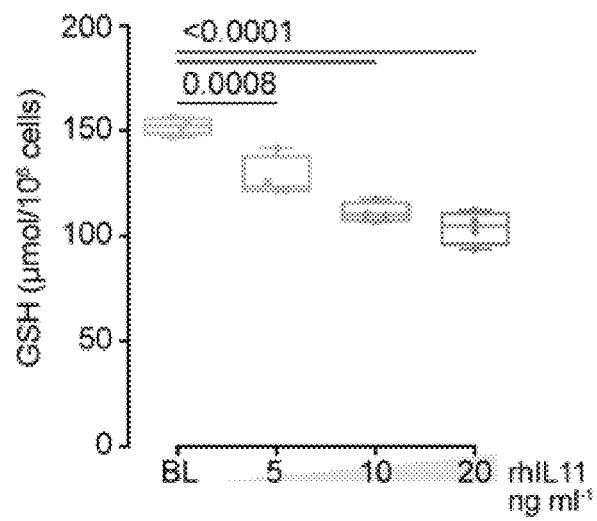
Figure 11K:
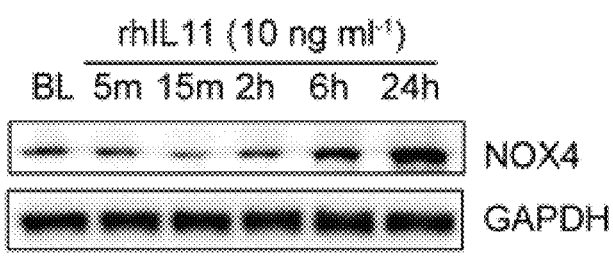
Figure 11L:
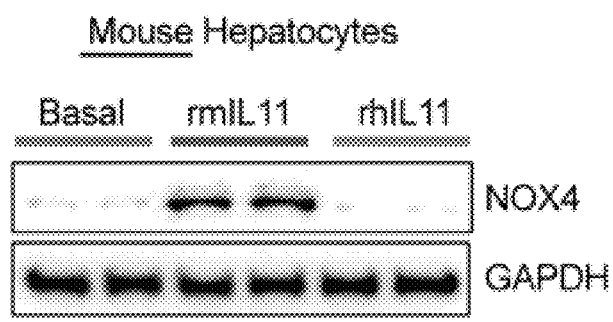

In fibroblasts, the expression of NOX4, an NADPH oxidase, and source of ROS, is strongly associated with IL11 expression (15, 25), and hepatocyte-specific Nox4 deletion prevents pathological activation of JNK (26). Therefore, the inventors investigated the relationship between IL11, NOX4, and ROS in greater detail. In Il11-Tg mice, hepatic Nox4 expression was upregulated (FIG. 11H). In primary human hepatocytes, IL11 stimulated dose-dependent GSH depletion over a time course that mirrored ERK and JNK activation and was accompanied by NOX4 upregulation (FIG. 9G and FIGS. 11I to 11K). As expected, only species-specific IL11 induced NOX4 upregulation and lowered GSH levels (FIG. 11L and FIGS. 20A to 20D).

Figure 11M:
Figure 11N:
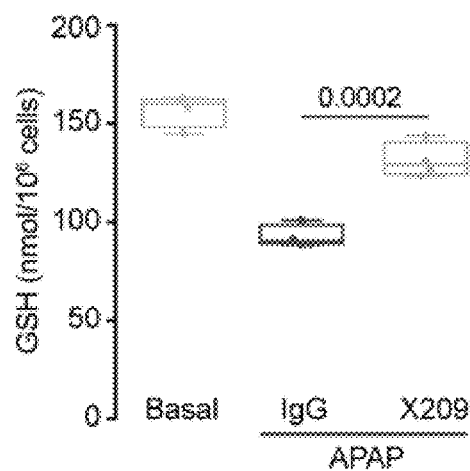
Figure 11O:
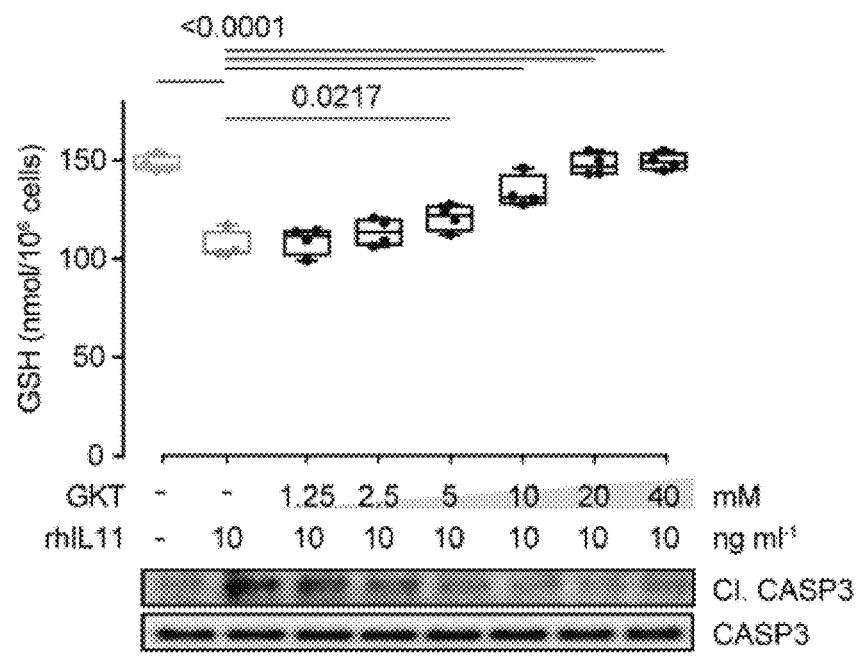
Figure 11P:
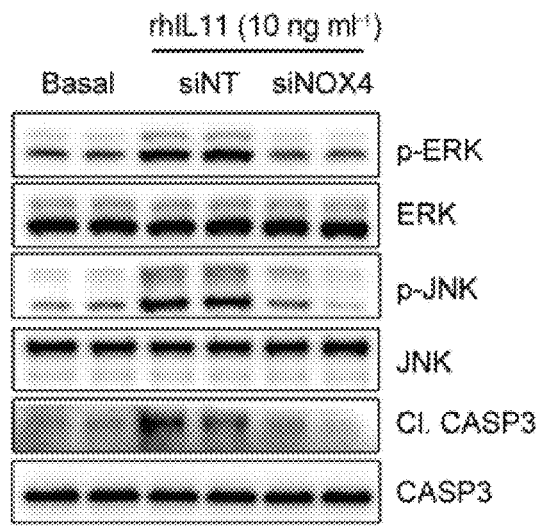
Figure 11Q:
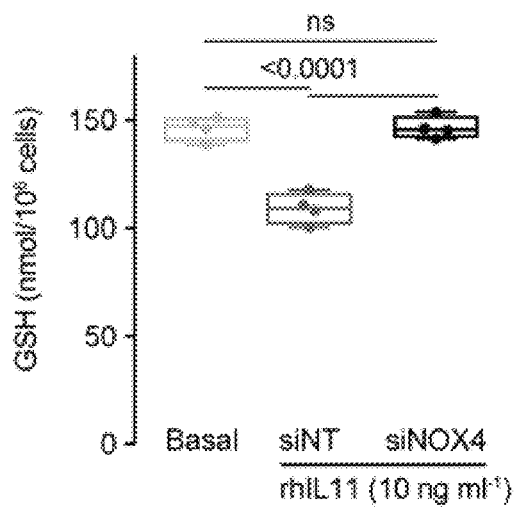
Figure 21A:
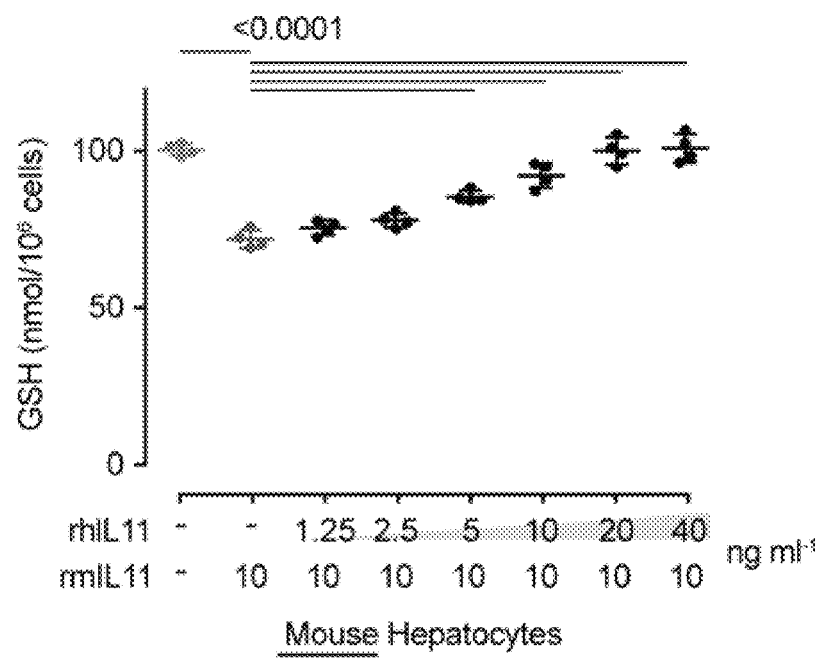
Figure 21B:
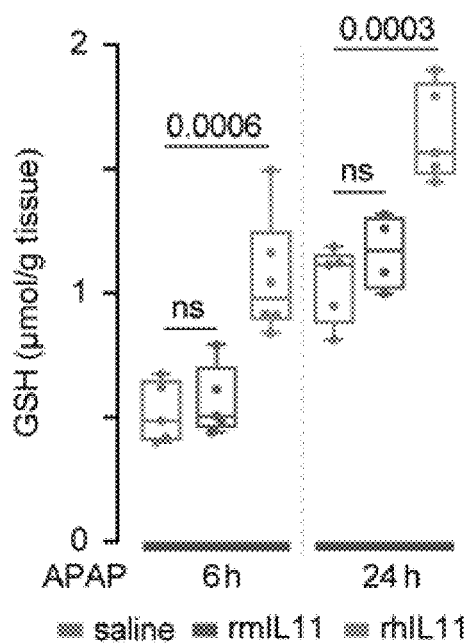

APAP stimulation also resulted in NOX4 upregulation in hepatocytes, coincident with depletion in hepatocyte GSH levels, which was blocked with the anti-IL11Rα antibody X209 (FIGS. 11M and 11N). The inventors reconsidered the effect of rhIL11 in inhibiting endogenous IL11-induced cell death in mouse hepatocytes (FIGS. 10J and 10K) and found clear, dose-dependent effects of rhIL11 in restoring GSH levels in rmIL11 stimulated mouse cells (FIG. 21A). Similarly, rhIL11 restored APAP-induced GSH depletion in the mice, while rmIL11 did not (FIG. 21B). GKT-13781, a specific NOX4 inhibitor, prevented IL11-stimulated GSH depletion, CASP3 activation and cell death in a dose-dependent manner (FIG. 11O and FIGS. 22A and 22B). The specificity of pharmacological inhibition of NOX4 was confirmed using siRNA, which prevented IL11-induced hepatotoxicity (FIGS. 11P and 11Q, and FIGS. 23A and 23B). Together these data show that IL11-stimulated NOX4 activity, which could also impact mitochondrial ROS, is important for GSH depletion in the context of AILI.

Figure 12A:
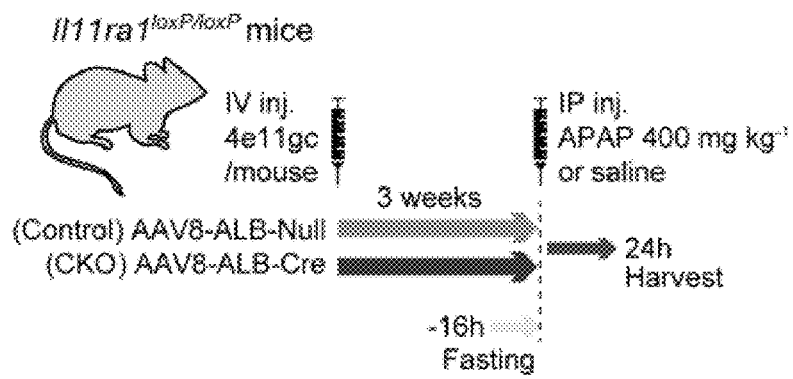
Figure 12B:
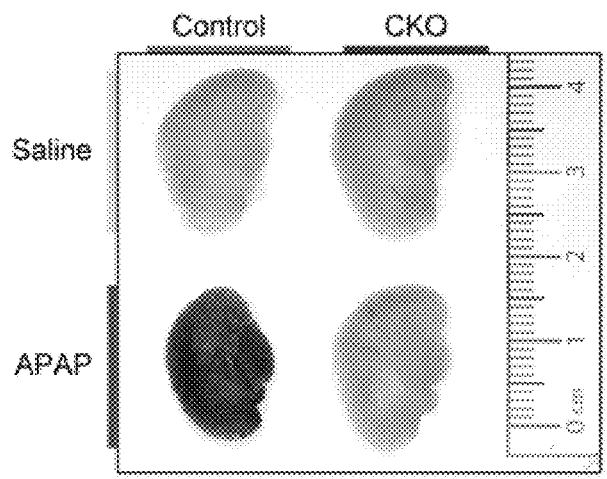
Figure 12C:
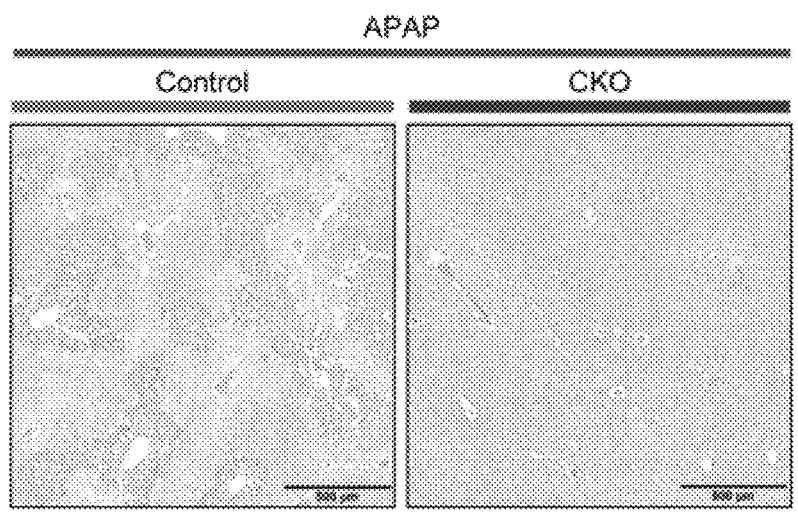
Figure 12D:
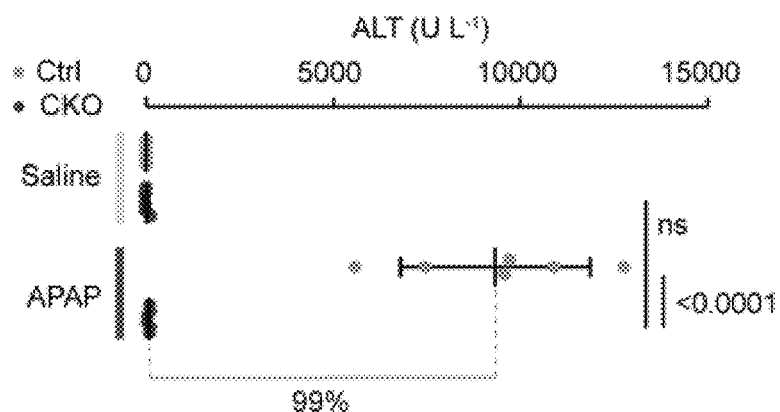
Figure 12E:
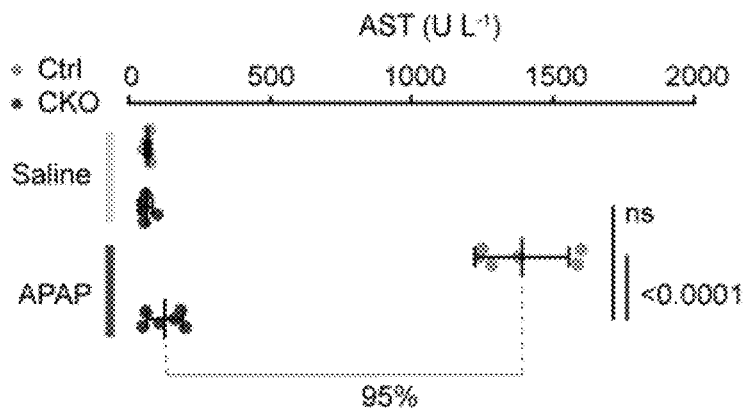
Figure 12F:
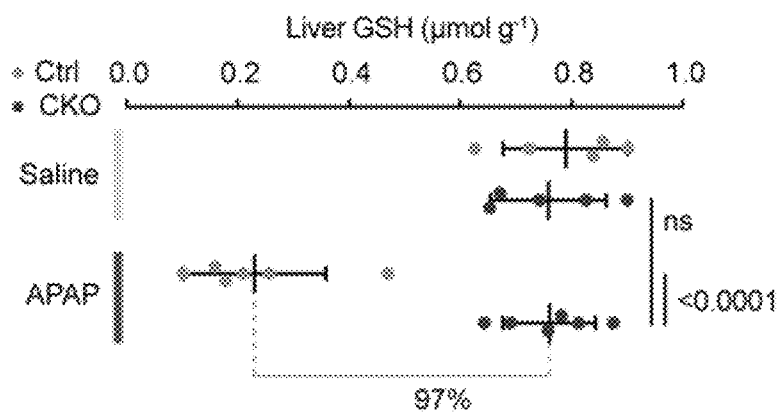

6.7 Hepatocyte-Specific Deletion of Il11Ra1 Prevents APAP-Induced Liver Failure To delete Il11ra1 specifically in adult mouse hepatocytes Il11ra1 conditional knockouts (CKOs) were created by injecting AAV8-ALB-Cre virus to mice homozygous for LoxP-flanked Il11ra1 alleles, along with wildtype controls. Three weeks after viral infection, control mice and CKOs were administered APAP (400 mg kg$^{-1}$) (FIG. 12A). The day after APAP administration, gross anatomy revealed small and discolored livers in control mice, whereas livers from CKO mice looked normal (FIG. 12B). Histology showed typical and extensive centrilobular necrosis in control mice, which was not observed in CKOs (FIG. 12C).

Figure 12G:
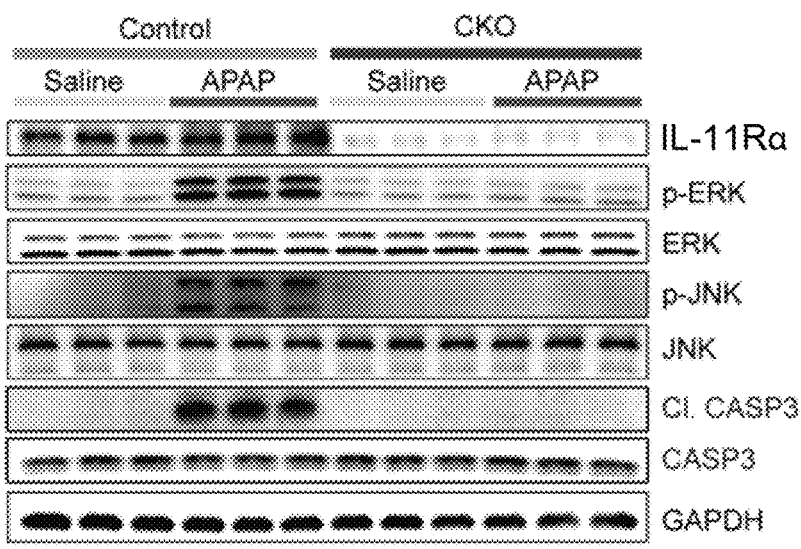
Figure 12H:
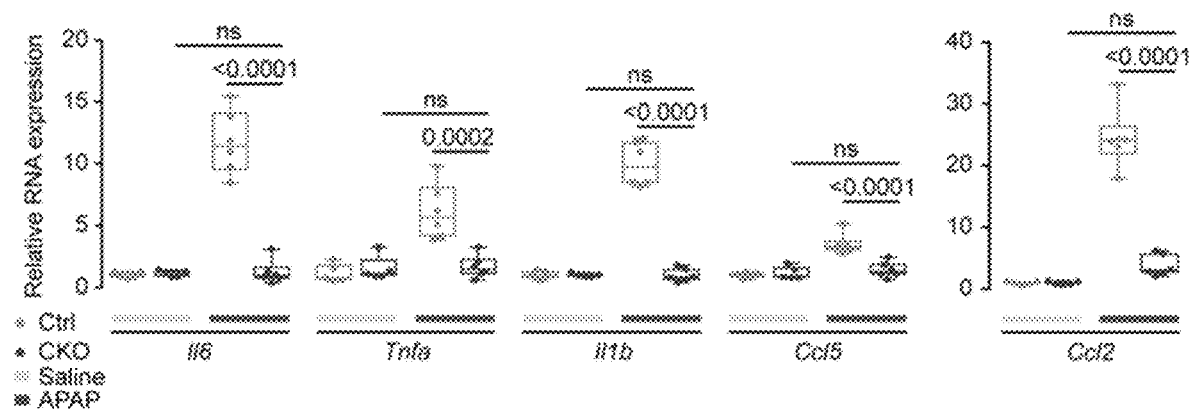

Strikingly, CKO mice had 99% and 95% lower ALT and AST levels, respectively, as compared to controls and GSH levels that were similar to baseline. Both groups had similar levels of APAP and APAP-Glutathione (APAP metabolite) in the serum and thus Il11ra1 deletion does not impact APAP metabolism (FIGS. 12D to 12F, and FIGS. 24A and 24B). ERK and JNK activation was observed in control mice, but not in the CKOs (FIG. 12G). Deletion of the receptor in hepatocytes also significantly reduced inflammatory markers, suggesting that inflammation in AILI is secondary to parenchymal injury. (FIG. 12H). Taken together, these data show a dominant role for hepatocyte-specific IL11 signaling in the pathogenesis of AILI. The fact that Il11ra1 deletion in hepatocytes is sufficient to protect from APAP OD indicates that free soluble Il11Rα1 in the serum or receptor shedding from other cellular sources does not contribute to disease pathogenesis via trans-signaling.

6.8 Effects of Anti-IL11Rα Administration Early During APAP-Induced Liver Injury The inventors next tested if therapeutic inhibition of IL11 signaling was effective in mitigating AILI by administering anti-Il11Rα (X209) antibody (14). Initially, a preventive treatment was performed by injecting X209 or control antibody (10 mg kg$^{-1}$) 16 h prior to APAP. This approach reduced serum markers of liver damage by over 70%, largely restored hepatic GSH levels, and limited histological evidence of centrilobular necrosis (FIGS. 13A to 13D, and FIG. 25A).

Next, anti-IL11Rα therapy was administered in a therapeutically-relevant mode by giving antibody 3 h after APAP, a time point by which APAP metabolism and toxicity is established and after which most interventions have no effect in the mouse model of AILI (FIG. 13E) (9). X209, across a range of doses (2.5-10 mg kg$^{-1}$), inhibited AILI with dose-dependent improvements in markers of liver damage and in hepatic GSH levels. Reduced JNK and ERK activation confirmed dose-dependent target coverage (FIGS. 13F to 13H, and FIG. 25B).

Figure 13I:
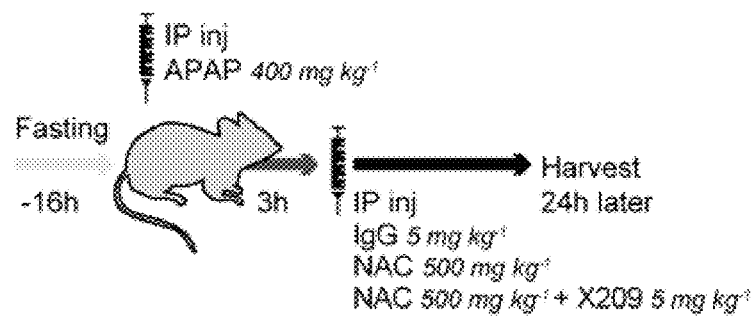
Figure 13J:
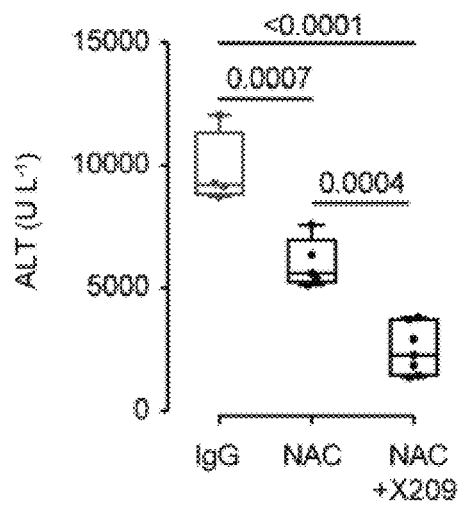
Figure 13K:
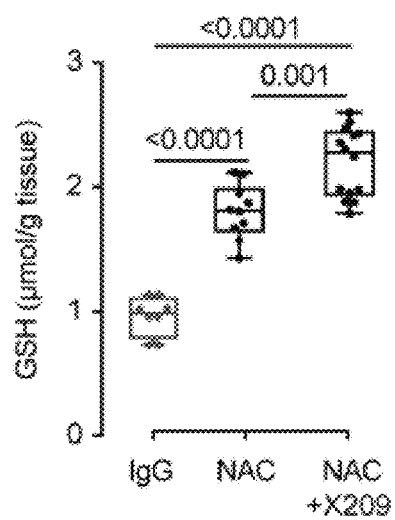
Figure 13L:
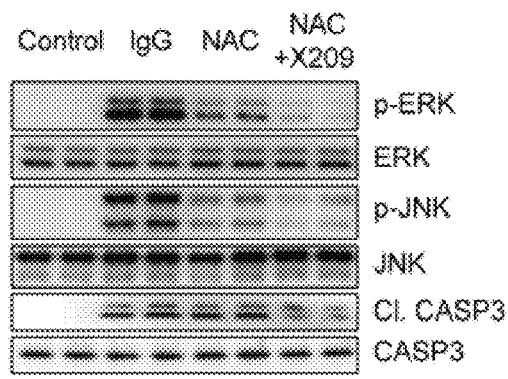

Lastly, it was determined whether inhibiting IL11 signaling had added value when given in combination with the current standard of care, NAC, 3 h after APAP dosing (FIG. 13I). Administration of NAC alone reduced serum levels of ALT and AST. However, NAC in combination with X209 was even more effective than either NAC or X209 alone (ALT reduction: NAC, 38%, P=0.0007; X209, 47%, P<0.0001; NAC+X209, 75%; P<0.0001) (FIGS. 13F, 13J and FIG. 25C). At the molecular level, the degree of ERK and JNK inhibition with NAC or NAC together with X209 mirrored the magnitude of ALT reduction in the serum and the restoration of hepatic GSH levels (FIGS. 13K and 13L). As such, anti-IL11Rα therapy has added benefits when given in combination with the current standard of care.

6.9 Liver Regeneration with Anti-IL11Rα Therapy

Figure 14F:
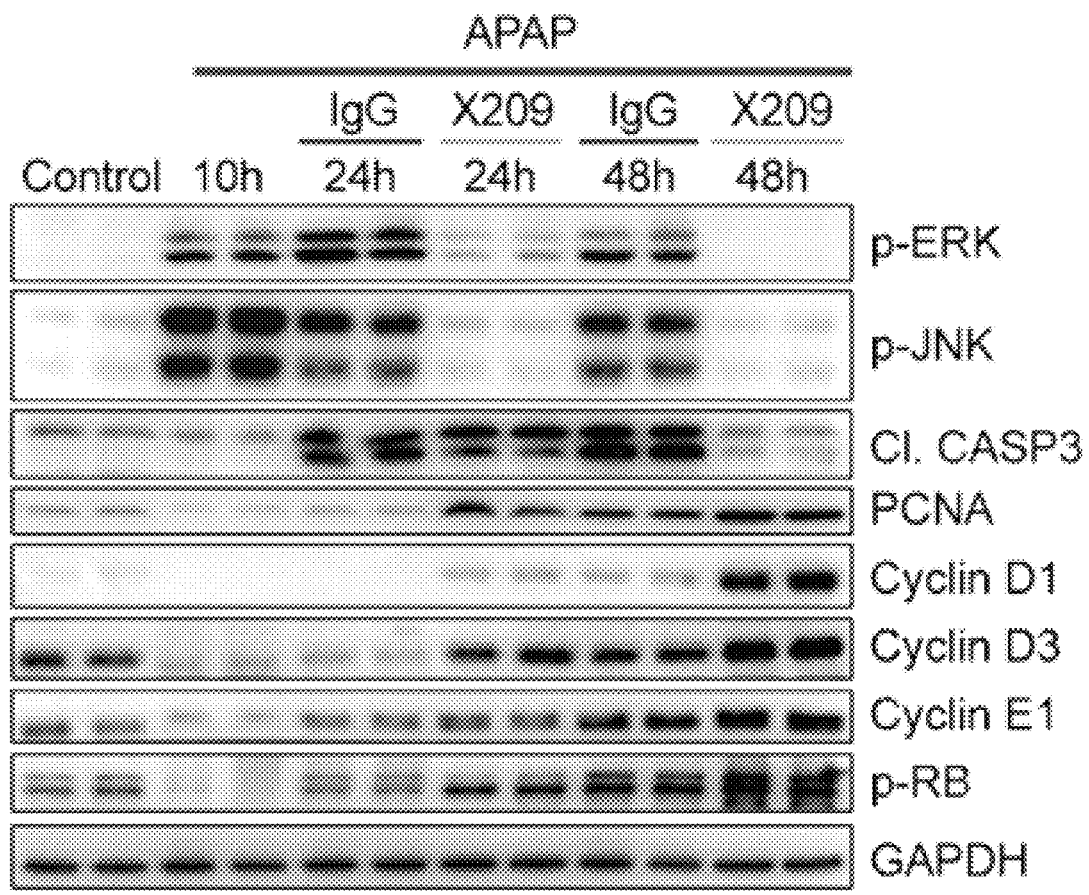

For patients presenting to the emergency room 8 h or later after APAP OD there is no effective treatment. This prompted us to test anti-IL11Rα 10 h after APAP (400 mg $kg^{-1}$) administration to mice (FIG. 14A). Given the accelerated metabolism of APAP in the mouse, therapy at 10 h in this model is equivalent to the treatment of a human up to 24 h post-APAP OD. APAP and APAP-Glutathione were quantified in serum by mass spectrometry and found levels to be elevated compared to saline-treated controls and equivalent between experimental groups, as expected (FIGS. 26A and 26B). Analysis of gross anatomy, histology and serum IL11, ALT and AST levels revealed that X209 largely reversed liver damage by the second day after APAP, whereas IgG treated mice had profound and sustained liver injury (FIGS. 14B to 14E, and FIG. 27A). The therapeutic antibody effectively blocked ERK and JNK activation throughout the course of the experiment and this preceded a reduction in cleaved CASP3 at 24 h (FIG. 14F and FIG. 27B).

Figure 14G:
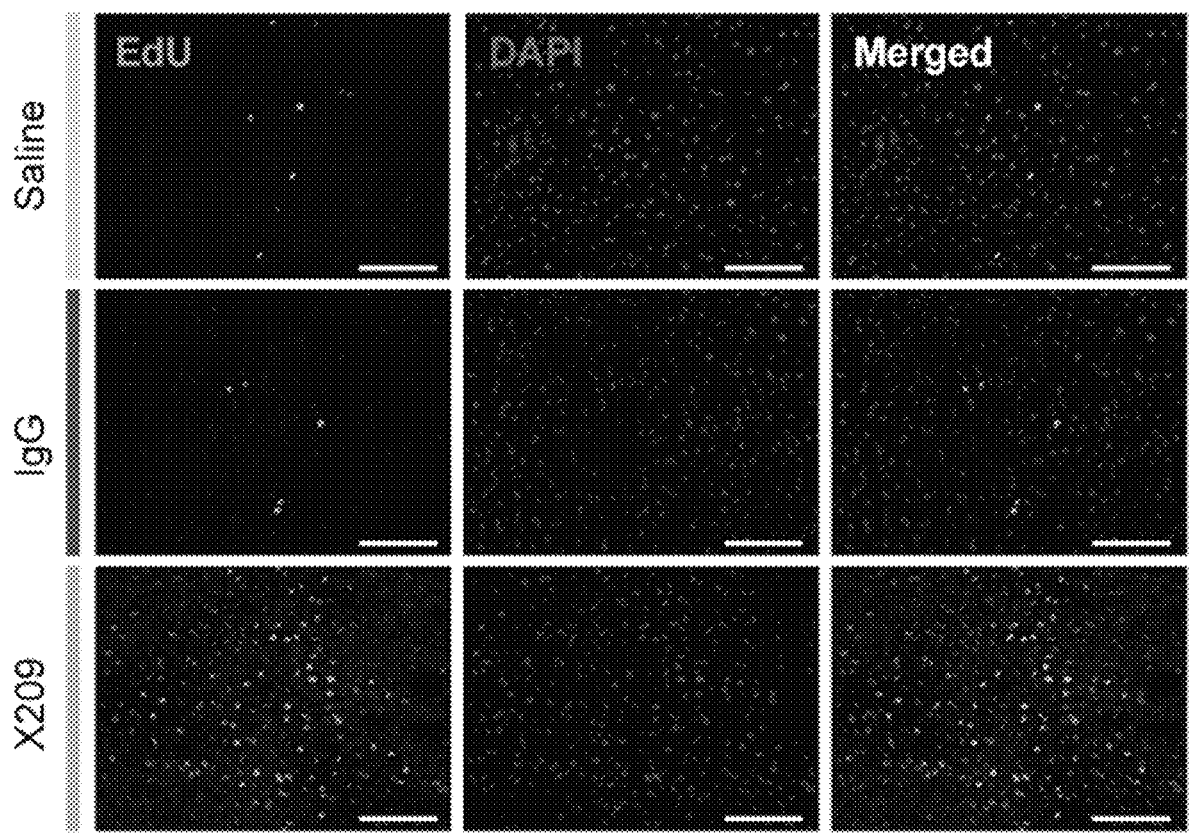
Figure 14H:
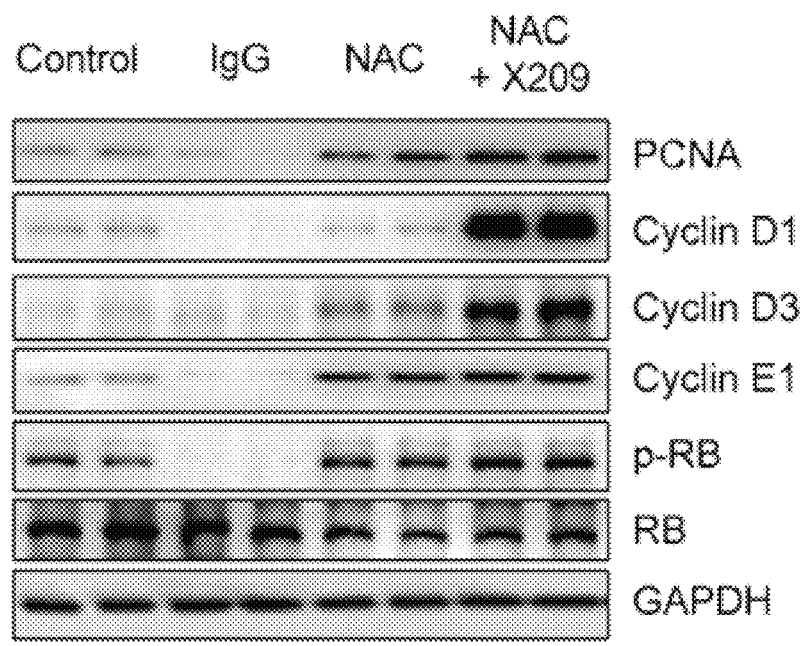

Interventions promoting liver regeneration, which has very large potential, may provide a new means of treating AILI (12). The status of genes important for liver regeneration was therefore assessed (10). Inhibition of IL11 signaling was associated with a robust signature of regeneration with strong upregulation of PCNA, Cyclin D1/D3/E1, and phosphorylation of RB, as seen during regeneration following partial hepatectomy (10). EdU injection and histological analyses showed very large numbers of nuclei with evidence of recent DNA synthesis in X209-treated mice as compared to controls (FIG. 14G). The effects X209 given 3 h post-APAP (FIG. 13I to 13L) was reassessed to see if regeneration was also associated with inhibition of IL11 signaling at earlier time points. This proved to be the case, and the combination of X209 and NAC was more effective than NAC alone in increasing molecular markers of regeneration, notably for Cyclin D1 and D3 (FIG. 14H).

Figure 14I:
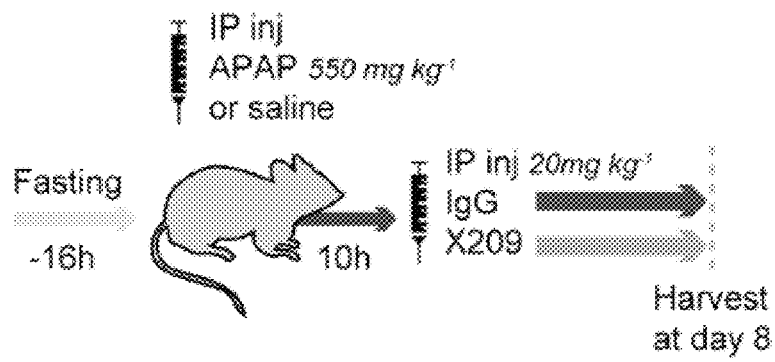
Figure 14J:
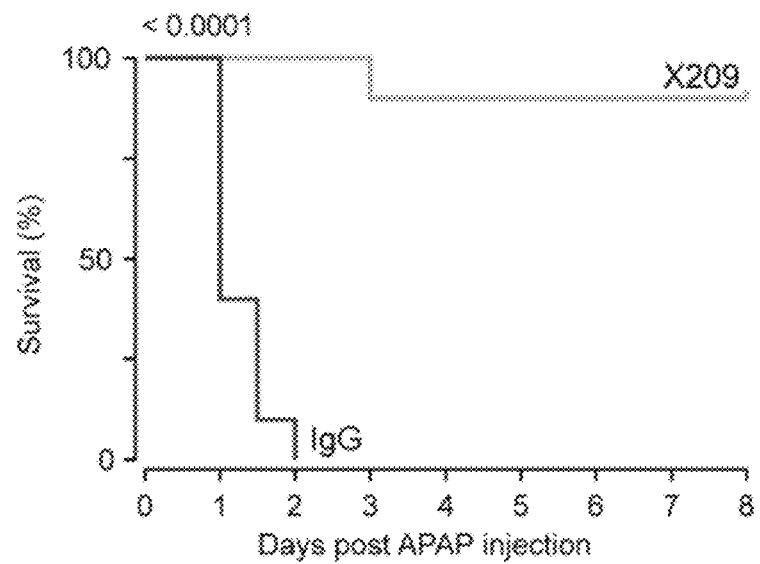
Figure 14K:
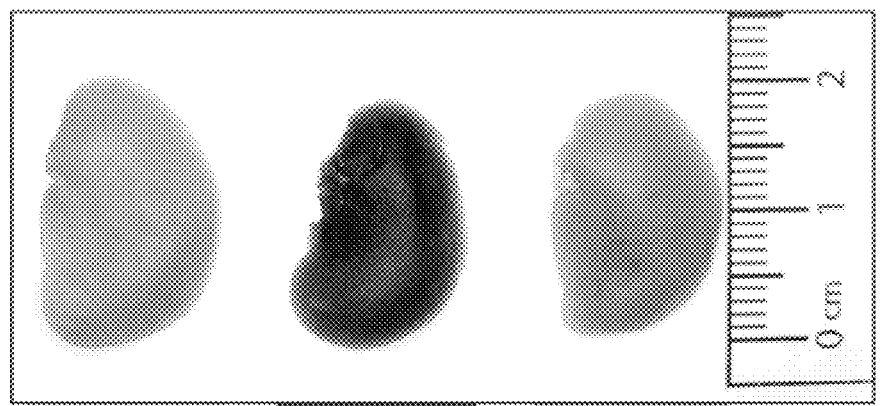

Finally, X209 (20 mg $kg^{-1}$) 10 h after a higher and lethal acetaminophen dose (550 mg $kg^{-1}$) at a time point when mice were moribund and livers undergoing fulminant necro-inflammation (FIG. 14I). X209-treated mice recovered and had a 90% survival by the study end. In contrast, IgG-treated mice did not recover and succumbed with a 100% mortality within 48 h, (FIG. 14J). On day 8 after the lethal dose of APAP, X209-treated mice appeared healthy with normal liver morphology and ALT levels were comparable to controls that had not received APAP (FIG. 14K, and FIGS. 28A and 28B).

6.10 Discussion

APAP OD is common with up to 50,000 individuals attending emergency departments every year in the UK, some who develop liver failure requiring transplantation (1). Here, IL11, which has previously been reported as protective against APAP-induced liver failure (17, 20), liver ischemia (18, 21), endotoxemia (22) and inflammation (19), is shown to actually be hepatotoxic and of central importance for liver failure following APAP OD.

The observation that endogenous IL11 is hepatotoxic is most surprising as over 30 publications have reported cytoprotective and/or anti-inflammatory effects of rhIL11 in rodent models of human disease (Tables 1 and 2). rhIL11 is shown to be a competitive inhibitor of mouse IL11 binding to IL11Rα1, which overturns previous understanding of the role of IL11 in AILI and liver disease more generally. This also implies that anti-IL11 therapies may be effective in additional diseases where rhIL11 had protective effects in mouse models such as rheumatoid arthritis (27) and colitis (28), among others (Table 2). Based on the erroneous assumption that rhIL11 effects in mice embodied beneficial IL11 gain-of-function, a number of clinical trials using rhIL11 were performed in patients (Table 3).

TABLE 1

List of publications showing protective effects of recombinant human IL11 (rhIL11) in rodent models of liver injury

| | |
|---|---|
| Yu et al. 2016. "*Interleukin-11 Protects Mouse Liver from Warm Ischemia/reperfusion (WI/Rp) Injury.*" *Clinics and Research in Hepatology and Gastroenterology* 40 (5): 562-70 | In vivo administration of rhIL11 (500 µg/kg, IV) prior to WI/Rp injury protects mouse livers. In vitro, pre-treatment with rhIL11 (2 µg/mL, 12 hours) reduces murine hepatocyte apoptosis due to hypoxia/reperfusion. |
| Zhu et al. 2015. "*IL-11 Attenuates Liver Ischemia/Reperfusion Injury (IRI) through STAT3 Signaling Pathway in Mice.*" *PloS One* 10 (5): e012629. | Hepatoprotective effects of rhIL11 in mice subjected to a single injection of rhIL11 (500 µg/kg, IP) one hour prior to IRI. In vitro, murine hepatocytes were treated with 1 µg/ml of rhIL11. |
| Nishina et al. 2012. "*Interleukin-11 Links Oxidative Stress and Compensatory Proliferation.*" *Science Signaling* 5 (207): ra5. | Administration of rhIL11 receptor superagonist, ($N_T$-3N, 500 µg/kg) 2 hours prior to acetaminophen (APAP) injection reduces acute liver injury in mice. |
| Maeshima et al. 2004. "*A Protective Role of Interleukin 11 on Hepatic Injury in Acute Endotoxemia.*" *Shock* 21 (2): 134-38. | The authors conclude that rhIL11 (150 µg/kg, IP) plays a significant protective role in LPS-induced hepatic injury (acute endotoxemia) in rats. |
| Trepicchio et al. 2001. "*Protective Effect of rhIL-11 in a Murine Model of Acetaminophen-Induced Hepatotoxicity.*" *Toxicologic Pathology* 29 (2): 242-249. | The authors indicate a protective role of rhIL11 (250 or 500 µg/kg, SC) against acetaminophen-induced liver damage, in which rhIL11 was injected to mice 2 hours before acetaminophen administration. |
| Bozza et al. 1999. "*Interleukin-11 Reduces T-Cell-Dependent Experimental Liver Injury in Mice.*" *Hepatology* 30 (6): 1441-47. | Administration of rhIL11 (50-500 µg/kg, IP) 2 hours prior to Concanavalin A-induced T-cell-mediated hepatotoxicity reduces liver necrosis and enhanced survival in mice. |

TABLE 2

List of publications showing protective and/or anti inflammatory effects of rhIL11 in other rodent disease models

| Category | Reference | Description |
| --- | --- | --- |
| Bowel | Gibson et al. 2010. "*Interleukin-11 Reduces TLR4-Induced Colitis in TLR2-Deficient Mice and Restores Intestinal STAT3 Signaling.*" *Gastroenterology* 139 (4): 1277-88. | The authors report that administration of rhIL11 (5 µg/kg, IP) ameliorates infection colitis and is cytoprotective in TLR2-deficient mice. |
| | Boerma et al. 2007. "*Local Administration of Interleukin-11 Ameliorates Intestinal Radiation Injury in Rats.*" *Cancer Research* 67 (19): 9501-6. | The authors conclude that IL11 ameliorates early intestinal radiation injury, in which rats were given daily injections of rhIL11 (2 mg/kg/d) from 2 days prior until 2 weeks after irradiation. |
| | Opal et al. 2003. "*Orally Administered Recombinant Human Interleukin-11 Is Protective in Experimental Neutropenic Sepsis.*" *The Journal of Infectious Diseases* 187 (1): 70-76. | The authors suggest that IL11 maintains epithelial cell integrity during cytoreductive chemotherapy by cyclophosphamide based on effects observed in rats receiving daily oral administration of rhIL11 (0.5 mg/kg/day), starting from 1 day before the first dose of cyclophosphamide for a total of 12 days. |
| | Ropeleski et al. 2003. "*Interleukin-11-Induced Heat Shock Protein 25 Confers Intestinal Epithelial-Specific Cytoprotection from Oxidant Stress.*" *Gastroenterology* 124 (5): 1358-68. | The authors conclude that IL11 confers epithelial-specific cytoprotection during intestinal epithelial injury. Rat, mouse and canine cell lines (IEC-18, YAMC, NIH3T3, MDCK-HR) were stimulated with high (50-100 ng/ml) levels of rhIL11. |
| | Greenwood-Van Meerveld et al 2000. "*Recombinant Human Interleukin-11 Modulates Ion Transport and Mucosal Inflammation in the Small Intestine and Colon.*" *Laboratory Investigation; a Journal of Technical Methods and Pathology* 80 (8): 1269-80. | The authors conclude that during intestinal inflammation IL11 acts as a modulator of epithelial transport or as an anti-inflammatory cytokine based on effects of rhIL11 on rat mucosal sheets (10-10,000 ng/ml) and in rats (33 µg/kg, alternate days for 1 or 2 weeks). |
| | Du et al 1997. "*Protective Effects of Interleukin-11 in a Murine Model of Ischemic Bowel Necrosis.*" *American Journal of Physiology-Gastrointestinal and Liver Physiology.* | Administration of rhIL11 (250 µg/kg/day) for 3 days prior to and for 7 days post bowel ischemia induction confers a protective effect against ischemic bowel necrosis and the authors suggest its use as a treatment for gastrointestinal mucosal diseases. |
| | Orazi et al. 1996. "*Interleukin-11 Prevents Apoptosis and Accelerates Recovery of Small Intestinal Mucosa in Mice Treated with Combined Chemotherapy and Radiation.*" *Laboratory Investigation; a Journal of Technical Methods and Pathology* 75 (1): 33-42. | Administration of rhIL11 (250 µg/kg) promotes recovery from chemotherapy and radiation-induced damage to the mice small intestinal mucosa. |
| | Potten et al 1996. "*Protection of the Small Intestinal Clonogenic Stem Cells from Radiation-Induced Damage by Pretreatment with Interleukin 11 Also Increases Murine Survival Time.*" *Stem Cells.* 1996 14(4): 452-9. | RhIL11 (100 µg/kg, SC), administered to mice prior to and after cytotoxic exposure, protects clonogenic cells in intestinal crypts and increases murine survival times following radiation exposure. |
| | Qiu et al. 1996. "*Protection by Recombinant Human Interleukin-11 against Experimental TNB-Induced Colitis in Rats.*" *Digestive Diseases and Sciences* 41 (8): 1625-30. | The authors describe protective effects of rhIL11 in trinitrobenzene sulfonic acid-induced colitis in rats. Rats were injected daily with rhIL11 (100, 300, or 1000 µg/kg, SC) 3 days before, or daily for 3-7-14 days after TNB administration. |
| | Du et al. 1994. "*A Bone Marrow Stromal-Derived Growth Factor, Interleukin-11, Stimulates Recovery of Small Intestinal Mucosal Cells after Cytoablative Therapy.*" *Blood* 83 (1): 33-37. | Administration of rhIL11 (250 µg/kg/d, SC) promotes recovery of small intestinal mucosa following combination radiation and chemotherapy in mice. |
| Heart | Tamura et al. 2018. "*The Cardioprotective Effect of Interleukin-11 against Ischemia-Reperfusion Injury in a Heart Donor Model.*" *Annals of Cardiothoracic Surgery* 7 (1): 99-105. | Administration of rhIL11 (18 µg/ml, IV, 10 minutes prior to heart collection) preserves heart function and lower apoptosis index in rat following ex vivo model of cold ischemia. |
| | Obana et al. 2012. "*Therapeutic Administration of IL-11 Exhibits the Postconditioning Effects against Ischemia-Reperfusion Injury via STAT3 in the Heart.*" *American Journal of Physiology. Heart and Circulatory Physiology* 303 (5): H569-77. | Administration of rhIL11 (20 µg/kg, IV at the start of reperfusion) prevents adverse cardiac remodeling and apoptosis after ischemia reperfusion injury-induced acute myocardial infarction in mice |
| | Obana et al. 2010. "*Therapeutic Activation of Signal Transducer and Activator of Transcription 3 by Interleukin-11 Ameliorates Cardiac Fibrosis after Myocardial Infarction.*" *Circulation* 121 (5): 684-91. | Administration of rhIL11 (8 µg/kg, IV) 24 hours following left coronary artery ligation-induced myocardial infarction (MI) and then consecutively every 24 hours for 4 days reduces post-MI scar volume in mice. |
| | Kimura et al. 2007. "*Identification of Cardiac Myocytes as the Target of Interleukin 11, a Cardioprotective Cytokine.*" *Cytokine* 38 (2): 107-115 | The authors conclude that IL11 is a cardioprotective based on effects of rhIL11 (8 µg/kg) administered to mouse 15 hours prior to cardiac ischemia-reperfusion |
| Immune System | Bozza et al. 2001. "*Interleukin-11 Modulates Th1/Th2 Cytokine Production from Activated CD4 T Cells.*" *Journal of Interferon & Cytokine Research* 21(1): 21-30. | The authors state that IL11 acts directly on activated murine CD4+ve T-cells and modulates, not represses, the immune response following stimulation with rhIL11 (1-500 ng/ml). |
| | Opal et al. 2000. "*Recombinant Human Interleukin-11 Has Anti-inflammatory Actions Yet Does Not Exacerbate Systemic Listeria Infection.*" *The Journal of Infectious Diseases* 181(2): 754-756 | Daily administration of rhIL11 (150 mg/kg, IV) for 7 days prior to *Listeria* infection reduces interferon-γ levels. Interestingly, the authors stated that inflammatory markers IL-6/IFN-γ trend down after anti-IL11mAb (10 mg/kg) treatment. |
| | Hill et al. 1998. "*Interleukin-11 Promotes T Cell Polarization and Prevents Acute Graft-versus-Host Disease after Allogeneic Bone Marrow* | The authors conclude that IL11 prevents Graft-vs-Host-Disease (GVHD) via T Cell polarization, based on experiments in which a high dose of rhIL11 (250 µg/kg, SC, twice daily) was injected into |

TABLE 2-continued

List of publications showing protective and/or anti inflammatory effects of rhIL11 in other rodent disease models

| | | |
|---|---|---|
| | Transplantation." *The Journal of Clinical Investigation* 102(1): 115-23. | a murine model of GVHD. |
| | Sonis et al. 1997. "*Mitigating Effects of Interleukin 11 on Consecutive Courses of 5-Fluorouracil-Induced Ulcerative Mucositis in Hamsters.*" *Cytokine* 9 (8): 605-12. | Administration of rhIL11 (50-100 µg/animal/day, SC) protects from 5-fluorouracil-induced ulcerative mucositis in hamsters. |
| | Trepicchio et al. 1997. "*IL-11 Regulates Macrophage Effector Function through the Inhibition of Nuclear Factor-kappaB.*" *Journal of Immunology* 159 (11): 5661-70. | The authors conclude that IL11 inhibits the secretion of pro-inflammatory cytokines by macrophages; murine primary macrophages were treated with rhIL11 (10-100 ng/ml). |
| | Trepicchio et al. 1996. "*Recombinant Human IL-11 Attenuates the Inflammatory Response through down-Regulation of Proinflammatory Cytokine Release and Nitric Oxide Production.*" *Journal of Immunology* 157 (8): 3627-34. | The authors report that IL11 reduces levels of TNF-α, IL-1β and IFN-γ in the serum of LPS-treated mice and in LPS-stimulated macrophage media. Mice and murine macrophages were treated with rhIL11 (500 µg/kg or 10-100 ng/ml, respectively). |
| Joint | Anguita et al. 1999. "*Selective Anti-Inflammatory Action of Interleukin-11 in Murine Lyme Disease: Arthritis Decreases While Carditis Persists.*" *The Journal of Infectious Diseases* 179 (3): 734-37. | Administration of rhIL11(0.1-2 µg/mouse/day, 5 days/week for 3 weeks) reduces arthritis, but not carditis, in *Borrelia burgdorferi*-infected mice (a murine model of Lyme disease). |
| | Walmsley et al. 1998. "*An Anti-Inflammatory Role for Interleukin-11 in Established Murine Collagen-Induced Arthritis.*" *Immunology* 95 (1): 31-37. | Daily administration of rhIL11 (0.3-100 µg/mouse/day, IP, 10 days) reduces inflammation in a murine model of collagen-induced arthritis. |
| Kidney | Lee et al. 2012. "*Interleukin-11 Protects against Renal Ischemia and Reperfusion Injury.*" *American Journal of Physiology. Renal Physiology* 303 (8): F1216-24. | The authors conclude that IL11 is renoprotective based on pre-treatment (10 minutes prior to IR) and post-treatment (30-60 minutes following IR) effects of rhIL11 and PEGylated rhIL11 (100-1000 µg/kg, IP) in mice. |
| | Stangou et al. 2011. "*Effect of IL-11 on Glomerular Expression of TGF-Beta and Extracellular Matrix in Nephrotoxic Nephritis in Wistar Kyoto Rats.*" *Journal of Nephrology* 24 (1): 106-111. | Administration of rhIL11 (800-1360 µg/kg, IP) 2 hours prior to nephrotoxic nephritis and then once daily for 6 days suppresses ECM deposition in rats. |
| Lung | Sheridan et al 1999. "*Interleukin-11 Attenuates Pulmonary Inflammation and Vasomotor Dysfunction in Endotoxin-Induced Lung Injury.*" *The American Journal of Physiology* 277 (5): L861-67. | The authors conclude that rhIL11 (200 mg/kg, IP) exerts an anti-inflammatory activity that protects against LPS-induced lung injury and lethality in rats |
| | Waxman et al. 1998. "*Targeted Lung Expression of Interleukin-11 Enhances Murine Tolerance of 100% Oxygen and Diminishes Hyperoxia-Induced DNA Fragmentation.*" *J. Clin. Invest.* 101(9): 1970-1982 | The authors conclude that IL11 protects from hyperoxic-induced lung injury, based on the effects of lung-specific human IL11 overexpression in mice. |

TABLE 3

List of publications from clinical trials where rhIL11 was administered to patients, based mainly on an inferred protective effect of rhIL11 use in rodent models of disease.

| | |
|---|---|
| Herrlinger et al. 2006. "*Randomized, Double Blind Controlled Trial of Subcutaneous Recombinant Human Interleukin-11 versus Prednisolone in Active Crohn's Disease.*" *The American Journal of Gastroenterology* 101 (4): 793-797. | RhIL11 (1 mg, weekly for 12 weeks, SC) was administered to 51 patients with active Crohn's disease and found to be significantly inferior as compared to prednisolone treatment. |
| Lawitz et al. 2004. "*A Pilot Study of Interleukin-11 in Subjects with Chronic Hepatitis C and Advanced Liver Disease Nonresponsive to Antiviral Therapy.*" *The American Journal of Gastroenterology* 99 (12): 2359-64. | RhIL11 (5 µg/kg, daily for 12 weeks, SC) was administered to 20 patients with chronic Hepatitis C and late stage liver disease. Lower serum ALT was observed by study end. The most common side effect is oedema in lower extremities, which was observed in all subjects. |
| Sands et al. 2002. "*Randomized, Controlled Trial of Recombinant Human Interleukin-11 in Patients with Active Crohn's Disease.*" *Alimentary Pharmacology & Therapeutics* 16 (3): 399-406. | RhIL11 (15 µg/kg, weekly for 6 weeks, SC) was administered to 49 patients with Crohn's disease. A greater proportion of patients receiving rhIL11 achieved remission compared to placebo. Side effects including oedema were observed. |
| Moreland et al. 2001. "*Results of a Phase-I/II Randomized, Masked, Placebo-Controlled Trial of Recombinant Human Interleukin-11 (rhIL-11) in the Treatment of Subjects with Active Rheumatoid Arthritis.*" *Arthritis Research* 3 (4): 247-252. | Administration of up to 15 µg/kg rhIL11 weekly for 12 weeks (SC) in rheumatoid arthritis patients is safe but no therapeutic benefit was observed. In addition, mild adverse effect (erythema with/without induration) at the injection site was seen in 60.6% of patients receiving rhIL11. |
| Trepicchio et al. 1999. "*Interleukin-11 Therapy Selectively Downregulates Type I Cytokine Proinflammatory Pathways in Psoriasis Lesions.*" *The Journal of Clinical Investigation* 104 (11): 1527-1537. | Patients with extensive psoriasis were treated with 2.5 or 5 mg/kg of rhIL11 (daily for 8 weeks, SC). A response (RNA expression of inflammatory markers) was observed in a subset (n = 7) of 12 patients; the other 5 patients were nonresponsive and no improvement was observed. |

The inventors propose a refined mechanism for APAP toxicity whereby NAPQI damaged mitochondria produce ROS that stimulates IL11-dependent NOX4 upregulation and further sustained ROS production (FIG. 29). This drives a dual pathology: killing hepatocytes via JNK and caspase activation and preventing hepatocyte regeneration, through mechanisms yet to be defined. The mouse model of AILI closely resembles human disease, and so therapies targeting IL11 signaling are expected to be useful for the treatment of patients with APAP-induced liver toxicity. Since IL11 neutralizing therapies are not dependent on altering APAP metabolism (FIG. 12F) and specifically stimulate tissue regeneration, they are effective much later than the current standard of care and might be particularly useful for patients presenting late to the emergency room.

6.11 Materials and Methods for Example 6

Antibodies

Cleaved Caspase 3 (9664, CST), Caspase 3 (9662, CST), Cyclin D1 (55506, CST), Cyclin D3 (2936, CST), Cyclin E1 (20808, CST), p-ERK1/2 (4370, CST), ERK1/2 (4695, CST), GAPDH (2118, CST), GFP (ab6673, Abcam), IgG (Aldevron), p-JNK (4668, CST), JNK (9258, CST), neutralizing anti-IL11Rα (X209, Aldevron; in vivo study), IL11Rα (130920, Santa Cruz; WB), NOX4 (110-58849, Novus Biologicals), PCNA (13110, CST), p-RB (8516, CST), RB (9313, CST), anti-rabbit HRP (7074, CST), anti-mouse HRP (7076, CST), anti-rabbit Alexa Fluor 488 (ab150077, Abcam), anti-rabbit Alexa Fluor 647 (ab150079, Abcam), anti-mouse Alexa Fluor 488 (ab150113, Abcam), anti-goat Alexa Fluor 488 (ab150129, Abcam).

Recombinant Proteins

Recombinant human IL11 (rhIL11, UniProtKB:P20809, Genscript), recombinant mouse IL11 (rmIL11, UniProtKB: P47873, Genscript), human IL11Rα (10252-H08H, SinoBiological), mouse IL11Rα (50075-M08H, SinoBiological).

Chemical

Acetaminophen (APAP, A3035, Sigma), DAPI (D1306, ThermoFisher Scientifics), D-Luciferin (L6882, Sigma), GKT-137831 (17764, Cayman Chemical), N-Acetyl-L-Csyteine (NAC, A7250, Sigma).

Reagents for LC-MS/MS

Reference Standard acetaminophen (APAP, P0300000, Sigma), internal standard (IS) acetaminophen-d4 (APAP-D4, A161222, Toronto Research Chemicals), IS acetaminophen glutathione (APAP GLUT, A161223, Toronto Research Chemicals), Acetronitrile (900667, Sigma), Ammonium formate (A115-50, Sigma), Formic acid (F0507, Sigma), mouse serum (IGMSCD1 SER50ML, i-DNA Biotechnology). All chemicals, reagents and solvents were of LC-MS grade quality.

Animal Models

Animal procedures were approved and conducted in accordance with the SingHealth Institutional Animal Care and Use Committee (IACUC). All mice were provided food and water ad libitum, except in the fasting period, during which only water was provided ad libitum.

Mouse Models of Acetaminophen Poisoning

Prior to APAP, 12-14 weeks old male mice (C57BL6/NTAC, unless otherwise specified) were fasted overnight. Mice were then given a severe (400 mg kg$^{-1}$) or lethal (550 mg kg$^{-1}$) dose of APAP by intraperitoneal (IP) administration. Mice were administered anti-IL11Rα (X209) or IgG isotype control antibody at different times and doses, as described above or in the figure legends. Mice were euthanized at various time points post APAP, from 10 h to 8 days, as described above or in the figure legends.

Il11-Luciferase mice

The mouse Il11 gene consists of 5 exons, with the ATG start codon in exon 1 and TGA stop codon in exon 5. Three transcripts of mouse Il11 have been identified (ENSMUSG00000004371): transcript Il11-201 is the longest and encodes a 199aa pro-peptide, whereas transcripts Il11-202 and Il11-203 contain an alternative first exon, and are both predicted to encode a shorter 140 aa isoform that lacks the signal peptide. Using the CRISPR/Cas9 technique, a Kozak-Luciferase-WPRE-polyA sequence was introduced to replace the ATG start codon in exon 1 of Il11-201 (ENSMUST00000094892.11), resulting in translational disruption of this specific transcript. Single guide RNAs (sgRNAs) with recognition sites in exon 1 along with Cas9 and the targeting construct containing a Kozak-Luciferase-WPRE-polyA sequence were microinjected into fertilized zygotes and subsequently transferred into pseudopregnant mice (Shanghai Model Organisms Center, Inc). Insertion of the luciferase cassette into the Il11 gene locus was verified by sequencing. Mutant Il11-Luciferase offsprings were generated on a C57BL/6 background and identified by genotyping to detect the insertion of the luciferase construct in exon 1, using primers which amplify a 818 bp region corresponding to the wildtype Il11 allele (5'-GGAGGGAGGGGACGC-CAATGACC-3' (SEQ ID NO:22) and 5'-TCTGCC TCCCCTGCCTGTTTCTCG-3' (SEQ ID NO:23)), and a second set of primers that amplifies a 928 bp region corresponding to the targeted allele containing the luciferase construct (5'-AATTCCGTGGTGTTGTCG-3' (SEQ ID NO:24) and 5'-TCTGCCTCCCCTGCCTGTTTCTCG-3' (SEQ ID NO:25)).

Heterozygous Il11-Luciferase were subjected to APAP-induced liver injury as described above. After 24 h, mice were injected intraperitoneally with 150 mg kg$^{-1}$ of D-Luciferin in PBS and bioluminescence images of the liver were subsequently acquired using the IVIS Lumina System (Perkin Elmer), according to the manufacturer's instructions.

Il11-EGFP Mice

Transgenic mice with EGFP constitutively knocked-in to the Il11 gene were generated by Cyagen Biosciences Inc. Briefly, knockin mice were generated to contain a 2A-EGFP cassette inserted into exon 5, which replaces the TGA stop codon sequence, and translation of the targeted transcript would give rise to full-length IL11 pro-peptide and EGFP separated by a 2A self cleaving peptide linker. The targeting vector homology arms of Il11 gene, containing a Neo cassette inserted into intron 4 (flanked by SDA: self-deletion anchor sites) and a 2A-EGFP cassette inserted into exon 5, were generated by PCR using BAC clones from the C57BL/6 library. C57BL/6 ES cells were used for gene targeting and successfully targeted clones were injected into C57BL/6 albino embryos, which were then re-implanted into CD-1 pseudo-pregnant females. Founder animals were identified by their coat color and germline transmission was confirmed by breeding with C57BL/6 females and subsequent genotyping of the offsprings. Genotyping primers were designed to amplify selected regions of intron 4, spanning the Neo cassette SDA sites, according to the following primer sequences: (5'-GAAATGAG AGCCTAGAGTCCAGAG-3' (SEQ ID NO:26) and 5'-GAGGCTTGGAAGAATGCACAATTA-3' (SEQ ID NO:27)).

Hepatocyte-Specific Il11 Overexpressing Mice (Il11-Tg)

Mice in which mouse Il11 cDNA was introduced into the Rosa26 locus under the control of loxP-Stop-loxP sites to allow for cell-type specific overexpression of Il11 following Cre recombinase-mediated excision have previously been described (15). These animals are made available at The Jackson Laboratory (C57BL/6N-Gt(ROSA)26Sortm1 (CAG-Il11)Cook/J). To induce the specific expression of Il11 in hepatocytes, heterozygous Il11-Rosa26 mice were injected intravenously (IV) with either $4 \times 10^{11}$ genome copies in PBS/mouse (VectorBiolabs) of AAV8-ALB-Null (Control) AAV8-ALB-Cre (Il11-Tg). Livers and serum were assessed after three weeks.

Hepatocyte-Specific Il11Ra1 Deleted Mice

Il11ra1-floxed mice were recently generated and validated, in which exons 4 to 7 of the Il11ra1 gene were flanked by loxP sites, allowing for the spatial and temporal deletion of Il11ra1 upon Cre recombinase-mediated excision (Ng et al., Sci Transl Med. (2019) 11(511) pii: eaaw1237). To induce the specific deletion of Il11 ra1 in hepatocytes, homozygous Il11ra1-floxed mice were IV injected with AAV8-ALB-Cre virus ($4 \times 10^{11}$ genome copies in PBS/ mouse, VectorBiolabs) via the tail vein. A similar amount of AAV8-ALB-Null virus were injected into homozygous Il11ra1-floxed mice as controls. The AAV8 treated mice were allowed to recover for three weeks prior to APAP injury. Knockdown efficiency was determined by Western blotting of hepatic IL11Rα.

Cell Culture

Both primary human and mouse hepatocytes were grown and maintained at 37° C. and 5% $CO_2$. The growth medium was renewed every 2-3 days and cells were passaged at 80% confluence, using standard trypsinization techniques. All the experiments were carried out at low cell passage (P1-P3). Stimulated cells were compared to unstimulated cells that have been grown for the same duration under the same conditions, but without the stimuli.

Primary Human Hepatocytes

Human hepatocytes (5200, ScienCell) were maintained in hepatocyte medium (520, ScienCell) supplemented with 2% fetal bovine serum, 1% Penicillin-streptomycin. Cells were serum-starved for 16 h prior to respective stimulations, as described above or in the figure legends, that were performed in serum-free hepatocyte media for 24 h.

Primary Mouse Hepatocytes

Mouse hepatocytes (ABC-TC3928, AcceGen Biotech) were maintained in mouse hepatocyte medium (ABC-TM3928, AcceGen Biotech) supplemented with 1% Penicillin-streptomycin. Cells were stimulated with different treatment conditions for 24 h, as described above or in the figure legends.

siRNA Transfection

Primary human hepatocytes were seeded at 60-70% confluency in 6-well plate, 16 h before transfection. Cells were transfected with 50 nM of NOX4 siRNA (ON-TARGETplus SMARTpool siRNA, L-010194-00-0005, Dharmacon) or control siRNA (D-001810-10-05, Dharmacon) for 24 h at 37° C. in OptiMEM (31985070, Thermo Fisher) containing Lipofectamine RNAiMAX Transfection Reagent (13778150, Thermo Fisher). Transfected cells were then stimulated with rhIL11 for 24 h. Knockdown efficiency was determined by immunoblotting of NOX4.

Flow Cytometry

Primary human hepatocytes ($5 \times 10^5$) were stained using FITC Annexin V/Dead Cell Apoptosis Kit (V13242, Thermo Fisher), according to the manufacturer's instructions. $PI^{+ve}$ cells were quantified with the flow cytometer (Fortessa, BD Biosciences) and analyzed with FlowJo version 7 software (TreeStar).

Colorimetric Assays

The levels of alanine transaminase (ALT) or aspartate aminotransferase (AST) in mouse serum and hepatocyte supernatant were measured using ALT Activity (ab105134, Abcam) or AST (ab105135, Abcam) Assay Kits. Liver glutathione sulfhydryl (GSH) measurements were performed using Glutathione Colorimetric Detection Kit (EIAGSHC, Thermo Fisher). All colorimetric assays were performed according to the manufacturer's protocol.

Enzyme-Linked Immunosorbent Assay (ELISA)

The levels of IL11 in mouse serum and hepatocyte supernatant were quantified using Mouse IL-11 DuoSet (DY418 and DY008, R&D Systems) and Human IL11 Quantikine ELISA kit D1100, R&D Systems), respectively, according to the manufacturer's protocol.

Competitive ELISA

Mouse IL11Rα (1 µg ml$^{-1}$ in PBS) was coated on a 96-well plate (overnight at 4° C.) and then blocked with blocking buffer (1% BSA in PBS containing 0.05% Tween20). Biotinylated mouse Il11 was prepared using Lightning-Link Rapid Biotin type A kit (Expedeon) according to the manufacturer's instructions. RhIL11 or rmIl11 was two-fold serially diluted in blocking buffer (starting at 5 µg ml$^{-1}$) and mixed with 0.01 µg ml$^{-1}$ biotinylated mouse IL11. The mixture of biotinylated mouse IL11 and either rhIL11 or rmIL11 was added into the coated plate and incubated for 1 h at RT. Color development was performed by adding Streptavidin-HRP (1:1000 in blocking buffer) and TMB chromogen solution (002023, ThermoFisher Scientific).

Immunoblotting

Western blots were carried out from hepatocyte and liver tissue lysates. Hepatocytes and tissues were homogenized in radioimmunoprecipitation assay (RIPA) buffer containing protease and phosphatase inhibitors (Thermo Fisher), followed by centrifugation to clear the lysate. Protein concentrations were determined by Bradford assay (Bio-Rad). Equal amounts of protein lysates were separated by SDS-PAGE, transferred to PVDF membrane, and subjected to immunoblot analysis for the indicated primary antibodies. Proteins were visualized using the ECL detection system (Pierce) with the appropriate secondary antibodies.

Quantitative Polymerase Chain Reaction (qPCR)

Total RNA was extracted from either the snap-frozen liver tissues or hepatocyte lysates using Trizol (Invitrogen) followed by RNeasy column (Qiagen) purification. cDNAs were synthesized with iScript™ cDNA synthesis kit (Bio-Rad) according to manufacturer's instructions. Gene expression analysis was performed on duplicate samples with either TaqMan (Applied Biosystems) or fast SYBR green (Qiagen) technology using StepOnePlus™ (Applied Biosystem) over 40 cycles. Expression data were normalized to GAPDH mRNA expression and fold change was calculated using $2^{-\Delta\Delta Ct}$ method. The sequences of specific TaqMan probes and SYBR green primers are available upon request.

Surface Plasmon Resonance (SPR)

SPR measurements were performed on a BIAcore T200 (GE Healthcare) at 25° C. Buffers were degassed and filter-sterilized through 0.2 µm filters prior to use. RhIL11 or rmIl11 was immobilized onto a carboxymethylated dextran (CM5) sensor chip using standard amine coupling chemistry. For kinetic analysis, a concentration series (3.125 nM to 100 nM) of human IL11Rα or mouse Il11 rα was injected over the rhIL11, rmIl11 and reference surfaces at a flow rate of 40 µl min$^{-1}$. All the analytes were dissolved in HBS-EP+

(BR100669, GE Healthcare) containing 1 mg ml$^{-1}$ BSA. The association and dissociation were measured for 150s and 200s respectively. After each analyte injection, the surface was regenerated by a 30 s injection of Glycine pH2.5, followed by a 5 min stabilisation period. All sensorgrams were aligned and double-referenced. Affinity and kinetic constants were determined by fitting the corrected sensorgrams with the 1:1 Langmuir model using BIAevaluation v3.0 software (GE Healthcare). The equilibrium binding constant KD was determined by the ratio of the binding rate constants kd/ka.

Histology
Hematoxylin&Eosin (H&E) Staining

Livers were fixed for 48 h at room temperature (RT) in 10% neutral-buffered formalin (NBF), dehydrated, embedded in paraffin blocks and sectioned at 7 µm. Sections were stained with H&E according to standard protocol and examined by light microscopy.

EdU Staining

Livers were rinsed in cold PBS and patted dry with a lint free paper and cryo-molded in OCT compound (4583, Tissue-Tek®). After the OCT compound is frozen, liver specimens were wrapped in aluminium foil and stored in −80° C. Cryo-embedded livers were cryosectioned (−20° C.) at 7 µm thickness and allowed to dry on the slides for 1 h before proceeding to EdU detection using Baseclick's EdU IV Imaging Kit 488L (BCK488-IV-IM-L) according to the manufacturer's protocol.

Immunofluorescence Staining

Livers were processed and frozen as mentioned above (EdU staining section). Frozen liver tissues were sectioned at 7 µm at −20° C. and left to dry for 1 h (RT). Liver sections were fixed in cold acetone for 15 min prior to brief PBS washes, permeabilized with 0.1% TritonX-100 (T8787, Sigma), and blocked with 2.5% normal goat serum (S-1012, Vector Labs) for 1 h (RT). Liver sections were incubated with GFP (1:500) and Caspase 3 (1:1000) primary antibodies overnight (4° C.), followed by incubation with the appropriate Alexa Fluor 488/647 secondary antibodies (1:250) for 1 h (RT). DAPI was used to stain the nuclei prior to imaging by fluorescence microscope (Leica).

LC-MS/MS

Mouse serum samples (20 µL), calibrators and QCs were transferred into a deep well 96-well plate, then spiked with 50 µL of 10 µg l$^{-1}$ of APAP-D4 heavy isotope standards. After treating with 360 µL of ice-cold Acetonitrile containing 0.1% Formic acid, the plate was mixed (1000 rpm min$^{-1}$, 10 min), followed by centrifugation (2270 g, 50 min, 4° C.). 140 µL of the supernatant was carefully transferred to a 96-microwell plate and loaded into the auto-sampler for analysis by LC-MS/MS. Ion counts were then normalized against that of the heavy isotope standard, before using the standard curve for quantification. Liquid chromatographic (LC) separation of the biomarkers was carried out on an Agilent 1290 Infinity II LC system (Agilent Technologies) with PEEK coated SeQuant®ZIC®-cHILIC 3 mm, 100 Å 100×2.1 mm HPLC column (Merck Pte Ltd) maintained at 40° C. The organic solvent was Acetonitrile containing 0.1% Formic acid (Solvent A) and the aqueous solvent was 20 mM Ammonium Formate pH 4.0 (Solvent B). A linear LC gradient on Binary Pump A (G7120A, Agilent Technologies) was set up with percentage of Solvent B as follows: 10% at 0 min, 70% at 9 min, 70% at 11 min, and 10% between 11.1 and 11.5 min, with a flow rate of 0.4 ml min$^{-1}$. The column was further equilibrated for 11.5 min with 10% Solvent B. An additional high speed pump, Binary Pump B, together with a Quick-Change valve head, 2-position/10-port, 1,300 bar (5067-4240, Agilent), were utilized to reduce the cycle times by automated alternating column regeneration. Percentage of Solvent B on BinaryPump B was maintained at 10% with a flow rate of 0.3 ml min$^{-1}$. For mass detection, the LC eluent is connected to an Agilent 6495 Triple Quadrupole MS system (G6495A, Agilent Technologies) operated with the electrospray source in either positive or negative ionization mode. The electrospray ionization source conditions were as follows: capillary voltage of 4.0 kV, nozzle voltage of 500 V, iFunnel parameter high/low pressure RF of 90 V, nebulizer pressure of 60 psi, gas temperature of 290° C., sheath gas temperature of 350° C., Nebulizer was 35 psi, and sheath gas flow of 12 l min$^{-1}$. The multiple reaction monitoring (MRM) conditions used for APAP and APAP-D4 were 152.1→110 with Collision Energy (CE) of 16 eV, Collision Accelerator Voltage (CAV) of 5 V and 156→114 with CE of 8 eV and CAV of 5 V, respectively. The MRM used for APAP-Glutathione was 457.1→140 with Collision Energy (CE) of 42 eV, Collision Accelerator Voltage (CAV) of 5 V.

Calibration and Linearity

Nine-point calibration curves were obtained by fortifying drug-free mouse serum with working solutions of APAP and APAP-Glutathione. The final concentrations of APAP were 0.32, 0.46, 2.6, 5.2, 10.3, 20.6, 41.3, 82.5 and 330 mg l$^{-1}$ (low QC: 1.29 mg l$^{-1}$; high QC: 165 mg l$^{-1}$). The final concentrations of APAP-Glutathione were 0.244, 0.49, 0.98, 1.95, 3.91, 7.81, 15.6, 62.5, 125 and 250 mg l$^{-1}$ (low QC: 1.95 mg l$^{-1}$; high QC of 31.3 mg l$^{-1}$). Standard curves corresponded to peak area ratios of each analyte to IS using weighted linear least-squares regression (1/x2) for APAP and (1/x) for APAP-Glutathione, the linearity coefficients of determination (r2) were 0.97807145 and 0.99655914, respectively. The precision and accuracy of the assay in the mice serum samples were determined as described previously (32).

Statistical Analysis

Statistical analyses were performed using GraphPad Prism software (version 6.07). P values were corrected for multiple testing according to Dunnett's (when several experimental groups were compared to one condition), Tukey (when several conditions were compared to each other within one experiment), Sidak (when several conditions from 2 different genotypes were compared to each other). Analysis for two parameters for comparison of two different groups were performed by two-way ANOVA. Survival curves were analyzed by Gehan-Breslow-Wilcoxon test. The criterion for statistical significance was P<0.05.

6.12 References to Example 6

1. W. Bernal, J. Wendon, Acute liver failure. N. Engl. J. Med. 370 (2014), pp. 1170-1171.
2. W. M. Lee, L. S. Hynan, L. Rossaro, R. J. Fontana, R. T. Stravitz, A. M. Larson, T. J. Davern 2nd, N. G. Murray, T. McCashland, J. S. Reisch, P. R. Robuck, Acute Liver Failure Study Group, Intravenous N-acetylcysteine improves transplant-free survival in early stage non-acetaminophen acute liver failure. Gastroenterology. 137, 856-64, 864.e1 (2009).
3. H. Jaeschke, Acetaminophen: Dose-Dependent Drug Hepatotoxicity and Acute Liver Failure in Patients. Dig. Dis. 33, 464-471 (2015).
4. A. L. Chiew, C. Gluud, J. Brok, N. A. Buckley, Interventions for paracetamol (acetaminophen) overdose. Cochrane Database Syst. Rev. 2, CD003328 (2018).
5. S. Win, T. A. Than, J. Zhang, C. Oo, R. W. M. Min, N. Kaplowitz, New insights into the role and mechanism of c-Jun-N-terminal kinase signaling in the pathobiology of liver diseases. Hepatology. 67, 2013-2024 (2018).
6. H. Zhang, J. Cook, J. Nickel, R. Yu, K. Stecker, K. Myers, N. M. Dean, Reduction of liver Fas expression by an antisense oligonucleotide protects mice from fulminant hepatitis. Nat. Biotechnol. 18, 862-867 (2000).
7. R. F. Schwabe, T. Luedde, Apoptosis and necroptosis in the liver: a matter of life and death. Nat. Rev. Gastroenterol. Hepatol. 15, 738-752 (2018).
8. B. K. Gunawan, Z. Liu, D. Han, N. Hanawa, W. A. Gaarde, N. Kaplowitz, c-Jun N-Terminal Kinase Plays a Major Role in Murine Acetaminophen Hepatotoxicity. Gastroenterology. 131 (2006), pp. 165-178.
9. Y. Xie, A. Ramachandran, D. G. Breckenridge, J. T. Liles, M. Lebofsky, A. Farhood, H. Jaeschke, Inhibitor of apoptosis signal-regulating kinase 1 protects against acetaminophen-induced liver injury. Toxicol. Appl. Pharmacol. 286, 1-9 (2015).
10. S. Sekiya, A. Suzuki, Glycogen synthase kinase 3 β-dependent Snail degradation directs hepatocyte proliferation in normal liver regeneration. Proc. Natl. Acad. Sci. U.S.A 108, 11175-11180 (2011).
11. A. Marcos, R. A. Fisher, J. M. Ham, M. L. Shiffman, A. J. Sanyal, V. A. Luketic, R. K. Sterling, A. S. Fulcher, M. P. Posner, Liver regeneration and function in donor and recipient after right lobe adult to adult living donor liver transplantation. Transplantation. 69, 1375-1379 (2000).
12. B. Bhushan, U. Apte, Liver Regeneration after Acetaminophen Hepatotoxicity: Mechanisms and Therapeutic Opportunities. Am. J. Pathol. 189, 719-729 (2019).
13. G. K. Michalopoulos, Hepatostat: Liver regeneration and normal liver tissue maintenance. Hepatology. 65, 1384-1392 (2017).
14. A. A. Widjaja, B. K. Singh, E. Adami, S. Viswanathan, J. Dong, G. A. D'Agostino, B. Ng, W. W. Lim, J. Tan, B. S. Paleja, M. Tripathi, S. Y. Lim, S. G. Shekeran, S. P. Chothani, A. Rabes, M. Sombetzki, E. Bruinstroop, L. P. Min, R. A. Sinha, S. Albani, P. M. Yen, S. Schafer, S. A. Cook, Inhibiting Interleukin 11 Signaling Reduces Hepatocyte Death and Liver Fibrosis, Inflammation, and Steatosis in Mouse Models of Non-Alcoholic Steatohepatitis. Gastroenterology (2019), doi:10.1053/j.gastro.2019.05.002.
15. S. Schafer, S. Viswanathan, A. A. Widjaja, W.-W. Lim, A. Moreno-Moral, D. M. DeLaughter, B. Ng, G. Patone, K. Chow, E. Khin, J. Tan, S. P. Chothani, L. Ye, O. J. L. Rackham, N. S. J. Ko, N. E. Sahib, C. J. Pua, N. T. G. Zhen, C. Xie, M. Wang, H. Maatz, S. Lim, K. Saar, S. Blachut, E. Petretto, S. Schmidt, T. Putoczki, N. Guimarães-Camboa, H. Wakimoto, S. van Heesch, K. Sigmundsson, S. L. Lim, J. L. Soon, V. T. T. Chao, Y. L. Chua, T. E. Tan, S. M. Evans, Y. J. Loh, M. H. Jamal, K. K. Ong, K. C. Chua, B.-H. Ong, M. J. Chakaramakkil, J. G. Seidman, C. E. Seidman, N. Hubner, K. Y. K. Sin, S. A. Cook, IL-11 is a crucial determinant of cardiovascular fibrosis. Nature. 552, 110-115 (2017).
16. S. Cook, B. Ng, J. Dong, S. Viswanathan, G. DAgostino, A. Widjaja, W.-W. Lim, N. Ko, J. Tan, S. Chothani, B. Huang, C. Xie, A.-M. Chacko, N. Guimaraes-Camboa, S. Evans, A. Byrne, T. Maher, J. Liang, P. Noble, S. Schafer, IL-11 is a therapeutic target in idiopathic pulmonary fibrosis (2018), doi:10.1101/336537.
17. T. Nishina, S. Komazawa-Sakon, S. Yanaka, X. Piao, D.-M. Zheng, J.-H. Piao, Y. Kojima, S. Yamashina, E. Sano, T. Putoczki, T. Doi, T. Ueno, J. Ezaki, H. Ushio, M. Ernst, K. Tsumoto, K. Okumura, H. Nakano, Interleukin-11 links oxidative stress and compensatory proliferation. Sci. Signal. 5, ra5 (2012).
18. M. Zhu, B. Lu, Q. Cao, Z. Wu, Z. Xu, W. Li, X. Yao, F. Liu, IL-11 Attenuates Liver Ischemia/Reperfusion Injury (IRI) through STAT3 Signaling Pathway in Mice. PLoS One. 10, e0126296 (2015).
19. M. Bozza, J. L. Bliss, R. Maylor, J. Erickson, L. Donnelly, P. Bouchard, A. J. Dorner, W. L. Trepicchio, Interleukin-11 reduces T-cell-dependent experimental liver injury in mice. Hepatology. 30, 1441-1447 (1999).
20. W. L. Trepicchio, M. Bozza, P. Bouchard, A. J. Dorner, Protective effect of rhIL-11 in a murine model of acetaminophen-induced hepatotoxicity. Toxicol. Pathol. 29, 242-249 (2001).
21. J. Yu, Z. Feng, L. Tan, L. Pu, L. Kong, Interleukin-11 protects mouse liver from warm ischemia/reperfusion (WI/Rp) injury. Clin. Res. Hepatol. Gastroenterol. 40, 562-570 (2016).
22. K. Maeshima, T. Takahashi, K. Nakahira, H. Shimizu, H. Fujii, H. Katayama, M. Yokoyama, K. Morita, R. Akagi, S. Sassa, A protective role of interleukin 11 on hepatic injury in acute endotoxemia. Shock. 21, 134-138 (2004).
23. H. Mühl, STAT3, a key parameter of cytokine-driven tissue protection during sterile inflammation—the case of experimental acetaminophen (Paracetamol)-induced liver damage. Front. Immunol. 7, 163 (2016).
24. K. Schleinkofer, A. Dingley, I. Tacken, M. Federwisch, G. Mu»ller-Newen, P. C. Heinrich, P. Vusio, Y. Jacques, A. Gro»tzinger, Identification of the Domain in the Human Interleukin-11 Receptorthat Mediates Ligand Binding. available online at http://www.idealibrary.com on J. Mol. Biol. 306, 263-274 (2001).
25. C. P. Denton, V. H. Ong, S. Xu, H. Chen-Harris, Z. Modrusan, R. Lafyatis, D. Khanna, A. Jahreis, J. Siegel, T. Sornasse, Therapeutic interleukin-6 blockade reverses transforming growth factor-beta pathway activation in dermal fibroblasts: insights from the faSScinate clinical trial in systemic sclerosis. Ann. Rheum. Dis. 77, 1362-1371 (2018).
26. A. Bettaieb, J. X. Jiang, Y. Sasaki, T.-I. Chao, Z. Kiss, X. Chen, J. Tian, M. Katsuyama, C. Yabe-Nishimura, Y. Xi, C. Szyndralewiez, K. Schröder, A. Shah, R. P. Brandes, F. G. Haj, N. J. Török, Hepatocyte Nicotinamide Adenine Dinucleotide Phosphate Reduced Oxidase 4 Regulates Stress Signaling, Fibrosis, and Insulin Sensitivity During Development of Steatohepatitis in Mice. Gastroenterology. 149, 468-80.e10 (2015).
27. M. Walmsley, D. M. Butler, L. Marinova-Mutafchieva, M. Feldmann, An anti-inflammatory role for interleukin-11 in established murine collagen-induced arthritis. Immunology. 95, 31-37 (1998).
28. B. S. Qiu, C. J. Pfeiffer, J. C. Keith, Protection by recombinant human interleukin-11 against experimental TNB-induced colitis in rats. Digestive Diseases and Sciences. 41 (1996), pp. 1625-1630.
29. T. V. A. Murray, X. Dong, G. J. Sawyer, A. Caldwell, J. Halket, R. Sherwood, A. Quaglia, T. Dew, N. Anilkumar, S. Burr, R. K. Mistry, D. Martin, K. Schroder, R. P. Brandes, R. D. Hughes, A. M. Shah, A. C. Brewer, NADPH oxidase 4 regulates homocysteine metabolism and protects against acetaminophen-induced liver damage in mice. Free Radic. Biol. Med. 89, 918-930 (2015).
30. L. Hecker, R. Vittal, T. Jones, R. Jagirdar, T. R. Luckhardt, J. C. Horowitz, S. Pennathur, F. J. Martinez, V. J. Thannickal, NADPH oxidase-4 mediates myofibroblast activation and fibrogenic responses to lung injury. Nat. Med. 15, 1077-1081 (2009).

31. P. J. Wermuth, F. A. Mendoza, S. A. Jimenez, Abrogation of transforming growth factor-β-induced tissue fibrosis in mice with a global genetic deletion of Nox4. Lab. Invest. 99, 470-482 (2019).

32. T. Gicquel, J. Aubert, S. Lepage, B. Fromenty, I. Morel, Quantitative Analysis of Acetaminophen and its Primary Metabolites in Small Plasma Volumes by Liquid Chromatography-Tandem Mass Spectrometry.
Journal of Analytical Toxicology. 37 (2013), pp. 110-116.

Example 7: IL-11 and IL-6 Receptor Expression and Signalling in Primary Human Hepatocytes

7.1 Introduction

IL11 is a member of the interleukin 6 (IL6) cytokine family and, like IL6, binds to its membrane-bound alpha receptor (IL11Rα) and glycoprotein 130 (gp130) to signal in cis. IL6 itself has been linked to liver function and publications suggest an overall beneficial effect (Klein et al., 2005; Kroy et al., 2010; Matthews et al., 2010; Schmidt-Arras and Rose-John, 2016; Wuestefeld et al., 2003). However, it is also thought that IL6 can bind to soluble IL6 receptor (sIL6R) and signal in trans, which is considered maladaptive (Schmidt-Arras and Rose-John, 2016). It is possible that IL11, like IL6, signals in a pathogenic mode in trans but experiments to date have found no evidence for this in tumors or reproductive tissues (Agthe et al., 2017; Balic et al., 2017).

7.2 Results

Figure 31A:
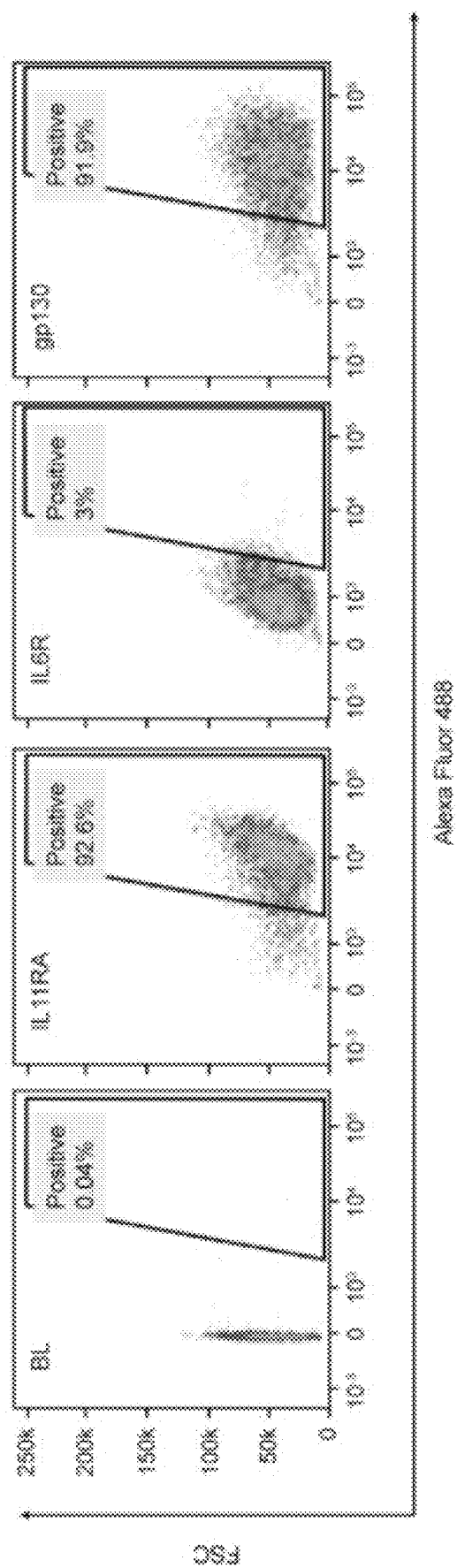
Figure 31B:
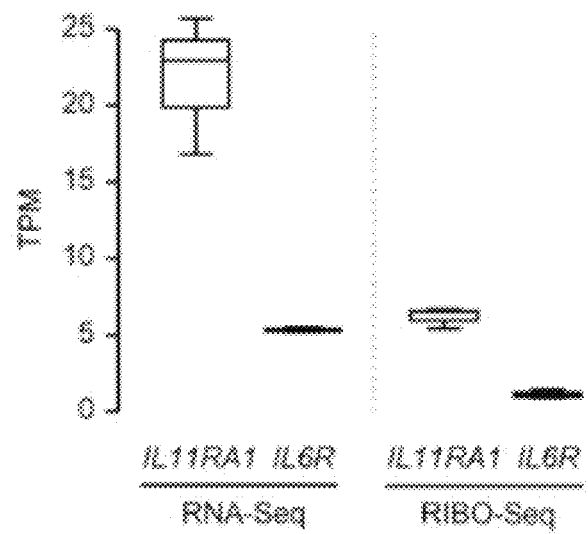
Figure 31C:
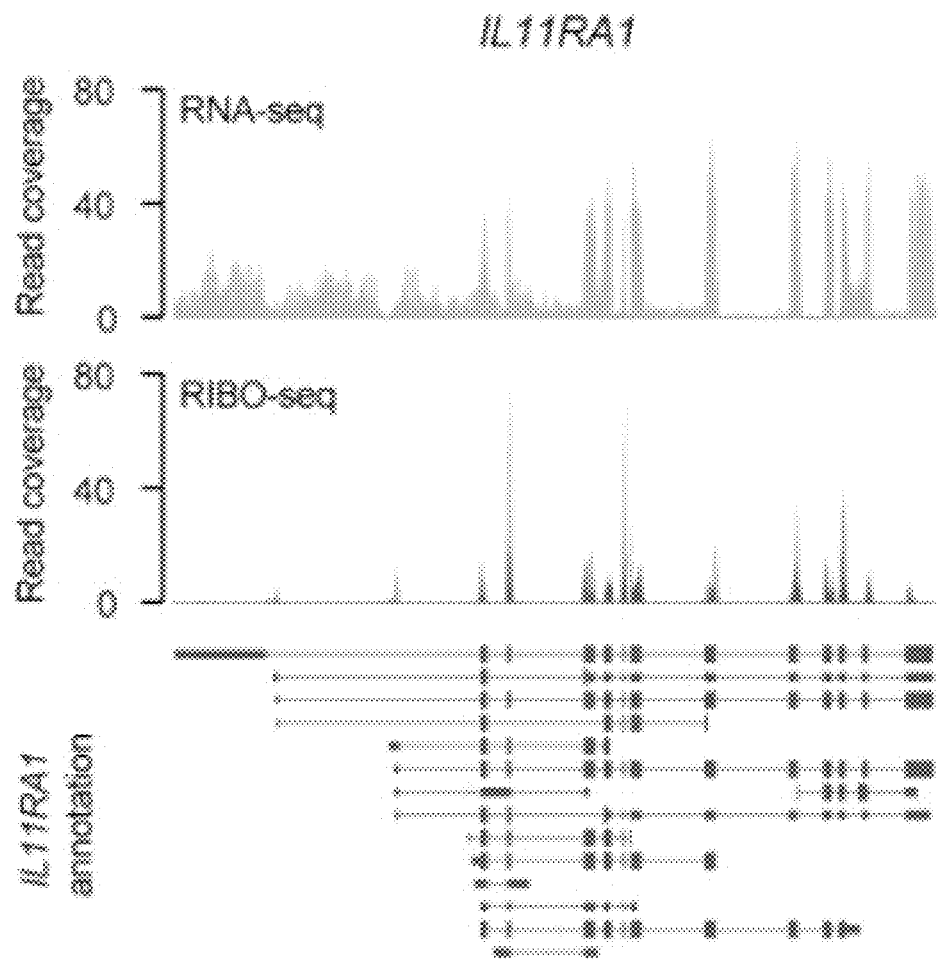
Figure 31D:
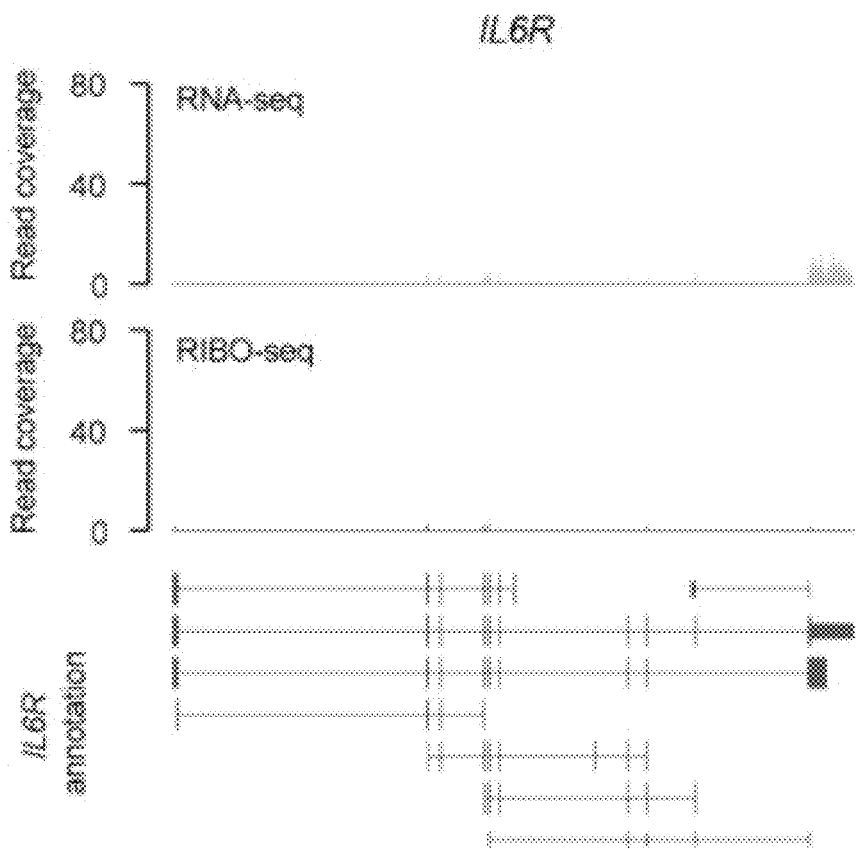
Figure 32A:
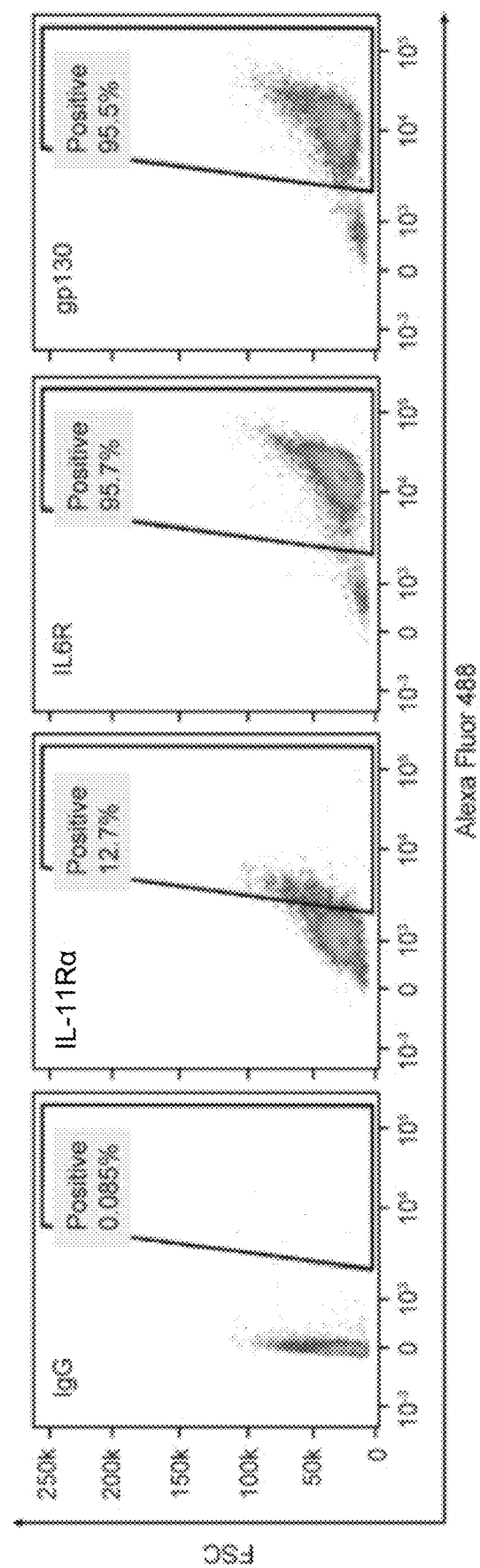
Figure 32B:
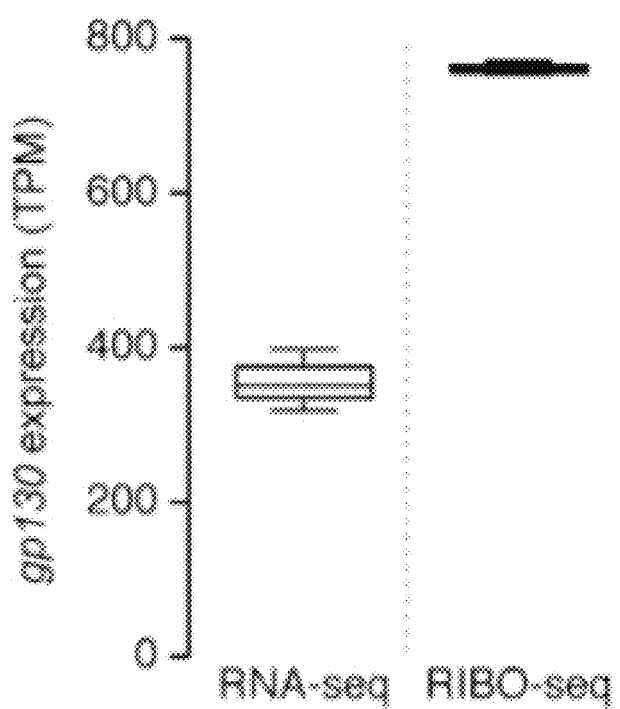
Figure 32C:
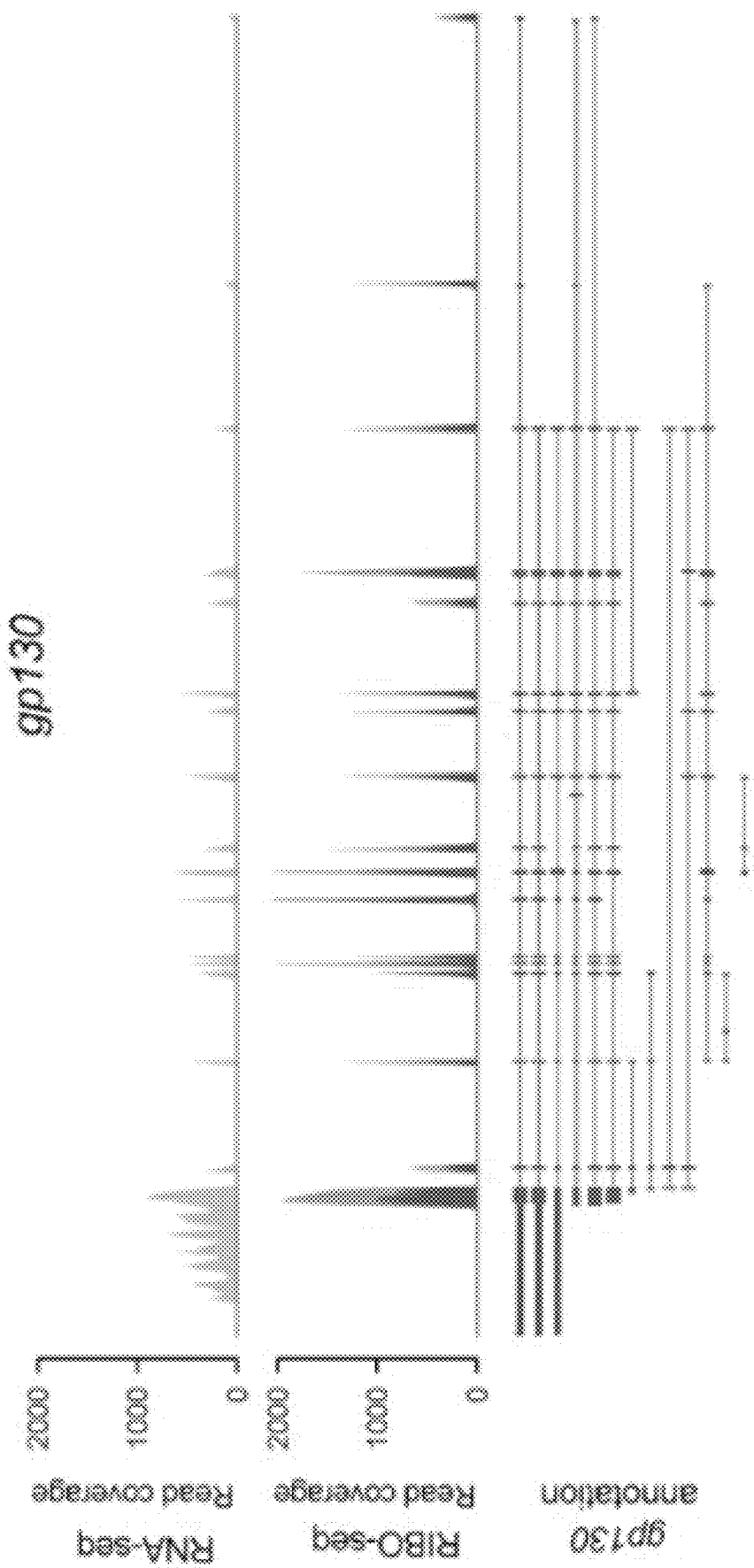
Figure 32D:
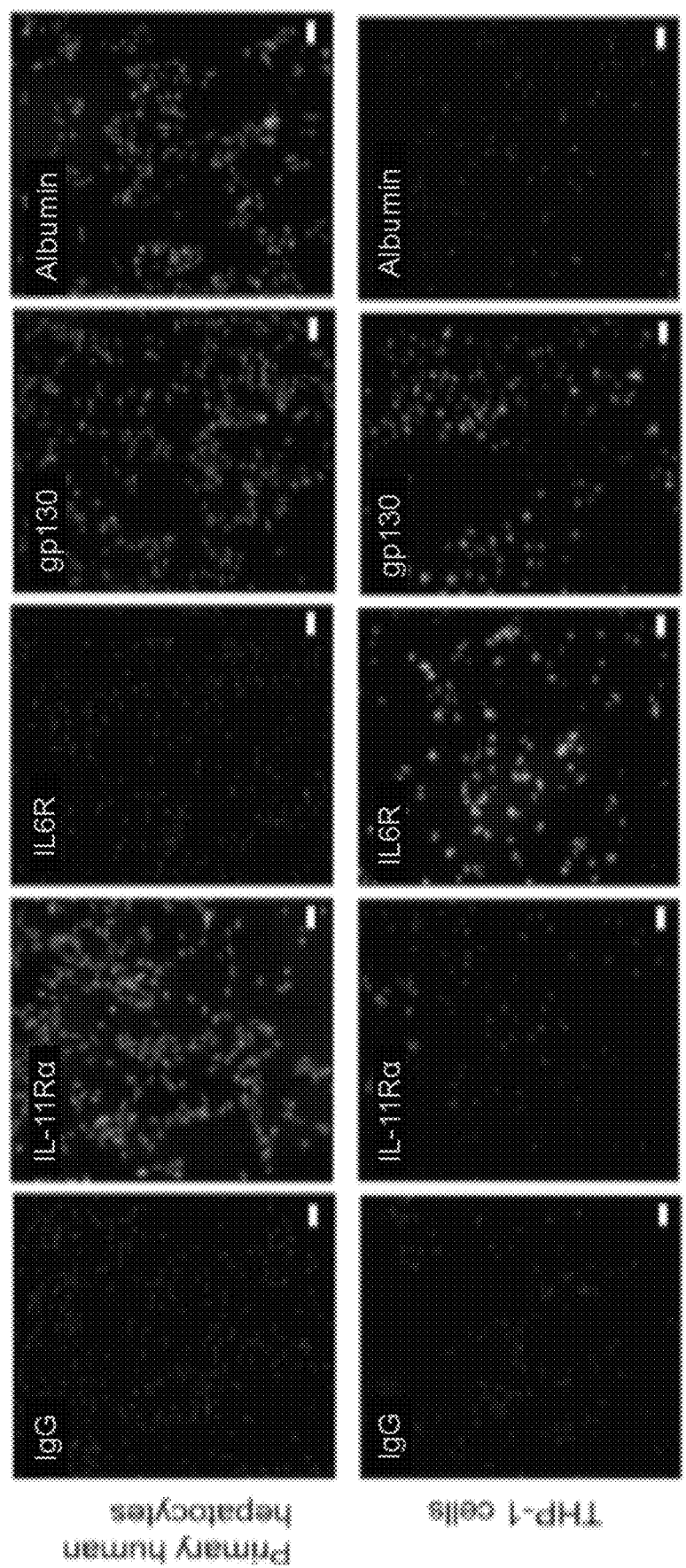
Figure 32E:
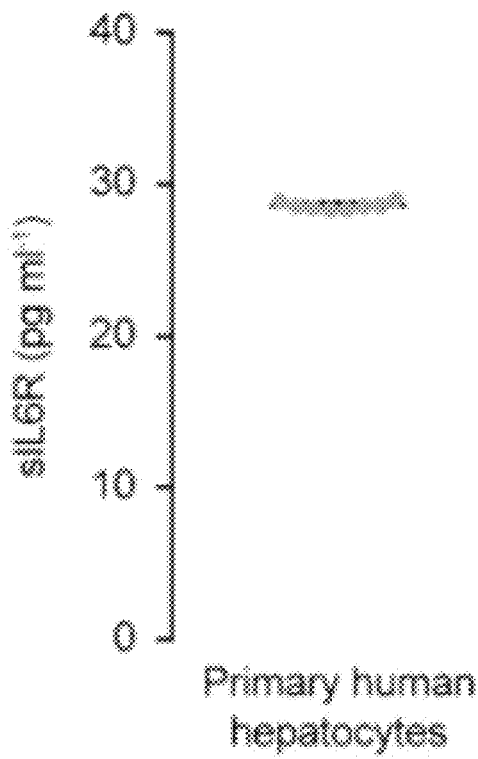

The inventors first assessed the expression levels of IL6R, IL11Rα and gp130 in primary human hepatocytes by flow cytometry. Robust expression of IL11Rα and gp130 was observed in the large majority of cells (92.6% and 91.9%, respectively) but only few hepatocytes (3.0%) expressed IL6R, and at low levels (FIGS. 31A and 32A). In accordance with this result, RNA-seq and Ribo-seq studies found IL11Rα and gp130 transcripts to be highly expressed and actively translated in hepatocytes. By contrast, few IL6R transcripts were observed, and there was almost no detectable IL6R translation (FIGS. 31B-31D, 32B, and 32C). Immunofluorescence staining of hepatocytes corroborated the results of the Ribo-seq data: high IL11Rα expression but no detectable IL6R expression (FIG. 32D). The inventors also did not detect significant levels of IL6R into culture media (levels were just above the lower limit of detection), and so they excluded the possibility that IL6R was being shed (FIG. 32E). Taken together these data show that IL6R is expressed at very low levels in primary human hepatocytes, implying a limited role for IL6 cis-signaling in these cells. However, these cells display strong co-expression of both IL11Rα and gp130.

Figure 31E:
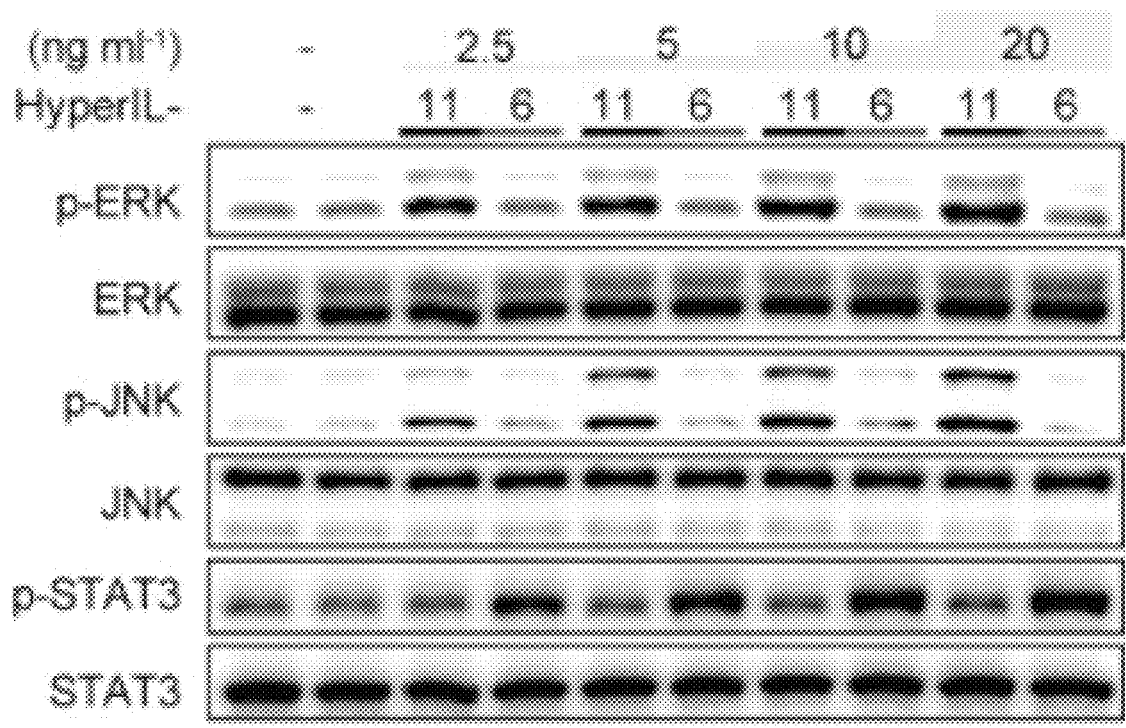

Given the lack of IL6R expression by human hepatocytes the inventors employed a synthetic IL6 trans-signaling construct (hyperIL6) to activate IL6 signaling in these cells and compared this with a synthetic IL11 trans-signaling complex (hyperIL11). HyperIL11, like IL11 itself (see Example 6), activated ERK and JNK in a dose-dependent manner (2.5 ng/ml to 20 ng/ml). By contrast, IL6 trans-signaling did not activate non-canonical signaling pathways but instead dose-dependently induced STAT3 activation (FIG. 31E). Thus, IL11 or IL6 in a pre-formed synthetic complex with their cognate receptors activate different intracellular pathways when bound to gp130 on hepatocytes, which is a novel and intriguing finding.

Figure 31F:
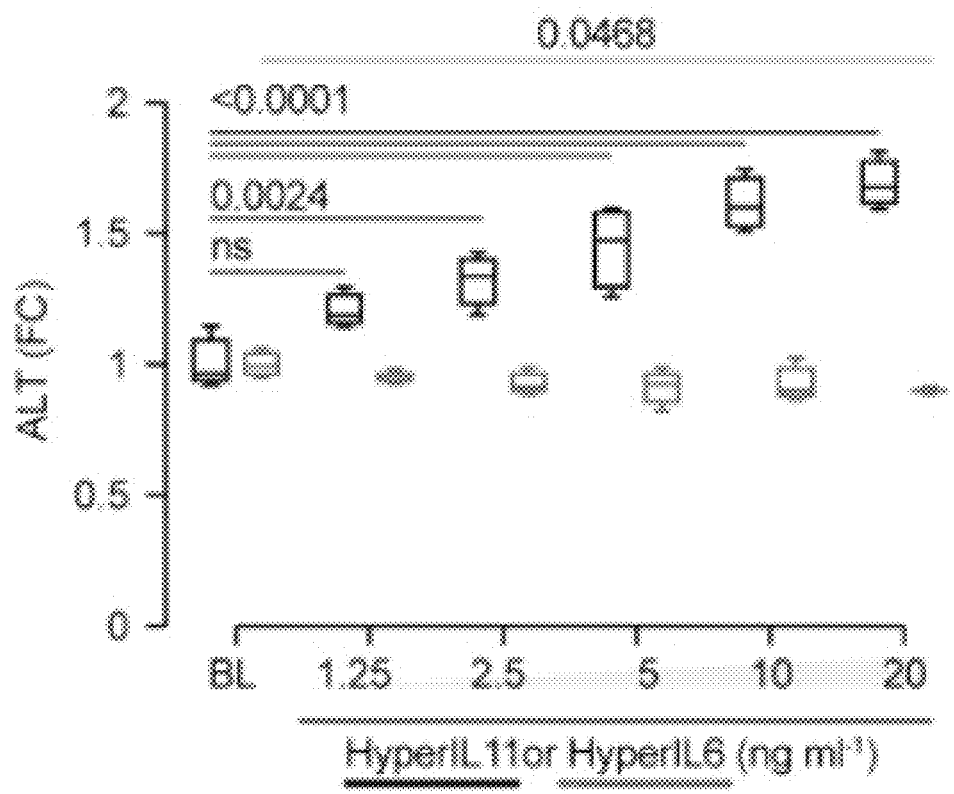
Figure 31G:
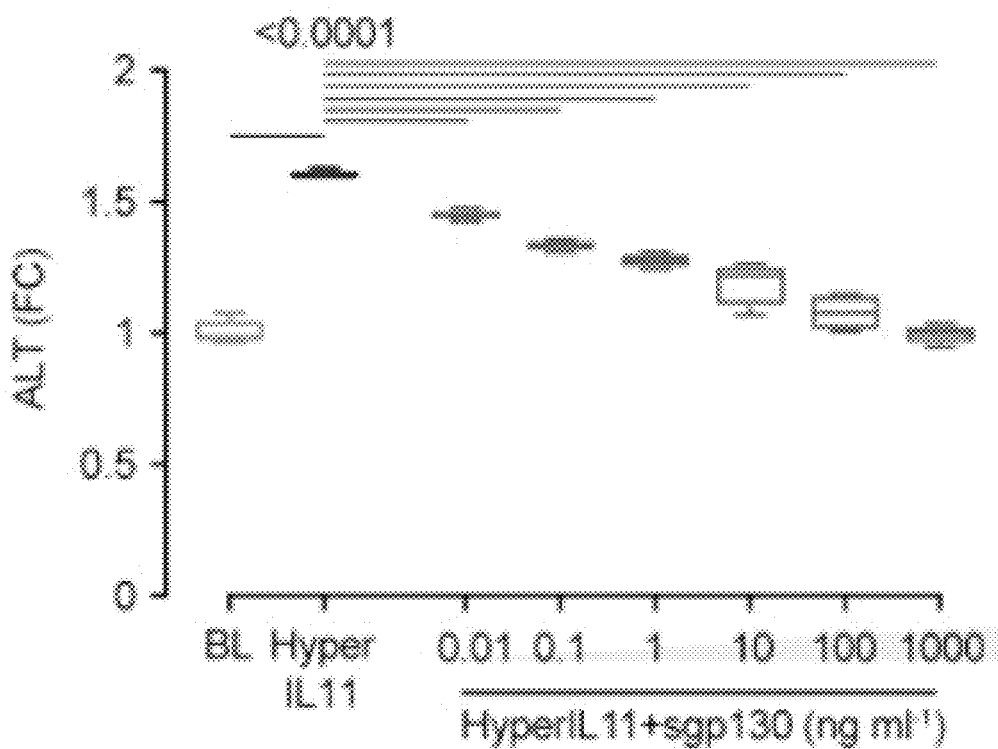
Figure 31H:
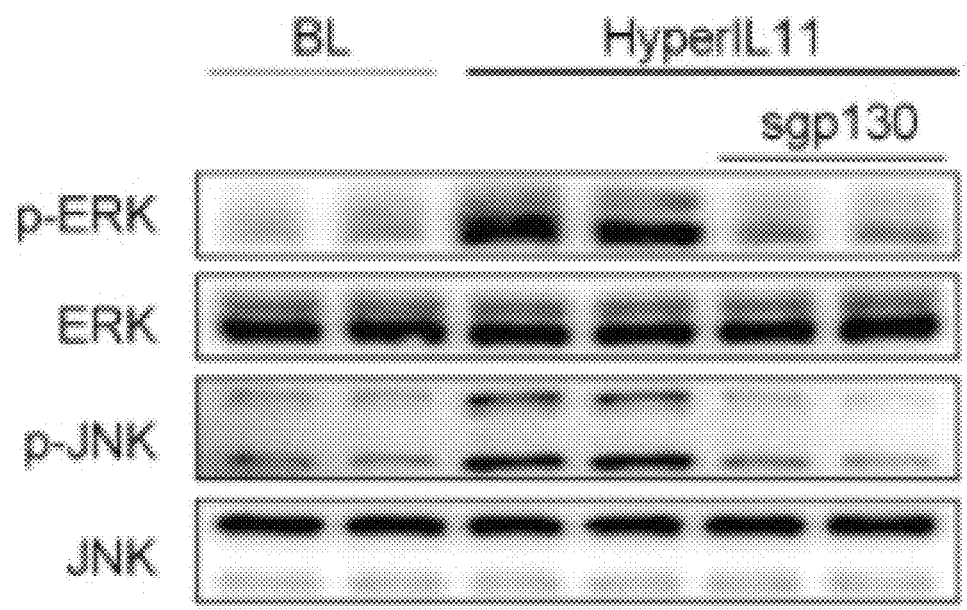
Figure 31I:
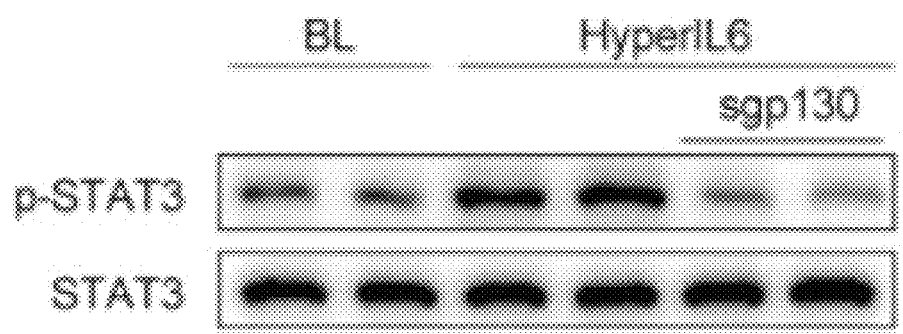

HyperIL11 caused a dose-dependent increase in alanine transaminase (ALT) in the media of primary human hepatocyte cell cultures whereas hyperIL6 (20 ng/ml) was found to have a significant, albeit limited, cytoprotective effect (fold change (FC)=0.9; P=0.0468) (FIG. 31F). Soluble gp130 (sgp130) is an inhibitor of trans-signaling complexes acting through gp130 (Schmidt-Arras and Rose-John, 2016). Consistent with its reported decoy effects, sgp130 blocked the activation of signaling pathways downstream of both hyperIL11 (p-ERK/p-JNK) and hyperIL6 (p-STAT3) and also inhibited the hepatotoxic effects of hyperIL11 (FIGS. 31G-31I).

Figure 31J:
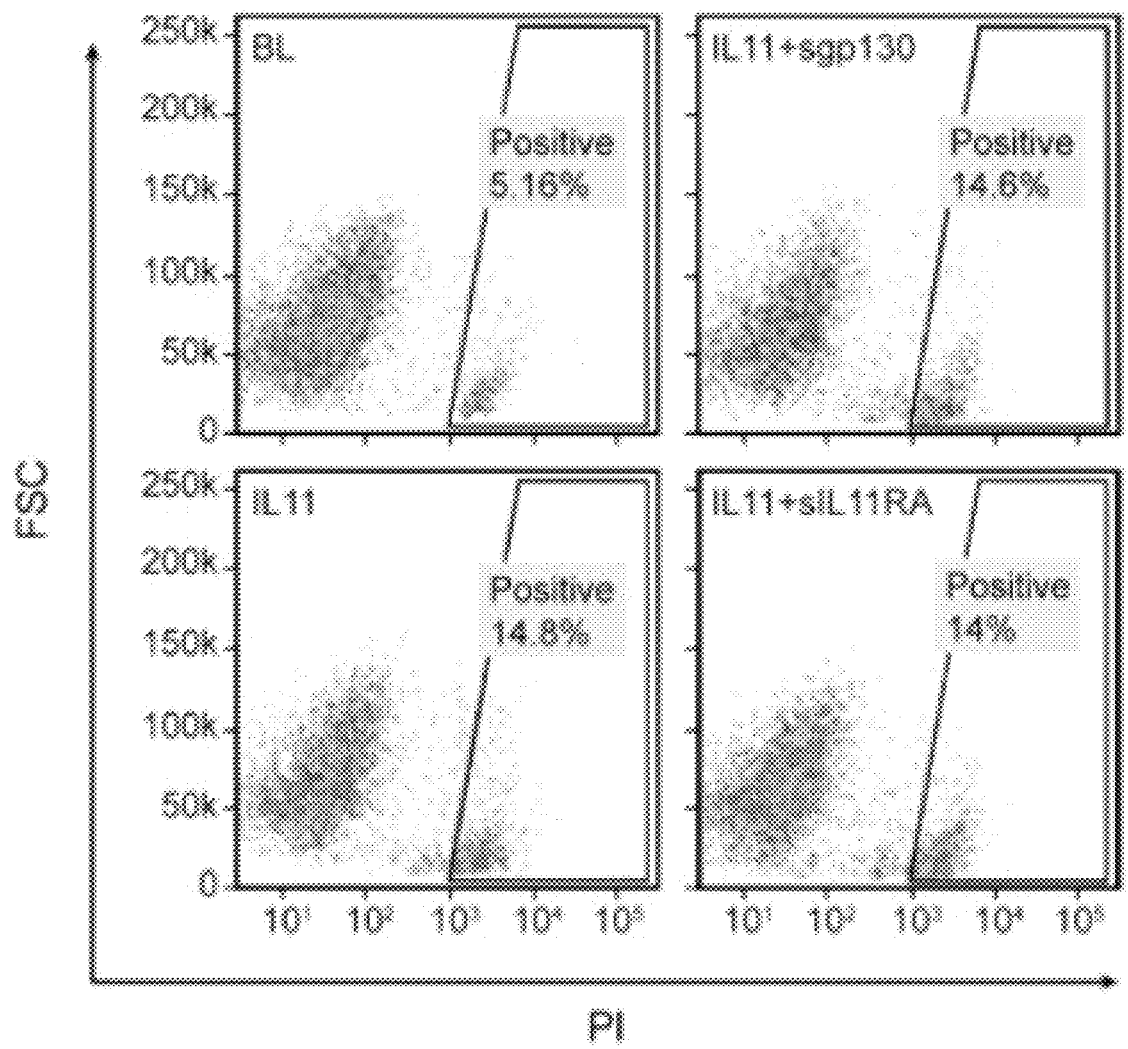
Figure 31K:
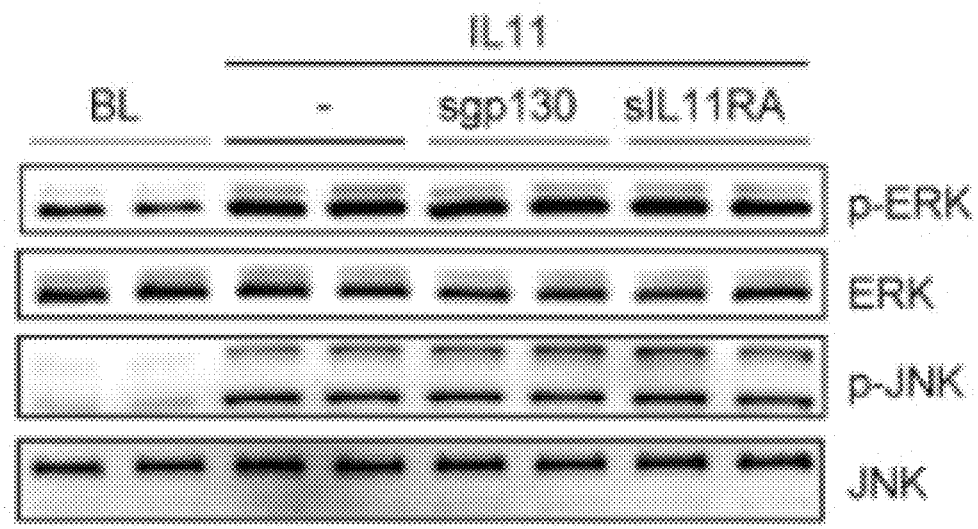
Figure 32F:
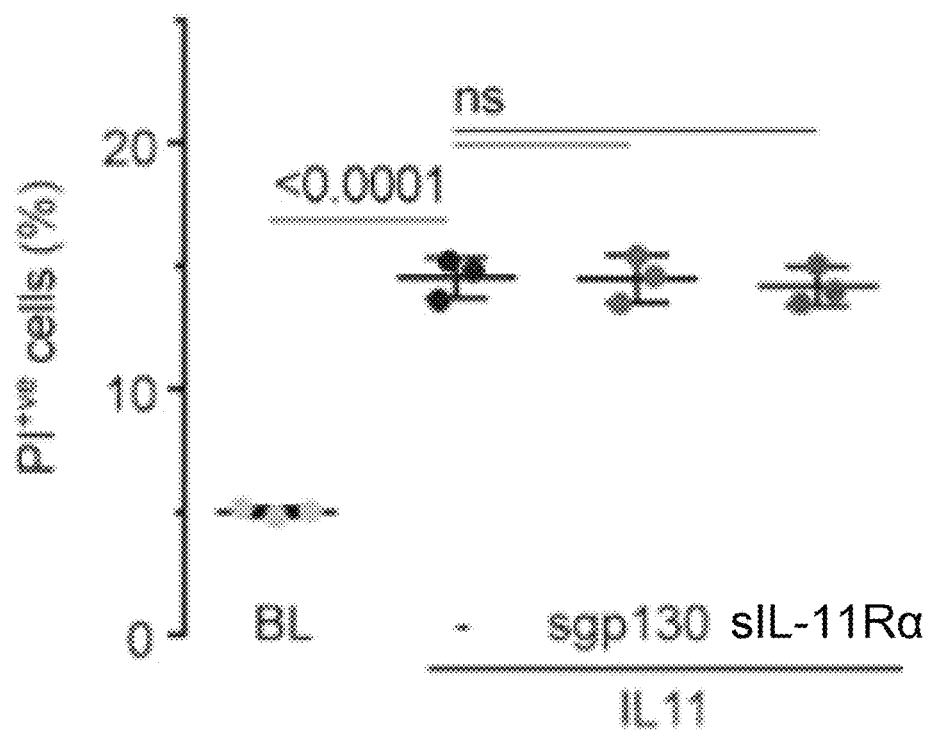
Figure 32G:
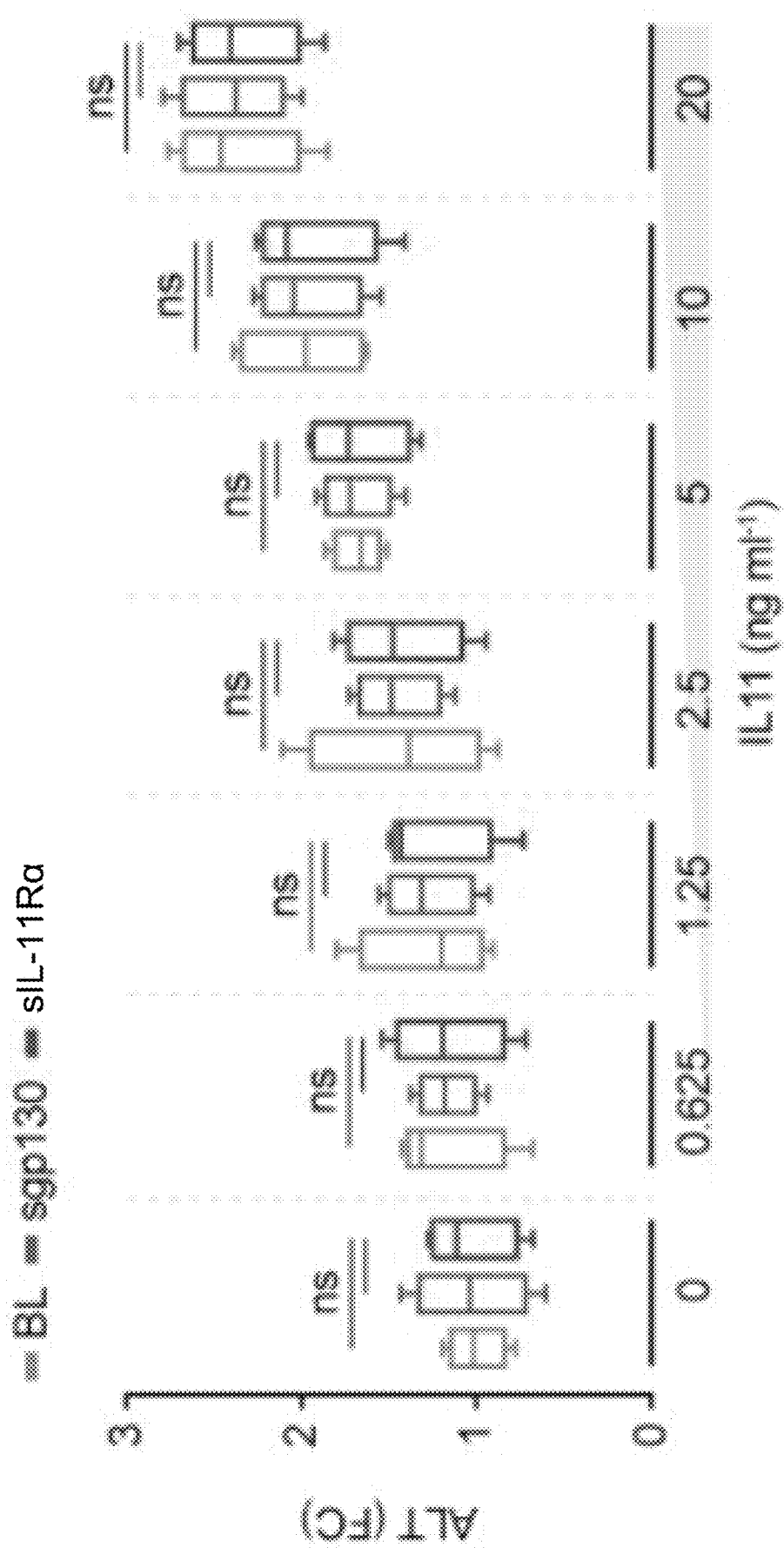
Figure 32H:
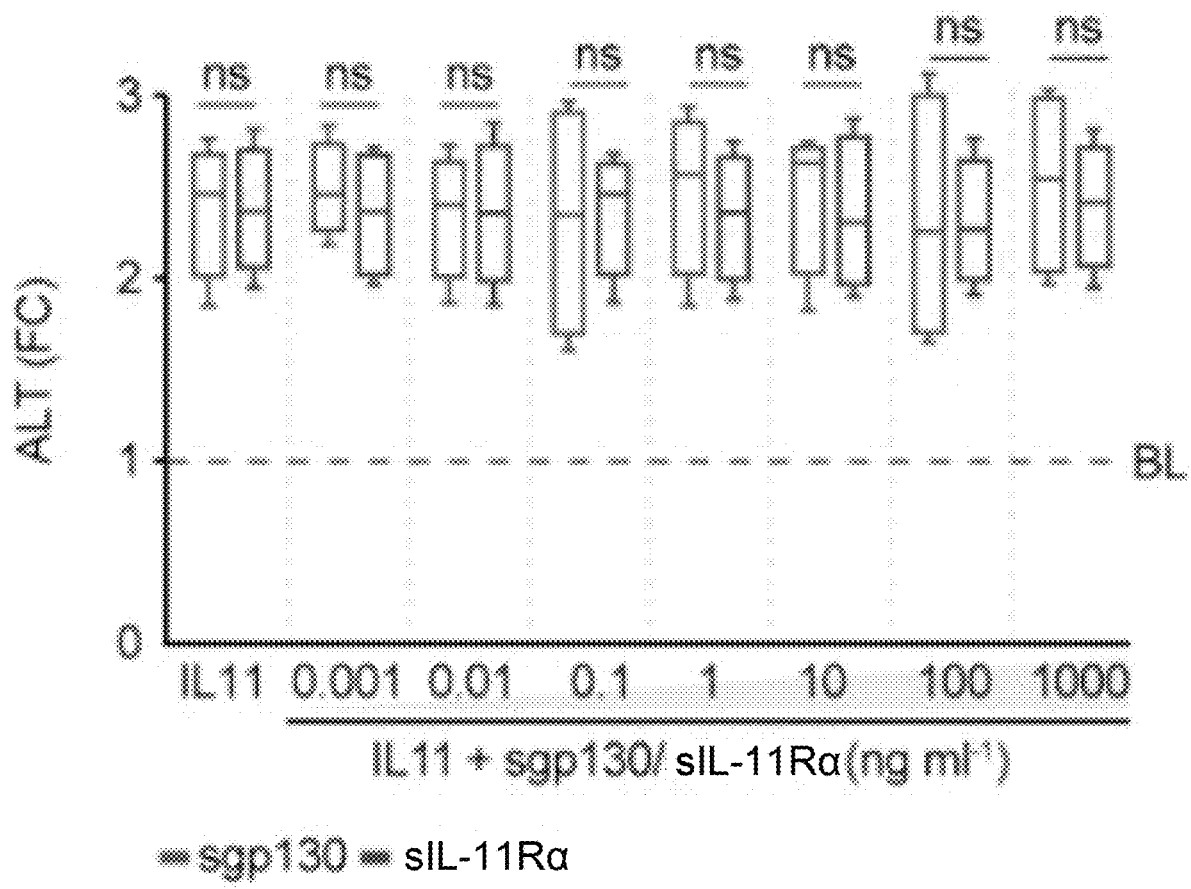

The inventors then performed experiments in order to detect IL11 trans-signaling in the absence of the artificial protein complexes hyperIL6 or hyperIL11. Cells were stimulated with IL11 in the presence of either soluble gp130 (sgp130, to inhibit putative trans-signaling) or soluble IL11Rα (sIL11Rα, to potentiate putative trans-signaling). IL11-induced hepatocyte death and signaling were unaffected by sgp130 or sIL11Rα (FIGS. 31J-31K and 32F). Furthermore, IL11 dose-dependently (0.625 ng/ml to 20 ng/ml) caused hepatocyte cell death, which was unaffected by the addition of sgp130 (1 µg/ml) or sIL11Rα (1 µg/ml) (FIG. 32G). Reciprocally, increasing doses of sgp130 or sIL11Rα had no effect on ALT release from IL11-stimulated hepatocytes (FIG. 32H). These data suggest that IL11 trans-signaling may not exist in the absence of synthetic constructs.

7.3 Materials and Methods for Example 7

Antibodies

Albumin (ab207327, Abcam), Alexa Fluor 488 secondary antibody (ab150077, Abcam), p-ERK1/2 (4370, CST), ERK1/2 (4695, CST), gp130 (PA5-28932, Thermo Fisher), IL6 (AF506, R&D systems), IL6R (flow cytometry, ab222101, Abcam), IL6R (for immunofluorescence staining, MA1-80456, Thermo Fisher), IL11 (Aldevron), IL11Rα (flow cytometry and immunofluorescence staining, ab125015, Abcam), IL11Rα (western blot, 130920, Santa Cruz), p-JNK (4668, CST), JNK (9258, CST), p-STAT3 (4113, CST), STAT3 (4904, CST), mouse HRP (7076, CST), rabbit HRP (7074, CST).

Recombinant Proteins

Commercial recombinant proteins: Human hyperIL6 (IL6R:IL6 fusion protein, 8954-SR, R&D systems), human soluble gp130 Fc (671-GP-100, R&D systems), human IL11Rα (8895-MR-050, R&D systems). Custom recombinant proteins: Human IL11 (UniProtKB:P20809, Genscript). Human hyperIL11 (IL11Rα:IL11 fusion protein), which mimics the trans-signalling complex, was constructed using a fragment of IL11Rα (amino acid residues 1-317; UniProtKB: Q14626) and IL11 (amino acid residues 22-199, UniProtKB: P20809) with a 20 amino acid linker (SEQ ID NO:20; Schafer et al., 2017).

Chemicals

Paraformaldehyde (PFA, 28908; Thermo Fisher), phorbol 12-myristate 13-acetate (PMA, P1585, Sigma), Triton X-100 (T8787, Sigma), and 4',6-diamidino-2-phenylindole (D1306; Thermo Fisher).

Primary Human Hepatocyte Culture

Primary human hepatocytes (5200, ScienCell) were maintained in hepatocyte medium (520, ScienCell) supplemented with 2% fetal bovine serum, 1% Penicillin-streptomycin at 37° C. and 5% $CO_2$. Hepatocytes (P2-P3) were serum-starved overnight unless otherwise specified in the methods prior to 24 hours stimulation with different doses of various recombinant proteins as outlined in the main text and/or figure legends.

THP-1 Culture

THP-1 (ATCC) were cultured in RPMI 1640 (A1049101, Thermo Fisher) supplemented with 10% FBS and 0.05 mM β-mercaptoethanol. THP-1 cells were differentiated with 10 ng/ml of PMA in RPMI 1640 for 48 hours.

Flow Cytometry

For surface IL11Rα, IL6R, and gp130 analysis, primary human hepatocytes and THP-1 cells were stained with IL11Rα, IL6R, or gp130 antibody and the corresponding Alexa Fluor 488 secondary antibody. Cell death analysis was performed by staining primary human hepatocytes with Dead Cell Apoptosis Kit with Annexin V FITC and PI (V13242, Thermo Fisher). PI+ve cells were then quantified with the flow cytometer (Fortessa, BD Biosciences) and analyzed with FlowJo version X software (TreeStar).

Immunofluorescence

Primary human hepatocytes were seeded on 8-well chamber slides (1.5×104 cells/well) 24 hours before the staining. Cells were fixed in 4% PFA for 20 minutes, washed with PBS, and non-specific sites were blocked with 5% BSA in PBS for 2 hours. Cells were incubated with IL11Rα, IL6R, gp130, or Albumin antibody overnight (4° C.), followed by incubation with the appropriate Alexa Fluor 488 secondary antibody for 1 hour. Chamber slides were dried in the dark and 5 drops of mounting medium with DAPI were added to the slides for 15 minutes prior to imaging by fluorescence microscope (Leica).

RNA-Sequencing (RNA-Seq) and Ribosome Profiling (Ribo-Seq)

RNA-seq and Ribo-Seq library preparations were performed as previously described (Chothani et al., 2019).

Generation of RNA-Seq Libraries

Total RNA was extracted from human hepatocytes using RNeasy columns (Qiagen). RNA was quantified using a Qubit RNA High-Sensitivity Assay kit (Life Technologies) and its quality was assessed on the basis of their RNA integrity number using the LabChip GX RNA Assay Reagent Kit (Perkin Elmer). TruSeq Stranded mRNA Library Preparation kit (Illumina) was used to measure transcript abundance following standard instructions from the manufacturer.

Generation of Ribo-Seq Libraries

Hepatocytes were grown to 90% confluence in a 10 cm culture dish and lysed in 1 mL cold lysis buffer (formulation as in TruSeq® Ribo Profile Mammalian Kit, RPHMR12126, Illumina) supplemented with 0.1 mg/mL cycloheximide. Homogenized and cleared lysates were then footprinted with Truseq Nuclease (Illumina) according to the manufacturer's instructions. Ribosomes were purified using Illustra Sephacryl S400 columns (GE Healthcare), and the protected RNA fragments were extracted with a standard phenol:chloroform:isoamylalcohol technique. Following ribosomal RNA removal (Mammalian RiboZero Magnetic Gold, Illumina), sequencing libraries were then prepared out of the footprinted RNA by using TruSeq® Ribo Profile Mammalian Kit according to the manufacturer's protocol. The final RNA-seq and ribosome profiling libraries were quantified using KAPA library quantification kits (KAPA Biosystems) on a StepOnePlus Real-Time PCR system (Applied Biosystems) according to the manufacturer's protocol.

The quality and average fragment size of the final libraries were determined using a LabChip GX DNA High Sensitivity Reagent Kit (Perkin Elmer). Libraries with unique indexes were pooled and sequenced on a NextSeq 500 benchtop sequencer (Illumina) using NextSeq 500 High Output v2 kit and paired-end 75-bp sequencing chemistry.

Data Processing and Analyses for RNA-Sequencing and Ribosome Profiling

Raw sequencing data were demultiplexed with bcl2fastq V2.19.0.316 and the adaptors were trimmed using Trimmomatic (Bolger et al., 2014) V0.36, retaining reads longer than 20 nt post-clipping. Ribo-seq reads were aligned using bowtie (Langmead et al., 2009) to known mtRNA, rRNA and tRNA sequences (RNACentral(The RNAcentral Consortium, 2017), release 5.0) and only unaligned reads were retained as Ribosome protected fragments (RPFs). Alignment to the human genome (hg38) was carried out using STAR (Dobin et al., 2012). Gene expression was quantified on the CDS (coding sequence) regions for Ribo-seq and exonic regions for RNA-seq using uniquely mapped reads (Ensembl database release GRCh38 v86) with feature counts (Liao et al., 2014). TPM was calculated and visualized using boxplot to compare baseline expression of IL11Rα (ENSG00000137070), IL6R (ENSG00000160712), and gp130 (ENSG00000134352). Read coverage using Ribo-seq and RNA-seq reads for IL11Rα, IL6R and gp130 was visualized using Gviz R package (Hahne and Ivanek, 2016) with strand specific alignment files.

Colorimetric Assays

Alanine Aminotransferase (ALT) activity in the cell culture supernatant was measured using ALT Activity Assay Kit (ab105134, Abcam) according to the manufacturer's protocol.

Immunoblotting

Western blots were carried out on total protein extracts from hepatocytes. Hepatocyte lysates were homogenized in RIPA Lysis and Extraction Buffer (89901, Thermo Scientific) containing protease and phosphatase inhibitors (Roche). Protein lysates were separated by SDS-PAGE and transferred to PVDF membranes. Protein bands were visualized using the ECL detection system (Pierce) with the appropriate secondary antibodies: anti-rabbit HRP or anti-mouse HRP.

Statistical Analysis

All statistical analyses were performed using GraphPad Prism software (version 6.07). P values were corrected for multiple testing according to Tukey when several conditions were compared to each other within one experiment. The criterion for statistical significance was set at $P<0.05$.

7.4 References to Example 7

Agthe, M., Garbers, Y., Putoczki, T., and Garbers, C. (2017). Interleukin-11 classic but not trans-signaling is essential for fertility in mice. Placenta 57, 13-16.

Balic, J. J., Garbers, C., Rose-John, S., Yu, L., and Jenkins, B. J. (2017). Interleukin-11-driven gastric tumourigenesis is independent of trans-signalling. Cytokine 92, 118-123.

Bolger, A. M., Lohse, M., and Usadel, B. (2014). Trimmomatic: a flexible trimmer for Illumina sequence data. Bioinformatics 30, 2114-2120.

Chothani, S., Schafer, S., Adami, E., Viswanathan, S., Widjaja, A. A., Langley, S. R., Tan, J., Wang, M., Quaife, N. M., Jian Pua, C., et al. (2019). Widespread Translational Control of Fibrosis in the Human Heart by RNA-Binding Proteins. Circulation 140, 937-951.

Dobin, A., Davis, C. A., Schlesinger, F., Drenkow, J., Zaleski, C., Jha, S., Batut, P., Chaisson, M., and Gingeras, T. R. (2012). STAR: ultrafast universal RNA-seq aligner. Bioinformatics 29, 15-21.

Hahne, F., and Ivanek, R. (2016). Visualizing Genomic Data Using Gviz and Bioconductor. In Statistical Genomics, (Humana Press, New York, N.Y.), pp. 335-351.

Klein, C., Wüstefeld, T., Assmus, U., Roskams, T., Rose-John, S., Müller, M., Manns, M. P., Ernst, M., and Trautwein, C. (2005). The IL-6-gp130-STAT3 pathway in hepatocytes triggers liver protection in T cell-mediated liver injury. J. Clin. Invest. 115, 860-869.

Kroy, D. C., Beraza, N., Tschaharganeh, D. F., Sander, L. E., Erschfeld, S., Giebeler, A., Liedtke, C., Wasmuth, H. E., Trautwein, C., and Streetz, K. L. (2010). Lack of interleukin-6/glycoprotein 130/signal transducers and activators of transcription-3 signaling in hepatocytes predisposes to liver steatosis and injury in mice. Hepatology 51, 463-473.

Langmead, B., Trapnell, C., Pop, M., and Salzberg, S. L. (2009). Ultrafast and memory-efficient alignment of short DNA sequences to the human genome. Genome Biol. 10, R25.

Liao, Y., Smyth, G. K., and Shi, W. (2014). featureCounts: an efficient general purpose program for assigning sequence reads to genomic features. Bioinformatics 30, 923-930.

Matthews, V. B., Allen, T. L., Risis, S., Chan, M. H. S., Henstridge, D. C., Watson, N., Zaffino, L. A., Babb, J. R., Boon, J., Meikle, P. J., et al. (2010). Interleukin-6-deficient mice develop hepatic inflammation and systemic insulin resistance. Diabetologia 53, 2431-2441.

Schafer, S., Viswanathan, S., Widjaja, A. A., Lim, W.-W., Moreno-Moral, A., DeLaughter, D. M., Ng, B., Patone, G., Chow, K., Khin, E., et al. (2017). IL-11 is a crucial determinant of cardiovascular fibrosis. Nature 552, 110-115.

Schmidt-Arras, D., and Rose-John, S. (2016). IL-6 pathway in the liver: From physiopathology to therapy. J. Hepatol. 64, 1403-1415.

The RNAcentral Consortium (2017). RNAcentral: a comprehensive database of non-coding RNA sequences. Nucleic Acids Res. 45, D128-D134.

Wuestefeld, T., Klein, C., Streetz, K. L., Betz, U., Lauber, J., Buer, J., Manns, M. P., Müller, W., and Trautwein, C. (2003). Interleukin-6/glycoprotein 130-dependent pathways are protective during liver regeneration. J. Biol. Chem. 278, 11281-11288.

---

The invention claimed is:

1. A method of treating acetaminophen (APAP) induced liver injury, the method comprising administering a therapeutically effective amount of an anti-IL-11 antibody or an antigen-binding fragment thereof which is an antagonist of the IL-11 mediated signaling to a subject.

2. The method according to claim 1, wherein the anti-IL-11 antibody or an antigen-binding fragment thereof which is an antagonist of the IL-11 mediated signaling is capable of preventing or reducing the binding of interleukin 11 (IL-11) to a receptor for interleukin 11 (IL-11R).

3. The method according to claim 2, wherein the interleukin 11 receptor is or comprises IL-11Rα.

4. The method according to claim 1, wherein the method of treating APAP-induced liver injury further comprises treatment with N-acetylcysteine.

5. The method according to claim 1, wherein the method of treating comprises administering the anti-IL-11 antibody or an antigen-binding fragment thereof which is an antagonist of the IL-11 mediated signaling to a subject in which expression of interleukin 11 (IL-11) or a receptor for IL-11 (IL-11R) is upregulated.

6. The method according to claim 1, wherein the method of treating comprises administering the anti-IL-11 antibody or an antigen-binding fragment thereof which is an antagonist of the IL-11 mediated signaling to a subject in which expression of interleukin 11 (IL-11) or a receptor for interleukin 11 (IL-11R) has been determined to be upregulated.

7. The method according to claim 1, wherein the method of treating comprises determining whether expression of interleukin 11 (IL-11) or a receptor for IL-11 (IL-11R) is upregulated in the subject and administering the anti-IL-11 antibody or an antigen-binding fragment thereof which is an antagonist of the IL-11 mediated signaling to a subject in which expression of interleukin 11 (IL-11) or a receptor for IL-11 (IL-11R) is upregulated.

* * * * *

UNITED STATES PATENT AND TRADEMARK OFFICE
CERTIFICATE OF CORRECTION

PATENT NO.        : 11,319,368 B2
APPLICATION NO.   : 16/748698
DATED             : May 3, 2022
INVENTOR(S)       : Stuart Alexander Cook et al.

It is certified that error appears in the above-identified patent and that said Letters Patent is hereby corrected as shown below:

On the Title Page

Under Item (30) Foreign Application Priority Data:
"Jan. 21, 2019 (GB)............1900811
Jun. 3, 2019 (GB)............1907839
Oct. 17, 2019 (GB)............1915003"

Should Read:
-- Jan. 21, 2019 (GB)............1900811.6
Jun. 3, 2019 (GB)............1907839.3
Oct. 17, 2019 (GB)............1915003.9 --

Signed and Sealed this
Twenty-third Day of August, 2022

Katherine Kelly Vidal
*Director of the United States Patent and Trademark Office*

SEQUENCE LISTING

```
<160> NUMBER OF SEQ ID NOS: 29

<210> SEQ ID NO 1
<211> LENGTH: 199
<212> TYPE: PRT
<213> ORGANISM: Homo sapiens

<400> SEQUENCE: 1

Met Asn Cys Val Cys Arg Leu Val Leu Val Val Leu Ser Leu Trp Pro
1               5                   10                  15

Asp Thr Ala Val Ala Pro Gly Pro Pro Gly Pro Pro Arg Val Ser
            20                  25                  30

Pro Asp Pro Arg Ala Glu Leu Asp Ser Thr Val Leu Leu Thr Arg Ser
        35                  40                  45

Leu Leu Ala Asp Thr Arg Gln Leu Ala Ala Gln Leu Arg Asp Lys Phe
    50                  55                  60

Pro Ala Asp Gly Asp His Asn Leu Asp Ser Leu Pro Thr Leu Ala Met
65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
            100                 105                 110

Arg Ala Gly Gly Ser Ser Leu Lys Thr Leu Glu Pro Glu Leu Gly Thr
        115                 120                 125

Leu Gln Ala Arg Leu Asp Arg Leu Leu Arg Arg Leu Gln Leu Leu Met
    130                 135                 140

Ser Arg Leu Ala Leu Pro Gln Pro Pro Asp Pro Pro Ala Pro Pro
145                 150                 155                 160

Leu Ala Pro Pro Ser Ser Ala Trp Gly Gly Ile Arg Ala Ala His Ala
                165                 170                 175

Ile Leu Gly Gly Leu His Leu Thr Leu Asp Trp Ala Val Arg Gly Leu
            180                 185                 190

Leu Leu Leu Lys Thr Arg Leu
    195
```

<210> SEQ ID NO 2
<211> LENGTH: 918
<212> TYPE: PRT
<213> ORGANISM: Homo sapiens

<400> SEQUENCE: 2

```
Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
```

```
              370                 375                 380
Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
                420                 425                 430

Phe Pro Lys Asp Asn Met Leu Trp Val Glu Trp Thr Thr Pro Arg Glu
            435                 440                 445

Ser Val Lys Lys Tyr Ile Leu Glu Trp Cys Val Leu Ser Asp Lys Ala
        450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
                500                 505                 510

Tyr Leu Lys Gln Ala Pro Pro Ser Lys Gly Pro Thr Val Arg Thr Lys
            515                 520                 525

Lys Val Gly Lys Asn Glu Ala Val Leu Glu Trp Asp Gln Leu Pro Val
        530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
                580                 585                 590

Ala Ala Tyr Thr Asp Glu Gly Gly Lys Asp Gly Pro Glu Phe Thr Phe
            595                 600                 605

Thr Thr Pro Lys Phe Ala Gln Gly Glu Ile Glu Ala Ile Val Val Pro
        610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
                660                 665                 670

Arg His Asn Phe Asn Ser Lys Asp Gln Met Tyr Ser Asp Gly Asn Phe
            675                 680                 685

Thr Asp Val Ser Val Val Glu Ile Glu Ala Asn Asp Lys Lys Pro Phe
        690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Ser Asp Glu Asn Glu Ser Ser Gln Asn
                740                 745                 750

Thr Ser Ser Thr Val Gln Tyr Ser Thr Val Val His Ser Gly Tyr Arg
            755                 760                 765

His Gln Val Pro Ser Val Gln Val Phe Ser Arg Ser Glu Ser Thr Gln
        770                 775                 780

Pro Leu Leu Asp Ser Glu Glu Arg Pro Glu Asp Leu Gln Leu Val Asp
785                 790                 795                 800
```

-continued

```
His Val Asp Gly Gly Asp Gly Ile Leu Pro Arg Gln Gln Tyr Phe Lys
            805                 810                 815

Gln Asn Cys Ser Gln His Glu Ser Ser Pro Asp Ile Ser His Phe Glu
        820                 825                 830

Arg Ser Lys Gln Val Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
                900                 905                 910

Gly Gly Tyr Met Pro Gln
            915
```

<210> SEQ ID NO 3
<211> LENGTH: 422
<212> TYPE: PRT
<213> ORGANISM: Homo sapiens

<400> SEQUENCE: 3

```
Met Ser Ser Ser Cys Ser Gly Leu Ser Arg Val Leu Val Ala Val Ala
1               5                   10                  15

Thr Ala Leu Val Ser Ala Ser Pro Cys Pro Gln Ala Trp Gly Pro
            20                  25                  30

Pro Gly Val Gln Tyr Gly Gln Pro Gly Arg Ser Val Lys Leu Cys Cys
        35                  40                  45

Pro Gly Val Thr Ala Gly Asp Pro Val Ser Trp Phe Arg Asp Gly Glu
    50                  55                  60

Pro Lys Leu Leu Gln Gly Pro Asp Ser Gly Leu Gly His Glu Leu Val
65                  70                  75                  80

Leu Ala Gln Ala Asp Ser Thr Asp Glu Gly Thr Tyr Ile Cys Gln Thr
                85                  90                  95

Leu Asp Gly Ala Leu Gly Gly Thr Val Thr Leu Gln Leu Gly Tyr Pro
            100                 105                 110

Pro Ala Arg Pro Val Val Ser Cys Gln Ala Ala Asp Tyr Glu Asn Phe
        115                 120                 125

Ser Cys Thr Trp Ser Pro Ser Gln Ile Ser Gly Leu Pro Thr Arg Tyr
    130                 135                 140

Leu Thr Ser Tyr Arg Lys Lys Thr Val Leu Gly Ala Asp Ser Gln Arg
145                 150                 155                 160

Arg Ser Pro Ser Thr Gly Pro Trp Pro Cys Pro Gln Asp Pro Leu Gly
                165                 170                 175

Ala Ala Arg Cys Val Val His Gly Ala Glu Phe Trp Ser Gln Tyr Arg
            180                 185                 190

Ile Asn Val Thr Glu Val Asn Pro Leu Gly Ala Ser Thr Arg Leu Leu
        195                 200                 205

Asp Val Ser Leu Gln Ser Ile Leu Arg Pro Asp Pro Pro Gln Gly Leu
    210                 215                 220

Arg Val Glu Ser Val Pro Gly Tyr Pro Arg Arg Leu Arg Ala Ser Trp
225                 230                 235                 240

Thr Tyr Pro Ala Ser Trp Pro Cys Gln Pro His Phe Leu Leu Lys Phe
```

```
                    245                 250                 255
Arg Leu Gln Tyr Arg Pro Ala Gln His Pro Ala Trp Ser Thr Val Glu
            260                 265                 270

Pro Ala Gly Leu Glu Glu Val Ile Thr Asp Ala Val Ala Gly Leu Pro
        275                 280                 285

His Ala Val Arg Val Ser Ala Arg Asp Phe Leu Asp Ala Gly Thr Trp
    290                 295                 300

Ser Thr Trp Ser Pro Glu Ala Trp Gly Thr Pro Ser Thr Gly Thr Ile
305                 310                 315                 320

Pro Lys Glu Ile Pro Ala Trp Gly Gln Leu His Thr Gln Pro Glu Val
            325                 330                 335

Glu Pro Gln Val Asp Ser Pro Ala Pro Pro Arg Pro Ser Leu Gln Pro
        340                 345                 350

His Pro Arg Leu Leu Asp His Arg Asp Ser Val Glu Gln Val Ala Val
    355                 360                 365

Leu Ala Ser Leu Gly Ile Leu Ser Phe Leu Gly Leu Val Ala Gly Ala
370                 375                 380

Leu Ala Leu Gly Leu Trp Leu Arg Leu Arg Arg Gly Gly Lys Asp Gly
385                 390                 395                 400

Ser Pro Lys Pro Gly Phe Leu Ala Ser Val Ile Pro Val Asp Arg Arg
            405                 410                 415

Pro Gly Ala Pro Asn Leu
            420

<210> SEQ ID NO 4
<211> LENGTH: 19
<212> TYPE: DNA
<213> ORGANISM: Artificial Sequence
<220> FEATURE:
<223> OTHER INFORMATION: siRNA target IL-11

<400> SEQUENCE: 4
ccttccaaag ccagatctt                                             19

<210> SEQ ID NO 5
<211> LENGTH: 19
<212> TYPE: DNA
<213> ORGANISM: Artificial Sequence
<220> FEATURE:
<223> OTHER INFORMATION: siRNA target IL-11

<400> SEQUENCE: 5
gcctgggcag gaacatata                                             19

<210> SEQ ID NO 6
<211> LENGTH: 19
<212> TYPE: DNA
<213> ORGANISM: Artificial Sequence
<220> FEATURE:
<223> OTHER INFORMATION: siRNA target IL-11

<400> SEQUENCE: 6
cctgggcagg aacatatat                                             19

<210> SEQ ID NO 7
<211> LENGTH: 19
<212> TYPE: DNA
<213> ORGANISM: Artificial Sequence
<220> FEATURE:
<223> OTHER INFORMATION: siRNA target IL-11
```

```
<400> SEQUENCE: 7
ggttcattat ggctgtgtt                                                    19

<210> SEQ ID NO 8
<211> LENGTH: 19
<212> TYPE: DNA
<213> ORGANISM: Artificial Sequence
<220> FEATURE:
<223> OTHER INFORMATION: siRNA target IL-11Ralpha

<400> SEQUENCE: 8
ggaccatacc aaaggagat                                                    19

<210> SEQ ID NO 9
<211> LENGTH: 19
<212> TYPE: DNA
<213> ORGANISM: Artificial Sequence
<220> FEATURE:
<223> OTHER INFORMATION: siRNA target IL-11Ralpha

<400> SEQUENCE: 9
gcgtctttgg gaatcctttt                                                   19

<210> SEQ ID NO 10
<211> LENGTH: 18
<212> TYPE: DNA
<213> ORGANISM: Artificial Sequence
<220> FEATURE:
<223> OTHER INFORMATION: siRNA target IL-11Ralpha

<400> SEQUENCE: 10
gcaggacagt agatccct                                                     18

<210> SEQ ID NO 11
<211> LENGTH: 19
<212> TYPE: DNA
<213> ORGANISM: Artificial Sequence
<220> FEATURE:
<223> OTHER INFORMATION: siRNA target IL-11Ralpha

<400> SEQUENCE: 11
gctcaaggaa cgtgtgtaa                                                    19

<210> SEQ ID NO 12
<211> LENGTH: 42
<212> TYPE: DNA
<213> ORGANISM: Artificial Sequence
<220> FEATURE:
<223> OTHER INFORMATION: siRNA to IL-11 (NM_000641.3)
<220> FEATURE:
<221> NAME/KEY: misc_feature
<222> LOCATION: (20)..(21)
<223> OTHER INFORMATION: n = deoxythymine
<220> FEATURE:
<221> NAME/KEY: misc_feature
<222> LOCATION: (41)..(42)
<223> OTHER INFORMATION: n = deoxythymine

<400> SEQUENCE: 12
ccuuccaaag ccagaucuun naagaucugg cuuuggaagg nn                          42

<210> SEQ ID NO 13
<211> LENGTH: 42
<212> TYPE: DNA
<213> ORGANISM: Artificial Sequence
<220> FEATURE:
<223> OTHER INFORMATION: siRNA to IL-11 (NM_000641.3)
```

```
<220> FEATURE:
<221> NAME/KEY: misc_feature
<222> LOCATION: (20)..(21)
<223> OTHER INFORMATION: n = deoxythymine
<220> FEATURE:
<221> NAME/KEY: misc_feature
<222> LOCATION: (41)..(42)
<223> OTHER INFORMATION: n = deoxythymine

<400> SEQUENCE: 13
gccugggcag gaacauauan nuauauguuc cugcccaggc nn                          42

<210> SEQ ID NO 14
<211> LENGTH: 42
<212> TYPE: DNA
<213> ORGANISM: Artificial Sequence
<220> FEATURE:
<223> OTHER INFORMATION: siRNA to IL-11 (NM_000641.3)
<220> FEATURE:
<221> NAME/KEY: misc_feature
<222> LOCATION: (20)..(21)
<223> OTHER INFORMATION: n = deoxythymine
<220> FEATURE:
<221> NAME/KEY: misc_feature
<222> LOCATION: (41)..(42)
<223> OTHER INFORMATION: n = deoxythymine

<400> SEQUENCE: 14
ccugggcagg aacauauaun nauauaguu ccugcccagg nn                           42

<210> SEQ ID NO 15
<211> LENGTH: 42
<212> TYPE: DNA
<213> ORGANISM: Artificial Sequence
<220> FEATURE:
<223> OTHER INFORMATION: siRNA to IL-11 (NM_000641.3)
<220> FEATURE:
<221> NAME/KEY: misc_feature
<222> LOCATION: (20)..(21)
<223> OTHER INFORMATION: n = deoxythymine
<220> FEATURE:
<221> NAME/KEY: misc_feature
<222> LOCATION: (41)..(42)
<223> OTHER INFORMATION: n = deoxythymine

<400> SEQUENCE: 15
gguucauuau ggcuguguun naacacagcc auaaugaacc nn                          42

<210> SEQ ID NO 16
<211> LENGTH: 42
<212> TYPE: DNA
<213> ORGANISM: Artificial Sequence
<220> FEATURE:
<223> OTHER INFORMATION: siRNA to IL-11Ralpha (U32324.1)
<220> FEATURE:
<221> NAME/KEY: misc_feature
<222> LOCATION: (20)..(21)
<223> OTHER INFORMATION: n = deoxythymine
<220> FEATURE:
<221> NAME/KEY: misc_feature
<222> LOCATION: (41)..(42)
<223> OTHER INFORMATION: n = deoxythymine

<400> SEQUENCE: 16
ggaccauacc aaaggagaun naucuccuuu gguauggucc nn                          42

<210> SEQ ID NO 17
<211> LENGTH: 42
<212> TYPE: DNA
<213> ORGANISM: Artificial Sequence
<220> FEATURE:
```

<223> OTHER INFORMATION: siRNA to IL-11Ralpha (U32324.1)
<220> FEATURE:
<221> NAME/KEY: misc_feature
<222> LOCATION: (20)..(21)
<223> OTHER INFORMATION: n = deoxythymine
<220> FEATURE:
<221> NAME/KEY: misc_feature
<222> LOCATION: (41)..(42)
<223> OTHER INFORMATION: n = deoxythymine

<400> SEQUENCE: 17
gcgucuuugg gaauccuuun naaaggauuc ccaaagacgc nn                42

<210> SEQ ID NO 18
<211> LENGTH: 42
<212> TYPE: DNA
<213> ORGANISM: Artificial Sequence
<220> FEATURE:
<223> OTHER INFORMATION: siRNA to IL-11Ralpha (U32324.1)
<220> FEATURE:
<221> NAME/KEY: misc_feature
<222> LOCATION: (20)..(21)
<223> OTHER INFORMATION: n = deoxythymine
<220> FEATURE:
<221> NAME/KEY: misc_feature
<222> LOCATION: (41)..(42)
<223> OTHER INFORMATION: n = deoxythymine

<400> SEQUENCE: 18
gcaggacagu agaucccuan nuagggaucu acuguccugc nn                42

<210> SEQ ID NO 19
<211> LENGTH: 42
<212> TYPE: DNA
<213> ORGANISM: Artificial Sequence
<220> FEATURE:
<223> OTHER INFORMATION: siRNA to IL-11Ralpha (U32324.1)
<220> FEATURE:
<221> NAME/KEY: misc_feature
<222> LOCATION: (20)..(21)
<223> OTHER INFORMATION: n = deoxythymine
<220> FEATURE:
<221> NAME/KEY: misc_feature
<222> LOCATION: (41)..(42)
<223> OTHER INFORMATION: n = deoxythymine

<400> SEQUENCE: 19
gcucaaggaa cguguguaan nuuacacacg uuccuugagc nn                42

<210> SEQ ID NO 20
<211> LENGTH: 21
<212> TYPE: PRT
<213> ORGANISM: Artificial Sequence
<220> FEATURE:
<223> OTHER INFORMATION: 20 amino acid linker

<400> SEQUENCE: 20

Gly Pro Ala Gly Gln Ser Gly Gly Gly Gly Ser Gly Gly Gly Ser
1               5                   10                  15

Gly Gly Gly Ser Val
            20

<210> SEQ ID NO 21
<211> LENGTH: 516
<212> TYPE: PRT
<213> ORGANISM: Artificial Sequence
<220> FEATURE:
<223> OTHER INFORMATION: Hyper IL-11 (IL-11RA:IL-11 fusion)

<400> SEQUENCE: 21

```
Met Ser Ser Ser Cys Ser Gly Leu Ser Arg Val Leu Ala Val Ala
1               5                   10                  15

Thr Ala Leu Val Ser Ala Ser Ser Pro Cys Pro Gln Ala Trp Gly Pro
            20                  25                  30

Pro Gly Val Gln Tyr Gly Gln Pro Gly Arg Ser Val Lys Leu Cys Cys
            35                  40                  45

Pro Gly Val Thr Ala Gly Asp Pro Val Ser Trp Phe Arg Asp Gly Glu
50                  55                  60

Pro Lys Leu Leu Gln Gly Pro Asp Ser Gly Leu Gly His Glu Leu Val
65                  70                  75                  80

Leu Ala Gln Ala Asp Ser Thr Asp Glu Gly Thr Tyr Ile Cys Gln Thr
                85                  90                  95

Leu Asp Gly Ala Leu Gly Gly Thr Val Thr Leu Gln Leu Gly Tyr Pro
                100                 105                 110

Pro Ala Arg Pro Val Val Ser Cys Gln Ala Ala Asp Tyr Glu Asn Phe
            115                 120                 125

Ser Cys Thr Trp Ser Pro Ser Gln Ile Ser Gly Leu Pro Thr Arg Tyr
    130                 135                 140

Leu Thr Ser Tyr Arg Lys Lys Thr Val Leu Gly Ala Asp Ser Gln Arg
145                 150                 155                 160

Arg Ser Pro Ser Thr Gly Pro Trp Pro Cys Pro Gln Asp Pro Leu Gly
                165                 170                 175

Ala Ala Arg Cys Val Val His Gly Ala Glu Phe Trp Ser Gln Tyr Arg
            180                 185                 190

Ile Asn Val Thr Glu Val Asn Pro Leu Gly Ala Ser Thr Arg Leu Leu
            195                 200                 205

Asp Val Ser Leu Gln Ser Ile Leu Arg Pro Asp Pro Pro Gln Gly Leu
            210                 215                 220

Arg Val Glu Ser Val Pro Gly Tyr Pro Arg Arg Leu Arg Ala Ser Trp
225                 230                 235                 240

Thr Tyr Pro Ala Ser Trp Pro Cys Gln Pro His Phe Leu Leu Lys Phe
                245                 250                 255

Arg Leu Gln Tyr Arg Pro Ala Gln His Pro Ala Trp Ser Thr Val Glu
                260                 265                 270

Pro Ala Gly Leu Glu Glu Val Ile Thr Asp Ala Val Ala Gly Leu Pro
            275                 280                 285

His Ala Val Arg Val Ser Ala Arg Asp Phe Leu Asp Ala Gly Thr Trp
    290                 295                 300

Ser Thr Trp Ser Pro Glu Ala Trp Gly Thr Pro Ser Thr Gly Pro Ala
305                 310                 315                 320

Gly Gln Ser Gly Gly Gly Gly Ser Gly Gly Ser Gly Gly Gly
                325                 330                 335

Ser Val Pro Gly Pro Pro Gly Pro Pro Arg Val Ser Pro Asp Pro
                340                 345                 350

Arg Ala Glu Leu Asp Ser Thr Val Leu Leu Thr Arg Ser Leu Leu Ala
                355                 360                 365

Asp Thr Arg Gln Leu Ala Ala Gln Leu Arg Asp Lys Phe Pro Ala Asp
    370                 375                 380

Gly Asp His Asn Leu Asp Ser Leu Pro Thr Leu Ala Met Ser Ala Gly
385                 390                 395                 400

Ala Leu Gly Ala Leu Gln Leu Pro Gly Val Leu Thr Arg Leu Arg Ala
                405                 410                 415
```

-continued

```
Asp Leu Leu Ser Tyr Leu Arg His Val Gln Trp Leu Arg Arg Ala Gly
            420                 425                 430

Gly Ser Ser Leu Lys Thr Leu Glu Pro Glu Leu Gly Thr Leu Gln Ala
        435                 440                 445

Arg Leu Asp Arg Leu Leu Arg Arg Leu Gln Leu Leu Met Ser Arg Leu
    450                 455                 460

Ala Leu Pro Gln Pro Pro Asp Pro Pro Ala Pro Pro Leu Ala Pro
465                 470                 475                 480

Pro Ser Ser Ala Trp Gly Gly Ile Arg Ala Ala His Ala Ile Leu Gly
                485                 490                 495

Gly Leu His Leu Thr Leu Asp Trp Ala Val Arg Gly Leu Leu Leu Leu
        500                 505                 510

Lys Thr Arg Leu
        515
```

```
<210> SEQ ID NO 22
<211> LENGTH: 23
<212> TYPE: DNA
<213> ORGANISM: Artificial Sequence
<220> FEATURE:
<223> OTHER INFORMATION: Il11 genotyping primer F

<400> SEQUENCE: 22
ggagggaggg gacgccaatg acc                                              23

<210> SEQ ID NO 23
<211> LENGTH: 24
<212> TYPE: DNA
<213> ORGANISM: Artificial Sequence
<220> FEATURE:
<223> OTHER INFORMATION: l11 genotyping primer R

<400> SEQUENCE: 23
tctgcctccc ctgcctgttt ctcg                                             24

<210> SEQ ID NO 24
<211> LENGTH: 18
<212> TYPE: DNA
<213> ORGANISM: Artificial Sequence
<220> FEATURE:
<223> OTHER INFORMATION: Il11-Luciferase genotyping primer F

<400> SEQUENCE: 24
aattccgtgg tgttgtcg                                                    18

<210> SEQ ID NO 25
<211> LENGTH: 24
<212> TYPE: DNA
<213> ORGANISM: Artificial Sequence
<220> FEATURE:
<223> OTHER INFORMATION: Il11-Luciferase genotyping primer R

<400> SEQUENCE: 25
tctgcctccc ctgcctgttt ctcg                                             24

<210> SEQ ID NO 26
<211> LENGTH: 24
<212> TYPE: DNA
<213> ORGANISM: Artificial Sequence
<220> FEATURE:
<223> OTHER INFORMATION: Il11-EGFP genotyping primer F

<400> SEQUENCE: 26
```

```
gaaatgagag cctagagtcc agag                                          24

<210> SEQ ID NO 27
<211> LENGTH: 24
<212> TYPE: DNA
<213> ORGANISM: Artificial Sequence
<220> FEATURE:
<223> OTHER INFORMATION: Il11-EGFP genotyping primer R

<400> SEQUENCE: 27
gaggcttgga agaatgcaca atta                                          24

<210> SEQ ID NO 28
<211> LENGTH: 5
<212> TYPE: PRT
<213> ORGANISM: Artificial Sequence
<220> FEATURE:
<223> OTHER INFORMATION: conserved motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 28

Trp Ser Xaa Trp Ser
1               5

<210> SEQ ID NO 29
<211> LENGTH: 54
<212> TYPE: DNA
<213> ORGANISM: Artificial Sequence
<220> FEATURE:
<223> OTHER INFORMATION: knock-in locus

<400> SEQUENCE: 29
aacccctggc ctgtggggac atgaactgta agttggttcc agttcatggg tgag         54
```